(12) United States Patent
Grabstein et al.

(10) Patent No.: US 9,732,367 B2
(45) Date of Patent: Aug. 15, 2017

(54) CELL LINES

(71) Applicant: MEDIMMUNE LIMITED, Cambridge (GB)

(72) Inventors: Kenneth H. Grabstein, Mercer Island, WA (US); Michael Van Brunt, Covington, WA (US); Marcello Marelli, Seattle, WA (US); William Brady, San Diego, CA (US); Jeffrey C. Johnson, Flemington, NJ (US)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 14/430,542

(22) PCT Filed: Sep. 24, 2013

(86) PCT No.: PCT/EP2013/069887
§ 371 (c)(1),
(2) Date: Mar. 23, 2015

(87) PCT Pub. No.: WO2014/044872
PCT Pub. Date: Mar. 27, 2014

(65) Prior Publication Data
US 2015/0259721 A1    Sep. 17, 2015

Related U.S. Application Data

(60) Provisional application No. 61/862,495, filed on Aug. 5, 2013, provisional application No. 61/705,116, filed on Sep. 24, 2012.

(51) Int. Cl.
| | |
|---|---|
| C12P 21/02 | (2006.01) |
| C07K 16/40 | (2006.01) |
| C12N 15/85 | (2006.01) |
| C07K 16/46 | (2006.01) |
| C07K 17/08 | (2006.01) |
| C07K 16/32 | (2006.01) |
| C07C 271/12 | (2006.01) |
| C07C 271/20 | (2006.01) |
| C07C 271/22 | (2006.01) |
| C07C 233/49 | (2006.01) |
| C07C 233/56 | (2006.01) |
| C07C 247/04 | (2006.01) |
| C07K 16/24 | (2006.01) |
| A61K 47/48 | (2006.01) |
| C07C 235/74 | (2006.01) |
| C07K 14/435 | (2006.01) |
| C07K 16/28 | (2006.01) |
| C12N 9/00 | (2006.01) |

(52) U.S. Cl.
CPC ........ *C12P 21/02* (2013.01); *A61K 47/48569* (2013.01); *C07C 233/49* (2013.01); *C07C 233/56* (2013.01); *C07C 235/74* (2013.01); *C07C 247/04* (2013.01); *C07C 271/12* (2013.01); *C07C 271/20* (2013.01); *C07C 271/22* (2013.01); *C07K 14/43595* (2013.01); *C07K 16/244* (2013.01); *C07K 16/248* (2013.01); *C07K 16/2863* (2013.01); *C07K 16/32* (2013.01); *C07K 16/40* (2013.01); *C07K 16/46* (2013.01); *C07K 17/08* (2013.01); *C12N 9/93* (2013.01); *C12N 15/85* (2013.01); *C07K 2317/14* (2013.01); *C07K 2317/24* (2013.01); *C07K 2317/31* (2013.01); *C07K 2317/40* (2013.01); *C07K 2317/51* (2013.01); *C12Y 601/01025* (2013.01)

(58) Field of Classification Search
None
See application file for complete search history.

(56) References Cited

U.S. PATENT DOCUMENTS

| | | | |
|---|---|---|---|
| 3,711,458 A | 1/1973 | Olofson | |
| 4,512,979 A | 4/1985 | Patchett | |
| 5,216,023 A | 6/1993 | Literati et al. | |
| 8,168,407 B2 | 5/2012 | Yokoyama et al. | |
| 2010/0304431 A1* | 12/2010 | Yokoyama ............... | C12N 9/93 435/69.1 |

FOREIGN PATENT DOCUMENTS

| | | |
|---|---|---|
| EP | 1911840 A1 | 4/2008 |
| GB | 2470770 A | 8/2010 |
| WO | 2004041752 A2 | 5/2004 |
| WO | 2011044255 A1 | 4/2011 |
| WO | 2011087810 A1 | 7/2011 |
| WO | 2012032181 A2 | 3/2012 |
| WO | 2012038706 A1 | 3/2012 |
| WO | 2014/036492 A1 | 3/2014 |

OTHER PUBLICATIONS

Coward et al, "Analogs of S-adenosylhomocysteine as potential inhibitors of biological transmethylation. Synthesis and biological activity of homocysteine derivatives bridged to adenine", J. Med. Chem., 15(4), 381-384 (1972).
Erickson et al, "Use of chlorinated benzyloxycarbonyl protecting groups to eliminate N. epsilon-branching at lysine during solid-phase peptide synthesis", J.A.C.S., 95(11), 3757-3763 (1973).
(Continued)

*Primary Examiner* — Addison D Ault
(74) *Attorney, Agent, or Firm* — Glance Law Group; Melissa Pytel

(57) ABSTRACT

There is provided inter alia a process for stabilizing a eukaryotic cell line which expresses PylRS and tRNAPyl and which is suitable for incorporation of a gene encoding a target protein containing one or more non-natural amino acids encoded by a nonsense codon which comprises culturing said cell line under conditions in which the adverse effect of tRNAPyl expression on cell viability and/or cell growth is reduced or eliminated.

6 Claims, 43 Drawing Sheets

(56) References Cited

OTHER PUBLICATIONS

Jermyn "Carbobenzoxy derivatives of S-aminoalkyl-L-cysteines", Australian Journal of Chemistry, 19(10), 1999-2000 (1966).

Jie Li et al: "Ligand-free palladium-mediated site-specific protein labelling inside gram-negative bacterial pathogens", J. A.C.S., 135(19), 7330-7338, (2013).

Kimbonguila et al, "Allylic protection of thiols and cysteine: I: The allyloxycarbonylaminomethyl group", Tetrahedron, 55(22), 6931-6944 (1999).

Ledger et al, "The use of sequestering agents in the preparation of [epsilon]-acyl-L-lysine and [delta]acyl-L-ornithine derivatives", Australian Journal of Chemistry, 18(6), 933-935, (1965).

Lindley "The preparation of compounds related to S-2-aminoethyl-L-cysteine" Australian Journal of Chemistry 12(2), 296-298, (1959).

Matsui, "Studies on acylase activity and microorganisms. XXIV. Properties of [delta]-ornithine acylase: 5-N-acylornithine amidohydrolase", Chem. Pharm. Bull., 15(10), 1586-1596 (1967).

Nishino et al, "Tandem enzymatic relsolution yielding L-alpha-aminoalkanedioic acid omega-esters", Chem. Pharm. Bull., 44(1), 212-214 (1996).

Noda et al, "Modified benzyloxycarbonyl groups for protection of [epsilon]-amino group of lysine", Bull. Chem. Soc. Japan, 43(6), 1883-1885 (1970).

Plass et al, "Genetically encoded copper-free click chemistry", Angewandte Chemie, Int Edition, 50(17), 3878-3881 (2011).

Popovitz-Biro et al, "A new series of amphiphilic molecules forming stable Z-type (polar) Langmuir-Blodgett films", 112(7), 2498-2506 (1990).

Spanton et al, "Chemical defence and self-defence: Biochemical transformations of contact insecticides produced by soldier termites", Tetrahedron, 38(13), 1921-1930 (1982).

Theodoropoulos, "Synthesis of [epsilon]-peptides of lysine", J. Org. Chem. 23(1), 140, (1958).

Xin Li et al, "N6-(2-(R)-propargylglycyl)lysine as a clickable pyrrolysine mimic", Chemistry—An Asian Journal, 5(8), 1765-1769 (2010).

Zhang et al, "Mechanism of inactivation of neuronal nitric oxide synthase by N[omega]-allyl-L-arginine", J.A.C.S., 119(45), 10888-10902 (1997).

Sun et al., "Vitamin K epoxide reductase significantly improves carboxylation in a cell line overexpressing factor X", Blood, 106(12):3811-3813 (2005).

Axup et al., "Synthesis of site-specific antibody-drug conjugates using unnatural amino acids", P.N.A.S. 109(40), (2012) 16101-16106.

Dose et al., "Single nucleotide specific detection of DNA by native chemical ligation of fluorescence labelled PNA-probes", Bioorg. Med. Chem., 16, (2008) 65-77.

Hancock et al., "Expanding the Genetic Code of Yeast for Incorporation of Diverse Unnatural Amino Acids via a Pyrrolysyl-tRNA Synthetase/tRNA Pair", J. Am. Chern. Soc., 132, (2010), 14819-14824.

Mukai et al., "Addling L-lysine derivatives to the genetic code of mammalian cells with engineered pyrrolysyl-tRNA synthetases", Biochemical and Biophysical Research Communications, 371 (2008), 818-822.

Vrabel et al., "Optimization of the posttranslational click modification of proteins", Collect. Czech. Chern. Commun. 76(9), (2011) 1089-1101.

Yasobu et al., "Design, Synthesis and Antitumor Activity of 4-Halocolchicines and their Pro-drugs Activated by Cathepsin B", ACS Med. Chem. Lett., 2, (2011) 348-352.

International Search Report mailed Nov. 14, 2013, in PCT/EP2013/069887 (5 pages).

International Search Report mailed Jan. 3, 2014, in PCT/EP2013/069888 (4 pages).

International Search Report mailed Jul. 4, 2015, in PCT/IB2014/002505 (8 pages).

* cited by examiner

Ab Attachment Site

Ab Attachment Site

Ab Attachment Site

Ab Attachment Site

CELL LINES

CROSS REFERENCE TO RELATED APPLICATIONS

This application is a national stage application under 35 U.S.C. §371(c) of PCT Application No. PCT/EP2013/069887, entitled "CELL LINES," filed on Sep. 24, 2013, which claims priority to U.S. Provisional Patent Application Nos. 61/705,116, filed Sep. 24, 2012 and 61/862,495, filed Aug. 5, 2013, the entire disclosures of which are incorporated by reference herein in their entirety.

REFERENCE TO SEQUENCE LISTING SUBMITTED ELECTRONICALLY

The content of the electronically submitted sequence listing in ASCII text file entitled Sequence Listing.txt and having a size of 164 kilobytes filed with the application is incorporated herein by reference in its entirety.

FIELD OF THE INVENTION

This invention relates to stable eukaryotic cell lines suitable for use in incorporating non natural amino acids into proteins and to processes for preparing them. This invention also relates to proteins with incorporated non natural amino acids which are suitable for conjugation with other proteins, with drugs or other moieties e.g. to allow half life extension and to corresponding protein conjugates. Further, the invention relates to novel amino acid derivatives.

BACKGROUND TO THE INVENTION

The site-specific introduction of non natural amino acids (nnAAs) into a target protein provides a significant advantage for the generation of functionalized protein conjugates over non specific methods (Wang et al., 2011). A variety of non natural amino acids are available that contain moieties that provide bioorthogonal sites for conjugation chemistry and enable specific reactions to occur at these sites. Control over the positions of the conjugation site enables products with optimal function by avoiding active sites and essential protein functional domains. In addition, this allows for the generation of a homogeneous and predictably modified product that improves the functional characteristics and purification of the product.

Site specific incorporation of nnAAs in bacterial cells has been achieved through amino acid substitution approaches and through the engineering of orthogonal aminoacyl tRNA synthetases that charge only their cognate tRNAs with a non natural amino acid. The position of the non natural amino acid in the target protein can be specified by a variety of codons within the gene sequence, but most often it is directed to amber codons. The variety of proteins that can be expressed in *E. coli* and other prokaryotic based systems, however, is limited by the protein folding machinery of these organisms. Eukaryotic expression systems (such as mammalian expression systems) are capable of expressing a wider variety of proteins including those that require glycosylation for optimal therapeutic function (e.g. G-CSF, insulin, epoietin alpha) exist as protein complexes (e.g. antibodies), or require posttranslational modifications such as disulfide bond formation (e.g. atrial natriuretic factor) that are not accessible in bacterial systems.

Systems for the introduction of nnAAs into mammalian cells have been developed either through transfection of in vitro charged tRNAs (Hecht et al., 1978; Kohrer et al., 2001; Kohrer et al., 2003) or genetically encoded using orthogonal aminoacyl tRNA synthetase/tRNA pairs (Mukai et al 2008, Liu W. et Al., 2007; Wang W., 2007; Ye, S. et Al., 2008; Sakamoto, K et Al., 2002; Takimoto, J. et Al., 2009; Chen, P. et Al., 2009). Chemically acylated tRNAs are not reacylated and thus their use is prohibitive to large scale protein synthesis whether in vitro or in vivo. Genomically encoded RS/tRNA pairs are required to be orthogonal to the host cell in order to retain the specificity of nnAA insertion.

In use of orthogonal aminoacyl tRNA synthetase/tRNA pairs, orthogonality of the RS and tRNA is achieved through mutations at key sites to enable specificity for a nnAA while at the same time reducing or eliminating recognition of canonical amino acids, and host tRNAs. The tRNA may also be modified to prevent cognition by host RSs and to recognize amber stop codons. Several RS/tRNA pairs have been developed including the *E. coli* TyrRS/*B. stearothermophilus* tRNAtyr (Liu, W., 2007; Ye et al., 2008; Sakamoto et al., 2002) and *E. coli* TyrRS/*E. coli* tRNAtyr (Wang, W., 2007; Takimoto et al., 2009).

It has been observed that one orthogonal RS/tRNA pair naturally evolved in a subset of archaeabacteria (methanogenic archaea bacteria that catabolize methylamines) which has specificity for the amino acid pyrrolysine. Pyrrolysine uses a 21st aminoacyl-tRNA synthetase, naturally evolved to be orthogonal to all other amino acids and tRNAs.

Pyrrolysine is a natural amino acid, the only one that is authentically specified by an amber codon. Blight et al., 2004 showed that PylRS and tRNApyl can incorporate Pyrrolysine at amber codons in *E. coli*. They also showed that the wild type ("WT") PyLRS is naturally promiscuous and can incorporate analogs of Lysine.

Yokoyama et al (EP1911840) demonstrated that the PylRS/tRNA system is orthogonal in eukaryotic cells and showed the incorporation of several nnAAs into a target proteins encoded by amber codons in bacterial cells. These authors also identified key amino acid residues in pylRS that form the amino acid binding pocket and function in selecting pyrrolysine over other canonical amino acids. Mutations at this site generated mutants able the recognize and aminoacylate the tRNApy with AzZ-lys (Yanagisawa 2008)

This orthogonality extends to bacteria and eukaryotic cells.

PylRS is a naturally promiscuous synthetase that has naturally evolved to exclude lysine, but will incorporate lysine analogs without mutation including azides, alkynes and alkenes, (Yanagisawa et al, 2008; Neumann et al. 2008; Mukai et al., 2008; Nguyen et al., 2009). The basis of this specificity is dependent on hydrophobic interactions between amino acid residues of the pylRS binding pocket with the pyrrol ring of pyrrolysine that stabilizes and correctly positions the amino acid in the active site of the synthetase (Kavran et al., 2007). This RS/tRNA pair has been introduced via transient transfection into bacterial, yeast and mammalian cells and shown to be effective for incorporation of a number of non-natural amino acids into target proteins.

For instance, EP 1911840 demonstrates incorporation of N-ε-boc-Lysine into a target protein in *E. coli* cells.

The expression of tRNA in eukaryotic cells requires two internal promoters within the tRNA coding sequence. The consensus sequences of such promoters are known as the A-Box and B-Box (Naykova et al., 2003).

Although certain prokaryotic-derived tRNAs naturally carry sequences that function as an internal promoter and can be expressed in animal cells without modifications, or with changes that generate an intragenic promoter sequence but do not alter the function of the tRNA or its recognition by its cognate RS, tRNAPyl does not contain such promoter. Furthermore, the D loop where A-Box and B-Box are normally present is unusually small and the introduction of said A-Box and B-Box would destroy its function as reported in yeast by Hancock et al (2010) and confirmed by the inventors in mammalian cells.

WO2007099854 describes the use of a eukaryotic snRNA promoter to drive tRNAPyl expression in eukaryotic cells. DNA constructs described therein comprise the tRNAPyl gene, a transcription terminator sequence placed 3' of said tRNA gene, and a promoter sequence that induces transcription by RNA Polymerase II or III such as U1 snRNA promoter or U6 snRNA promoter placed 5' to said tRNAPyl gene.

Mammalian expression is of particular interest as it allows for the production of fully folded proteins and protein complexes like full length antibodies that are challenging or currently inaccessible to prokaryotic systems or yeast cells.

Transient transfection experiments of genes encoding the pyrrolysine aminoacyl tRNA synthetase (pylRS) and its tRNAPyl, in both human (HEK293) and hamster (CHO) cells, have shown that the pylRS/tRNA pair efficiently incorporates nnAAs into a target protein at sites designated by an amber stop codon in mammalian cells (see for instance Mukai 2008).

EP1911840 teaches the introduction of a vector carrying a WT PylRS, a vector carrying a tRNAPyl gene, and a vector carrying a target gene where an amber mutation is introduced at the site where the lysine derivative is to be inserted. The only technique utilized to introduce the vectors is transient transfection. In fact, nowhere in the patent application the selection of stable clones is mentioned nor applied experimentally.

WO09038195 describes the generation of mutant PylRS enzymes in order to improve its catalytic activity, and allow incorporation of non natural aminoacids derived from lysine with bulky side chain structures.

In particular, WO09038195 describes a mutation at position 384 (referred to *methanosarcina mazei* PylRS aminoacid sequence) whereby Tyr384 is replaced with Phenylalanine, among other amino acids. It is hypothesized that due to the fact that Tyr384 interacts with a substrate aminoacid, particularly with its main chain (Kavran 2007, Nozawa 2009) there is likelihood that the enzyme catalytic activity would be enhanced independently of the substrate.

As noted above, expression based on the PylRS and tRNAPyl orthogonal pair has hitherto only been achieved in transiently stable eukaryotic cell lines. Transiently stable cell lines are not suitable for the reliable manufacture of commercial products; indeed the present inventors believe that the biologic products on the market today derived from mammalian cells are exclusively generated by stable cell lines.

Therefore there remains a need in the art to develop methods for the production of stable eukaryotic cells containing the PylRS and tRNAPyl orthogonal pair thereby to facilitate production of proteins containing nnAAs on a commercial scale.

The present invention addresses the aforementioned need.

Pyrrolysine analogs, defined as amino acid derivatives recognized by either native or genetically evolved PylRS and incorporated into proteins at amber codon sites, have been disclosed in the past few years and reviewed, for instance, by Fekner et. al (Fekner, Li, & Chan, 2010) and Liu et al. Analogs bearing functional groups or post translational modifications have been site-specifically incorporated into proteins using pylRS-tRNAPyl systems. Several studies, see e.g. Yanagisawa et al, focused on mutations within the PylRS enzyme in order to accommodate analogs in which the N6 substituent were an aromatic ring within the binding pocket pyrrolysine. Others, for instance Nguyen et al (also in WO2010/139948), and Li et al (also in WO2011/044255) focused on identification of pyrrolysine analogs which do not carry a bulky N6 substituent, with the result of obtaining simpler analogs which would be simple to synthesize and interact with native pylRS/tRNAPyl pairs. There remains a need to develop further pyrrolysine analogs. Whilst pyrrolysine analogs made thus far have been restricted to those evolved from a lysine backbone, the present inventors have generated pyrrolysine analogs successfully incorporated into proteins with native pylRS/tRNAPyl pairs starting from a variety of amino acid structures.

Antibody drug conjugates (ADCs), composed of recombinant chimeric, humanized or human antibodies covalently bound by means of synthetic linkers to highly cytotoxic drugs, have been developed in recent years in order to target cytotoxic drugs to tumor cells. The right combination of antibodies targeting tumor associated antigens, a potent toxins and appropriate conjugation chemistry can be very effective at delivering the toxin directly to the tumor cells, while avoiding toxicity of the drug to normal tissue.

ADCs developed so far are heterogeneous mixtures of conjugated and unconjugated antibody, depending on the chemistry of the conjugation used when generating the ADC. In particular, the random nature of the most commonly used conjugation protocols results in a collection of species with varying numbers of drugs conjugated per antibody molecule (DAR) as well as varying conjugation sites. Common conjugation chemistries include lysine side-chain based conjugation, which results in a wide range of species due to the large availability of lysine residues in a typical antibody. More site-specific conjugations have been obtained through engineering of cysteine residues to produce reactive thiol groups, resulting in nearly homogeneous ADCs.

Her2 tumor associated antigen, a member of the EGFR family, has been successfully targeted in breast cancer with Herceptin, an anti-Her 2 antibody, however, the antibody itself is effective in a limited group of patients. A more potent form, ado-trastuzumab emtansine, which has a toxin linked to it, is now available. Ado-trastuzumab emtansine is able to effectively treat patients who are refractory to Herceptin, due to the ability of ado-trastuzumab emtansine to deliver a toxin to the cytoplasm of the cancer cell. The conjugation chemistry being used by ado-trastuzumab emtansine and Brentuximab vedotin, exploits existing cysteine residues that normally form disulfide bonds, and more recently, engineered free cysteine residues. This approach has led to the production of heterogeneous mixtures of ADC with different numbers of drug at different positions on the mAb. The linkers used include thioether (Kadcyla) as well as dipeptide linkers (Adcetris), the latter being specifically cleaved by lysosomal acid hydrolases. Both types of linkers appear to be effective, but not optimal. Conventional Cys or Lys directed bioconjugation methods such as those used for manufacture of by ado-trastuzumab emtansine, Brentuximab vedotin, and gemtuzamab ozogamicin permit premature release of toxin prior to tumor cell engagement. Gemtuzamab ozogamicin, which was approved in 2000, was withdrawn from the market in 2010, due to high toxicity due to the use of an acid labile linker which caused intolerable release of the toxin from the ADC in the blood.

Therefore there remains a need in the art to develop highly homogeneous ADCs, where the conjugation sites and the number of drugs per antibody are well controlled.

The present inventors have found that through use of site specific incorporation of nnAAs and subsequent conjugation of antibodies at the site of nnAA it is possible to generate homogeneous and potent ADCs. Furthermore, the present inventors have found sites, within the IgG constant region, which can be used for conjugation without disrupting the specificity of the binding of the antibody or its pharmacokinetic properties in vivo.

SUMMARY OF THE INVENTION

According to the present invention there is provided a process for preparing a stable eukaryotic cell line which expresses pylRS and tRNApyl and which is suitable for incorporation of a gene permitting expression of a target protein containing one or more non-natural amino acids encoded by an amber codon.

The invention is derived from the inventors' findings concerning the source of instability of cell lines prepared by prior art methods.

It may be observed that conventional eukaryotic cells such as CHO, and HEK293 cells that express pylRS and tRNApyl without any gene permitting expression of a target protein containing one or more non-natural amino acids encoded by an amber codon adopt a phenotype indicative of cellular toxicity, including higher proportion of dead cells in the culture, a rounded cellular morphology, loose attachment of the cells to the growth plates, and decreased cell growth rates. The inventors observed that upon subsequent expression of said gene permitting expression of a target protein the health of cells appeared to improve noticeably. It appears to the inventors that the toxicity is associated with the expression in the system of high amounts of the tRNApyl which in the absence of nnAA induces the extension of essential) housekeeping genes that terminate in an amber stop codon (Liebman and Sherman 1976; Liebman et al., 1976).

Thus, without being bound by theory, toxic effects of tRNApyl may be a consequence of imperfect orthogonality occurring when high levels of tRNApyl are present in the absence of a target protein.

While the tRNApyl is for the most part orthogonal in mammalian cells, it is possible that the tRNApyl may be inefficiently aminoacylated by one of the host RSs in the absence of nnAA (where the natural enzyme, pylRS is vacant). In cells expressing high levels of the tRNA a significant amount of aminoacylated tRNA may be generated which forces irregular amber suppression of essential genes.

Accordingly the inventors have surmised that stable cell lines may be produced by processes which have as their objective a reduction in or masking of the apparently toxic effects of tRNApyl.

As a first aspect of the invention, therefore, there is provided a process for stabilizing a eukaryotic cell line (particularly a mammalian cell line) which expresses PylRS and tRNAPyl and which is suitable for incorporation of a gene encoding a target protein containing one or more non-natural amino acids encoded by an amber codon which comprises culturing said cell line under conditions in which the adverse effect of tRNAPyl expression on cell viability and/or cell growth is reduced or eliminated.

As a second aspect of the invention, there are provided decoy amino acids (dnnAAs) of formula VII as described herein, which have the merit of reducing or masking the toxic effects of tRNApyl when added to the culture media during the production or maintenance of said stable cell lines.

According to a third aspect of the invention, there are provided novel non natural aminoacids analogs of pyrrolysine of Formulae V and VI as described herein, which have the merit of being straightforward to prepare, in being readily incorporated into proteins (typically without loss of bioactivity when used appropriately) and in providing useful means for bioconjugation.

According to a fourth aspect of the invention, there are provided methods to obtain highly homogeneous and active Antibody Drug Conjugates through site specific insertion of non natural aminoacids at pre-determined positions.

BRIEF DESCRIPTION OF THE SEQUENCE LISTING

Figure 1:
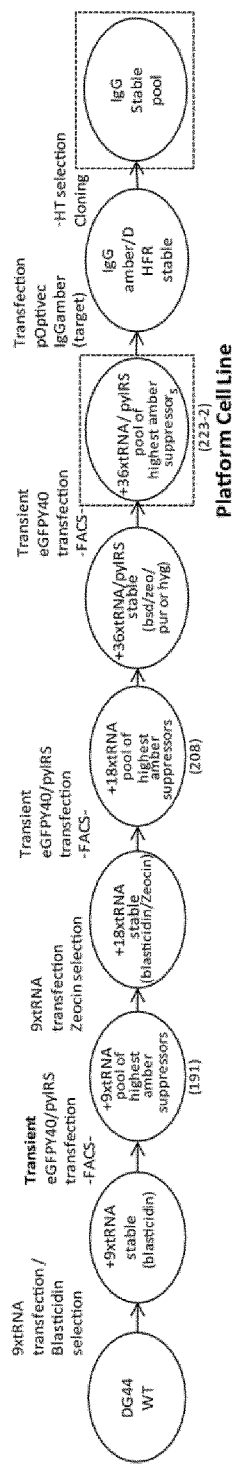
FIG. 1. Scheme detailing the iterative introduction of RS/tRNA elements and selection steps performed for the development of a platform cell line and subsequent expression cell line.

SEQ ID No 1: PylRS *Methanosarcina mazei* WT amino acid sequence
SEQ ID No 2: PylRS *Methanosarcina mazei* Y384F mutant amino acid sequence
SEQ ID No 3: PylRS *Methanosarcina barkeri* WT amino acid sequence
SEQ ID No 4: PylRS *Desulfitobacterium hafniense* amino acid sequence
SEQ ID No 5: PylRS *Methanosarcina acetivoran* amino acid sequence
SEQ ID No 6: PylRS *Methanococcoides burtonii* amino acid sequence
SEQ ID No 7: PylRS *Methanosarcina thermophila* amino acid sequence
SEQ ID No 8: PylRS *Methanosalsum zhilinae* amino acid sequence
SEQ ID No 9: PylRS *Methanohalobium evestigatum* amino acid sequence
SEQ ID No 10: PylRS *Methanohalophilus mahii* amino acid sequence
SEQ ID No 11: PylRS *Desulfotomaculum gibsoniae* amino acid sequence
SEQ ID No 12: PylRS *Desulfosporosinus meridiei* amino acid sequence
SEQ ID No 13: PylRS *Desulfotomaculum acetoxidans* amino acid sequence
SEQ ID No 14: PylRS *Methanosarcina mazei* WT nucleotide sequence
SEQ ID No 15: PylRS *Methanosarcina mazei* Y384F mutant nucleotide sequence
SEQ ID No 16: PylRS Codon optimized *Methanosarcina mazei* nucleotide sequence
SEQ ID No 17: PylRS *Methanosarcina barkeri* nucleotide sequence
SEQ ID No 18: PylRS *Desulfitobacterium hafniense* nucleotide sequence
SEQ ID No 19: PylRS *Methanosarcina acetivorans* nucleotide sequence
SEQ ID No 20: PylRS *Methanococcoides burtonii* nucleotide sequence
SEQ ID No 21: PylRS *Methanosarcina thermophila* nucleotide sequence
SEQ ID No 22: PylRS *Methanosalum zhilinae* nucleotide sequence
SEQ ID No 23: PylRS *Methanohalobium evestigatum* nucleotide sequence
SEQ ID No 24: PylRS *Desulfotomaculum gibsoniae* nucleotide sequence
SEQ ID No 25: PylRS *Methanohalophilus mahii* nucleotide sequence
SEQ ID No 26: tRNApyl *Methanosarcina barkeri*
SEQ ID No 27: tRNApyl *Methanosarcina acetivorans*
SEQ ID No 28: tRNApyl *Methanosarcina mazei*
SEQ ID No 29: tRNApyl *Methanococcoides burtonii*
SEQ ID No 30: tRNApyl *Desulfobacterium hafniense*
SEQ ID No 31: H1/TO Promoter
SEQ ID No 32: U6 snRNA Promoter
SEQ ID No 33: SNR52 Promoter
SEQ ID No 34: H1 Promoter
SEQ ID No 35: U6-tRNApyl construct
SEQ ID No 36: GFP nucleotide sequence
SEQ ID No 37: GFP amino acid sequence
SEQ ID No 38: GFPY40 Aminoacid Sequence
SEQ ID No 39: anti-IL-6 (28D2) Gamma Nucleotide Sequence
SEQ ID No 40: anti-IL-6 (28D2) Gamma Aminoacid Sequence
SEQ ID No 41: anti-IL-6 (28D2) Gamma_amber K274 Nucleotide Sequence
SEQ ID No 42: anti-IL-6 (28D2) Gamma_amber K274 Aminoacid Sequence
SEQ ID No 43: anti-IL-6 (28D2) Kappa Nucleotide Sequence
SEQ ID No 44: anti-IL-6 (28D2) Kappa Aminoacid Sequence
SEQ ID No 45: anti-Her2 (4D5) gamma Nucleotide sequence
SEQ ID No 46: anti-Her2 (4D5) gamma amino acid sequence
SEQ ID No 47: anti-Her2 (4D5) gamma_K274amber nucleotide sequence
SEQ ID No 48: anti-Her2 (4D5) gamma_K274amber amino acid sequence
SEQ ID No 49: anti-Her2 (4D5) gamma_T359amber nucleotide sequence
SEQ ID No 50: anti-Her2 (4D5) gamma_T359amber amino acid sequence
SEQ ID No 51: anti-Her2 (4D5)Kappa nucleotide sequence
SEQ ID No 52: anti-Her2 (4D5)Kappa amino acid sequence
SEQ ID No 53: anti-Her2 (4D5)Kappa D70amber nucleotide sequence
SEQ ID No 54: anti-Her2 (4D5)Kappa D70amber amino acid sequence
SEQ ID No 55: anti-Her2 (4D5)Kappa E81amber nucleotide sequence
SEQ ID No 56: anti-Her2 (4D5)Kappa E81amber amino acid sequence SEQ ID No 57: anti-PSMA scFv nucleotide sequence
SEQ ID No 58: anti-PSMA scFv amino acid sequence
SEQ ID No 59: anti-PSMA scFv_117amber nucleotide sequence
SEQ ID No 60: anti-PSMA scFv_117amber aminoacid sequence
SEQ ID No 61: FGF21 WT nucleotide sequence
SEQ ID No 62: FGF21 WT amino acid sequence
SEQ ID No 63: FGF21 R131amber nucleotide sequence
SEQ ID No 64: FGF21 R131amber amino acid sequence
SEQ ID No 65: FGF21 F12amber nucleotide sequence
SEQ ID No 66: FGF21 F12amber aminoacid sequence
SEQ ID No 67: FGF21 L60amber nucleotide sequence
SEQ ID No 68: FGF21 L60amber amino acid sequence
SEQ ID No 69: FGF21P 90amber nucleotide sequence
SEQ ID No 70: FGF21P 90amber amino acid sequence
SEQ ID No 71: FGF21 P140amber nucleotide sequence
SEQ ID No 72: FGF21 P140amber amino acid sequence
SEQ ID No 73: GFPY40 nucleotide Sequence
SEQ ID No 74: Herceptin nucleotide sequence Heavy Chain
SEQ ID No 75: Herceptin amino acid sequence Heavy Chain
SEQ ID No 76: Herceptin H274 Nucleotide sequence Heavy Chain
SEQ ID No 77: Herceptin H274 amino acid sequence Heavy Chain
SEQ ID No 78: Herceptin nucleotide sequence Light Chain
SEQ ID No 79: Herceptin amino acid sequence Light Chain
SEQ ID No 80: 3× Flag tag sequence
SEQ ID No 81: 5×Pro-6×His tag
SEQ ID No 82: portion of human IgG1 Heavy Chain (constant region)
SEQ ID No 83: portion of SEQ ID No 52 (framework region)
SEQ ID No 84: portion of SEQ ID No 52 (framework region)

DETAILED DESCRIPTION OF THE INVENTION

Definitions

The term "alkyl" refers to an aliphatic linkage or substituent, typically containing 1-6 e.g. 1-4 carbon atoms and can be straight chain or branched. Examples include methyl, ethyl, n-propyl, i-propyl, n-butyl and t-butyl.

The term "alkenyl" refers to an aliphatic linkage or substituent, typically containing 2-6 e.g. 2-4 carbon atoms and can be straight chain or branched and which is unsaturated in respect of containing at least one C=C moiety. A specific example is a terminal alkene group in which the C=C moiety is at the terminus. Examples of alkenyl include ethenyl, propen-1-yl, propen-2-yl, and 2-methyl-propen-2-yl.

The term "alkyne" or "alkynyl" refers to an aliphatic linkage or substituent, typically containing 2-6 e.g. 2-4 carbon atoms and can be straight chain or branched and which is unsaturated in respect of containing at least one C≡C moiety. A specific example is a terminal alkyne group in which the C≡C moiety is at the terminus. Examples of alkynyl groups include —C≡CH and —C≡C—CH₃.

The term "aryl" refers to an aromatic ring structure that can be part of a linkage or part of a substituent. Aryl moieties may contain one ring (e.g. phenyl) or two rings (e.g. naphthyl) or more than two rings, provided that at least one ring is aromatic. Aryl groups may be substituted e.g. by one or more (e.g. one or two, such as one) substituent selected from alkyl, alkenyl, alkynyl, fluoroalkyl, halogen, alkoxy, nitro and cyano. An exemplary aryl is phenyl.

The term "heteroaryl" refers to a heteroaromatic ring structure that can be part of a linkage or part of a substituent. The heteroaromatic ring may contain 1-4 (more usually 1-3 e.g. one or two) heteroatoms selected from O, N and S. Heteroaryl moieties may contain one ring or two rings or more than two rings, provided that at least one ring is heteroaromatic. Example groups containing one 6 membered ring include pyridine and pyrimidine. Example groups containing one 5 membered ring include pyrrole, furan, thiophene, oxazole, thiazole, diazole, thiadiazole and tetrazole. Heteroaryl moieties that contain two rings may contain heteroatoms in one or both rings. Examples include quinoline and isoquinoline. Heteroaryl groups may be substituted e.g. by one or more (e.g. one or two, such as one) substituent selected from alkyl, alkenyl, alkynyl, fluoroalkyl, halogen, alkoxy, nitro and cyano.

The term "methyl" or "Me" refers to a CH₃ group
The term "OMe" refers to a O—CH₃ group.
The term "ethyl" or "Et" refers to a CH₂CH₃ group.
The term "OEt" refers to a O—CH₂CH₃ group
The term "tBu" refers to a C(CH₃)₃ group
The term "OtBu" refers to a O—C(CH₃)₃ group.
The term "OBn" or "OBenzyl" refers to a O—CH₂-Ph group
The term "OFmoc" or "OCH₂Fluorene" refers to the following structure:

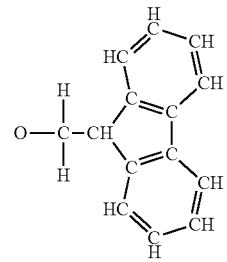 [SMILES: OCC1c2ccccc2-c2ccccc21]

The term "Phenyl" or "Ph" refers to a benzene ring as in the following structure:

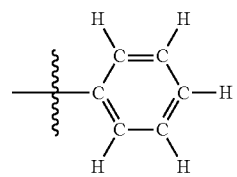 [SMILES: *c1ccccc1]

The term "allyl" refers to a CH₂—CH=CH₂ group
The term "ethyl chloride" refers to a CH₂CH₂—Cl group
The term "azide" and "azido" refers to a N=N(+)=N(−) or N₃ functional group.

The term "azidoalkyl" means alkyl substituted by azido, especially terminal azido. Examples include —(CH₂)ₙN₃ wherein n=1-4.

The term "haloalkyl" means alkyl substituted by one or more (e.g. 1, 2 or 3, especially 1 or 2 such as 1) halogen atoms (eg Cl or F atoms). Examples include —CF₃ and —CH₂CH₂Cl.

The term "propargyl" refers to a methyl group appended to a terminal alkyne. It is denoted by —CH$_2$—C≡C—H.

The term "amide" refers to a —C(=O)—NH— linkage.

The term "carbamate" refers to a —O—C(=O)—NH— linkage.

The term "ester" refers to a —C—C(=O)—O—C linkage

The term "alkoxy" refers to the group —O-alkyl.

The term "ketone" refers to a C—C(=O)—C linkage.

The term "pyrrolysine analog" means an amino acid derivative recognized by either native or genetically evolved PylRS and incorporated into proteins at a nonsense codon site.

The term "the side chain of one of the 20 natural amino acids" refers to the group R in the formula HOOC—CHR—NH$_2$ relating to the 20 natural amino acids known by their single letter codes A, C, D, E, F, G, H, I, K, L, M, N, P, Q, R, S, T, V, W and Y. Either L or S stereochemistry (or a mixture thereof) is intended, although L stereochemistry is preferred.

The term "cell viability" refers to a determination of living (viable) or dead cells, based on a total cell sample, within the context of cells cultured in vitro. A cell is considered viable if it has the ability to grow and develop. Viability assays are based on either the physical properties of viable cells such as membrane integrity or on their metabolic activity.

The term "cell growth" refers to cellular proliferation as measured by the number of cell divisions over a period of time. Growth is measured by tracking the cell density (cell/mL) of a culture over time.

The term "stable expression" refers to the expression of a protein which is achieved by integration of the gene (or corresponding cDNA) of interest into the target cell's chromosome.

The term "stable integration" therefore refers to the integration of the gene (or corresponding cDNA) of interest into the target cell's chromosome: Initially the gene of interest has to be introduced into the cell, subsequently into the nucleus and finally it has to be integrated into chromosomal DNA. Stably transfected cells can be selected and cultured in various ways: for instance, a selection marker is co-expressed on either the same or on a second, co-transfected vector. A variety of systems for selecting transfected cells exists, including resistance to antibiotics such as neomycin phosphotransferase, conferring resistance to G418, dihydrofolate reductase (DHFR), or glutamine synthetase. The culture of the transfected cells can be done either in bulk to obtain a mixed population of resistant cells, or via single cell culture, to obtain cell clones from one single integration event.

The term "target gene" refers to the gene encoding for the protein to be modified via insertion of nnAAs.

Various Embodiments According to the Invention

"Decoy Amino Acid" Approach

According to an embodiment, there is provided a process wherein the conditions in which the adverse effect of tRNApyl on cell viability and/or cell growth is reduced or eliminated include conditions in which there is present in the medium in which the cell line is cultured a decoy amino acid which is a substrate for PylRS (i.e. is aminoacylated and is loaded onto the tRNApyl) but which is incapable of being incorporated into an extending protein chain.

Thus, a process to incorporate non natural amino acids into a protein may include the following steps:

1. Introduce a decoy amino acid into the growth medium of cells that is readily recognized and activated by the orthogonal RS for the cognate tRNA
2. Introduce the RS and tRNA into a eukaryotic cell, on one or more plasmids
3. Select for cells containing the RS and tRNA expression cassettes
4. Isolate one or more stable clones expressing the RS protein and tRNA thereby generating a platform cell line. Cells capable of non natural amino acid incorporation rates of greater than 30%, for example greater than 40% or 50% or 60% or 70% or 80% or preferably greater than 90% are selected.
5. Introduce the cDNA of the target protein whereby one or more amber codons has been introduced at the position or positions into which the non natural amino acid is to be incorporated
6. Isolate a stable clone expressing high levels (greater than 0.5-10 pg/cell/day) of the target gene product
7. Grow the cell line in the absence of the decoy amino acid, but in the presence of the non natural amino acids allowing for incorporation at the amber codon.

According to this embodiment, when the decoy amino acid is present in the cell-line containing the PylRS and tRNA synthetase pair, it binds to the PylRS and is aminoacylated to the tRNA. It is then passed on to the ribosome, where the tRNA binds the amber codon, but the acylated amino-blocked decoy is disabled from forming a peptide bond, thus the protein terminates at this site.

In one embodiment, the decoy is not present once the cDNA of the target protein is introduced in the cell.

Alternatively, the decoy amino acid is maintained in the culture medium when the cDNA encoding the target protein is introduced into the cell.

In an alternative embodiment, expression of the target protein occurs in the presence of the decoy amino acid. Thus according to this embodiment, the decoy amino acid and a desired non-natural amino acid which is preferentially used by the PylRS are both added to (or present in) the fermentation medium during target protein production.

A decoy amino acid should not be added to or present in the fermentation medium if it competes with the desired non-natural amino acid for binding to the PylRS to any significant extent.

In another embodiment, expression of the target protein does not occur in the presence of the decoy amino acid (e.g. following elimination from the fermentation medium). Thus according to this embodiment, the decoy amino acid is not introduced into the fermentation media during the expression of the target protein. Only the desired non-natural amino acid which preferentially binds the PylRS is added to (or present in) the fermentation during target protein production. According to this embodiment, the decoy amino acid is utilized in the culture medium throughout the selection and isolation of platform cell lines containing the pylRS/tRNA. After introduction and selection of a target gene containing one or more amber codons, the decoy amino acid is removed.

A plurality of (e.g. 2, 3, 4, 5, 6 or 7 or more) decoy amino acids may be employed if desired.

A further aspect of the invention is a process for production of a stable eukaryotic cell line which is capable of expressing PylRS and tRNAPyl and which is suitable for incorporation of a gene encoding a target protein containing one or more non-natural amino acids encoded by an nonsense codon which comprises (a) in one or more steps introducing into a eukaryotic cell line genes encoding PylRS and tRNAPyl and such that PylRS and tRNAPyl are stably expressed in said cell line (b) culturing or selecting the resultant cell line in the presence of a decoy amino acid which is a substrate for PylRS but which is incapable of incorporation into an extending protein chain thereby to reduce the adverse effect of tRNAPyl on cell viability and/or cell growth.

A further aspect of the invention is a process for production of a stable eukaryotic cell line which is capable of expressing PylRS, tRNAPyl and a target protein containing one or more non-natural amino acids encoded by a nonsense codon which comprises (a) in one or more steps introducing into a eukaryotic cell line genes encoding PylRS and tRNAPyl such that PylRS and tRNAPyl are stably expressed in said cell line (b) culturing or selecting the resultant cell line in the presence of a decoy amino acid which is a substrate for PylRS but which is incapable of incorporation into an extending protein chain thereby to reduce the adverse effect of tRNAPyl on cell viability and/or cell growth (c) introducing into said eukaryotic cell line a gene encoding a target protein containing one or more non-natural amino acids such that said target protein is stably expressed in said cell line and (d) expressing the target protein in the absence of said decoy amino acid.

A further aspect of the invention is a process for production of a stable eukaryotic cell line according to any one of the aforementioned aspects wherein the culturing or selection of the cell line is performed in the presence of a decoy amino acid which is a substrate for PylRS but which is incapable of incorporation into an extending protein chain thereby reducing the adverse effect of tRNAPyl on cell viability and/or cell growth.

"Target First" Approach

According to an alternative embodiment, there is provided a process wherein the conditions in which the adverse effect of tRNAPyl on cell viability and/or cell growth is reduced or eliminated include conditions in which a target protein containing one or more non-natural amino acids encoded by a nonsense codon is also expressed by said cell line.

Thus, a process to incorporate non natural amino acids into a protein may include the following steps:
1. Introduce the target gene containing an amber codon at a position into which the non natural amino acid is to be incorporated into a eukaryotic cell on one or more plasmids
2. Isolate a pool of cells or clone that expressed the target protein at high levels (greater than 0.5 or greater than 10 pg/cell/day)
3. Introduce the RS and tRNA into these cells, on one or more plasmids, and select for clones containing the RS and tRNA
4. Grow the cell line in the presence of the non natural amino acids allowing for incorporation at the amber codon and isolate cells which show an incorporation efficiency of the non natural amino acid at the desired sites of greater than 30%, for example greater than 40% or 50% or 60% or 70% or 80% or preferably greater than 90%.

A further embodiment is a stable eukaryotic cell line which expresses PylRS and tRNAPyl and also expresses under the control of an inducible promoter a decoy protein containing one or more non-natural amino acids encoded by an amber codon.

A further aspect of the invention is a process for production of a stable eukaryotic cell line which expresses PylRS, tRNAPyl and a target protein containing one or more non-natural amino acids encoded by an amber codon which comprises (a) introducing into a eukaryotic cell line a gene encoding a target protein containing one or more non-natural amino acids encoded by an nonsense codon such that said gene is stably integrated in said cell line (b) in one or more steps further introducing into said cell line genes encoding PylRS and tRNAPyl such that PylRS and tRNAPyl are stably expressed in said cell line and (c) culturing the resultant cell line in the presence of a source of the one or more non-natural amino acids under conditions whereby tRNAPyl is expressed only by said cell line at the same time as the target protein is also expressed by said cell line thereby to reduce the adverse effect of tRNAPyl on cell viability and/or cell growth.

"Repressible tRNA" Approach

According to an alternative embodiment, there is provided a process wherein the conditions in which the adverse effect of tRNAPyl on cell viability and/or cell growth is reduced or eliminated include conditions in which the expression of tRNAPyl occurs under the control of a repressible promoter.

There is also provided a eukaryotic cell line which expresses or is capable of expressing PylRS and tRNAPyl in which expression of tRNAPyl occurs under the control of a repressible promoter.

Thus, a process to incorporate non natural amino acids into a protein may include the following steps:
1. Introduce the RS and tRNA, on one or more plasmids into a eukaryotic cell, the latter containing a repressible promoter element that enables control of tRNA expression.
2. Select for cells containing the RS and tRNA expression cassettes under repressed conditions
3. Induce tRNA expression and isolate one or more stable clones expressing high levels of the RS protein and tRNA or demonstrating efficient suppression of amber codons in a reporter gene thereby generating a platform cell line. Cells capable of non natural amino acid incorporation rates of greater than 30%, for example greater than 40% or 50% or 60% or 70% or 80% or preferably greater than 90% are selected.
4. Introduce the cDNA of the target protein whereby an amber codon has been introduced at the position where the non natural amino acid is to be incorporated
5. Isolate a stable clone expressing high levels (greater than 0.5-20 pg/cell/day) of the target gene product
6. Grow the cell line in presence of the non natural amino acids allowing for incorporation at the amber codon.

According to this embodiment, high levels of expression of the suppressor tRNA are avoided and amber suppression related cytotoxicity is prevented.

In such a process expression of the tRNA is suitably under the control of repressible promoter such as the H1 and U6 promoters containing tetracycline responsive elements (TetO or TtA) (Herold 2008). A further aspect of the invention is a stabilized cell line which has been prepared according to one of the aforementioned processes.

A further aspect of the invention is a process for production of a stable eukaryotic cell line which is capable of expressing PylRS, tRNAPyl and which is suitable for incorporation of a gene encoding a target protein containing one or more non-natural amino acids encoded by an nonsense codon which comprises (a) in one or more steps introducing into a eukaryotic cell line genes encoding PylRS and tRNAPyl which tRNAPyl is under the control of a repressible promoter and such that PylRS and tRNAPyl are stably expressed in said cell line (b) culturing the resultant cell line in the presence of a repressor such that expression of tRNAPyl is repressed thereby to reduce the adverse effect of tRNAPyl on cell viability and/or cell growth.

A further aspect of the invention is a process for production of a stable eukaryotic cell line which is capable of expressing PylR, tRNAPyl and a target protein containing one or more non-natural amino acids encoded by an nonsense codon which comprises (a) in one or more steps introducing into a eukaryotic cell line genes encoding PylRS and tRNAPyl which tRNAPyl is under the control of a repressible promoter and such that PylRS and tRNAPyl are stably expressed in said cell line (b) culturing the resultant cell line in the presence of a repressor such that expression of tRNAPyl is repressed thereby to reduce the adverse effect of tRNAPyl on cell viability and/or cell growth (c) introducing into said eukaryotic cell line a gene encoding a target protein containing one or more non-natural amino acids such that said target protein is stably expressed in said cell line and (d) expressing the target protein in the absence of said repressor such that tRNAPyl is expressed.

"Decoy Protein" Approach

According to an alternative embodiment, there is provided a process wherein the conditions in which the adverse effect of tRNAPyl on cell viability and/or cell growth is reduced or eliminated include conditions in which a decoy protein containing one or more non-natural amino acids encoded by an amber codon is also expressed under the control of an inducible promoter by said cell line.

For example, the decoy protein is selected from: Green fluorescence protein, Red Fluorescence Protein, Yellow Fluorescence Protein, Cyan Fluorescence Protein, blue fluorescence protein, albumin, SEAP, Actin, b-2 microglobulin, glutathione-s-transferase, IgG, or a poly amber containing peptide.

Thus, a process to incorporate non natural amino acids into a protein may include the following steps:
1. Introduce a gene for a decoy protein containing an amber codon into a eukaryotic cell which is under control of an inducible promoter
2. Isolate a pool of cells or clone that contains the decoy construct and upon induction is capable of expression of this protein at high levels (greater than 0.1 or greater than 1 pg/cell/day)
3. Introduce the RS and tRNA into these cells, on one or more plasmids, and select for clones containing the RS and tRNA
4. Isolate clones capable of incorporation efficiency of the non natural amino acid at desired sites at rates greater than 30%, for example greater than 40% or 50% or 60% or 70% or 80% or preferably greater than 90% in the presence of the non natural amino acid using the integrated decoy construct
5. Introduce the target gene containing an amber codon at a position into which the non natural amino acid is to be incorporated into a eukaryotic cell
6. Isolate clones capable of expression levels greater than 1 pg/cell/day of the target protein
7. Grow the cell line in the presence of the non natural amino acids allowing for incorporation at the amber codon and isolate cells which show an incorporation efficiency of the non natural amino acid at the desired sites of greater than 30%, for example greater than 40% or 50% or 60% or 70% or 80% or preferably greater than 90%

A further aspect of the invention is a stable eukaryotic cell line which expresses pylRS, tRNApyl and a decoy protein under the control of an inducible promoter.

According to this embodiment, expression of the decoy protein can be discontinued (e.g. by removal of the inducer for the promoter) when the expression of target protein is commenced.

Suitable inducible promoters systems include conditionally activated promoters and promoter systems such as the tetracycline regulated promoters (TetO or tTA; TetOn and TetOFF), doxycycline-inducible (TRE) promoters, cAMP inducible promoters, glucocorticoid activated promoter systems, IPTG inducible promoters (lac), Cd2+ or Zn2+ inducible promoters (methalloprotein promoters), interferon dependent promoters (e.g. murine MX promoter), HIV LTR promoters (Tat), DMSO inducible promoters (GLVP/TAXI, ecdysone), and rapamycin inducible promoters (CID).

According to this embodiment, expression of the decoy protein can be discontinued (e.g. by removal of the gene) when the expression of target protein is commenced using a recombination system.

Suitable systems include targeting recombination systems such as the Cre/lox, the phi31C-based integration system, and Flp-FRT recombination technology or by homologous recombination of the inserted cassettes.

A further aspect of the invention is a process for production of a stable eukaryotic cell line which is capable of expressing PylRS, tRNAPyl and a decoy protein containing one or more non-natural amino acids encoded by an nonsense codon and which is suitable for incorporation of a gene encoding a target protein containing one or more non-natural amino acids encoded by a nonsense codon which comprises (a) in one or more steps introducing into a eukaryotic cell line genes encoding pylRS, tRNApyl and said decoy protein and such that PylRS tRNAPyl and the decoy protein are stably expressed in said cell line (b) culturing the resultant cell line under conditions whereby tRNApyl is expressed only by said cell line at the same time as the decoy protein is also expressed by said cell line thereby to reduce the adverse effect of tRNApyl on cell viability and/or cell growth.

A further aspect of the invention is a process for production of a stable eukaryotic cell line which is capable of expressing PylRS, tRNAPyl, a decoy protein and a target protein containing one or more non-natural amino acids encoded by an nonsense codon which comprises (a) in one or more steps introducing into a eukaryotic cell line genes encoding pylRS, tRNApyl and a decoy protein said decoy protein being expressed under the control of an inducible promoter and such that PylRS, tRNAPyl and the decoy protein are stably expressed in said cell line (b) culturing the resultant cell line under conditions whereby tRNApyl is expressed only by said cell line at the same time as the decoy protein is also expressed by said cell line thereby to reduce the adverse effect of tRNApyl on cell viability and/or cell growth (c) introducing into said eukaryotic cell line a gene encoding a target protein containing one or more non-natural amino acids such that said target protein is stably expressed in said cell line and (d) expressing the target protein without expressing the decoy protein.

General

A further aspect of the invention is a stable eukaryotic cell line obtained by or obtainable by any one of the aforementioned processes.

A further aspect of the invention is a stable eukaryotic cell line obtained by or obtainable by a process according to a combination of two or more of the aforementioned processes of modification of the system (i.e. use of decoy protein, decoy amino acid, repressible promoter/inducible promoter, introduction of the nonsense codon containing target gene prior to introduction of the Pyl-tRNA etc).

A further aspect of the invention is a process for preparing a target protein containing one or more non-natural amino acids encoded by an nonsense codon which comprises culturing a stable eukaryotic cell line as aforementioned in the presence of a source of the one or more non-natural amino acids.

A further aspect of the invention is a process for preparing a target protein containing one or more non-natural amino acids encoded by an amber codon which comprises introducing into a stable eukaryotic cell line as aforesaid a gene encoding a target protein containing one or more non-natural amino acids encoded by a nonsense codon such that the target protein is stably expressed in said cell line and expressing said target protein in the presence of a source of the one or more non-natural amino acids and in the absence of any inducer of expression of the decoy protein.

A further aspect of the invention is a process for preparing a target protein containing one or more non-natural amino acids encoded by an nonsense codon which comprises introducing into a stable eukaryotic cell line as aforesaid a gene encoding a target protein containing one or more non-natural amino acids encoded by a nonsense codon such that the target protein is stably expressed in said cell line and expressing said target protein in the presence of a source of one or more non-natural amino acids and in the absence of any decoy amino acid.

A further aspect of the invention is a process for preparing a target protein containing one or more non-natural amino acids encoded by an nonsense codon which comprises introducing into a stable eukaryotic cell line as aforesaid a gene encoding a target protein containing one or more non-natural amino acids encoded by a nonsense codon such that the target protein is stably expressed in said cell line and expressing said target protein in the presence of a source of the one or more non-natural amino acids and in the absence of any repressor of expression of the tRNAPyl.

A further aspect of the invention is a process for preparing a target protein containing one or more non-natural amino acids encoded by an nonsense codon which comprises introducing into a stable eukaryotic cell line as aforesaid a gene encoding a target protein containing one or more non-natural amino acids encoded by a nonsense codon such that the target protein is stably expressed in said cell line and expressing said target protein in the presence of a source of the one or more non-natural amino acids.

A further aspect of the invention is process for preparing a chemically modified target protein which comprises preparing a target protein containing one or more non-natural amino acids encoded by a nonsense codon which comprises introducing into a stable eukaryotic cell line as aforesaid a gene encoding a target protein containing one or more non-natural amino acids encoded by a nonsense codon such that the target protein is stably expressed in said cell line, expressing said target protein in the presence of a source of the one or more non-natural amino acids, and chemically modifying the resultant target protein.

Cell Lines for Use According to the Invention

The invention related to stable eukaryotic cell lines. Suitably the cell lines are mammalian cell lines.

More preferably, the cell line is a CHO cell line, but also may be a HEK293, PERC6, COS-1, HeLa, VERO, or mouse hybridoma cell line. Further examples are COS-7 and mouse myeloma cell lines.

CHO and HEK293 cells lines are particularly suitable.

Certain elements of the present invention may be used in the context of a cell-free expression system wherein a synthesis reaction lysate obtained from a host cell comprises at least one component required for the synthesis of polypeptides.

The synthesis reaction lysate may be obtained from bacterial or eukaryotic cells. Preferably, the synthesis reaction lysate is obtained from eukaryotic cells, more preferably, from rabbit reticulocytes or wheat germ.

The cell-free expression system is capable of expressing WT PylRS and tRNApyl of the present invention, wherein tRNApyl is introduced into the cells used to obtain the synthesis reaction lysate with DNA constructs of the invention.

Cell-free expression systems suitable for use in the present invention are described for instance in WO201008110, WO2010081111, WO2010083148, incorporated in their entirety herein by reference.

pylRS to be Expressed in Cell Lines According to the Invention

As used herein, pylRS relates to an amino acyl tRNA synthetase which will aminoacylate a suitable tRNA molecule with pyrrolysine or a derivative thereof.

The pylRS of the present invention is suitably a Pyrrolysyl-tRNA Synthetase orthogonal in eukaryotic cells which is derived from methanogenic archaea spp.—i.e. it is wild-type in methanogenic archaea spp. or is a mutant thereof.

Preferably, the pylRS of the present invention is a Pyrrolysyl-tRNA Synthetase derived from one of the following: *Methanosarcina mazei* (SEQ ID NO. 1, SEQ ID NO. 2, SEQ ID NO. 14, SEQ ID NO. 15, SEQ ID NO. 16), *Methanosarcina barkeri* (SEQ ID NO. 3, SEQ ID NO. 17)i, *Desulfitobacterium hafniense*(SEQ ID NO. 4, SEQ ID NO. 18), *Methanosarcina acetivorans* (SEQ ID NO. 5, SEQ ID NO. 19), *Methanosarcina burtonii* (SEQ ID NO. 6, SEQ ID NO. 20), *Methanosarcina thermophila* (SEQ ID NO. 7, SEQ ID NO. 21), *Methanosalsum zhilinae* (SEQ ID NO 8, SEQ ID NO. 22), *Methanohalobium evastigatum* (SEQ ID NO. 9, SEQ ID NO. 23), *Methanohalophilus mahii* (SEQ ID NO. 10, SEQ ID NO. 24), *Desulfotomaculum gibsoniae* (SEQ ID NO. 11, SEQ ID NO. 25), *Desulfosporosinus meridei* (SEQ ID NO. 12, SEQ ID NO. 26) and *Desulfotomaculum acetoxidans* (SEQ ID NO. 13, SEQ ID NO. 27).

Most preferably, the pylRS of the present invention is the pyrrolysyl tRNA synthetase (pylRS) derived from *Methanosarcina mazei* (SEQ ID NO. 1)

The pylRS of the present invention may be a wild type synthetase.

Alternatively, the pylRS of the present invention may be mutated at one or more positions e.g. in order to increase its catalytic activity and/or to modify its selectivity for substrate amino acids (Yanagisawa 2008).

Preferably, the pylRS of the present invention may be mutated at position corresponding to Tyr 384 of SEQ ID NO. 1 or its equivalent. Most preferably, Tyr 384 is mutated into Phenylalanine (SEQ ID NO. 2).

In one embodiment, the pylRS of the present invention may be mutated at one or more positions in order to modify its substrate specificity and allow (or improve) incorporation of pyrrolysine analogs Further mutant PylRS enzymes are described in WO09038195 and in WO2010114615 each document incorporated herein by reference in its entirety.

tRNApyl to be Expressed in Cell Lines According to the Invention

The tRNApyl to be expressed in combination with the PylRS of the present invention has an anticodon and a tertiary structure which are complementary to the amber nonsense codon UAG, in order to function as a suppressor tRNA.

An artificial tRNA could be constructed that is complementary to other nonsense codons such as UGA, opal; UAA, ochre codons in order to function as a suppressor tRNA.

Thus it will be understood that although the present invention is substantially described and exemplified by reference to use of the amber codon for coding the nnAA and with discussion of the concept of amber suppression, the amber codon can be replaced with an another nonsense codon such as opal or ochre codons and would be expected to work in the same way.

However use of amber codon is preferred.

Engineering of tRNApyl sequences in order to optimize expression in eukaryotic cell lines has been described in WO2007099854, incorporated herein by reference.

WO2007099854 provides inter alia DNA constructs comprising a tRNA gene deriving from Archaeabacteria, preferably tRNApyl, a transcription terminator sequence placed 3' of said tRNA gene, a promoter sequence that induces transcription by RNA Polymerase II or III such as U1 snRNA promoter or U6 snRNA promoter placed 5' to said tRNApyl gene.

Preferably, the tRNApyl of the present invention is a tRNApyl derived from one of the following bacterial strains: *Methanosarcina mazei* (SEQ ID NO 28), *Methanosarcina barkeri* (SEQ ID NO 26), *Desulfitobacterium hafniense* (SEQ ID NO 30), *Methanosarcina acetivorans* (SEQ ID NO 27), *Methanosarcina burtonii* ((SEQ ID NO 29), or *Methanosarcina thermophila*.

More preferably, the tRNApyl of the present invention is a tRNApyl derived from *Methanosarcina mazei* (SEQ ID NO 28)

In one embodiment of the present invention, the tRNApyl is expressed in eukaryotic cells, preferably in animal cells, more preferably in mammalian cells.

In a preferred embodiment, the tRNApyl, naturally lacking promoter elements for expression in eukaryotic cells, is expressed under an external eukaryotic promoter.

In a particularly preferred embodiment, the external promoter is a U6 promoter.

In a particularly preferred embodiment, the external promoter is an H1 promoter.

In a further embodiment, the plasmid carrying the tRNApyl gene contains a transcriptor terminator sequence 3' to the tRNApyl gene, a U6 promoter sequence placed 5' to the tRNApyl gene and a CMV enhancer region placed 5' to the promoter region.

In a particularly preferred embodiment, the insert of the plasmid carrying the tRNApyl gene has SEQ ID NO 35.

In one embodiment of the present invention, the external promoter is a repressible promoter In a preferred embodiment, the repressible promoter is selected from H1 containing elements that allow for the repression of this promoter, such as TetO (H1/TetO; SEQ ID NO 31), or the promoter of human U6 snRNA containing elements that allow for the repression of expression (e.g. U6/TetO).

It will be understood that if the stop codon indicating the end of the target gene is an amber codon, and it is intended to use an amber codon to encode the nnAA, then the stop codon will be changed to another stop codon (e.g. ochre or opal). The same applies mutatis mutandis if it is intended to use another nonsense codon to encode the nnAA.

Vectors for Transformation of Eukaryotic Cell Lines with Genes Encoding pylRS and tRNApyl The present invention provides a plasmid for efficient expression of tRNApyl in eukaryotic cells. Preferably, the tRNApyl expression plasmid includes multiple repeats of the tRNA gene of SEQ ID 28) under a U6 promoter. More preferably, the tRNApyl expression plasmid includes tandem repeats of the tRNA gene of SEQ ID 28) under a U6 promoter According to the present invention, the Pyl tRNA gene and the PylRS cDNA are carried by the same or different plasmids.

In one embodiment the tRNApyl gene and the PylRS cDNA are present on the same plasmids.

In one embodiment the tRNApyl gene and the PylRS cDNA are present on different plasmids Vectors for Transformation of Eukaryotic Cell Lines with Genes Encoding Target Protein The present invention provides a vector comprising a nucleotide sequence of the present invention optionally, operably linked to a promoter sequence.

Vectors utilized in the present invention include: pJTI-Fast-DEST (Life technologies), pSelect-Blasti and pSelect-Zeo vectors (invivogen). pENTR P5-P2 vector (Life Technologies), pOptivec (Life Technologies), pFUSE-CHIg-hG1 (invivogen) and pFUSE-CHLIg-hK (invivogen).

Examples of suitable promoters include, but are not limited to, CMV promoter, SV40 Large T promoter, EF1alpha promoter, MCK promoter, and LTR promoter.

Construction of Stable Cell Lines and Selection of Stable Clones

The inventors have found that the construction of a cell line stably expressing the elements necessary for site specific nnAA incorporation requires a sequential introduction of plasmids for the expression of the different elements of the system (pylRS, tRNA, and target) each followed by a selection step and a sorting step (cloning step) to identify stable clones with high activity.

In one embodiment of the invention, a stable cell was obtained expressing all the elements for efficient nnAA introduction to serve as a starting point for the introduction of a target gene and subsequent isolation of the target protein modified at a desired position.

Suitably, this approach involves an iterative selection process whereby an expression cassette for tRNA is first introduced into the host cells and a pool of cells containing the constructs selected by virtue of antibiotic resistance conferred by the vector. Next, surviving cells are selected by the introduction of a reporter construct encoding green fluorescence protein (GFP) from *Aequoria victoria* containing an amber stop codon interrupting its open reading frame by transient transfection. The selection process consists in identifying those clones which, upon amber suppression, generate full length GFP which fluorescence is quantified by flow cytometry. High functioning cells from this population are thus isolated using fluorescence activated cell sorting. The best clones propagated and subsequently transfected with additional copies of the tRNA followed by an iteration of the selection method described above. The process continues with introduction of an integrating expression construct containing cassettes for the expression of pylRS and multiple copies of tRNA until optimal levels of expressin of each component and test amber suppressin are obtained.

Incorporation of Non-Natural Amino Acids Encoded for by Amber Codon

In proteins prepared using cell lines of the invention, one or more nnAAs may be incorporated. Suitably one nnAA is incorporated into a protein chain. In the case of the protein being an antibody, one nnAA may be incorporated into the light chain or the heavy chain or both.

In other embodiments more than one e.g. up to four e.g. two (or perhaps three) nnAAs may be incorporated into a protein chain. Suitably all the incorporated nnAAs are the same.

Non-Natural Amino Acids that May be Encoded by Amber Codon for Incorporation into Target Proteins The use of non-natural amino acids to allow for conjugating moieties to peptides is disclosed in WO 2007/130453, incorporated herein by reference.

As used herein an "non-natural amino acid" refers to any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

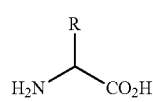

Formula I

An non-natural amino acid is typically any structure having Formula I wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids. For example, R in Formula I optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thioether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, cycloalkynes such as the constrained ring such as a cyclooctyne, cycloalkenes such as a norbornenes, transcycloalkenes, cyclopropenes, tetrazines, pyrones, thioester, enone, imine, aldehyde, ester, thioacid, hydroxylamine, amino, carboxylic acid, alpha-keto carboxylic acid, alpha or beta unsaturated acids and amides, glyoxyl amide, or organosilane group, or the like or any combination thereof.

In addition to non-natural amino acids that contain novel side chains, non-natural amino acids also optionally comprise modified backbone structures, e.g., as illustrated by the structures of Formula II and III:

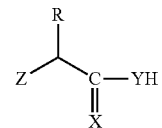

Formula II

Formula III wherein Z typically comprises OH, NH.sub.2, SH, NH.sub.2O—, NH—R', R'NH—, R'S—, or S—R'—; X and Y, which may be the same or different, typically comprise S, N, or O, and R and R', which are optionally the same or different, are typically selected from the same list of constituents for the R group described above for the non-natural amino acids having Formula I as well as hydrogen or (CH.sub.2).sub.x or the natural amino acid side chains. For example, non-natural amino acids disclosed herein optionally comprise substitutions in the amino or carboxyl group as illustrated by Formulas II and III. Non-natural amino acids of this type include, but are not limited to, .alpha.-hydroxy acids, .alpha.-thioacids .alpha.-aminothiocarboxylates, or .alpha.-.alpha.-disubstituted amino acids, with side chains corresponding e.g. to the twenty natural amino acids or to non-natural side chains. They also include but are not limited to .beta.-amino acids or .gamma.-amino acids, such as substituted .beta.-alanine and .gamma.-amino butyric acid. In addition, substitutions or modifications at the .alpha.-carbon optionally include L or D isomers, such as D-glutamate, D-alanine, D-methyl-O-tyrosine, aminobutyric acid, and the like.

Other structural alternatives include cyclic amino acids, such as proline analogs as well as 3-, 4-, 6-, 7-, 8-, and 9-membered ring proline analogs. Some non-natural amino acids, such as aryl halides (p-bromo-phenylalanine, p-iodo-phenylalanine, provide versatile palladium catalyzed cross-coupling reactions with ethyne or acetylene reactions that allow for formation of carbon-carbon, carbon-nitrogen and carbon-oxygen bonds between aryl halides and a wide variety of coupling partners.

For example, many non-natural amino acids are based on natural amino acids, such as tyrosine, glutamine, phenylalanine, and the like. The structures of a variety of exemplary non-limiting non-natural amino acids are provided in US 2003/0108885 A1, see the figures, e.g., FIGS. 29, 30, and 31, the entire content of which document which is incorporated herein by reference.

Other examples of amino acid analogs include (but are not limited to) an non-natural analog of a Lysine or Pyrrolysine amino acid which include one of the following functional groups; an alkyl, aryl, acyl, azido, nitrile, halo, hydrazine, hydrazide, hydroxyl, alkenyl, cycloalkenes, alkynyl, cycloalkynes, cycloalkynes such as the constrained ring such as a cyclooctyne, cycloalkenes such as a norbornenes, transcycloalkenes, cyclopropenes, aryl halide, vinyl halide, alkyl halide, aziridine, nitro, hydroxyl, ether, epoxide, vinyl ethers, silyl enol ethers, thiol, thioether, sulfonamide, sulfonyl, sulfone, seleno, ester, thioacid, boronic acid, boronate ester, borane, phosphono, phosphine, heterocyclic, pyridyl, naphthyl, benzophenone, tetrazines, pyrones, enone, imine, aldehyde, hydroxylamine, keto, thioester, ester, thioacid, organosilane group, amino, a photoactivatable cross-linker; a spin-labeled amino acid; a fluorescent amino acid; an amino acid that covalently or noncovalently interacts with another molecule; a metal binding amino acid; a metal-containing amino acid; a radioactive amino acid; a photocaged amino acid; a photoisomerizable amino acid; a biotin or biotin-analogue containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group Non-natural amino acids suitable for use in the methods of the invention also include those that have a fluorescent amino acids such as those containing naphthyl or dansyl or 7-aminocoumarin or 7-hydroxycoumarin side chains, photocleavable or photoisomerizable amino acids such as those containing azobenzene or nitrobenzyl Cys, Ser or Tyr side chains, p-carboxy-methyl-L-phenylalanine, homoglutamine, 2-aminooctanoic acid, p-azidophenylalanine, p-benzoylphenylalanine, p-acetylphenylalanine, m-acetylphenylalanine, 2,4-diaminobutyric acid (DAB) and the like. The invention includes unprotected and acetylated forms of the above. (See also, for example, WO 03/031464 A2, entitled "Remodeling and Glycoconjugation of Peptides"; and, U.S. Pat. No. 6,331,418, entitled "Saccharide Compositions, Methods and Apparatus for their synthesis;" Tang and Tirrell, J. Am. Chem. Soc. (2001) 123: 11089-11090; and Tang et al., Angew. Chem. Int. Ed., (2001) 40:8, all of which are incorporated herein by reference in their entireties).

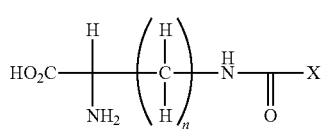

Formula IV

In the present invention, non natural amino acids (nnAA) of Formula IV above may be utilized for the production of proteins.

In an embodiment, the X group attached to the amido moeity could be an alkyl azide, alkoxy azide, alkoxy epoxide, alkyl-alkyne, alkoxy alkyne, alkoxy alkene, alkyl-alkene, alkyl chain, alkyl cyclohexene, alkyl cycloalkyne, alkoxyl cycloalkene, alkoxyl cycloalkyne, amido cycloalkyne, amido cycloalkene, transcycloalkene, cyclopropenes, tetrazines, pyrones, norbornenes, aryl azide, azido, a hydroxyl amine, a hydrazide, a vinyl halide, a aryl halide, a tetrazine, a pyrone, an imine, boronic ester or acid, a cyano group, a carbonyl group such as an aldehyde or ketone. In a preferred embodiment, non natural amino acids (nnAA) of the general structure above can have an alkyl chain from the amino acid terminus to the amido group at the opposite terminus of 1-12 methylene groups.

Preferably, non natural amino acids (nnAA) of the general structure above can contain cycloalkanes and aromatic rings as part of the connective structure.

In an embodiment, non natural amino acids (nnAA) of the general structure above interact with a pyrrolysyl tRNA synthetase (PyRS) and tRNApyl. Said amino acids include: (S)-2-Amino-6-((2-azidoethoxy)carbonylamino)hexanoic acid (Lys-azide), (S)-2-Amino-6-((prop-2-ynyloxy)carbonylamino)hexanoic acid (Lys-Alkyne), S)-2-amino-6((2-oxo-2-phenylacetamide)hexanoic acid, S)-2-amino-6((2-oxo-2-propanamide)hexanoic acid, (2S)-2-amino-6-({[(2-azidocyclopentyl)oxy]carbonyl}amino)hexanoic acid, (2S)-2-amino-6-({[(2-ethynylcyclopentyl)oxy]carbonyl}amino) hexanoic acid, (2S)-2-amino-6-{[(cyclooct-2-yn-1-yloxy)carbonyl]amino}hexanoic acid, (2S)-2-amino-6-({[2-(cyclooct-2-yn-1-yloxy)ethoxy]carbonyl}amino)hexanoic acid, (2S)-2-amino-6-[({bicyclo[2.2.1]hept-5-en-2-yloxy}carbonyl)amino]hexanoic acid, (2S)-2-amino-6-[({bicyclo[2.2.1]hept-5-en-2-ylmethoxy}carbonyl)amino] hexanoic acid, (2S)-2-amino-6-{[({4-[(6-methyl-1,2,4,5-tetrazin-3-yl)amino]phenyl}methoxy)carbonyl] amino}hexanoic acid, (2S)-2-amino-6-({[(4E)-cyclooct-4-en-1-yloxy]carbonyl}amino)hexanoic acid, (2S)-2-amino-6-{[(cycloprop-2-en-1-yloxy)carbonyl]amino}hexanoic acid, (2S)-2-amino-6-{[(cycloprop-2-en-1-ylmethoxy)carbonyl]amino}hexanoic acid, (2S)-2-amino-6-{[(3-azidopropyl)carbamoyl]oxy}hexanoic acid, (2S)-2-amino-6-{[(but-3-yn-1-yloxy)carbonyl]amino}hexanoic acid, (2S)-2-amino-6-(2-azidoacetamido)hexanoic acid, (2S)-2-amino-6-(3-azidopropanamido)hexanoic acid, (2S)-2-amino-6-(5-azidopentanamido)hexanoic acid.

The nnAA will be a substrate for the pylRS.

Suitably, nnAAs of the present invention are derived from lysine.

WO2010139948 incorporated herein by reference describes several nnAAs of interest for the present invention, in particular the following lysine derivatives:

(S)-2-amino-6((prop-2-ynyloxy)carbonylamino)hexanoic acid (LysAlkyne):

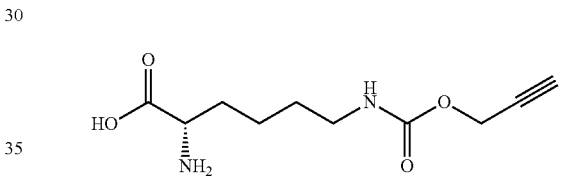

(S)-2-amino-6((2azidoethoxy)carbonylamino)hexanoic acid (Lys azide):

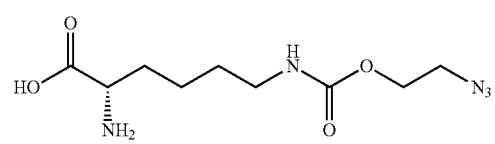 [SMILES: [N-]=[N+]=NCCOC(=O)NCCCC[C@H](N)C(=O)O]

Other suitable nnAAs are:

(S)-2-amino-6((2-oxo-2-phenylacetamide)hexanoic acid:

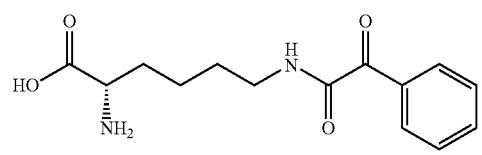 [SMILES: N[C@@H](CCCCNC(=O)C(=O)c1ccccc1)C(=O)O]

(S)-2-amino-6((2-oxo-2-propanamide)hexanoic acid:

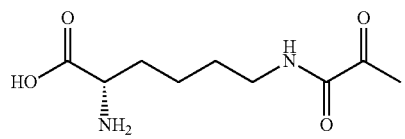

(S)-2-amino-6-(acetamide)hexanoic acid:

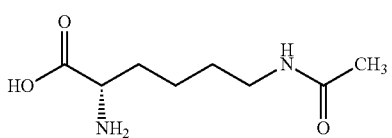

(S)-2-amino-6-(allyloxylcarbonylamino)hexanoic acid:

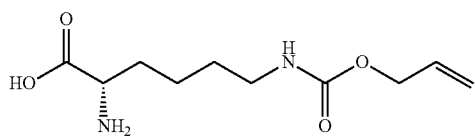

(2S)-2-amino-6-({[(2-azidocyclopentyl)oxy]carbonyl}amino)hexanoic acid:

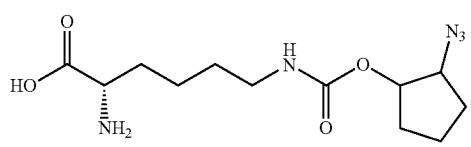 [SMILES: [N-]=[N+]=NC1CCCC1OC(=O)NCCCC[C@H](N)C(=O)O]

(2S)-2-amino-6-({[(2-ethynylcyclopentyl)oxy]carbonyl}amino)hexanoic acid:

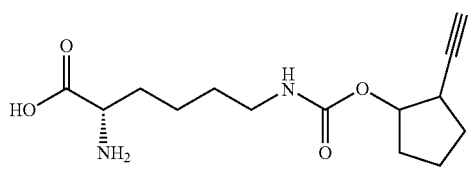 [SMILES: C#CC1CCCC1OC(=O)NCCCC[C@H](N)C(=O)O]

(2S)-2-amino-6-{[(clooct-2-yn-1-yloxy)carbonyl]amino}hexanoic acid:

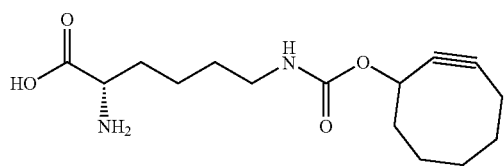 [SMILES: N[C@@H](CCCCNC(=O)OC1C#CCCCCC1)C(=O)O]

(2S)-2-amino-6-({[2-(clooct-2-yn-1-yloxy)ethoxy]carbonyl}amino)hexanoic acid:

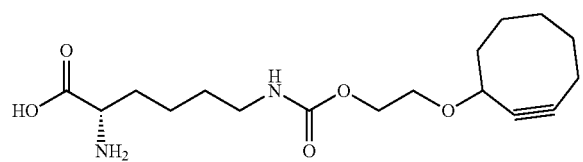 [SMILES: N[C@@H](CCCCNC(=O)OCCOC1C#CCCCCC1)C(=O)O]

(2S)-2-amino-6-[({bicyclo[2.2.1]hept-5-en-2-yloxy}carbonyl)amino]hexanoic acid:

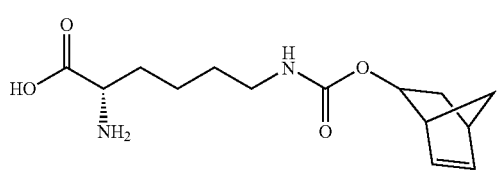 [SMILES: N[C@@H](CCCCNC(=O)OC1CC2C=CC1C2)C(=O)O]

(2S)-2-amino-6-[({bicyclo[2.2.1]hept-5-en-2-ylmethoxy}carbonyl)amino]hexanoic acid:

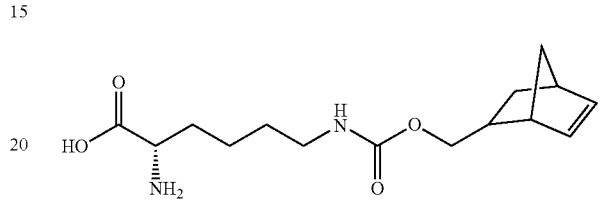

(2S)-2-amino-6-{[({4-[(6-methyl-1,2,4,5-tetrazin-3-yl)amino]phenyl}methoxy)carbonyl]amino}hexanoic acid:

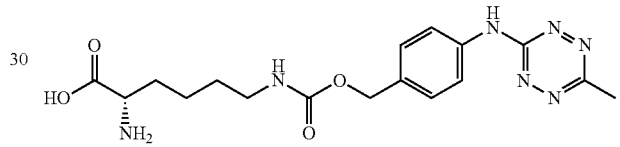

(2S)-2-amino-6-({[(4E)-clooct-4-en-1-yloxy]carbonyl}amino)hexanoic acid:

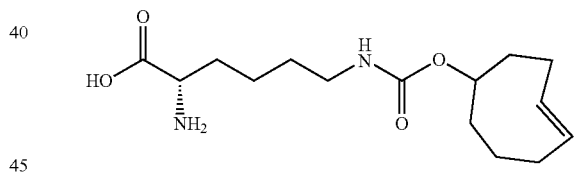

(2S)-2-amino-6-{[(cycloprop-2-en-1-yloxy)carbonyl]amino}hexanoic acid:

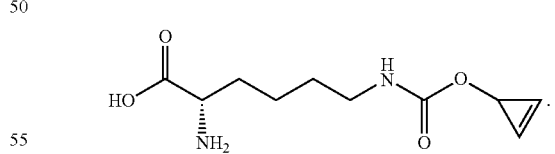

(2S)-2-amino-6-{[(cycloprop-2-en-1-ylmethoxy)carbonyl]amino}hexanoic acid:

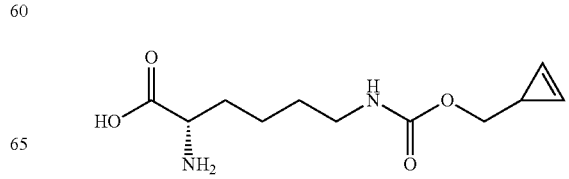

(2S)-2-amino-6-{[(3-azidopropyl)carbamoyl]oxy}hexanoic acid:

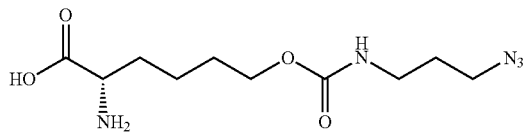 [SMILES: [N-]=[N+]=NCCCNC(=O)OCCCC[C@H](N)C(=O)O]

(2S)-2-amino-6-{[(but-3-yn-1-yloxy)carbonyl]amino}hexanoic acid:

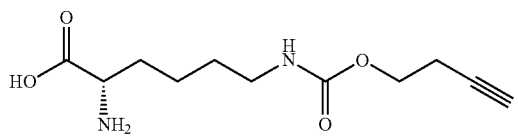 [SMILES: C#CCCOC(=O)NCCCC[C@H](N)C(=O)O]

(2S)-2-amino-6-(3-azidopropanamido)hexanoic acid:

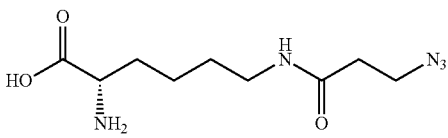 [SMILES: [N-]=[N+]=NCCC(=O)NCCCC[C@H](N)C(=O)O]

(2S)-2-amino-6-(5-azidopentanamido)hexanoic acid:

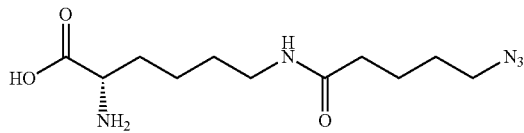 [SMILES: [N-]=[N+]=NCCCCC(=O)NCCCC[C@H](N)C(=O)O]

(2S)-2-amino-6-(pent-4-enamido)hexanoic acid:

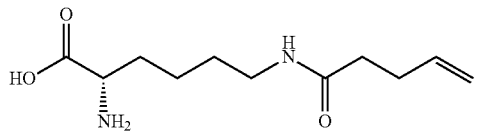 [SMILES: C=CCCC(=O)NCCCC[C@H](N)C(=O)O]

Further nnAAs include: (2S)-2-amino-6-{[(3-azidopropyl)carbamoyl]oxy}hexanoic acid, (2S)-2-amino-6-{[(3-azidopropyl)carbamoyl]oxy}hexanoic acid, (2S)-2-amino-6-{[(prop-2-yn-1-yl)carbamoyl]oxy}hexanoic acid, (2S)-2-amino-6-{[(but-3-yn-1-yl)carbamoyl]oxy}hexanoic acid, (2S)-2-amino-6-{[(prop-2-en-1-yl)carbamoyl]oxy}hexanoic acid, (2S)-2-amino-6-{[(but-3-en-1-yl)carbamoyl]oxy}hexanoic acid.

Suitably, nnAAs of the present invention are derived from (2S)-2-amino-6-hydroxyhexanoic acid.

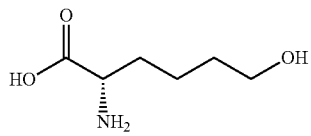

For example:

(2S)-2-amino-6-{[(2-azidoethyl)carbamoyl]oxy}hexanoic acid:

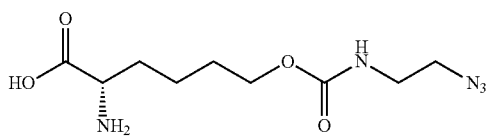

(2S)-2-amino-6-{[(3-azidopropyl)carbamoyl]oxy}hexanoic acid:

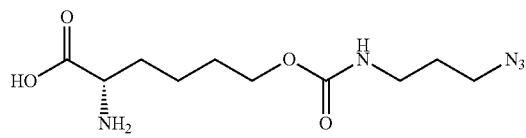

(2S)-2-amino-6-{[(prop-2-yn-1-yl)carbamoyl]oxy}hexanoic acid:

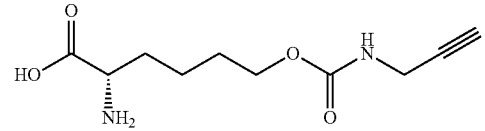 [SMILES: C#CCNC(=O)OCCCC[C@H](N)C(=O)O]

(2S)-2-amino-6-{[(but-3-yn-1-yl)carbamoyl]oxy}hexanoic acid:

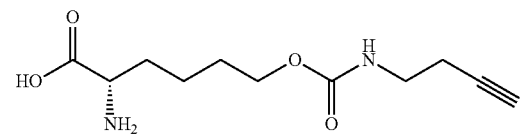 [SMILES: C#CCCNC(=O)OCCCC[C@H](N)C(=O)O]

(2S)-2-amino-6-{[(prop-2-en-1-yl)carbamoyl]oxy}hexanoic acid:

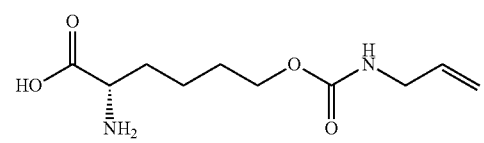

(2S)-2-amino-6-{[(but-3-en-1-yl)carbamoyl]oxy}hexanoic acid:

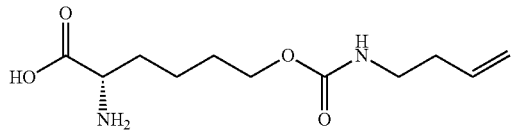

Further non natural amino acid analogs suitable for use in the present invention are pyrrolysine analogs which have the structure of Formula V Formula V

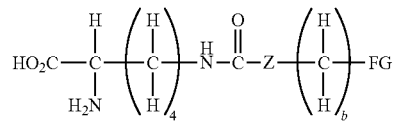

wherein
Z=bond, $CH_2$, CH—$NH_2$, CH—OH, NH, O, S or CH—$NH_2$;
b is 0 or an integer 1-7; and
FG=azide, alkene, alkyne, ketone, ester, aryl or cycloalkyne.

In formulae V when FG represents aryl, an example is aromatic halide e.g. 4-halo phenyl such as 4-iodo phenyl.
Moiety $Z(CH_2)_b FG$ may, for example, represent CO-aryl e.g. CO-phenyl or —COalkyl e.g. —COMe.

Exemplary compounds of formula V are the following:
(2S)-2-amino-6-{[(2-azidoethoxy)carbonyl]amino}hexanoic acid Formula V.1

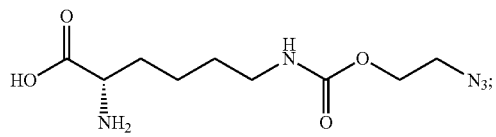

(2S)-2-amino-6-{[(prop-2-yn-1-yloxy)carbonyl]amino}hexanoic acid

Formula V.2

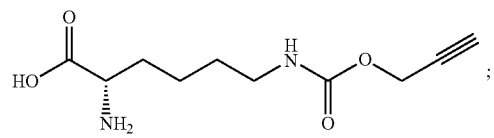

(2S)-2-amino-6-{[(prop-2-en-1-yloxy)carbonyl]amino}hexanoic acid

Formula V.3

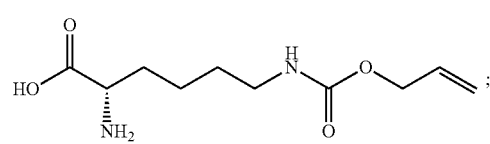

(2S)-2-amino-6-(3-azidopropanamido)hexanoic acid

Formula V.4

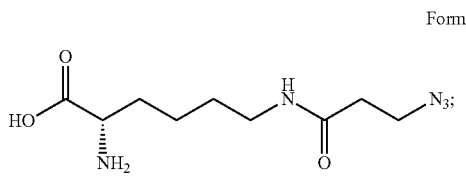

(2S)-2-amino-6-(pent-4-enamido)hexanoic acid

Formula V.5

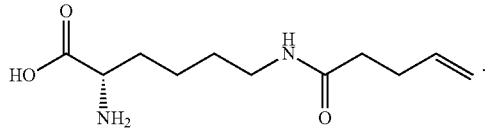

(S)-2-amino-6((2-oxo-2-phenylacetamide)hexanoic acid

Formula V.6

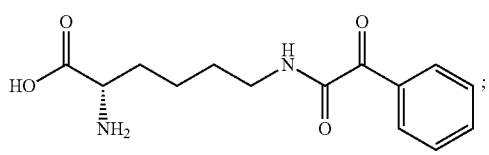

(S)-2-amino-6((2-oxo-2-propanamide)hexanoic acid

Formula V.7

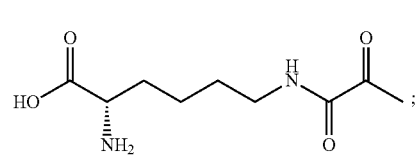

and
(2S)-2-amino-6-(2-azidoacetamido)hexanoic acid

Formula V.8

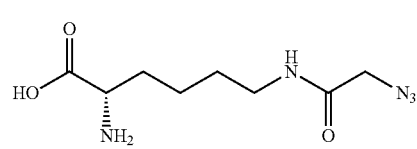

Alternative pyrrolysine analogs suitable for use as non natural amino acids in the present invention have the structure of Formula VI:

Formula VI

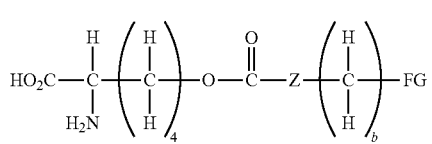

wherein

Z=CH$_2$, CH—NH$_2$, CH—OH, NH, O or S;

FG=azide, alkene, alkyne, ketone, ester, aryl or cycloalkyne; and b=an integer 1-4.

In formulae VI when FG represents aryl, an example is aromatic halide e.g. 4-halo phenyl such as 4-iodo phenyl.

Exemplary compounds of Formula VI are:

(2S)-2-amino-6-{[(2-azidoethyl)carbamoyl]oxy}hexanoic acid

Formula VI.1

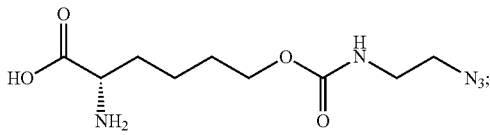

(2S)-2-amino-6-{[(prop-2-yn-1-yl)carbamoyl]oxy}hexanoic acid

Formula VI.2

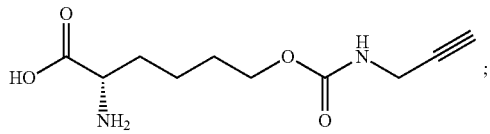

and (2S)-2-amino-6-{[(prop-2-en-1-yl)carbamoyl]oxy}hexanoic acid

Formula VI.3

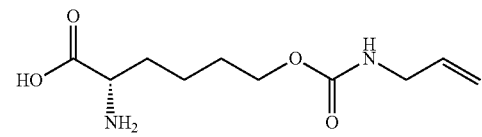 [SMILES: C=CCNC(=O)OCCCC[C@H](N)C(=O)O]

In structures of formulae V and VI, when FG represents alkene, it suitably represents —CH=CH$_2$ or —CH=CH—CH$_3$, preferably —CH=CH$_2$.

In structures of formulae V and VI, when FG represents alkyne, it suitably represents —C≡CH or —C≡C—CH$_3$, preferably —C≡CH.

In structures of formulae V and VI, when FG represents ketone, it suitably represents —C(=O)—CH$_3$ or —C(=O)—CH$_2$—CH$_3$, preferably —C(=O)—CH$_3$.

In structures of formulae V and VI, when FG represents ester, it suitably represents —C(=O)—Oalkyl e.g. —C(=O)—Omethyl.

In structures of formulae V and VI, when FG represents aromatic halide, it suitably represents phenyl substituted by halogen, especially iodine (e.g. 4-iodo-phenyl).

In structures of formulae V and VI, when FG represents cycloalkyne, it suitably represents cyclooctyne, e.g. cyclooct-4,5-yne.

Advantageously, the nnAAs of formulas V and VI of the present invention have been shown to have good incorporation as demonstrated by GFP assay. Formula VI.1 had a similar level of translational competency to Formula V.1 in the GFP assay incorporation assay. Both the Formula V and VI are easily modified to incorporate a variety of useful functional groups which can be used for site selective post translational modification. Alkynes and alkenes are readily incorporated. The pyrrolysine analogs disclosed herein can be made using various methods. The reaction conditions can generally be determined by one of the ordinary skill in the art.

Formula V analogs are readily prepared by the addition of an activated carbonyl group, such as a chloroformate, activated carboxylic acid ester, isocyanate, activated carbonate or sulfonyl halide to a mono-protected diamino substrate of type 1, in which the α-amino group is protected by a protecting group ("PG") such as a Boc, Cbz, TFA, Acetyl or Fmoc group (see Scheme 1). The coupled product 3 can undergo further modifications, such as the displacement of halides with an azido nucleophile to install the desired functionality. Otherwise, the intermediate 3 is deprotected to remove the α-amino acid masking group to afford the desired Formula V analog.

Scheme 1:

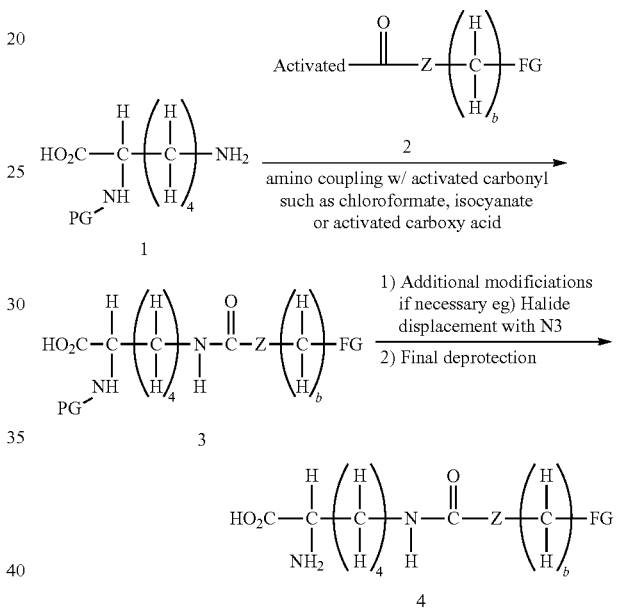

Formula VI analogs were prepared by conjugation of hydroxyl amino acids 9 to substrates with activated carbonyls such as carboxylic acid ester, isocyanate, acid chlorides, activated carbonates or sulfonyl halides. The coupled product 11 can undergo further modifications, such as the installation of the azide functional group by displacement of leaving groups such as halides or activated alcohols. The desired amino acid analog 12 is obtained by final deprotection to remove the α-amino acid masking group. Protecting groups may be used as per Scheme 1.

Scheme 2:

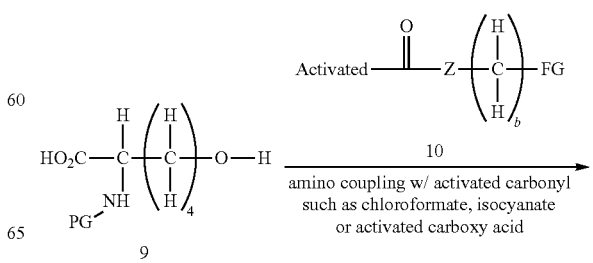

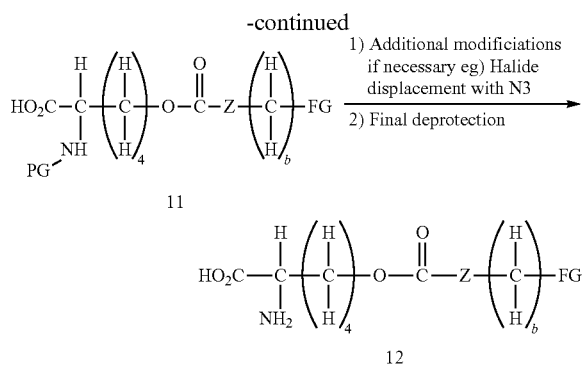

Many of the non-natural amino acids provided above are commercially available, e.g., from Sigma Aldrich (USA). Those that are not commercially available are optionally synthesized as provided in the examples of US 2004/138106 A1 (incorporated herein by reference) or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York), and WO 02/085923, all of which are hereby incorporated by reference.

Other nnAAs of the invention may be synthesized by published methods. For instance, synthesis of (S)-2-amino-6((prop-2-ynyloxy)carbonylamino)hexanoic acid and S)-2-amino-6((2azidoethoxy)carbonylamino)hexanoic acid is published in WO2010139948 and Nguyen et al. 2009.

S)-2-amino-6((2-oxo-2-phenylacetamide)hexanoic acid, S)-2-amino-6((2-oxo-2-propanamide)hexanoic acid, (2S)-2-amino-6-({[(2-azidocyclopentyl)oxy]carbonyl}amino) hexanoic acid, (2S)-2-amino-6-({[(2-ethynylcyclopentyl) oxy]carbonyl}amino)hexanoic acid, (2S)-2-amino-6-{[(cyclooct-2-yn-1-yloxy)carbonyl]amino}hexanoic acid, (2S)-2-amino-6-({[2-(cyclooct-2-yn-1-yloxy)ethoxy] carbonyl}amino)hexanoic acid, (2S)-2-amino-6-[({bicyclo [2.2.1]hept-5-en-2-yloxy}carbonyl)amino]hexanoic acid, (2S)-2-amino-6-[({bicyclo[2.2.1]hept-5-en-2-ylmethoxy}carbonyl)amino]hexanoic acid, (2S)-2-amino-6-{[({4-[(6-methyl-1,2,4,5-tetrazin-3-yl)amino] phenyl}methoxy)carbonyl]amino}hexanoic acid, (2S)-2-amino-6-({[(4E)-cyclooct-4-en-1-yloxy]carbonyl}amino) hexanoic acid, (2S)-2-amino-6-{[(cycloprop-2-en-1-yloxy) carbonyl]amino}hexanoic acid, (2S)-2-amino-6-{[(cycloprop-2-en-1-ylmethoxy)carbonyl]amino}hexanoic acid are disclosed in Hao, Z., Chem. Comm., 47, 4502, 2011, Schultz P G, et. al., Nat. Methods, 4, 239-244, 2007, Schultz P G, et. al., Bioorg. Med. Chem. Lett., 15, 1521-1524, 2005, Dieters A., et. al., J. Am. Chem. Soc., 125, 11782-11783, 2005, Wang, Y S, et. al., J. Am. Chem. Soc., 134, 2950-2953, 2012, Fekner, T., et. al., Angew Chem Int Ed Engl 45, 1633-1635, 2009, Plass, T., et. al. Angew Chem Int Ed Engl, 51, 4166-4170, 2012, Lang, K. J. Am. Chem. Soc., 134, 10317, 2012 and, Devaraj N K, Angew Chem Int Ed Engl, 48, 7013-7016, 2009.

Uses of Proteins with Incorporated Non-Natural Amino Acids

Proteins having incorporated non-natural amino acids using methods according to the invention may be used for the preparation of functionalized protein conjugates. Molecules that may be conjugated to proteins having incorporated non-natural amino acids include (i) other proteins, e.g. antibodies especially monoclonal antibodies and (ii) polymers especially PEG groups or other groups that may cause half life extension in the system. Moreover these modified proteins can be conjugated to drugs or nucleotides for targeted delivery of these potent compounds. Thus further molecules that may be conjugated to proteins having incorporated non-natural amino acids include (iii) cytotoxic agents and (iv) drug moieties.

More details of certain embodiments are given below in the discussion of antibody drug conjugates.

Non-natural amino acids may conveniently contain a unique chemical group permitting conjugation in a targeted fashion without risk of side reaction with other amino acids. For example non-natural amino acids conveniently contain azide or alkyne groups permitting reaction with a molecule to be conjugated which contains a corresponding alkyne or azide group using the Huisgen 1,3-dipolar cycloaddition reaction.

Site Specific Conjugation

A further aspect of the invention is a process for preparing a chemically modified target protein which comprises preparing a target protein according to the process according to an aspect of the invention and chemically modifying the resultant target protein.

Preferred conjugation chemistries of the invention include reactions which are orthogonal to the natural twenty amino acids. Such reactions do not interact or cause side reactions with the native 20 amino acids, they are specific to the functional groups associated with the reaction. Suitably the necessary functional groups are incorporated into the target protein via the nnAA.

Further, said reactions proceed under conditions which are not destructive to the protein, for instance aqueous solvents, with a pH range which is acceptable to the protein and maintains its solubility, at a temperature which does not lead to deleterious effects upon the protein.

Increasing the stability of the attachment moiety between the protein and the linker can be advantageous. Conventional methods conjugate to the thiol groups of cysteine by reaction with a maleimide forming a thiol ether. The thiol ether can undergo the reverse reaction releasing the linker drug derivative from the antibody. In an embodiment of the invention, the conjugation chemistry employed between an azide and an alkyne results in an aromatic triazole which is significantly more stable, and not as prone to reversibility.

In addition, the product of the reaction, the linkage between protein and payload, ought to be stable, equal to or greater than the stability associated with conventional linkages (amide, thiol ether). Though not an impediment to conjugation, it is often advantageous if the conjugation reactions can be done under native conditions, as this will eliminate an extra refolding processing step.

Preferred chemical conjugations for production of conjugates of the invention include: a 3+2 alkyne-azide cycloaddition; 3+2 dipolar cycloaddition; palladium based couplings including the Heck reaction; Sonogashira reaction; Suzuki reaction; Stille coupling; Hiyama/Denmark reaction; olefin metathesis; Diels-alder reaction; carbonyl condensation with hydrazine, hydrazide, alkoxy amine or hydroxyl amine; strain promoted cycloadditions, including Strain promoted azide alkyne cycloaddition; metal promoted azide alkyne cycloaddition; electron promoted cycloaddition; fragment extrusion cycloaddition; alkene cycloaddition followed by a b-elimination reaction.

According to one preferred embodiment, the incorporated amino acid contains an azide or an alkyne group and the process of chemical modification comprises reacting said azide or alkyne group with a reagent comprising an alkyne or azide group. The envisaged reaction is a Huisgen 1,3-dipolar cycloaddition reaction which leads to production of a triazole linkage. The reagent comprising an alkyne or azide group may be a protein (eg an antibody) or a toxin or a cytotoxic drug or a substance suitable for half life extension (eg a PEG group) which carries an alkyne or azide group optionally via a linker.

The alkyne group of use in said reaction is, for example, a cyclooctyne such as a bicyclo[6.1.0]non-4-yne moiety (BCN).

In a variant reaction, the incorporated amino acid contains an azide or an alkene group and the process of chemical modification comprises reacting said azide or alkene group with a reagent comprising an alkene or azide group. The reagent comprising an alkene or azide group may be a protein (eg an antibody) or a toxin or a substance suitable for half life extension (eg a PEG group) which carries an alkyne or alkene group optionally via a linker.

In an embodiment, conjugation chemistry of the invention is used for preparing an antibody drug conjugate.

Chemical Modification of Product

As noted elsewhere herein, cell lines according to the invention are useful for production of proteins containing incorporated non-natural amino acids. Said non-natural amino acids may usefully be employed in further chemical reactions.

A further aspect of the invention is a process for preparing a chemically modified target protein which comprises preparing a target protein according to the process according to an aspect of the invention and chemically modifying the resultant target protein.

Preferred conjugation chemistries of the invention include reactions which are orthogonal to the natural twenty amino acids. Such reactions do not interact or cause side reactions with the native 20 amino acids, they are specific to the functional groups associated with the reaction.

Further, said reactions proceed under conditions which are not destructive to the protein, for instance aqueous solvents, with a pH range which is acceptable to the protein and maintains its solubility, at a temperature which does not lead to deleterious effects upon the protein.

According to one embodiment, the incorporated amino acid contains an azide or an alkyne group and the process of chemical modification comprises reacting said azide or alkyne group with a reagent comprising an alkyne or azide group. The envisaged reaction is a Huisgen 1,3-dipolar cycloaddition reaction which leads to production of a triazole linkage. The reagent comprising an alkyne or azide group may be a protein (eg an antibody) or a drug moiety (e.g. a toxin or a cytotoxic drug) or a substance suitable for half life extension (eg a PEG group) which carries an alkyne or azide group optionally via a linker.

Optionally, the Huisgen 1,3-dipolar cycloaddition reaction can be performed in the presence of Cu(I) catalysis.

Preferably, copper catalyzed cycloaddition reactions are carried at room temperature, in aqueous solution in presence of cysteine and tris[(1-benzyl-1H-1,2,3-triazol-4-yl)methyl] amine (TBTA). Alternatively, the copper catalyzed cycloaddition reactions are carried out from 4° C. to 50° C. in aqueous solution in the presence of sodium ascorbate and tris(3-hydroxypropyltriazolylmethyl)amine (THPTA). The reactions can also be carried out in mixed aqueous/organic solution with the organic component consisting of DMSO, DMF, methanol, ethanol, t-butanol, trifluoroethanol, propylene glycol, ethylene glycol and hexylene glycol.

In a variant reaction, the incorporated amino acid contains an azide or an alkene group and the process of chemical modification comprises reacting said azide or alkene group with a reagent comprising an alkene or azide group. The reagent comprising an alkene or azide group may be a protein (eg an antibody) or a toxin or a substance suitable for half life extension (eg a PEG group) which carries an alkyne or alkene group optionally via a linker.

When more than one nnAA is incorporated into a target protein (eg an antibody), the chemical modification may be the same or different. For example if two nnAAs are incorporated, one may be modified to be conjugated to a drug moiety and one may be modified to be conjugated to a PEG moiety.

Target Proteins

Target proteins include antibodies, particularly monoclonal antibodies.

Antibodies of the invention include full length antibodies and antibody fragments including Fab, Fab2, and single chain antibody fragments (scFvs) directed to TROP-2, SSTR3, B7S1/B7x, PSMA, STEAP2, PSCA, PDGF, RaSL, C35D3, EpCam, TMCC1, VEGF/R, Connexin-30, CA125 (Muc16), Semaphorin-5B, ENPP3, EPHB2, SLC45A3 (PCANAP), ABCC4 (MOAT-1), TSPAN1, PSGRD-GPCR, GD2, EGFR (Her1), TMEFF2, CD74, CD174 (IeY), Muc-1, CD340 (Her2), Muc16, GPNMB, Cripto, EphA2, 5T4, Mesothelin, TAG-72, CA9 (IX), a-v-Integrin, FAP, Tim-1, NCAM/CD56, alpha folate receptor, CD44v6, Chondroitin sulfate proteoglycan, CD20, CA55.1, SLC44A4, RON, CD40, HM1.24, CS-1, Beta2 microglobulin, CD56, CD105, CD138, Lewis Y, GRNMP, Tomoregulin, CD33, FAP, CAIX, FasL Receptor, MMPmatrix metallo proteases.

In a preferred embodiment of the invention, antibodies of the invention directed to tumor targets are conjugated to protein moieties selected from the following: immunostimulatory and proapoptotic proteins, particularly Immune stimulators such as IL-1alpha, IL-1beta, other IL-1 family members, any of the interleukins, including but not limited to IL-2, IL-4, IL-5, IL-6, IL-7, IL-12, IL-13, IL-15, IL-17 family, IL-18, IL-21, IL-22, IL-23, IL-28, or costimulatory ligands such as B7.1 and B7.2, TACI. Interferons such as any of the Type I IFN family (IFN alpha and beta and lambda) or the Type II IFN gamma. Hematopoietic growth factors such as GM-CSF. Chemokines including CXCL-1, CXCL-2, CXCL-5, CXCL-6, CXCL-8, CXCL-9, CXCL-10, and CXCL-11, CXCL-13, CCL-2, CCL-3, CCL-4, CCL-5, CCL-21, IP-10, Eotaxin, RANTES, PF4, GRO related peptides, IL-8. Proapoptotic ligands such as those of the TNF superfamily including FasL, TNF, PD-L1. Antimicrobial peptides such as alpha and beta defensins and cathelicidin LL37/hCAP18, histatins, cathepsin G, azurocidin, chymase, eosinophil derived neurotoxin, high mobility group 1 nuclear proteins, HMGB1, lactoferrin. ROS and RNS producing enzymes such as the members of NADPH oxidases (NOXs), nitric oxide synthase NOS, INOS), neutrophil granule proteins including proteases such as elastases and cathepsins, Azurocidin (also known as CAP37 or HBP), myeloperoxidase, perforin, granzymes.

In one embodiment the target protein is an anti-Her-2 antibody.

In one embodiment, the target protein is an anti-IL-6 antibody.

In one embodiment, the target protein is an anti-PSMA antibody.

In a preferred embodiment, the anti-PSMA antibody is an scfv.

In one embodiment, the target protein is FGF21 for example having the sequence of SEQ ID No 62 or a sequence having 95% identity therewith (e.g 96, 97, 98 or 99% identity therewith). The sequence identify is calculated taking the whole protein as the window of comparison. Conventional sequence comparing programs such as BLAST may be used.

In a preferred embodiment, FGF21 is modified to contain non natural aminoacid lys-azide or propargyl lysine at position R131 (see SEQ ID No. 64) and conjugated to a PEG moiety via a triazole linker.

Decoy Amino Acid

A decoy amino acid of use in processes according to the invention is an amino acid derivative which is not incorporated into the extending protein. Alternatively, a decoy amino acid is an amino acid derivative which is incorporated into the extending protein but inhibits protein elongation.

Decoy amino acids of the present invention have general Formula VII:

Formula VII

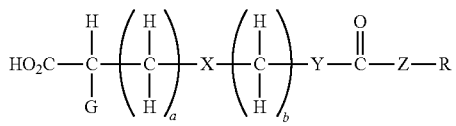

wherein
G=H, OH, —OCH$_3$, OCH$_2$CH$_3$, O—C(=O)—CH$_3$ or NH—K-Q;
X=bond, CH$_2$, S, O, NH, N—(C=O)— or CH-J;
J=alkyl, aryl, heteroaryl or the side chain of one of the 20 natural amino acids;
Y=bond, NH, O, S, CH$_2$;
Z=O, NH, CH$_2$, S, CH—NH$_2$,
K=CO or SO$_2$;
a=0, 1, 2 or 3;
b=0, 1, 2 or 3;
Q=—H, C$_{1-6}$alkyl, aryl, heteroaryl OC$_{1-6}$alkyl, —OCH$_2$aryl, —OCH$_2$heteroaryl, —C$_{2-6}$alkenyl or —OC$_{2-6}$alkenyl; and
R=C$_{1-6}$alkyl, C$_{2-6}$ alkenyl, —CH$_2$aryl, C$_{2-6}$alkynyl, C$_{1-6}$haloalkyl or C1-6azidoalkyl.

An example aryl group within the definition of Q is phenyl.

Example R groups include —CH$_2$CH=CH$_2$, —CH$_2$CH$_2$Cl, —CH$_2$CH$_2$N$_3$, —CH$_2$Ph, —C(CH$_3$)$_3$, —CH$_2$CH$_2$CH$_3$, —CH$_2$CH$_3$, —CH$_3$, —CH(CH$_3$)$_2$—, and —CH$_2$—C≡C—H.

An example aryl group within the definition of Q is phenyl.

Examples groups for Q include H, —CH$_3$, -Et, Ph, —OtBu, —OFmoc, —OBn, —OMe, —OEt and —OCH2CH=CH$_2$, In one embodiment K is CO. In another embodiment K is SO$_2$.

Suitably Y represents NH, O or S and Z represents O, NH, CH$_2$, S or CH—NH$_2$ or Y represents bond, NH, O, S or CH$_2$ and Z represents O, NH or S.

Suitably Y represents NH, O or S. Suitably Z represents NH, O or S. Suitably Y represents NH, O or S and Z represents NH, O or S.

In one embodiment Y is NH and Z is O. In another embodiment Y is O and Z is NH.

When J represents the side chain of one of the 20 natural amino acids, examples include the side chains of cysteine, serine, threonine, aspartic acid, glutamic acid, alanine, phenylalanine, isoleucine, valine, tyrosine and tryptophan.

In an embodiment, a decoy amino acids of the invention is an amino acid substrate for pylRS with a chemical modified amine group, for example an N-acylated amino acid of Formula VIIA:

Formula VIIA

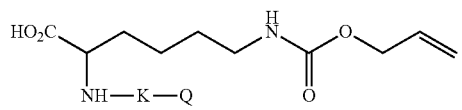

wherein
K is CO or SO$_2$;
Q=H, C$_{1-6}$alkyl, aryl, heteroaryl —OC$_{1-6}$alkyl, —OCH$_2$aryl, —OCH$_2$heteroaryl, —C$_{2-6}$alkenyl or —OC$_{2-6}$alkenyl.

Advantageously, decoy nnAAs of the present invention are able to prevent the toxic effects of amber suppression caused by the expression of the PyltRNA. The decoy prevents amber suppression by enabling the termination of protein translation at the amber codon, in the presence of the amber suppressor tRNA. Suitably, a decoy amino acid of Formula VII, that lacks amino terminal group necessary to propagate polypeptide synthesis as in Formula VIIB:

Formula VIIB

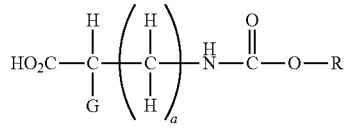

wherein
G=H;
a=4 or 5; and
R=C$_{1-6}$alkyl, C$_{2-6}$ alkenyl, —CH$_2$aryl, C$_{2-6}$alkynyl, C$_{1-6}$haloalkyl or C$_{1-6}$azidoalkyl.

An example aryl group within the definition of Q is phenyl.

When R represents C$_{1-6}$azidoalkyl it suitably represents C$_{2-6}$azidoalkyl e.g. C$_{2-4}$azidoalkyl.

Example R groups include —CH$_2$CH=CH$_2$, —CH$_2$CH$_2$Cl, —CH$_2$CH$_2$N$_3$, —CH$_2$Ph, —C(CH$_3$)$_3$, —CH$_2$CH$_2$CH$_3$, —CH$_2$CH$_3$, —CH$_3$, —CH(CH$_3$)$_2$, and —CH$_2$—C≡C—H.

In one embodiment a is 4. In another embodiment a is 5.

Exemplary decoy amino acids of Formula VIIB are the following:

6-{[(prop-2-en-1-yloxy)carbonyl]amino}hexanoic acid

Formula VIIB.1

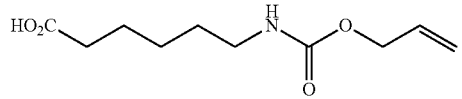

5-{[(prop-2-en-1-yloxy)carbonyl]amino}pentanoic acid

Formula VIIB.2

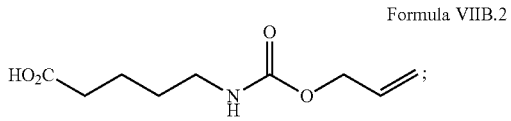

6-{[(2-chloroethoxy)carbonyl]amino}hexanoic acid

Formula VIIB.3

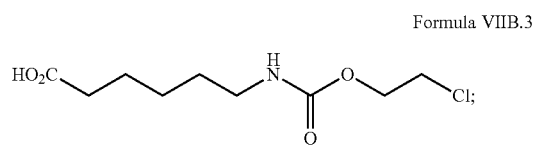 [SMILES: O=C(O)CCCCCNC(=O)OCCCl]

6-{[(tert-butoxy)carbonyl]amino}hexanoic acid

Formula VIIB.4

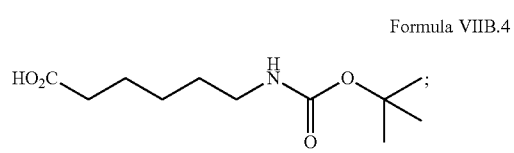 [SMILES: CC(C)(C)OC(=O)NCCCCCC(=O)O]

6-{[(prop-2-yn-1-yloxy)carbonyl]amino}hexanoic acid

Formula VIIB.5

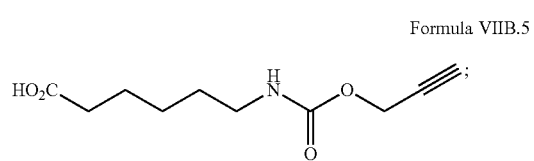

and 6-{[(2-azidoethoxy)carbonyl]amino}hexanoic acid

Formula VIIB.6

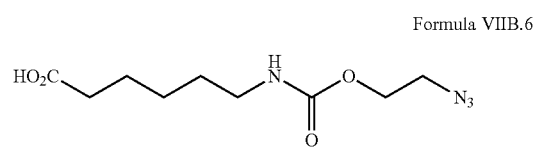 [SMILES: [N-]=[N+]=NCCOC(=O)NCCCCCC(=O)O]

Based on the data in Example 12, the decoy nnAA is able to prevent the toxic effects of amber suppression caused by the expression of the PyltRNA. The decoy prevents amber suppression by enabling the termination of protein translation at the amber codon, in the presence of the amber suppressor tRNA.

Decoy Protein

A decoy protein of use in process according to the invention is a benign protein containing one or more non-natural amino acids encoded by an amber codon that is not a target.

Decoy proteins on the invention are selected from: Green fluorescence protein, Red Fluorescence Protein, albumin, SEAP, Actin, b-2 microglobulin, glutathione-s-transferase and poly amber containing peptide. A further example is IgG.

A decoy protein of the invention is suitably under the control of an inducible promoter selected from conditionally activated promoters and promoter systems such as the tetracycline regulated promoters (TetO or tTA; TetOn and TetOFF), doxycycline-inducible (TRE) promoters, cAMP inducible promoters, glucocorticoid activated promoter systems, IPTG inducible promoters (lac), $Cd^{2+}$ or $Zn^{2+}$ inducible promoters (methalloprotein promoters), interferon dependent promoters (e.g. murine MX promoter), HIV LTR promoters (Tat), DMSO inducible promoters (globin promoter globin LCR), hormone modulated promoters (GLVP/TAXI, ecdysone), and rapamycin inducible promoters (CID).

PEG Moieties

Target proteins may be conjugated to PEG moieties. PEG moieties may be incorporated into antibody drug conjugates. The PEG moiety may typically have a molecular weight ranging between 0.5 kDa and 40 kDa e.g. 5 kDa and 40 kDa. More preferably, the PEG moiety may have a molecular weight of around 20 kDa. In addition, the PEG moieties can have a molecular weight range from 100-2000 Da. PEG moieties may be straight chain or branched or multi armed The PEG moieties can be functionalized with terminal alkynes, azides, cyanides, cycloalkynes, alkenes, aryl halides. The PEG can be functionalized in such as way as to be monofunctional, homobifunctional, heterobifunctional, and multi-homofunctional.

Antibody Drug Conjugates (ADCs)

Cell lines according to the invention are particularly useful for production of Antibody Drug Conjugates (recombinant antibody covalently bound by a synthetic linker to a given drug, typically a cytotoxic drug, or else a protein or a PEG group) which are homogeneous in nature, in which the number of drugs (or other conjugated molecule) per antibody and position of those drugs upon the antibody are explicitly controlled, whereby monoclonal antibodies containing incorporated non-natural amino acids are obtained and site specifically conjugated to a linker carrying a drug moiety (or other conjugated molecule) through orthogonal chemistry.

Suitably, the present invention provides a process to obtain ADCs including the following steps:

1. Introducing into a stable cell line of the invention one or more plasmids carrying the DNA sequence coding for a full length antibody, whereby a stop codon is introduced at specific positions within the sequence 2. Purify the modified antibody with non natural amino acid (nnAA) installed at desired position(s).

3. React a cytotoxin-linker derivative modified to include a functional group complimentary to the nnAA installed in the antibody with the modified antibody containing a complementary reactive group through an orthogonal chemistry 4. Purify the resulting ADC Thus, the present invention also provides ADCs whereby the antibody component has been modified to incorporate non natural aminoacids bearing a unique reactive functional group at desired positions, whereby such functional group allows conjugation to a drug moiety (or protein or PEG group).

In an embodiment the present invention provides an antibody conjugate comprising an anti-Her-2 antibody which is conjugated to one or more moieties (e.g. one, two, three or four, preferably one or two, especially one) selected from protein, drug and PEG moieties via linkers comprising a triazole moiety.

In particular, the triazole moiety may be formed by reaction of an azide or alkyne moiety in the side chain of a non-natural amino acid incorporated into the sequence of the anti-Her-2 antibody and an alkyne or azide moiety attached to the protein, drug or PEG moiety.

In one embodiment, the triazole moiety is formed by reaction of an azide or alkyne moiety in the side chain of a non-natural amino acid incorporated into the sequence of the anti-Her-2 antibody and an alkyne or azide moiety attached to the protein, drug or PEG moiety under conditions of Cu(I) catalysis.

Cu(I) catalysis is accomplished by using either a native Cu(I) source such as Copper iodide, copper bromide, copper chloride, copper thiolate, copper cyanide. The Cu(I) species can also be generated in situ by using a copper (II) source and a reducing agent. The copper (II) source can be copper sulfate, copper (II) chloride, or copper acetate. The reducing agent can be sodium ascorbate, dithiothreitol, TCEP, b-mercaptoethanol, hydrazine, hydroxylamine, sodium bisulfite, cystamine, cysteine Suitably, Cu(I) catalyzed cycloaddition are carried out in presence of ligands to stabilize the Cu(I) species present at the start of the reaction or generated in situ by reduction of a Cu(II) source such as sodium sulfate with sodium ascorbate, including TBTA, THPTA, phenanthroline derivatives, pyridylmethanimine derivatives, diethylenetriamine, bipyridine derivatives, TMEDA, N,N-bis(2-pyridylmethyl)amine (BPMA) derivatives, N,N,N',N'-tetrakis(2-pyridylmethyl) ethylenediamine (TPEN) derivatives, trialkylamines such as triethylamine, diisopropyl ethylamine, HEPES and MES.

In another embodiment, an antibody conjugate comprises an antibody which is conjugated to one or more moieties selected from drug and PEG moieties via linkers comprising a triazole moiety in which the triazole moiety is formed by reaction of an azide moiety in the side chain of a non-natural amino acid incorporated into the sequence of the antibody and an alkyne moiety attached to the drug or PEG moiety and in which the alkyne moiety is a cyclooctyne moiety.

In another embodiment, an antibody conjugate comprises an antibody which is conjugated to one or more moieties selected from drug and PEG moieties via linkers comprising a triazole moiety in which the triazole moiety is formed by reaction of an alkyne moiety in the side chain of a non-natural amino acid incorporated into the sequence of the antibody and an azide moiety attached to the drug or PEG moiety and in which the alkyne moiety is a cyclooctyne moiety.

The cyclooctyne moiety may, for example, be a bicyclo [6.1.0]non-4-yne moiety.

The non-natural amino acid incorporated into the sequence of the antibody is suitably a non-natural amino acid substrate for PylRS, particularly a non natural lysine analog such as (S)-2-amino-6((2-azidoethoxy)carbonylamino)hexanoic acid.

Antibodies

In the present invention ADCs include the use of full length antibodies as well as antibody fragments such as, but not limited to Fab, Fab2, and single chain antibody fragments.

Antibodies suitable for conjugation to cytotoxins include those targeted against: anti-Her2, anti-IL-6, TROP-2, SSTR3, B7S1/B7x, PSMA, STEAP2, PSCA, PDGF, RaSL, C35D3, EpCam, TMCC1, VEGF/R, Connexin-30, CA125 (Muc16), Semaphorin-5B, ENPP3, EPHB2, SLC45A3 (PCANAP), ABCC4 (MOAT-1), TSPAN1, PSGRD-GPCR, GD2, EGFR (Her1), TMEFF2, CD74, CD174 (IeY), Muc-1, CD340 (Her2), Muc16, GPNMB, Cripto, EphA2, 5T4, Mesothelin, TAG-72, CA9 (IX), a-v-Integrin, FAP, Tim-1, NCAM/CD56, alpha folate receptor, CD44v6, Chondroitin sulfate proteoglycan, CD20, CA55.1, SLC44A4, RON, CD40, HM1.24, CS-1, Beta2 microglobulin, CD56, CD105, CD138, Lewis Y, GRNMP, Tomoregulin, CD33, FAP, CAIX, FasL Receptor, MMPmatrix metallo proteases.

In a preferred embodiment, antibodies of the invention are of the IgG type.

In a particularly preferred embodiment of the invention, the antibody is modified to comprise one or more non-natural amino acids, wherein the positions of such non-natural amino acids are conserved amongst IgG immunoglobulins and are selected from positions K157 of SEQ ID No 82, representing a conserved constant region of the heavy chain for an IgG, corresponding to position 274 of the anti-Her 2 antibody of SEQ ID Nos 46 and 75 and position T242 of SEQ ID 82 corresponding to position 359 of the anti-Her 2 antibody of SEQ ID Nos 46 and 75 and positions D70 and L81 in the framework region of the light chain of IgG, following Kabat numbering and corresponding to D70 and L81 of SEQ ID Nos 52 and 79. For clarity, the D70 is found in the following amino acid context: sgsrsgtdftltisslq and E81 in the following amino acid context: sslqpedfatyycqq.

One particular antibody of interest is an anti-Her-2 antibody.

The anti-Her2-antibody may, for example, have the light chain sequence of SEQ ID No 52 or a derivative having a sequence identity of 95% (e.g. 96, 97, 98 or 99%) or more thereto and having the same CDRs and the heavy chain sequence of SEQ ID No 46 or a derivative having a sequence identity of 95% (e.g. 96, 97, 98 or 99%) or more thereto and having the same CDRs. The sequence identify is calculated taking the whole antibody, but excluding the CDRs, as the window of comparison. Conventional sequence comparing programs such as BLAST may be used. The mAb sequence described in this document has high similarity to the sequence of Herceptin. The mAb sequence utilized here was generated by placing the antigen binding sites sequence found in Herceptin into a germline IgG1. The variable regions of the mouse antibody 4D5 directed to the extracellular domain of Her2 was generated by gene synthesis using overlapping oligomers and cloned into a shuttle vector. The variable regions were then grafted onto the human frameworks encoded by pFUSE-CHIg-hG1 and pFUSE-CHLIg-hK (Invivogen) to generate a mouse-human hybrid. Sequence comparison showed that the constructed antibody had six amino acid substitutions relative to Herceptin. These corresponded to 5 heavy chain positions and one light chain site. None of these sites correspond to CDR regions or sites adjacent to the CDRs.

According to an embodiment, the non-natural amino acid used for conjugation is in position 274 of the heavy chain sequence of each heavy chain of said anti-Her2-antibody.

According to an embodiment, the non-natural amino acid used for conjugation is in position 70 of the light chain sequence of each heavy chain of said anti-Her2-antibody.

According to an embodiment, the non-natural amino acid used for conjugation is in position 274 of the heavy chain sequence of each heavy chain of said anti-Her2-antibody and also in position 70 of the light chain sequence of each light chain of said anti-Her2-antibody.

According to an embodiment, the non-natural amino acid used for conjugation is in position 359 of the heavy chain sequence of each heavy chain of said anti-Her2-antibody.

According to an embodiment, the non-natural amino acid used for conjugation is in position 81 of the light chain sequence of each heavy chain of said anti-Her2-antibody.

According to an embodiment, the non-natural amino acid used for conjugation is in position 274 of the heavy chain sequence of each heavy chain of said anti-Her2-antibody and also in position 81 of the light chain sequence of each light chain of said anti-Her2-antibody.

According to an embodiment, the non-natural amino acid used for conjugation is in position 359 of the heavy chain sequence of each heavy chain of said anti-Her2-antibody and also in position 70 of the light chain sequence of each light chain of said anti-Her2-antibody.

According to an embodiment, the non-natural amino acid used for conjugation is in position 359 of the heavy chain sequence of each heavy chain of said anti-Her2-antibody and also in position 81 of the light chain sequence of each light chain of said anti-Her2-antibody.

Another particular antibody of interest is an anti-PSMA antibody, especially a scfv. The anti-PSMA antibody may, for example, have the scfv sequence of SEQ ID No 58 or a derivative having a sequence identity of 95% (e.g. 96, 97, 98 or 99%) or more thereto and having the same CDRs. The sequence identify is calculated taking the whole antibody, but excluding the CDRs, as the window of comparison. Conventional sequence comparing programs such as BLAST may be used.

In a particular embodiment, an anti-PSMA scfv is modified to contain non natural amino acid lys-azide at position 117 (SEQ ID 60). Said scfv may, for example, be conjugated to a MMAF-valine-citruline-p-amino-benzoyl-carbonate-cycloalkyne derivative Site Specific Modification of Antibodies for Production of ADCs In the present invention, selection of conjugation sites for the incorporation of nnAAs into the antibody included the following steps:

Initial selection of sites was conducted using in silico predictive methods that took into account the three dimensional structure of the antibody, its functional domains and critical amino acid residues that play a role in the structure or function of the antibody. Selected sites were then screened for their physico-chemical properties and stability.

Suitably, criteria for selection of optimal conjugation sites included the following:

Preferred sites are: residues distal to the binding sites of the antibody; surface/solvent exposed residues (to enhance access to conjugate formation and enable efficient conjugate formation); Sites were empirically found to allow efficient amber suppression; sites that were empirically found to retain the stability of the expressed protein and conjugate Avoided sites are: residues important for function (eg FcRN binding, FcGamma interactions), amino acid residues known to be important for folding or structure (e.g. Cys, proline)

Six sites in human IgG1 have been identified following the criteria outline above. These include four heavy chain positions (T114, K274, K288 and T359) and two light chain sites (D70 and E81). HC K274, K288 and T359; and LC D70, E81 were shown to efficiently incorporate nnAAs and enable conjugate formation.

Linkers

According to the present invention, the target protein or antibody may be directly linked to the protein or drug moiety or PEG moiety or else linked through a linker or spacer.

Linkers of the invention may be cleavable or non cleavable.

Thus the invention provides an antibody conjugate wherein the or a linker comprising a triazole moiety is a cleavable linker by virtue of the presence in the linker of a spacer containing a cleavage site. The cleavage site may be an enzymatically labile cleavage site. An example of an enzymatically labile cleavage site is the incorporation of a valine-citrulline peptide which recognized by the enzyme cathepsin B and which cleaves the peptide at the citruline C-terminus In an embodiment, the or a linker of the antibody conjugate comprises a triazole moiety that is not a cleavable linker.

The use of cleavable linkers is driven by the need for the cytotoxin to be released within its target in an unaltered state. This is exemplified by cytotoxins such as monomethylauristate E <(Pettit 1997, Senter 2003)>. The mechanism for release in a cleavable linker can be chemical such as acid lability, or enzymatic by inclusion of a cleavable peptide within the linker. The mechanism can also be externally triggered by a light or other radiation source or a chemical trigger such as fluoride.

Non cleavable linkers do not have to be removed from the cytotoxin in order to achieve the desired potency or cell killing effect during therapy. Thus, antibody is internalized and reduced to its amino acid components in the lysosome, with the drug-linker released. It is this compound which requires no additional release in order to be potent. Non-cleavable linkers have no internal mechanism for releasing the intact cytotoxin, instead they rely on the benign-ness of their inclusion on a cytotoxins framework. Non cleavable linkers can have a number of varied structures, from relatively simple to more complex entities.

Further, linkers are defined by the manner in which they are attached both the cytotoxin and the antibody. For conventional approaches this includes chemistry for attaching to either cysteine thiols (maleimide) or lysine amines (activated acids). Linkers of the invention incorporate alkyne or azide groups.

Figure 43:
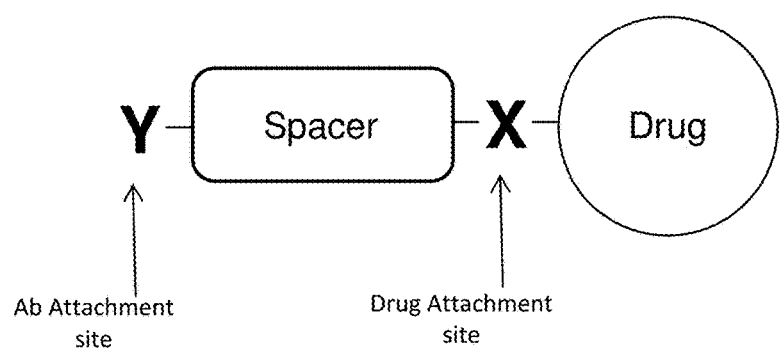
FIG. 43. A schematic showing a non-cleavable linker with a functional handle (Y) for attaching to the antibody at one terminus, a spacer which bridges the two components of the antibody drug conjugate (ADC) and provides the functional groups necessary to attach to the antibody and to the drug. and a complimentary functional group (X) for coupling to the drug.

Suitably, non cleavable linkers of the invention include a functional handle (Y) for attaching to the antibody at one terminus, a spacer which bridges the two components of the ADC and provides the functional groups necessary to attach to the antibody and to the drug. and an the complimentary functional group (X) for coupling to the drug. (See FIG. 43)

Suitably, the preferred functional handles are those chemical moieties which are complementary reactive partners to the functional group on the non-natural amino acid installed into the target protein. The spacer portion of the molecule is a non-functional chemical bridge which contains the two complimentary functional groups necessary to attach to the antibody and to the drug. In this embodiment of the linker, this spacer has no cleavage site.

Figure 44:
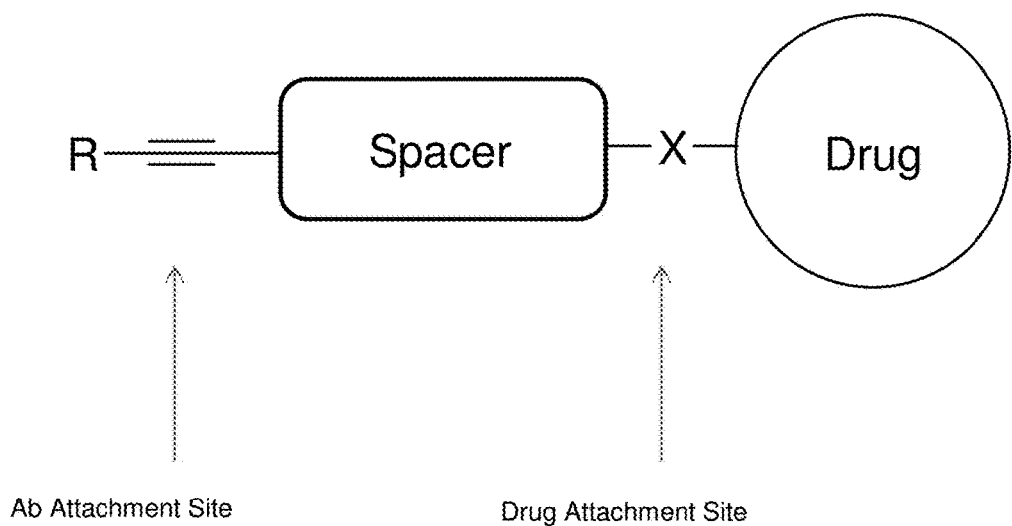
FIG. 44. A schematic showing a linker with a functional handle (Y) that includes an alkyne group.

In a preferred embodiment of the invention, the functional handle (Y) includes an alkyne group. (See FIG. 44)

Preferably, the alkyne may be a terminal alkyne, an internal alkyne, a cyclic alkyne and an Silyl-protected alkyne.

Preferably, the internal alkyne would contain electron withdrawing groups adjacent to the alkyne. Preferably, the cyclic alkyne would be an alkyne contained within a 7, 8 or 9 membered ring.

These electron withdrawing groups include halogens such as fluorine, bromine chlorine and iodine. Additional electron withdrawing groups in include hydroxyl, ethers, acetals, ketals, ketones, aldehydes, carboxylic acids, esters, nitriles, nitro, amides.

More preferably, the ring would be included in a bicyclic ring system in which the 8 membered ring is fused to another ring of 3, 4, 5, or 6 atoms as described for instance in van Delft, F., Angew. Chem. Int. Ed, 49, 1-5, 2012. M. D. Best, Biochemistry 2009, 48, 6571-6584; E. M.

Sletten, C. R. Bertozzi, Angew. Chem. 2009, 121, 7108-7133; Angew. Chem. Int. Ed. 2009, 48, 6974-6998; J. A. Prescher, C. R. Bertozzi, Nat. Chem. Biol. 2005, 1, 13-21. J. A. Codelli, J. M. Baskin, N. J. Agard, C. R. Bertozzi, J. Am. Chem. Soc. 2008, 130, 11486-11493. Incorporated herein by reference.

Particularly preferred cyclic alkynes are described in U.S. Pat. No. 7,807,619 and U.S. Ser. No. 12/049,034, incorporated herein by reference.

Particularly preferred bicyclic alkynes are bicyclononynes as described in WO2011/136645 (incorporated herein by reference):

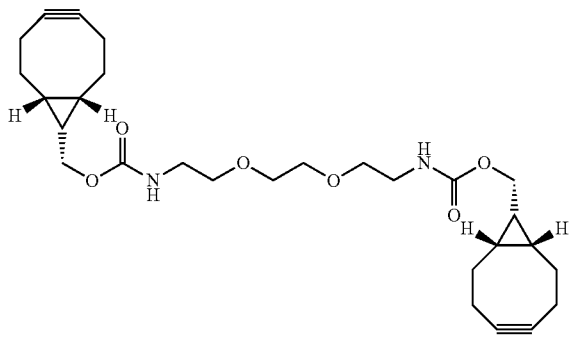

SX-BCN-BCN
120 mg
Oil
SX-JV-133
MW = 508.6

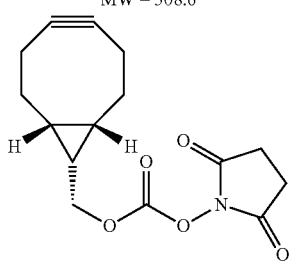

SX-BCN-OSu
Cat #: SX-A1028
120 mg, White Solid
SX-JV-94
MW = 291.3

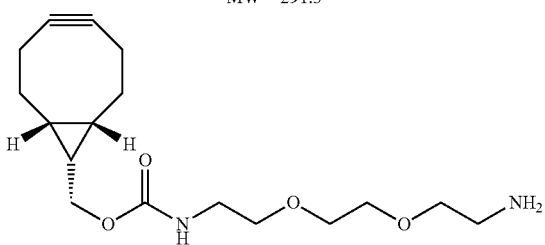

SX-A1054
120 mg, oil
SX-JV-94
MW = 324

In an embodiment, a non cleavable linker of the invention may contain an alkene as functional handle (Y) at the antibody attachment site.

Suitably, the alkene can be mono, di, tri or tetra substituted.

Suitably, the alkene can be incorporated as part of a ring.

In the preferred embodiment, the alkene can be part of a 3-12 membered ring.

Figure 45:
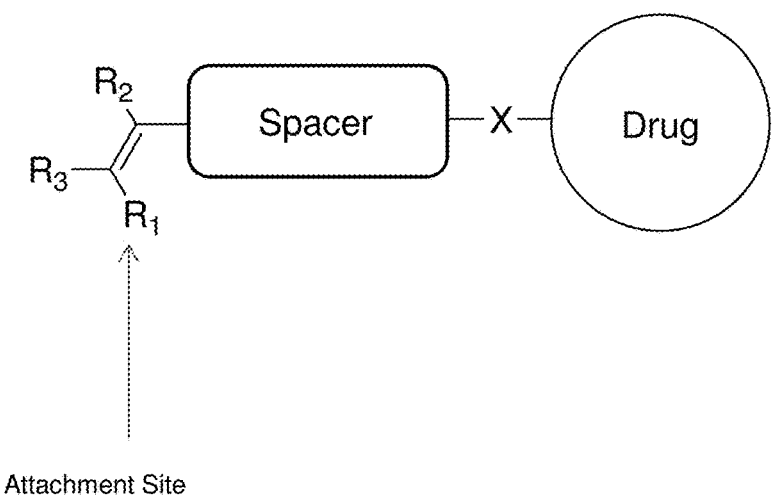
FIG. 45. A schematic showing a non-cleavable linker with a functional handle (Y) at the antibody attachment site that includes a vinyl halide.

In a further preferred embodiment, the alkene can be part of a bicyclic ring system such as norbornene, bicyclic furan or bicyclic pyrrole system. (See FIG. 45)

Preferably, the functional handle (Y) at the antibody attachment site includes a vinyl halide.

Preferably, the vinyl halide includes a halide such as fluorine, chloride, bromine, or iodine at either the Z or Y positions or both. Furthermore, the vinyl halide can be terminal in which the R-group is a hydrogen. The vinyl halide group can also contain additional substitution at the R position, including alkyl and aryl groups, carbonyl groups.

Preferably, the vinyl halide is part of a cyclic compound.

More preferably, the vinyl halide is part of rings with 3, 4 and 5 atoms.

Figure 46:
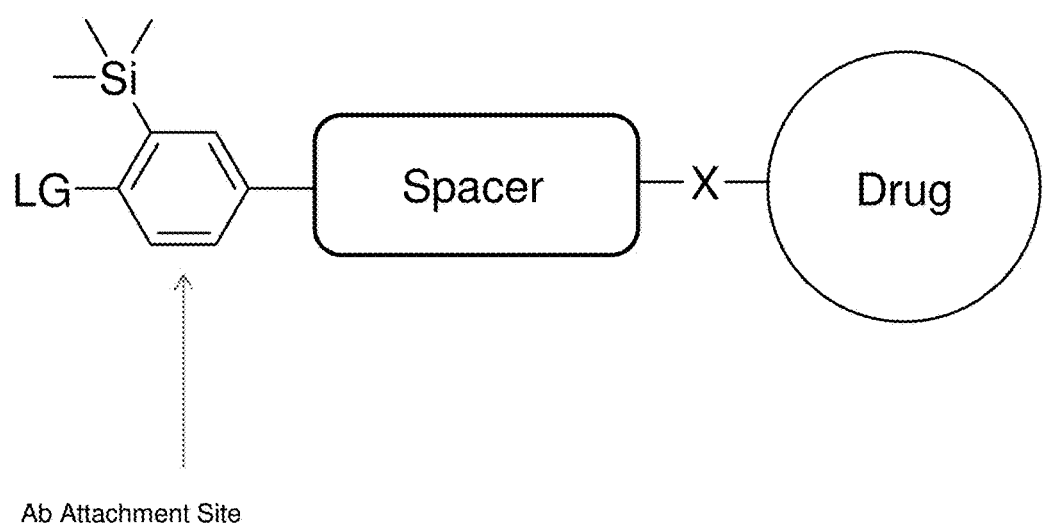
FIG. 46. A schematic showing a non-cleavable linker with a functional handle (Y) at the antibody attachment site that includes a reactive aromatic ring substituted with a silyl group and either a halide or triflate, tosylate or mesylate at the LG position.

In an embodiment, the functional handle (Y) at the antibody attachment site includes a reactive aromatic ring substituted with a silyl group and either a halide or triflate, tosylate or mesylate at the LG position. (See FIG. 46)

Figure 47:
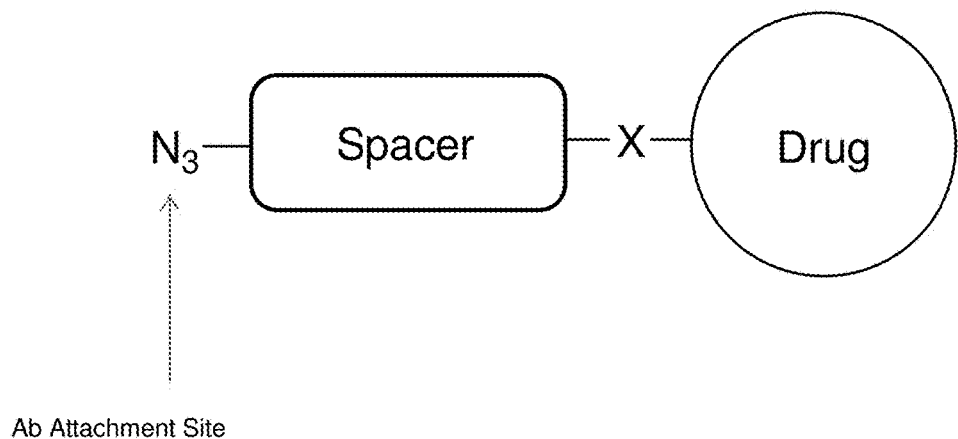
FIG. 47. A schematic showing a non-cleavable linker with a functional handle (Y) at the antibody attachment site that includes a reactive azide group at the terminus.

In a further embodiment, the functional handle (Y) at the antibody attachment site includes a reactive azide group at the terminus. (See FIG. 47)

Figure 48:
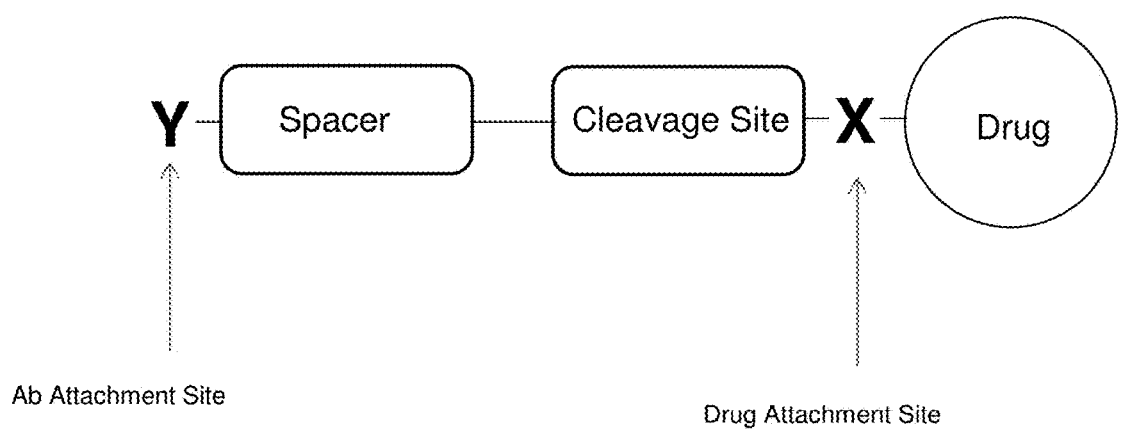
FIG. 48. A schematic showing a cleavable linker for an antibody drug conjugate (ADC) that includes a cleavage site.

Suitably, a cleavable linker of the invention includes a functional handle (Y) for attaching to the antibody at one terminus, a spacer and an the complimentary functional group (X) for coupling to the drug. (See FIG. 48)

Suitably, cleavable linkers of the ADCs of the invention include a cleavage site.

Suitably, the cleavage site may be triggered enzymatically, chemically, or externally.

In an embodiment, the cleavage site is placed at the drug attachment site.

Figure 49:
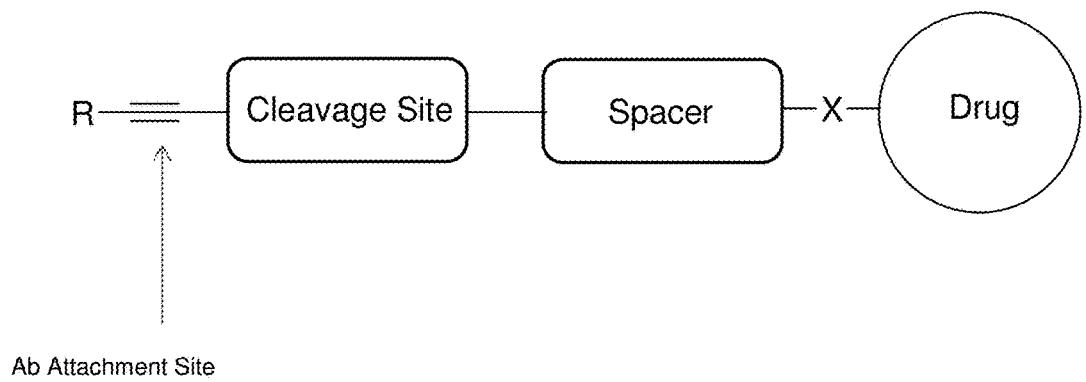
FIG. 49. A schematic showing a cleavable linker with a functional handle (Y) at the antibody attachment site that includes an alkyne.

In an alternative embodiment, the cleavage site is at the drug attachment site. (See FIG. 49)

In an embodiment, the cleavable linker includes a functional handle (Y) at the antibody attachment site with an alkyne.

Preferably, the alkyne may be a terminal alkyne, an internal alkyne, a cyclic alkyne and an Silyl-protected alkyne.

Preferably, the internal alkyne would contain electron withdrawing groups adjacent to the alkyne. These electron withdrawing groups include halogens such as fluorine, bromine chlorine and iodine. Additional electron withdrawing groups in include hydroxyl, ethers, acetals, ketals, ketones, aldehydes, carboxylic acids, esters, nitriles, nitro, amides.

Preferably, the cyclic alkyne would be an alkyne contained within a 7, 8 or 9 membered ring.

More preferably, the ring would be included in a bicyclic ring system in which the 8 membered ring is fused to another ring of 3, 4, 5, or 6 atoms.

Figure 50:
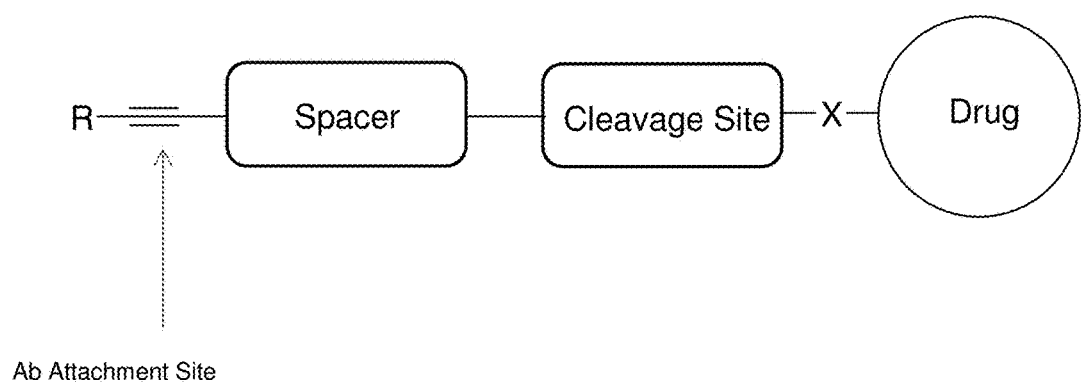
FIG. 50. A schematic showing a cleavable linker in which the cleavage site and spacer are reversed in order with the cleavage site at the drug attachment site.

In an alternative embodiment, the cleavage site and spacer are reversed in order with the cleavage site is at the drug attachment site. (See FIG. 50)

In an embodiment, a cleavable linker of the invention may contain an alkene as functional handle (Y) at the antibody attachment site.

Suitably, the alkene can be mono, di, tri or tetra substituted.

Suitably, the alkene can be incorporated as part of a ring.

In a preferred embodiment, the alkene can be part of a 3-12 membered ring.

In a further preferred embodiment, the alkene can be part of a bicyclic ring system such as norbornene, bicyclic furan or bicyclic pyrrole system.

Figure 51:
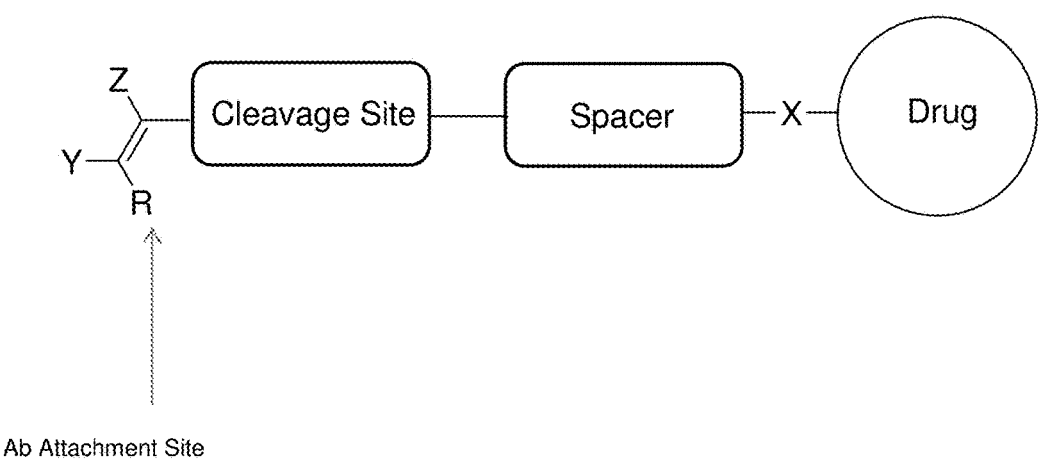
FIG. 51. A schematic showing a cleavable linker with a functional handle (Y) at the antibody attachment site that includes a vinyl halide.

Preferably, the functional handle (Y) at the antibody attachment site includes a vinyl halide. (See FIG. 51)

Preferably, the vinyl halide includes a halide such as fluorine, chloride, bromine, or iodine at either the Z or Y positions or both. Furthermore, the vinyl halide can be terminal in which the R-group is a hydrogen. The vinyl halide group can also contain additional substitution at the R position, including alkyl and aryl groups, carbonyl groups.

Preferably, the vinyl halide is part of a cyclic compound.

More preferably, the vinyl halide is part of rings with 3, 4 and 5 atoms.

Figure 52:
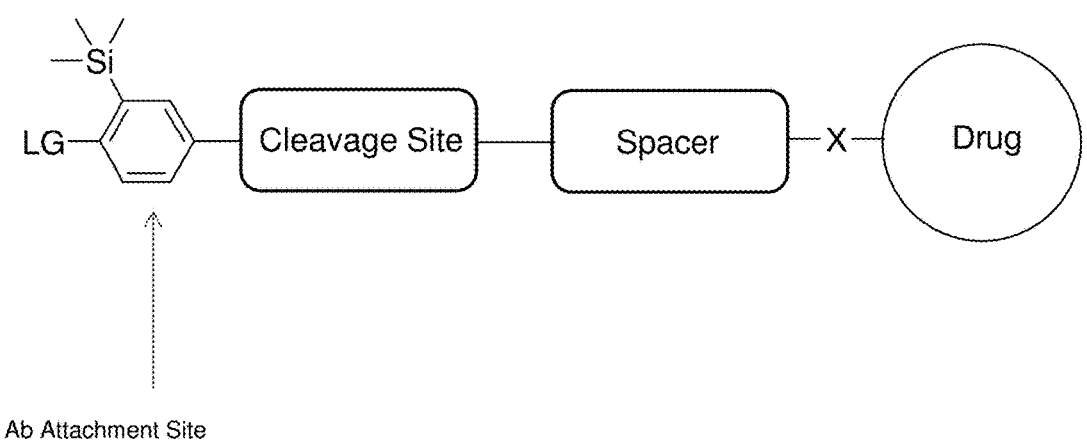
FIG. 52. A schematic showing a cleavable linker with a functional handle (Y) at the antibody attachment site that includes a reactive aromatic ring substituted with a silyl group and either a halide or triflate, tosylate or mesylate at the LG position.

In an alternative embodiment, the cleavage site and spacer are reversed in order with the cleavage site is at the drug attachment site In an embodiment, the functional handle (Y) at the antibody attachment site includes a reactive aromatic ring substituted with a silyl group and either a halide or triflate, tosylate or mesylate at the LG position. (See FIG. 52)

In an alternative embodiment, the cleavage site and spacer are reversed in order with the cleavage site is at the drug attachment site.

Figure 53:
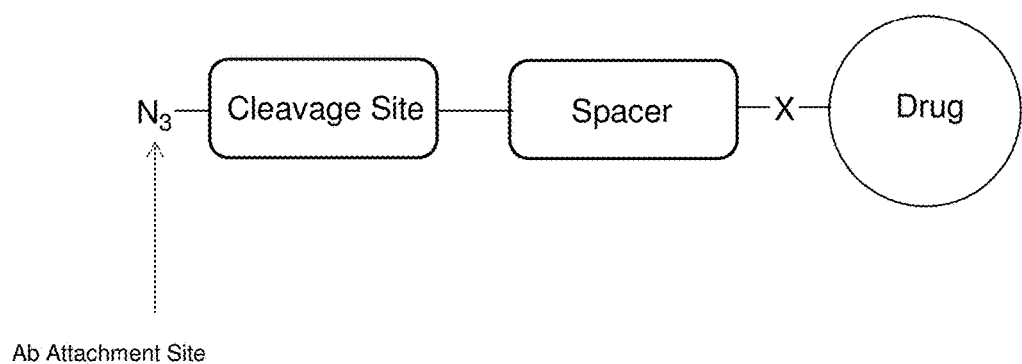
FIG. 53. A schematic showing a cleavable linker with a functional handle (Y) at the antibody attachment site that includes a reactive azide group at the terminus.

In a further embodiment, the functional handle (Y) at the antibody attachment site includes a reactive azide group at the terminus. (See FIG. 53)

In an alternative embodiment, the cleavage site and spacer are reversed in order with the cleavage site is at the drug attachment site In an embodiment of the present invention, the spacer portion of both cleavable and non-cleavable linker can be structurally diverse and include alkyl chains, alkyl rings, aromatic rings, aniline derivative including p-amino-benzyl carbonate, alkenes, polymers such as polyethylene glycol.

Figure 54:
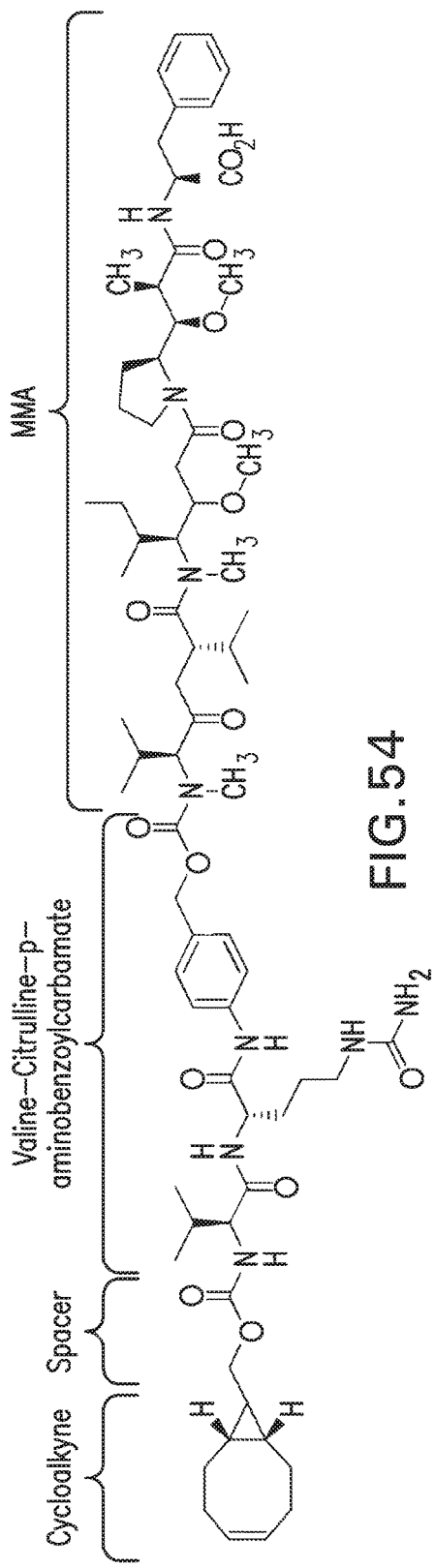
FIG. 54. A schematic showing a linker that includes a cycloalkyne at one terminus for attachment to the antibody via azidealkyne cycloaddition; a carbon chain spacer attached to the cycloalkyne which is then attached to a valinecitrulline peptide; wherein the C-terminus of citrulline is coupled to a p-amino-benzoyl carbamate (PABC) which is connected to the N-terminus of monomethyl auristatin F (MMAF).

In a preferred embodiment of the invention, the linker is composed of a cycloalkyne at one terminus for attachment to the antibody via azide-alkyne cycloaddition. Attached to the cycloalkyne is carbon chain which is then attached to a valine-citrulline peptide. The C-terminus of citrulline is coupled to a p-amino-benzoyl carbamate (PABC). This is turn is connected to the N-terminus of MMAF. (See FIG. 54) This valine-citrulline peptide is recognized by the enzyme cathepsin B, which cleaves the peptide at the citrulline c-terminus. Follow the cleavage, the p-aminobenzoyl undergoes an elimination reaction to extrude CO2 and the MMAF group. Thus, the entire cyclo-alkyne-val-cit-PABC combination is a cleavable linker.

In an embodiment of the invention, the linker releases the drug from the ADC upon a trigger Suitably, a trigger may be found near or within the target cell.

Preferably, the linker is found within the cell. Suitably an intracellular trigger includes an enzymatic trigger.

Suitably, enzymatic cleavage sites include aminoacid sequences specifically recognized by intracellular enzymes.

Preferred enzymatic cleavage site of the invention are Cathepsin (Valine-Citrulline) and Furin (Arg-N-Arg-Arg), Alternatively, chemical triggers are found within the target cell.

Suitably, chemical triggers include acid hydrolysis of chemical moieties including, esters, amides, acetals, ketals, nitriles, ether cleavage, carbamates, ureas, sulfonamides, sulfonyl, sulfenyl, phosphinamides, phosphoramidates, enamines, imines, silyl ethers, ortho esters, boronates.

Alternatively, chemical triggers can also include reduction of chemical moieties including disulfides, fluoride addition to silyl groups, reverse cycloadditions and reverse Michael additions.

Alternatively, release of the drug from the linker can be achieved by extracellular stimuli such as exposure to radiation of a particular wavelength.

Drug Moieties

Drug moieties of the present invention, such as cytotoxin drug moieties, include small molecules, natural products, synthetically derived drugs, proteins such as immunotoxins, and radionuclides.

In an embodiment, the drug moiety is an auristatin moiety eg auristatin or a derivative thereof such as monomethyl auristatin E (MMAE)(Vedotin) or monomethyl auristatin F (MMAF), Auristatin F (AF), Amanitin, Paclitaxel and doxorubicin.

Other drug moieties include maytansine, paclitaxel, doxorubicin and immunotoxins such as exotoxin or bouganin as well as radionuclides such as Iodine-131, Yttrium-90, Samarium-135, and Strontium-89 which may also be incorporated into organic molecules. (see for instance: MMAE: Senter, P E, et. al, BLOOD, 102, 1458-1465. MMAF: Senter, P E, et. al., Bioconj. Chem. 2006, 17, 114-124. Maytansine: Lewis-Phillips G D, Cancer Res., 63, 9280-9290, 2008. Bouganin: MacDonald G C, et. al, J. Immunotherapy, 32 574-84, 2009.

Most suitably the drug moiety is a moiety selected from a doxorubicin, paclitaxel and auristatin moiety.

Salts

Amino acids, amino acid derivatives, decoy amino acids and pyrrolysine analogs described herein may optionally be employed in the form of a salt. Any such salts form an aspect of the invention. Salts of carboxylic acids may include salts formed with Group 1 and Group 2 metals, especially soluble salts such as sodium and potassium salts. Salts of amines may include salts formed with weak and strong acids, such as HCl, HBr or acetic acid.

INCORPORATION BY REFERENCE

All references cited herein, including patents, patent applications, papers, text books and the like, and the references cited therein, to the extent that they are not already, are hereby incorporated herein by reference in their entirety.

EXAMPLES

Example 1: Generation of a Stable Cell Line

The generation of a platform cell line capable of site specific integration of nnAAs into a target protein required the stepwise construction of a cell line stably expressing the pylRS and the pyltRNA. This was accomplished by sequential introduction of the pylRS/tRNA expression elements and iterative selection steps to identify high functioning cells (FIG. 1).

Figure 2:
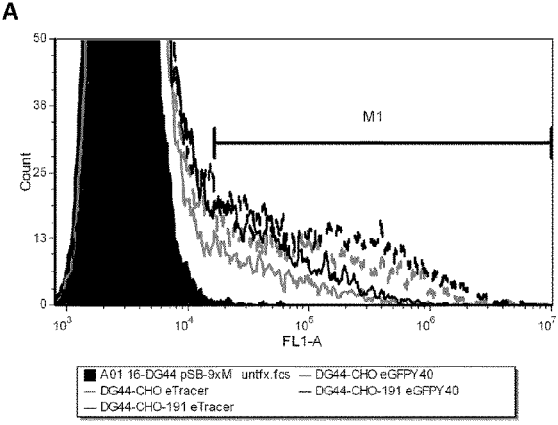
FIG. 2. Functional comparison of parental and sorted cells isolated during the development of a platform cell line.
Figure 2:
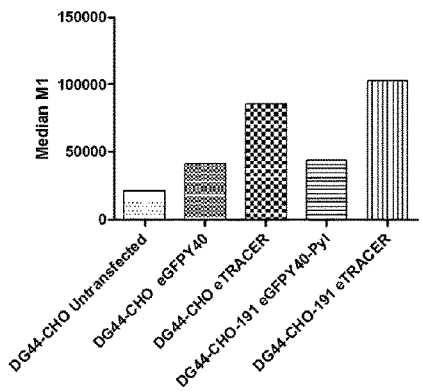
Figure 2:
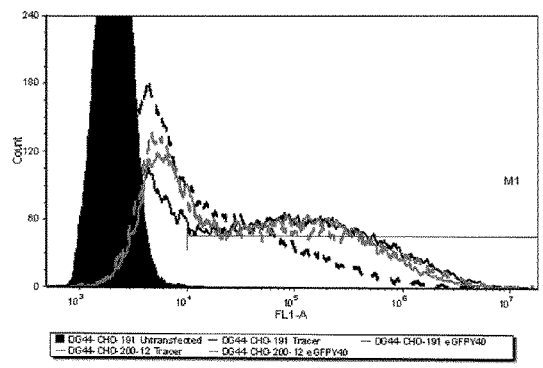
Figure 2:
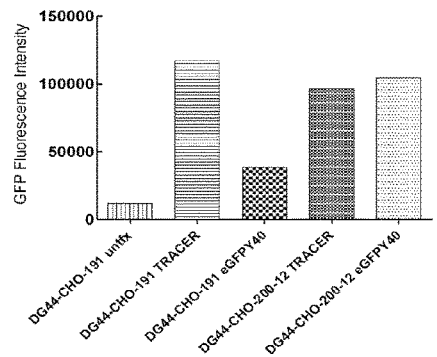
Figure 2:
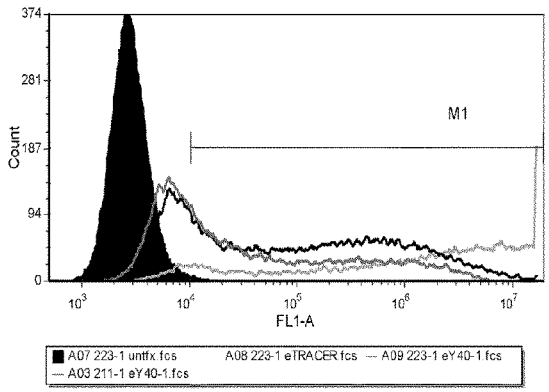
Figure 2:
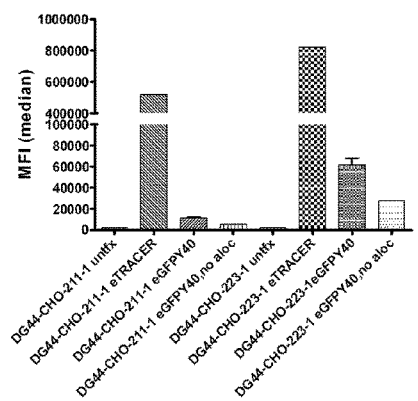

A plasmid containing nine copies of the U6-pyltRNA expression cassette as well as a sequence encoding the human INFβ Matrix Attachment Region (pSB-9xtRNA-MARS whereby the U6 is defined in SEQ ID 32, the tRNA sequence in Seq ID28), a sequence element that mediates the organization of chromatin in the nucleus and plays a role in the regulation of gene expression and enhances stability of these elements through replication (Klar 2005; Heng 2004; Piechaczek 1999) were transfected into DG44-CHO cells and selected in ProCHO4 medium supplemented with HT supplement containing 0.1 mM hypoxanthine and 0.016 mM thymidine, 8 mM glutamine, 5 ug/mL blasticidin (ProCHO4-C). Cells were then selected for tRNA function using a GFP reporter assay and cell sorting. Briefly, cells were transfected with pJTI-R4 PylRS eGFPY40, encoding a FLAG tagged pylRS (SEQ ID 2) and the reporter eGFP containing an amber codon in place of the codon encoding tyrosine at position 40 (eGFPY40, SEQ ID 38, and cells exposed to 2 mM nnAA ALOC (Nε-Allyloxycarbonyl-L-Lysine) for 14 h. 30,000 cells showing the highest levels of fluorescence were collected into fresh ProCHO4-C medium using a BD FACS Aria II cell sorter and expanded. This population of cells represents a sorted pool containing pyltRNA activity. To test whether the sorted pool showed improved function over the parental, pre-sorted pool, both populations were transiently transfected with pJTI-R4 PylRS eGFPY40 a GFP control (pTracer EF/HisA; Life technologies modified to contain F64L and S65T mutations) encoding a wild type eGFP (SEQ ID37). Transfected cells were grown for 24 h in ProCHO4-C medium containing 2 mM ALOC and analysed using a Accuri flow cytometer and the fluorescence levels quantified in these and control cells (FIG. 2A) These data show that the sorted cell population has higher amber suppression efficacy in the presence of nnAA as compared to the parental strain or untransfected controls. This intermediate cell population is referred to as DG44-CHO-191. While the DG44-CHO-191 cells were capable of amber suppression their efficacy was limited, with less than 43% amber suppression based on the GFPY40. The levels of tRNA were shown to be the limiting factor in the efficacy of amber suppression. Therefore, sorted DG44-CHO-191 cells were transfected with pSZ-9×tRNA and cells selected in DMEM-BZ (DMEM (Life Technologies), 2 mM glutamax, 1 mM sodium pyruvate, 6 mM glutamine, 1× non essential amino acids (Gibco CAT#11140-050), 10% fetal bovine serum, HT supplement, 5 ug/ml Blasticidin, 0.5 mg/mL Zeocin). The surviving cell pool, referred to as DG44-CHO-200-12, and DG44-CHO-191 cells were transfected with pJTI-R4 PylRS eGFPY40 or pTracer. Cells containing additional copies of the tRNA expression cassettes demonstrate increased eGFPY40 dependent fluorescence and thus amber suppression efficacy (FIG. 2B). These data show that the stepwise, iterative selection and cell sorting methodology results in the identification of cells with improved function. With the understanding that tRNA is a limiting component of the system, and to further increase the expression levels of the pyltRNA and thus efficacy of amber suppression of this cell population, DG44-CHO-200-12 cells were subjected to cell sorting to isolate cells with high amber suppression capabilities. Here DG44-CHO-200-12 cells (Containing pSB-9×-MARS and pSZ-9×) were transiently transfected with pJTI-R4-pylRS-eGFPY40 and cells grown in medium containing 2 mM ALOC. 7,000 cells showing the highest 1% fluorescence levels were isolated using the BD FACS Aria II cell sorter and propagated in DMEM-BZ. This resulted in the cell pool referred to as DG44-CHO-208-2.

The completion of the platform cell line required the stable introduction of a cassette for the expression of pyrlRS. Thus, 208-2 cells were transfected with pMOAV2 or pMOAV2-puro carrying the cDNA sequence coding for pylRS of SEQ ID No 2 (Y384F mutant) or SEQ ID 1 (WT), and transformants selected in DMEM-BSD-Zeo containing 0.5 mg/mL hygromycin (DMEM-HBZ), or DMEM-BZ containing 7.5 ug/ml puromycin (DMEM-PBZ), to generate a selected pool of cells called DG44-CHO-211-1 (hygro) or DG44-CHO-211-2 (puro). Antibiotic resistant cells were cultured and transfected with pENTR-P5-P2 eGFPY40 encoding the eGFP reporter construct and cells cultured in the presence of 2 mM ALOC for 1 hour and 20 min and subsequently cells showing high fluorescence levels were isolated using cell sorting. Here, 1331 cells (from 1,712,332 events) of the 211-1 and 1169 of 211-2 were isolated. The sorted populations called DG44-CHO-223-1 or DG44-CHO-223-2 were cultured in DMEM-HBZ or DMEM-PBZ.

To determine whether sorting of pylRS containing populations improved the efficacy of amber suppression transient transfections of DG44-CHO-223-1 and its parental cell line DG44-CHO-211-1 were conducted with a reporter plasmid encoding GFP containing an amber codon interrupting its open reading frame (P2-P5 eGFPY40), eTracer, or left untransfected. Transfected cells were incubated with 2 mM ALOC for 28 h and fluorescence quantified by flow cytometry utilizing an Accuri flow cytometer (FIG. 2C). While DG44-CHO-211-1 and DG44-CHO-223-1 showed equivalent transfectability (eTracer control), DG44-CHO-223-1 showed a greater than 5-fold more eGFPY40 dependent fluorescence than the parental cell line. This result indicates that sorting cells enables the isolation of highly active amber suppressing cells and the isolation of an efficient platform cell line.

Next, the platform cell line was used to develop an expression cell line containing a stably integrated gene target coding for the protein to be modified with a nnAA.

Figure 3:
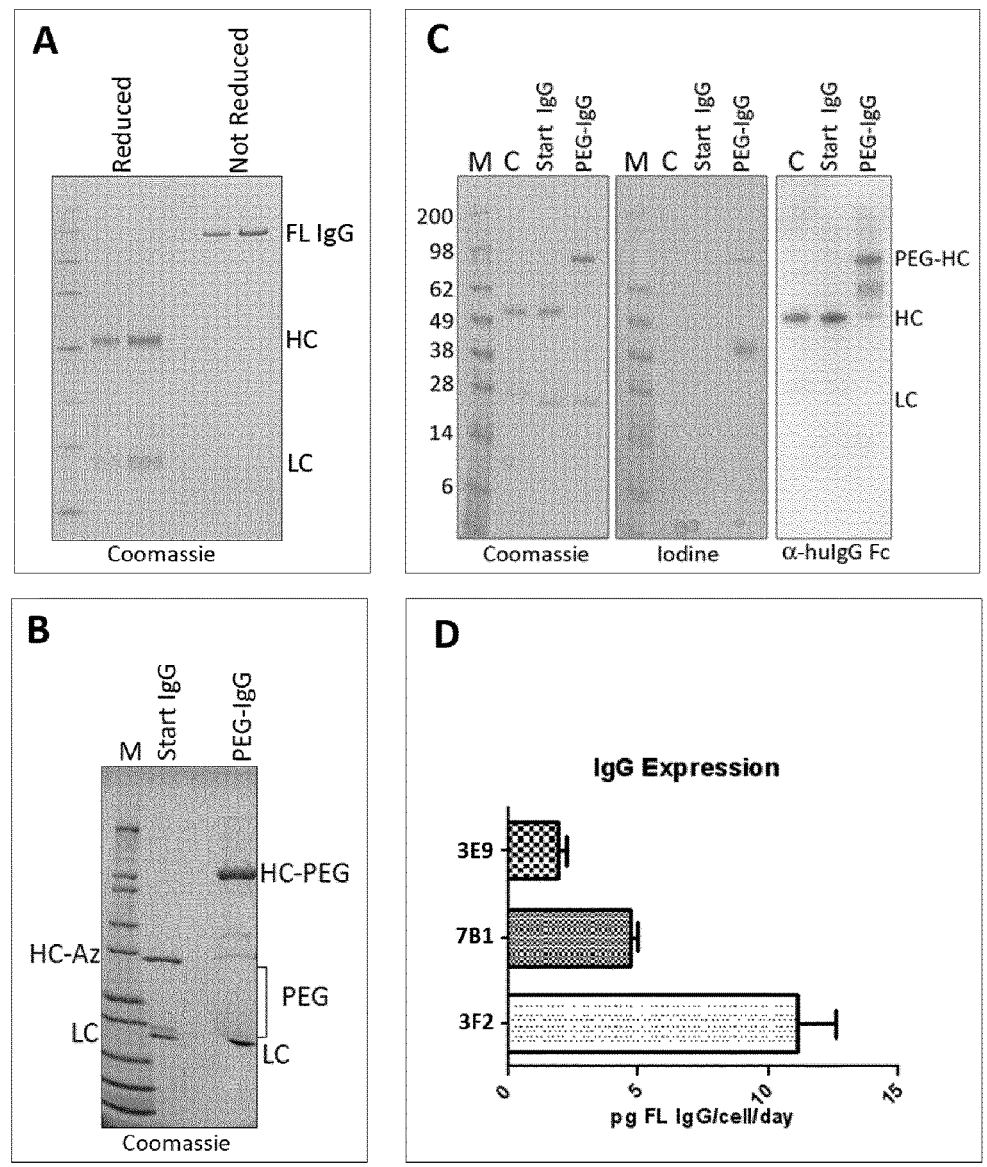
FIG. 3. Characterization of expressed anti-IL-6 IgG K274 containing a lys-azide nnAA from a stable cell line.

The DG44-CHO-223-2 cell line was transfected with pOtivec-28D2amb274 plasmid containing genes for the expression of an IgG directed against human IL-6 with an amber codon at position K274 of the heavy chain cDNA. To do this an antibody directed against the human cytokine IL-6 was generated by grafting the Variable regions of a rabbit antibody directed against the human cytokine IL-6 were grafted onto a human frameworks by PCR amplification and cloning into the vectors pFUSE-CHIg-hG1 (heavy chain, SEQ ID 40) and pFUSE-CHLIg-hK (Light chain, SEQ ID 44)(Invivogen) to generate a rabbit-human hybrid, as described in WO2012032181, incorporated in its entirety herein by reference. An amber codon was introduced at position K274 of the heavy chain constant region by site directed mutagenesis (SEQ ID 42). Clones containing the amber codons were identified by DNA sequencing. To generate an integrating construct this IgG, the promoters and ORF for the heavy chain was amplified by PCR and cloned by restriction enzyme digestion and ligation into pOptivec (Life technologies). The light chain and a single copy of the tRNA were joined by two step PCR method using overlapping oligomers and cloned into available sites into the pOptivec plasmid containing the heavy chain. The resulting vector was introduced by transfection into the platform cell line DG44-CHO-223-2 and cells selected by growth of the culture in growth medium lacking hypoxanthine and thymidine, DMEM-HT (DMEM, 2 mM glutamax, 1 mM sodium pyruvate, 6 mM glutamine, 1× non essential amino acids (Gibco CAT#11140-050), 10% dialyzed fetal bovine serum, 5 ug/ml Blasticidin, 0.5 mg/mL Zeocin, 0.75 ug/mL Puromycin). The Optivec vector also contains the gene for dihydrofolate reductase (DHFR), which enables growth of DG44 CHO cells in medium lacking HT supplements and in the presence of methotrexate. Cells were further selected in medium lacking DMEM-HT and containing 10 nM, 50 nM, and 100 nM methotrexate (MTX). Live cells were harvested and distributed at 50 cells/well into 96 well trays in the same medium with half the antibiotic concentrations used previously outlined. In the absence of a nnAA in the growth medium, the pylRS/tRNA pair is inactive and amber suppression does not occur. Thus, a truncated IgG heavy chain is expressed and secreted into the growth medium. After 10-12 days, wells were monitored for growth and ELISA assays used to identify wells which contain colonies that express high levels of truncated IgG. To do this ELISA plates were coated with 1 ug/mL 3×FLAG-IL-6-Avi in phosphate buffered saline (PBS) for 1 h or overnight at 4 C. After washing in water and blocking in PBS containing 1% BSA, 15 ul of expression medium was diluted with 35 ul of PBS containing 0.1% skim milk and added to each of the wells for 1 h at room temperature. Wells were washed in water several times and 50 ul of a 1:10,000 dilution of the secondary antibody conjugated to horse raddish peroxidase (anti-human H+L-HRP; Jackson Laboratories) for 1 h at room temperature. Wells were then washed and 50 ul of Sureblue Reserve TMB (KPL) added to each well. After 5-10 minutes 0.1N H2SO4 was added to stop the reaction and color development quantified using a plate reader at 450 nM wavelength. Wells containing cells that expressed high levels of the truncated IgG were propagated and expanded. This assay led to the identification of seven clones showing high truncated IgG expression. To determine if the isolated clones showed efficient amber suppression, the clones were exposed to 2 mM ALOC and the expression levels of the full length IgG were measured by ELISA. Briefly, a goat human anti-FC antibody (Jackson labs) was used to specifically capture full length IgG, and not truncated IgG. Out of the seven clones tested, one showed high levels of full length expression (3F2, SEQ ID 42). To demonstrate the efficiency of amber suppression, the 3F2 clone was utilized for the expression and purification of IgG. The 3F2 clone was cultured to 90% confluence in a tissue culture flask in medium containing 50 nM MTX and cells incubated with 2 mM lys-azide(nnAA) in expression medium (DMEM, 2 mM glutamax, 1 mM sodium pyruvate, 6 mM glutamine, 1× non essential amino acids (Gibco CAT#11140-050), 10% low IgG fetal calf serum, 5 ug/ml Blasticidin, 0.5 mg/mL Zeocin, 0.75 ug/mL Puromycin). Cells were allowed to express antibody for 7 days and medium harvested. Antibody from the expression supernatant was captured on a protein A column and washed with PBS. Bound protein was eluted in 50 mM glycine pH3.0 and peak fractions containing the IgG dialyzed to PBS. Purified antibody containing a lys-azide nnAA are referred to as AzAb. Representative samples were resuspended in SDS-PAGE loading buffer and 0.5 ug and 1 ug respectively resolved by SDS-PAGE under reducing and non reducing conditions and stained with coomassie blue (FIG. 3A). To demonstrate that the expressed product contained a nnAA (lys-azide) the expressed protein was incubated with a 100 fold excess of 20 KDa-PEG containing a cyclic alkyne functional group, for 4 h at room temperature. Equal amounts of the starting material and the PEG-IgG conjugate were resolved by SDS-PAGE and visualized by coomassie staining (FIG. 3B). The PEG alters the molecular weight of the conjugate resulting in a retardation of gel mobility. When the reaction mixture was resolved under denaturing and reducing conditions, it was observed that only the heavy chain of the IgG, which was designed to contain the nnAA integration site (at position 274) shows a gel mobility shift. In contrast, the light chain does not appear to be altered by the conjugation reaction. These data demonstrate that the expressed protein contains a moiety that is specifically modified and that the conjugation conditions are specific to the heavy chain. To further demonstrate that the mobility shift observed with the conjugate represents PEGylation of the IgGanti-IL-6 AzAb, a control IgG, the starting material for the conjugation reaction and the conjugated IgG were bound to protein A. The bound material was washed with PBS to remove unconjugated PEG, and protein eluted with 2% SDS. This material was then resolved by SDS-PAGE under reducing conditions and proteins visualized by Coomassie-blue staining, iodine staining to visualize PEG, and Western blotted using an anti-human FC specific antibody (Jackson labs) to detect the heavy chain (FIG. 3C). These data show that the conjugate is formed specifically at the heavy chain and that the molecular weight increase is due to the formation of the conjugate with PEG.

A second clone expressing an antibody to IL-6 was identified and characterized in parallel (7B1, SEQ ID 42) as was a clone generated as indicated above for an antibody directed against her2/neu (3E9, SEQ ID 48), containing an amber codon encoded into the heavy chain at the same position described above (K274, SEQ ID 48). The expression levels of these cell lines was quantified and a per cell production determined in expression medium in the presence of lys-azide (FIG. 3D). These data demonstrate the applicability of the present process to the expression of different antibodies containing nnAAs.

Example 2: Amber Suppression Associated Toxicity

Figure 4:
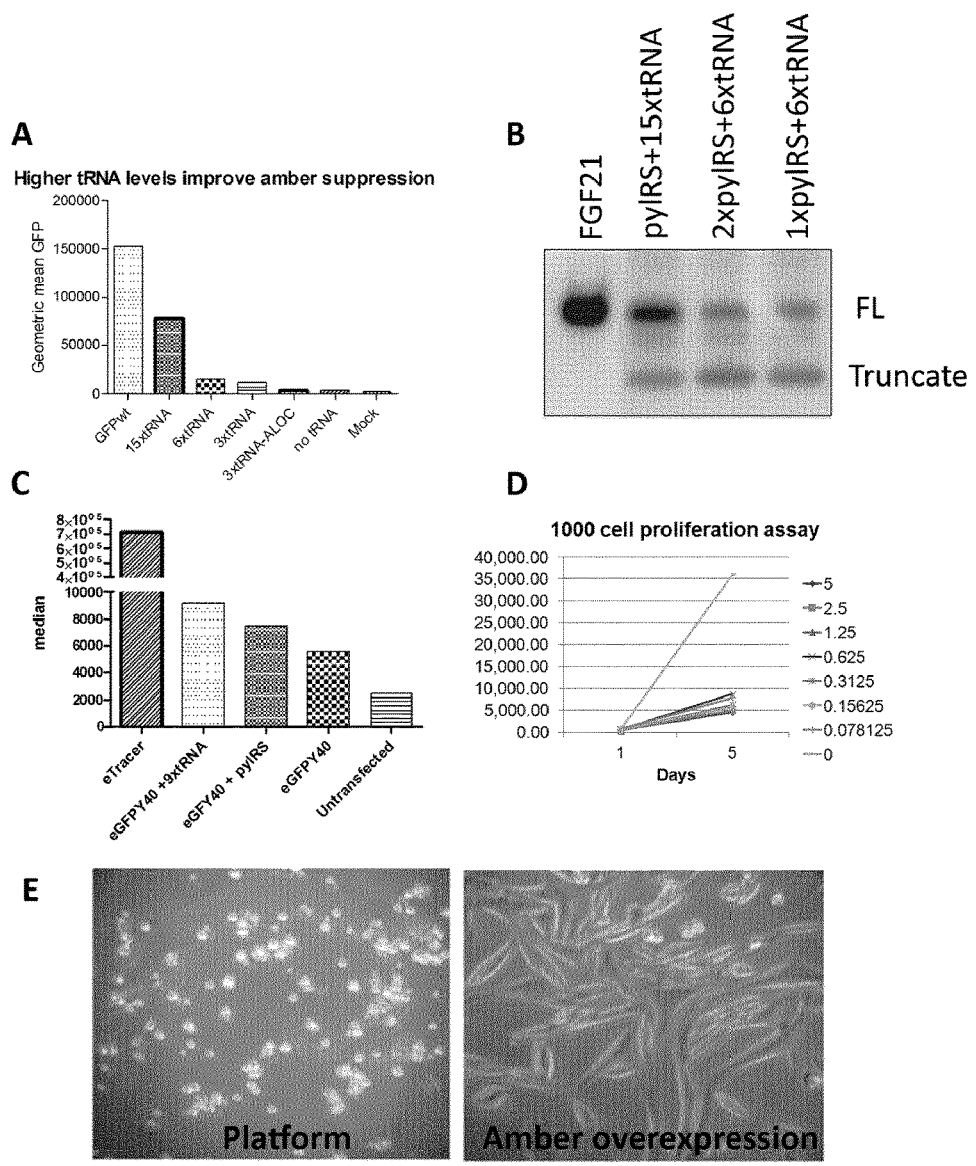
FIG. 4. Illustration of how tRNA is the limiting component to the system and background activity has a cytostatic effect.

During the course of the platform cell line isolation the inventors observed that as an increasing amount of the pylRS/tRNApyl was introduced in order to improve the efficiency of the system, the viability of the cells deteriorated. In particular increasing tRNApyl levels were found to have the greatest impact on amber suppression efficacy. This was observed in cells transiently transfected with pJTI-R4-pylRS-eGFPY40 and vectors encoding different numbers of U6-tRNA expression cassettes and the mean fluorescence was determined using an Accuri flow cytometer (FIG. 4A). We observed that cells lacking a tRNA expression cassette, or cells grown in the absence of ALOC did not show a significant GFP signal. However, the expression level of GFP increased with the number of tRNA gene copies indicating that tRNA is an important component of the amber suppression system. To further refine the effect of tRNA levels in amber suppression we transiently transfected different amounts of vectors encoding pylRS or tRNA genes and gauged the efficacy of amber suppression on a target protein containing an amber stop codon in the presence of 2 mM ALOC. When an expression construct encoding the human cytokine, FGF21 containing an amber codon at amino acid residue 131 (where the initiator methionine is 1-SEQ ID63, SEQ ID 64), was co transfected with pylRS and 6 gene copies of the U6-tRNA cassette we observed an approximately 50% conversion of truncate to full length FGF21 (FIG. 4B). Doubling the amount of pylRS vector in the transfection did not significantly alter the ratio between truncated and full length FGF21 (2×pylRS). However, introducing additional copies of the tRNA cassettes (15×U6-tRNA) resulted in a significant increase in the relative expression of full length FGF21. This indicated that the tRNA levels were the greatest limiting factor to amber suppression.

Thus, the generation of a cell line with efficient amber suppression properties requires high levels of tRNA expression. However, the inventors found that the expression of the tRNA plasmids in particular were deleterious to cell growth. The inherent toxicity of the tRNA expression cassettes was reflected in observable morphological changes and decreased growth rates of high functioning platform cells as compared to the parental lines.

While the efficacy of the platform cell lines is impacted directly by tRNA levels, high levels of tRNApyl led to cytotoxic effects. The inventors observed that while introduction of high numbers of U6-tRNA genes improved amber suppression in the presence of a nnAA and the pylRS, high levels of the tRNA also led to cytotoxicity. To confirm whether this effect was associated with tRNA expression a CHO cell line selected for the presence of pSB-9xtRNA (DG44-CHO-191) was transiently transfected with a vector encoding eGFPY40 (P5-P2 eGFPY40) alone or in combination with a vector encoding pylRS under control of the CMV promoter (pCEP4-pylRS), or a vector containing nine copies of the U6-tRNA in a plasmid also containing a pOriP element (pOriP-9xtRNA) and allows for prolonged retention of the plasmid in cells expressing EBNA-1 (Shan 2006 and EP1992698 incorporated herein in its entirety by reference), and the cells incubated at 37 C for 48 h. The fluorescence levels were quantified using a flow cytometer (FIG. 4C). While the addition of pylRS expression cassettes in a background of cells expressing pyltRNA leads to an increased level of amber suppression in the absence of a nnAA, this effect was amplified in cells transfected with additional copies of the tRNA. These data suggest that high levels of the tRNApyl induce background amber suppression levels well above wild type cells. The toxicity associated with amber suppression is documented in the literature for various systems and is largely attributed to the extension of essential genes that normally terminate in amber codons (Liebman and Sherman 1976; Liebman et al., 1976). It is current thinking that the extension of these genes beyond their natural stop, can alter, decrease or eliminate the function of these proteins. Finally, to determine whether amber suppression led to cytostatic effects, 1000 HEK293 c18 cells plates in a 96 well plate and transiently transfected with pCEP4-pylRS and pOriP-9xtRNA constructs. Cells were grown in DMEM-C medium containing a titration of nnAA (ALOC) starting with 5 mM to 0.08 mM. Cell viability was assayed at the time of the transfection, and after 5 days growth using an MTS colorimetric assays (FIG. 4D). The data show that even small concentrations of the nnAA led to a cytotstatic effect. Upon the current hypothesis, the toxicity associated with amber suppression is inherent to the system and cannot be avoided. Thus, a platform cell line containing tRNApyl and PylRS is not suitable for manufacturing of protein based drugs which require high productivity as measured by amount of protein produced per cell.

However, upon transfection of a target protein containing an amber codon, and subsequent selection, the inventors observed that the cells regained a spindle shape and flattened appearance that is characteristic to untransfected cells and showed an improved growth rate (FIG. 4E).

This suggests that the presence of high levels of a message containing an amber codon absorbs the background amber suppression and limits the impact upon essential genes. Thus, the construction of a cell line may require a preexisting and high expressing target containing an amber codon that would enable the isolation of very high functioning amber suppressing cells.

Example 3—Techniques to Mitigate Amber Suppression Associated Toxicity

The toxicity associated with amber suppression led us to conceive of alternative approaches that would mitigate this toxicity in the development of an expression cell line while enabling the isolation of highly active amber suppressor cells.

"Target First" Approach

One approach to mitigate the observed toxicity in the development of a stable expression cell line while enabling the isolation of highly active amber suppressor cells requires the introduction of a highly expressed target gene that contains an amber codon prior to the introduction of the pylRS and pyltRNA. High levels of message from this gene effectively compete with endogenous gene expression for the activated pyltRNA available in the cell and thus reducing the impact to the cell's functional machinery. To do this an eukaryotic expression host cell is transfected with a gene intended for expression and containing one or more amber stop codons, such as an IgG cloned into the vector pOptivec (Life Technologies). Transfected cells are selected by virtue of their resistance to, and ability to grow in medium lacking HT and in medium lacking HT and supplemented with 10 nM, 50 nM or 100 nM MTX. Surviving cells are cloned by transferring 1-50 cells to each well of a 96-well plate and allowed to populate the well. Wells are then be assayed by ELISA to identify wells containing high titers of truncated antibody. For this, ELISA plates are coated with antigen (for example 1 ug 3xFLAG-IL-6-Avor 0.5 ug/mL Her2 extracellular domain) in phosphate buffered saline (PBS) for 1 h or overnight at 4 C. After washing and blocking in PBS containing 10% goat serum or 1% BSA, 40 ul of PBS containing 10% goat serum or 35 ul of 1% skim milk and 10 ul of expression medium are added to appropriate wells for 1 h at room temperature. Wells are washed in water several times and 50 ul of a 1:4,000 dilution of the secondary antibody conjugated to horse radish peroxidase (anti-human Kappa-HRP)(Jackson Labs) are added to each well for 1 h at room temperature. Wells will then be washed and 50 ul of Sureblue Reserve TMB (KPL) added to each well. After 5-10 minutes color development is stopped by the addition of 0.1N H2SO4 and color generation quantified using a plate reader at 450 nM wavelength. A control IgG of known concentration is used to establish a standard curve. Wells containing cells that expressed high levels of the truncated IgG are propagated and expanded.

Functional elements for the introduction of nnAAs are introduced and selected either sequentially or concurrently. In one example, cells showing high expression of the target gene are transfected with pMOAV2 or pMOAV2puro, containing genes for pylRS and pyltRNA. Transfected cells are selected in DMEM containing 2 mM glutamax, 1 mM sodium pyruvate, 6 mM glutamine, 1x non essential amino acids (Gibco CAT#11140-050), 10% fetal bovine serum, and 0.5 mg/mL hygromycin or 7.5 ug/ml puromycin. Surviving cells are propagated and 1-50 cells from this population seeded into each well of 96 well plates. Once the cells have expanded and colonies form, cells are exposed to nnAA at 2 mM and functionally assayed using ELISA assays to identify clones with amber suppression efficiencies greater than 40% or 50% or preferably greater than 60 or 80% or 90%. To quantify full length IgG expression ELISA plates are coated with 1 ug/mL anti-human FC (Jackson Labs) antibodies in phosphate buffered saline (PBS) for 1 h or overnight at 4 C. After washing and blocking in PBS containing 10% goat serum, 40 ul of PBS containing 10% goat serum and 10 ul of expression medium are added to appropriate wells for 1 h. at room temperature. Wells are washed in water several times and 50 ul of a 1:10,000 dilution of the secondary antibody conjugated to horse raddish peroxidase (anti-human H+L-HRP)(Jackson Labs) is added to each well for 1 h at room temperature. Wells will then be washed and 50 ul of Sureblue Reserve TMB (KPL) added to each well. After 5-10 minutes color development is stopped by the addition of 0.1N H2SO4 and color generation quantified using a plate reader at 450 nM wavelength. A control IgG of known concentration is used to establish a standard curve. This assay will determine the expression levels of full length IgG. To determine truncated IgG levels, ELISA plates are coated with antigen, for example Jug/mL 3×FLAG-IL-6-Avor 0.5 ug/mL Her2 extracellular domain in phosphate buffered saline (PBS) for 1 h or overnight at 4 C. After washing and blocking in PBS containing 1% BSA, 35 ul of PBS containing 0.1% skim milk and 15 ul of expression medium are added to appropriate wells for 1 h. at room temperature. Wells are washed in water several times and 50 ul of a 1:10,000 dilution of the secondary antibody conjugated to horse raddish peroxidase (anti-human kappa-HRP) (Jackson Labs) are added to each well for 1 h at room temperature. Wells will then washed and 50 ul of Sureblue Reserve TMB (KPL) added to each well. After 5-10 minutes color development is stopped by the addition of 0.1N H2504 and color generation quantified using a plate reader at 450 nM wavelength. A control IgG of known concentration is used to establish a standard curve. The ratio of truncated to full length IgG in each well is determined and wells showing high amber suppression activity, where the full length IgG levels are at least 25 or 50%, preferably 40-60% or 80-90% or greater of the total produced IgG are propagated.

If necessary, additional tRNA genes will be introduced into these selected pools of cells to further improve the efficacy of amber suppression. To do this, pSB-9×tRNA-MARS expression cassette is transfected into these cells and transfectants selected by virtue of antibiotic resistance in DMEM containing 2 mM glutamax, 1 mM sodium pyruvate, 6 mM glutamine, lx non essential amino acids (Gibco CAT#11140-050), 10% fetal bovine serum, and 0.5 mg/mL hygromycin or 7.5 ug/ml puromycin containing 5 ug/mL blasticidin (DMEM-BSD) or alternatively ProCHO4 (Lonza) or equivalent medium containing, 8 mM glutamine, 0.5 mg/mL hygromycin or 7.5 ug/ml puromycin and 5 ug/mL blasticidin (ProCHO4-BSD). Cells with the highest activity of the tRNA are selected using the ELISA assays described above to determine full length and truncated IgG production yields in cells exposed to nnAA. Cells showing improved full length IgG to truncated IgG ratios over parental cells are propagated. If additional tRNA gene insertions are required the process is repeated as described above with pSZ-9×tRNA and cells selected in medium containing 5 ug/mL Zeocin followed by a functional selection screen.

"Decoy Protein" Approach

An alternative approach to mitigate the observed toxicity in the development of a stable expression cell line while enabling the isolation of highly active amber suppressor cells, involves the introduction of a surrogate gene containing an amber codon expressed at high levels, which expression is driven by an inducible promoter to enable the down regulation of its expression during the expression of the target gene. This has the advantage that stable cell lines expressing the PylRS/tRNApyl orthogonal machinery can be generated and used to modify multiple targets. To do this a eukaryotic expression host cell such as CHO cells are transfected with a gene intended for expression and containing one or more amber stop codons, such as but not limited to GFP, eGFP, red fluorescent protein, glutathione-S-transferase, b-microglobulin, or B-galactoside cloned into a mammalian expression vector preferably containing an inducible promoter such as the Tet-On 3G (Clontech), T-Rex (Life Technologies), ecdysone-inducible, or steroid-inducible promoters. Transfected cells are selected by virtue of their resistance to, and ability to grow in medium containing an appropriate antibiotic. Surviving cells are cloned by transferring 1-50 cells to each well of a 96-well plate and allowed to populate the well. Wells will then be assayed by ELISA assays, to identify wells containing high titers of truncated protein. A highly expressed surrogate protein containing one or more amber codons will function as an amber sink to absorb amber suppression activity and protect the cell from the deleterious effect of amber suppression. Functional elements such as U6-tRNA cassettes and pylRS genes, for the introduction of nnAAs, are introduced into the host cell and selected either sequentially or concurrently. In one example, cells showing high expression of the surrogate target gene are transfected with pMOAV2 or pMOAV2puro, containing genes for pylRS and pyltRNA. Transfected cells are selected in DMEM containing 2 mM glutamax, 1 mM sodium pyruvate, 6 mM glutamine, 1× non essential amino acids (Gibco CAT#11140-050), 10% fetal bovine serum, and 0.5 mg/mL hygromycin or 7.5 ug/ml puromycin. Surviving cells are propagated and 1-50 cells from this population seeded into each well of 96 well plates. Once the cells have expanded and colonies form, cells are exposed to nnAA at 2 mM and functionally assayed using ELISA assays to identify clones with amber suppression efficiencies greater than 40% or 50% or preferably 40-60% or greater than 80 or 90% using a reporter protein (eGFPY40) or the surrogate target protein. High functioning clones are isolated by limiting dilution cloning or cell sorting. Genes encoding protein therapeutics will then be introduced into these cells and selected. High expressing clones are isolated and identified by ELISA assays. High expressing clones will then be screened for amber suppression efficacy. The ratio of truncated to full length protein in each well is determined and wells showing high amber suppression activity, clones showing amber suppression levels of at least 40% or 50%, but preferably 40-60% or 80-90% or greater of the full length protein containing nnAA are propagated.

If necessary additional tRNA genes will be introduced into these selected pools of cells to further improve the efficacy of amber suppression as just discussed above.

"Repressible tRNA" Approach

An alternative strategy has been engineered to regulate the tRNA expression levels and mitigate tRNA associated cytotoxicity. To do this, promoter elements such as U6 or H1 necessary for tRNA expression are modified to include sequence elements that enable the suppression of gene expression such as the TetO repressor elements. This enables the downregulation of tRNA expression during growth phase and the induction of tRNA expression during expression of the target genes.

"Decoy Amino Acid" Approach

An alternative strategy to regulate the effects of background amber suppression has been engineered by introducing an amino acid analogue recognized by pylRS, and activated to the tRNApyl, but modified so as to not allow peptide bond formation. The activation of this decoy amino acid onto the tRNApyl will effectively compete with native amino acid activation by host RSs or pylRS and generate a cellular pool of decoy amino acid activated tRNA. This pool will also compete with mis-acylated tRNApyl for amber codons. The pool of decoy amino acid activated tRNA will therefore allow for normal termination of protein synthesis at amber stop codons. During the course of platform cell line construction, cells such as DG44 CHO cells are grown in medium containing the decoy amino acid and the genes encoding tRNA and pylRS stably integrated into these cells. Transfected cells are selected by growth in medium containing appropriate antibiotics and surviving cells expanded. This pool is transiently transfected with a vector encoding eGFPY40 and cells grown in medium containing a nnAA that allows peptide bond formation enabling amber codon readthrough, and lacking the decoy amino acid. High functioning cells will then be identified by virtue of expression levels of the eGFPY40 reporter and cells isolated using flow cytometry using a BD FACS Aria II. Sorted cells are expanded and the efficacy of amber suppression in this sorted pool gauged using available reporters (e.g. eGFPY40 or FGF21-131amb). Iterative additions of tRNA or pylRS genes and selection using flow cytometry can be performed to enhance the efficiency of amber suppression if necessary. Platform cells will then be transfected with a target gene such as an IgG directed to a desirable antigen, containing an amber codon, in a vector containing the DHFR gene such as the Optivec plasmid (Life Technologies) or a plasmid containing the Glutamine Synthetase gene (Lonza) to allow for gene expression selection. Cells expressing high levels of the truncated protein are grown under appropriate selection, methotrexate or methionine sulphoximine respectively, to select for high expressing cells. Clones are isolated using limiting cell dilutions and cells capable of efficient amber suppression and high expression yields are identified using ELISA assays.

Example 4: Modification of Target Proteins to Enable nnAA Incorporation

An amber codon was introduced into the ORF of the green fluorescence protein-blasticidin fusion in the vector pTracer His EF/HISA (Life Technologies) to generate the GFPY40 reporter construct. Briefly, site-directed mutagenesis was used to change the a single nucleotide at position +120 (where +1 is the A of the start codon) of the GFP ORF from a cytosine to a guanine, and thereby generating an in-frame amber stop codon.

FGF21 ORF was generated by gene synthesis using overlapping oligomers and PCR to regenerate the sequence for human FGF21 as shown in SEQ ID61, nucleotide sequence; SEQ ID62 amino acid sequence) containing an additional amino terminal 3× Flag tag (encoding dykdh-dgdykdhdidykddddks) (3×FLAG-FGF21, SEQ ID 80). The construct was cloned into the pJ201 shuttle vector and transferred by restriction enzyme digestion using HinDIII and XhoI and ligation to pCEP4 (Life Technologies). The resulting construct placed the ORF of FGF21 downstream and under control of a CMV promoter for expression in mammalian cells. Amber codons were introduced by site directed mutagenesis at positions F12 (SEQ ID 66), L66 (SEQ ID68), P90 (SEQ ID70), R131 (SEQ ID64), and P140 (SEQ ID71) of the FGF21 ORF. A two step PCR amplification scheme was used to replace the 3×FLAG tag with a 6×His tag using overlapping oligomers. Briefly, two PCR reactions were set up, one to amplify the CMV promoter and a second to amplify the FGF21 ORF and in frame with a 5' 6×His tag. Flanking oligomers were then used in a third PCR reaction to join the CMV promoter to the 6×His-FGF21 construct. The product was cloned by Gateway into a pDONR 221 P4r-P3r vector to generate both 6×HIS-FGF21 wt and 6×HIS-FGF21 R131.

An antibody directed against IL-6 was modified to enable the integration of a nnAA and its subsequent conjugation. To generate this molecule the variable regions of a rabbit antibody directed against the human cytokine IL-6 were grafted onto a human frameworks by PCR amplification (See WO12032181) and cloning into the vectors pFUSE-CHIg-hG1 (heavy chain) and pFUSE-CHLIg-hK (Light chain)(Invivogen) to generate a rabbit-human hybrid. Additional mutations were also incorporated adjacent to the IL-6 CDRs to humanize the antibody. The resulting vector pairs pFuse-28D2gamma and pFUSE-28D2kappa and served for cotransfection and expression of the anti-IL-6 IgG by transient transfections. The sites for nnAA incorporation were generated by introducing an amber codon at the desired sites by site-directed mutagenesis and mutants screened by sequencing. This resulted in a heavy chain clone containing an amber codon at sites 274 (pFuse-28D2gamma_K274am) (SEQ ID 41). Co transfection of the heavy chain constructs and the light chain constructs allows expression of the anti-IL-6 antibody. An integrating construct containing the anti-IL-6 IgG heavy chain (containing an amber at position K274) was cloned into pOptivec by TOPO cloning. The Light chain expression construct, including its promoter and poly A sequence was amplified by PCR and a single copy of the tRNA were joined by two step PCR method using overlapping oligomers and cloned into available sites into the pOptivec plasmid containing the heavy chain (pOtivec-28D2-GKt). Transient expression and stable expression of these antibodies was performed to integrate lysine-azide, ALOC, propargyl-lysine and lysine-chloride nnAAs.

Expression and Purification

For all experiments protein was isolated from stable cell lines (Example 1). Alternatively, transiently transfected cell lines were utilized CHO or HEK293 cells were plated to approximately 90% confluence and grown at 37 C. The following day, the plated cells were incubated with the appropriate DNA previously treated with a lipophilic reagent (Lipofectamine 2000, 293 fectin (invitrogen), according to the specific manufacturer's instructions. Following 2-5 days of growth in the presence of nnAA, ALOC, Lys-azide, propargyl Lysine or Lys-chloride) the growth medium was harvested and either used directly or the expressed proteins purified by an appropriate method. For expression of IgG, cells were grown in medium containing low IgG fetal bovine serum. Stably transfected cell lines were grown adherently in flasks to 90% confluence and exposed to nnAA (selected from the following: ALOC (Nε-Allyloxycarbonyl-L-Lysine), lys azide, propargyl lysine, (2S)-2-amino-6-{[(2-azidoethyl)carbamoyl]oxy}hexanoic acid (Formula VI.1)) for 5-7 days, and the growth medium harvested and either used directly or the expressed proteins purified by an appropriate method. For expression of IgG, cells were grown in medium containing low IgG fetal bovine serum.

Expressed IgGs, scFvs, or FGF21 described here were purified from growth medium following stable or transient expression of eukaryotic cells. In each case 0.1 volumes of 10×PBS was added to the expression supernatant to equilibrate the salts and pH of the sample. For purification of 6×His tagged proteins, the supernatant was dialysed at 4° C. for 16 to PBS. Protein was bound to Nickle-NTA beads by batch binding or gravity flow and washed extensively with wash buffer (recipe). Bound material was eluted with (50 mM sodium phosphate pH7.4, 300 mM NaCl, 250-500 mM imidazole). Fractions containing the target protein were identified by SDS-PAGE and coomassie staining. Peak fractions were pooled and dialysed against PBS prior to further use.

IgGs were purified by protein A affinity chromatography. Briefly, expression supernatants were supplemented with 0.1 volumes of 10×PBS and passaged through a 1 mL or 5 mL Protein A sepharose Fast Flow column (GE). Bound material was washed with 5-10 column volumes of PBS and eluted with 3-5 volumes of 0.1 M glycine pH3.0. Fractions were subsequently neutralized by the addition of 0.05 volumes of 20×PBS to achieve a neutral pH. Elution fractions were analysed by SDS-PAGE and coomassie staining and peak protein fractions pooled and dialysed to PBS at 4° C. for 16 hours.

This method was used to prepare: Anti-IL-6-LysAzide274h, FGF21 modified to include the NNAA (S)-2-amino-6((prop-2-ynyloxy)carbonylamino)hexanoic acid (Lys-Alkyne) at position 131

Example 5: Conjugation of nnAA-Containing Proteins

Figure 55:
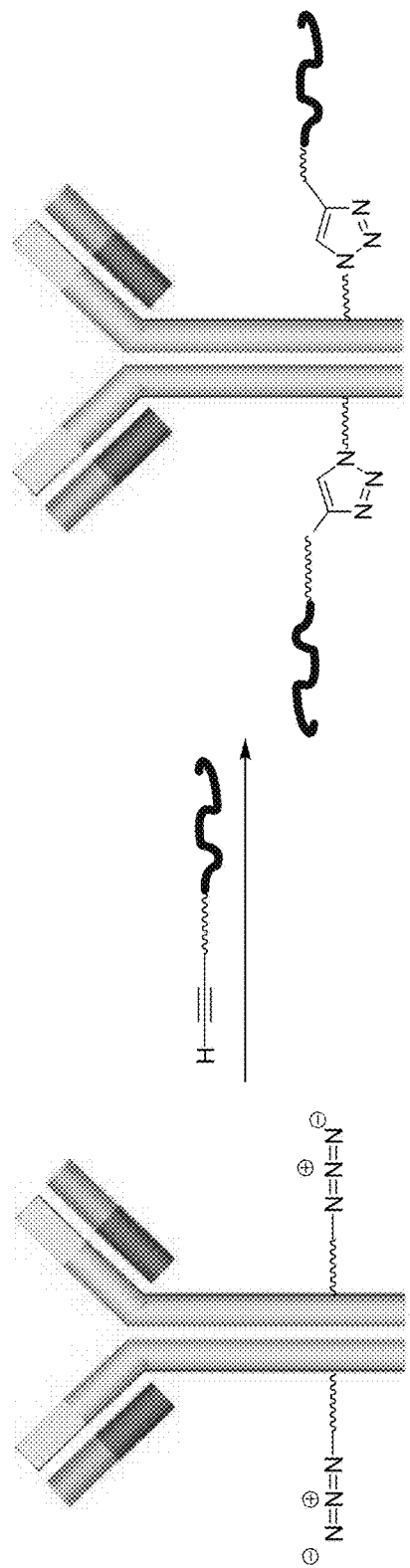
FIG. 55. A schematic showing PEGylation of anti-IL-6 antibody with NNAA Lys-Azide incorporated at position 274 of heavy chain with 20KPEG terminal alkyne (Anti-IL-6-LysAzide274h).

PEGylation of Anti-IL-6 Antibody with NNAA Lys-Azide Incorporated at Position 274 of Heavy Chain with 20KPEG Terminal Alkyne (Anti-IL-6-LysAzide274h). (See FIG. 55)

In a 8×30 mm glass vial with small magnetic stirrer was placed a dichloromethane solution of TBTA (80 mM, 3.75 mL), the solvent was evaporated by gently blowing nitrogen over the tube. To this was added a phosphate buffer (125 mM, pH=7.4, 53 uL) and an aqueous solution of 20KPEG alkyne (3 mM, 33 uL). A solution of the Anti-IL-6-LysAzide274h was added (0.4 mg/mL, 6.26 uL) followed by a solution of cysteine (100 mM, 2 uL) and copper sulfate (80 mM, 1.9 uL). The vial was blanketed with argon, capped and mixed gently for 4 h.

A portion of the reaction mixture was removed (15 uL) and mixed with non-reducing gel loading buffer (4×, NuPage, Invitrogen, 7.5 uL). The entire volume was loaded onto a SDS-PAGE gel for analysis (FIG. 5A): SDS-PAGE indicated the copper conditions afforded a mixture of monoPEGylated and bis-PEGylated antibody species. PDSi densitometry indicated the monoPEGylated species in approximately 1:1 ratio (mono=47%, bis=53%). The antibody with no azides failed to react under similar conditions, speaking to the specificity for the azide.

Figure 56:
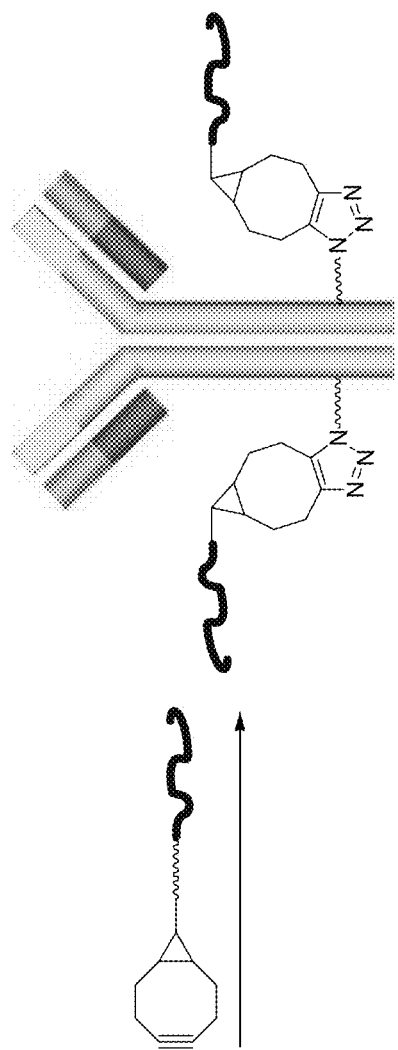
FIG. 56. A schematic showing PEGylation of anti-IL-6 antibody with NNAA Lys-Azide incorporated at position 274 of heavy chain (Anti-IL-6-LysAzide274h) with 20KPEG CYCLOOCTYNE (bicyclo[6.1.0]non-4-yne-linked PEG).
Figure 56:
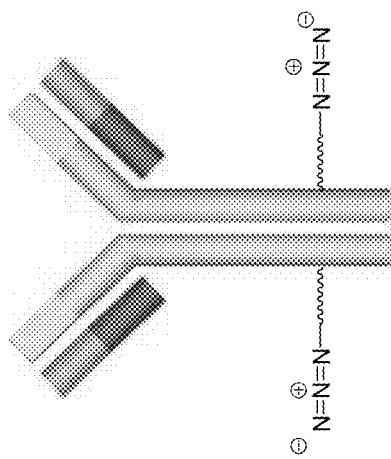

PEGylation of Anti-IL-6 Antibody with NNAA Lys-Azide Incorporated at Position 274 of Heavy Chain (Anti-IL-6-LysAzide274h) with 20KPEG CYCLOOCTYNE (Bicyclo[6.1.0]Non-4-Yne-Linked PEG). (See FIG. 56)

In a 8×30 mm glass vial with small magnetic stirrer was placed phosphate buffer (125 mM, pH=7.4, 60 uL) and an aqueous solution of 20KPEG cyclooctyne (bicyclicnonyne) (3 mM, 33 uL). A solution of the Anti-IL-6-LysAzide274h was added (0.4 mg/mL, 6.26 uL) and the vial was capped and mixed gently for 4 h.

A portion of the reaction mixture was removed (15 uL) and mixed with non-reducing gel loading buffer (4×, NuPage, Invitrogen, 7.5 uL). The entire volume was loaded onto a SDS-PAGE gel for analysis.

Figure 5:
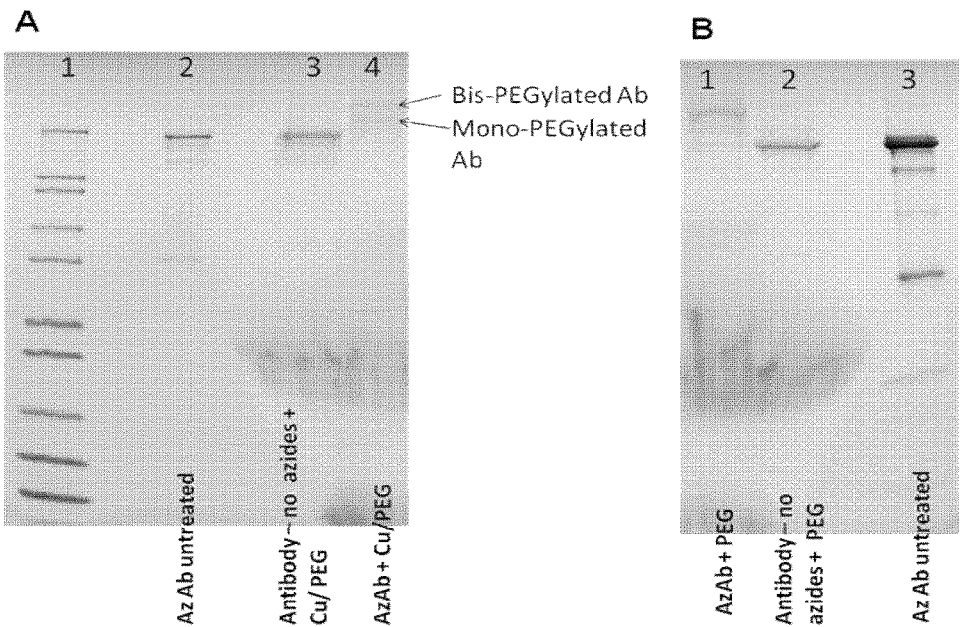
FIG. 5. Non-Reducing SDS-PAGE gel of PEGylation of an anti-IL-6 AzAb with a linear 20kPEGAlkyne (A) and Non-Reducing SDS-PAGE gel of PEGylation of Anti-IL-6-LysAzide274h with 20KPEG cyclooctyne (B).

SDS-PAGE gel analysis, (FIG. 5B: Lane 1: (Anti-IL-6-LysAzide274h) treated with 20KPEG cyclooctyne, Lane 2: Antibody with no azides treated with 20K PEG cyclooctyne, Lane 3: Antibody untreated), indicated a mixture of monoPEGylated and bis-PEGylated antibody species. Densitometry of the resulting gel indicated a mixture of monoPEGylated (10%) and bis-PEGylated antibody (76%), with the starting material consumed. The azide containing antibody was the only species to react.

To test the activity of antibodies directed against IL-6 and determine whether the modification of this antibody altered the binding properties of this antibody we established an in vitro IL-6 neutralization assay. To do this, IL-6 dependent murine B-cell hybridoma cells (B9) were seeded into 96 well plates in medium containing 50 pg/mL of IL-6. Different concentrations of an anti-IL-6 antibody and controls were added to a series of wells and grown for 3 days at 37° C.

The viability of the cells was then determined using alamar blue a colorimetric assay that allows to quantitatively measure the health of cells. Briefly, 25 uL of reagent is added to each well and cells allowed to continue growing for 8-16 hr. After the incubation the panels are read spectrophotometrically at 570 nm and 600 nm wavelength. The measures absorbance is plotted versus the corresponding antibody concentrations. The data indicates that the site specific pegylation of the anti-IL-6 antibody does not decrease the functional characteristics of the antibody as compared to naked unmodified antibody.

Figure 8:
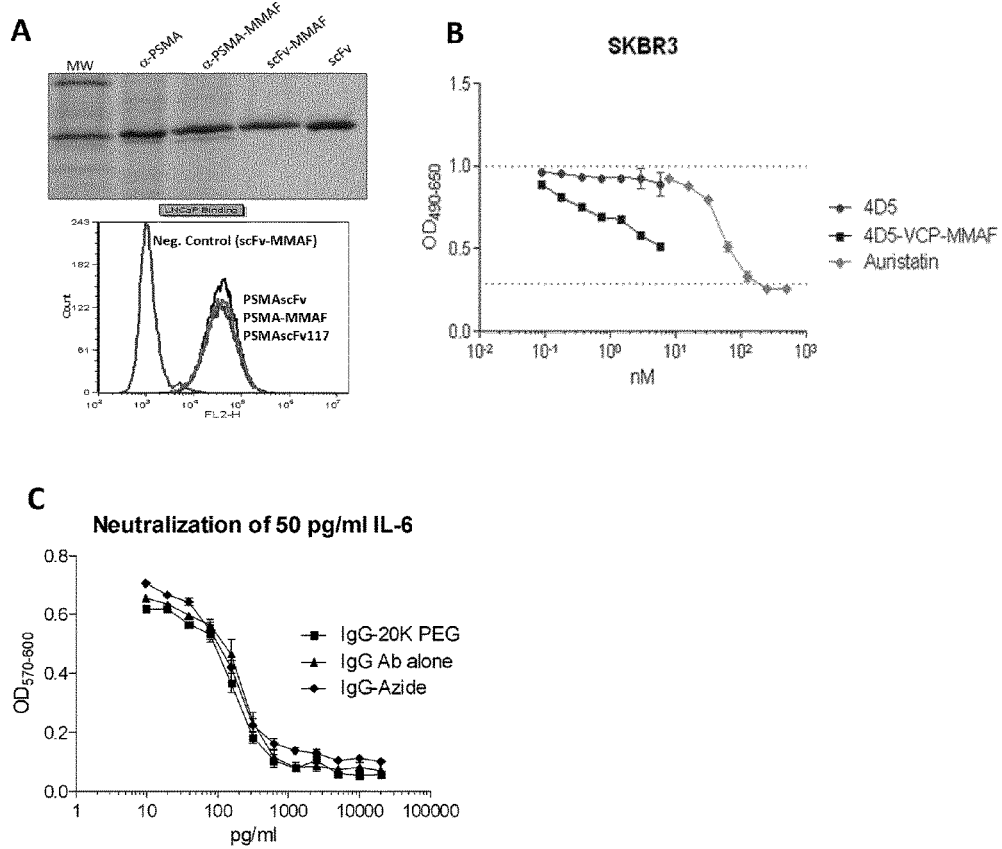
FIG. 8. Evidence that toxin conjugated antibodies and antibody fragments demonstrate specific activity in vitro.

IL-6 inhibition assay (FIG. 8C). To test the activity of antibodies directed against IL-6 an IL-6 neutralization assay was used. IL-6 dependent B9 cells were seeded into 96 well plates in medium containing 50 pg/mL of IL-6. Different concentrations of a anti-IL-6 antibody and controls were added to a series of wells and grown for 3 days at 37° C. The viability of the cells was determined using alamar blue. Briefly, 25 uL of reagent is added to each well and cells allowed to continue growing for 8-16 hr. After the incubation the panels are read spectrophotometrically at 570 nm and 600 nm wavelength. The measures absorbance is plotted versus the corresponding antibody concentrations.

Figure 57:
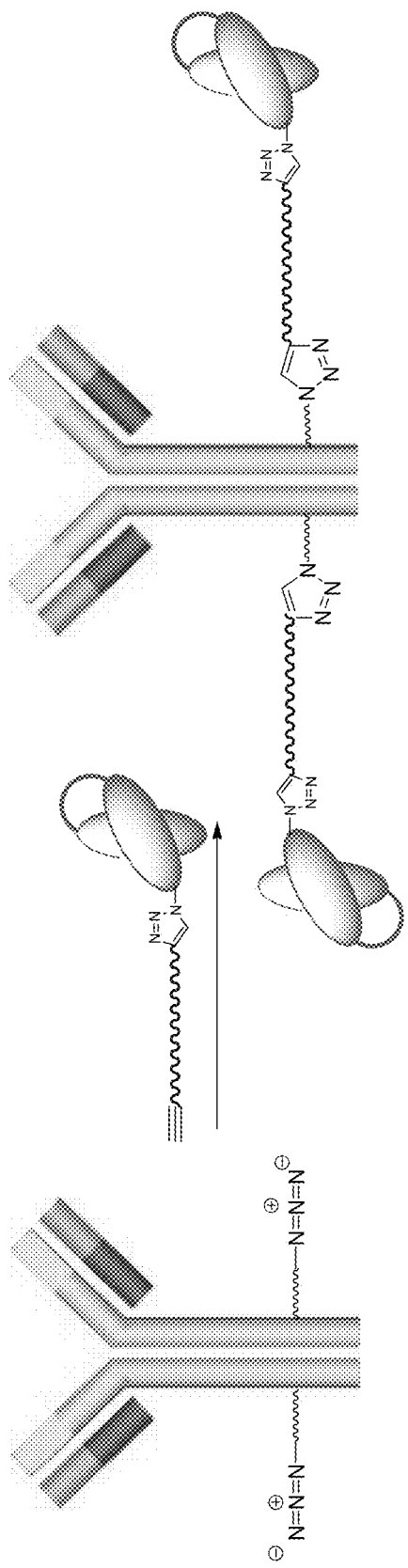
FIG. 57. A schematic showing conjugation of an anti-IL-6 (antibody)-anti IL-23 (scFv-PEG) bispecific antibody.

Preparation of an Anti-IL-6 (Antibody)-Anti IL-23 (scFv-PEG) Bispecific. (See FIG. 57)

The generation of an scFv directed against the human cytokine IL23 was generated using an *E. coli* expression system that enables site specific incorporation of an azidohomo alanine at desired sites. Briefly, a methionine auxotrophic strain of *E. coli* (B834) was transformed with an expression plasmid encoding the scFv to hIL23 (WO2012/032181, incorporated herein by reference). The scFv gene encodes only two methionines, the initiator methionine that is cleaved post-translationally and a methionine at the c-terminus of the molecule. The transformed cells were fermented in rich medium and the culture allowed to grow reach a growth plateau. At this point the cells were induced with IPTG to derepress expression of the scFv and the medium supplemented with AHA. The cells were then allowed to grow for an additional four hours and the bacterial cells harvested by centrifugation. The expressed scFv was purified from inclusion bodies and folded in vitro. The expressed scFv contains an azide containing amino acid that allows for conjugation with alkyne containing moieties. To generate a bi-specific antibody construct the Anti-IL-6-LysAzide274h was ligated to the anti-IL23 scFv with bis-alkyne PEG moiety (WO2012/032181, incorporated herein by reference). To do this a 8×30 mm glass vial with small magnetic stirrer was placed phosphate buffer (20 mM, pH=7.4, 80 uL). A solution of the Anti-IL-6-LysAzide274h was added (0.4 mg/mL, 6.3 uL), followed by a solution of the anti-IL23 scFv previously conjugated to a −20KPEG alkyne (1 mg/mL, 2.1 uL). To this solution was added a solution of BME (100 mM, 3 uL) and a solution of copper sulfate (80 mM, 2.81 uL). The mixture was allowed to stir for 4 h.

Figure 6:
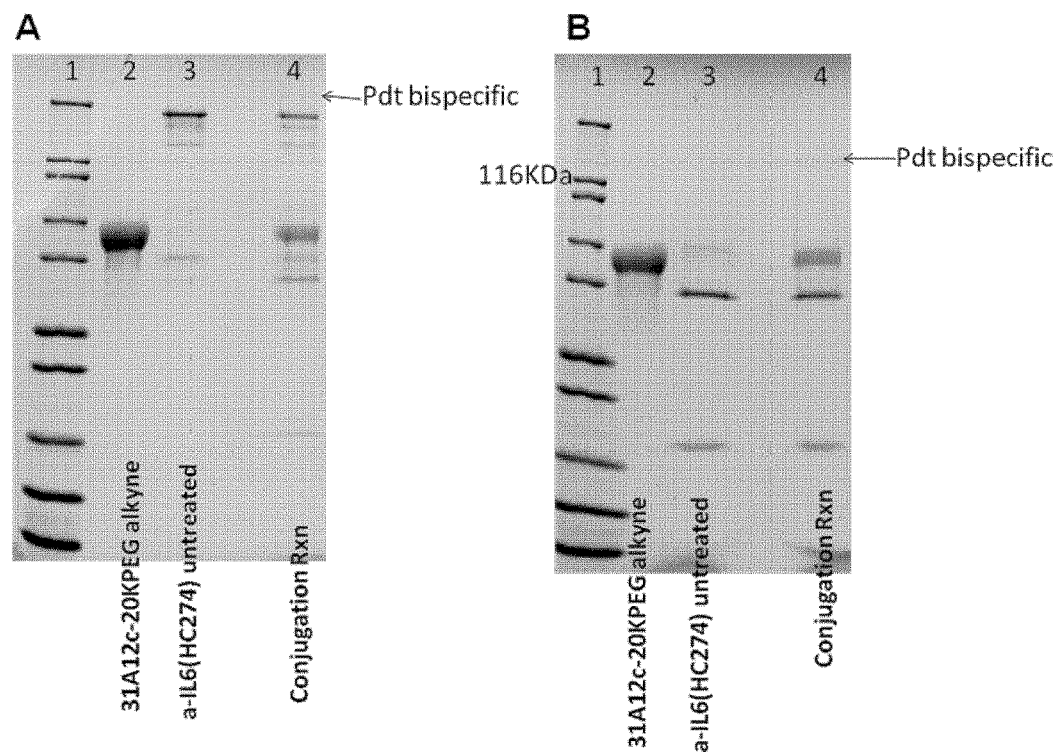
FIG. 6. Non-Reducing SDS-PAGE gel of Bispecific Conjugation of an Anti-IL-6-LysAzide274h to 31A12-20KPEG alkyne (A) and Reducing SDS-PAGE gel of Bispecific Conjugation of an Anti-IL-6-LysAzide274h to 31A12-20KPEG alkyne (B).

A portion of the reaction mixture was removed (15 uL) and mixed with non-reducing gel loading buffer (4×, NuPage, Invitrogen, 7.5 uL). The entire volume was loaded onto a SDS-PAGE gel for analysis. A very small amount of the bispecific was produced as evidenced by the new higher molecular band above the antibody band (FIG. 6A).

For reducing gels, a portion of the reaction mixture was removed (15 uL) and mixed with reducing gel loading buffer (4×, NuPage, Invitrogen, 30% BME, 7.5 uL). The entire volume was loaded onto a SDS-PAGE gel for analysis. A very small amount of the bispecific was produced as evidenced by the new higher molecular band above the heavy chain band, consistent with the anticipated MW change (FIG. 6B).

PEGylation of FGF-21 (Modified to Include NNAA Lys-Alkyne) with 20K Linear PEG Bis Azide For all experiments standard transfection conditions were use. Briefly, a clone of 293 cells previously selected for stable pylRS expression were plated to approximately 90% confluence and grown at 37° C. for 16 h. The following day, the plated cells were treated with the 6×HIS-FGF21 R131 previously combined with a lipophilic reagent (Lipofectamine 2000, 293 fectin (invitrogen), according to the specific manufacturer's instructions. Cells were then grown in DMEMcomplete (DMEM, 2 mM glutamax, 1 mM sodium pyruvate, 6 mM glutamine, 1× non essential amino acids, 10% fetal calf serum) medium containing 2 mM propargyl-lysine nnAA, for 5-7 days. The growth medium was harvested and FGF21 purified by affinity chromatography on a 5 mL prepacked nickel-NTA column (GE).

The expressed 6×HIS-FGF21 was purified from the growth medium. Here, 0.1 volumes of 10×PBS was added to the expression supernatant to equilibrate the salts and pH of the sample. And the medium was dialysed at 4° C. for 16 to PBS. The expressed FGF21 was bound to a Nickel-NTA beads (GE) by batch binding or gravity flow and washed extensively with wash buffer (50 mM sodium phosphate pH7.4, 300 mM NaCl, 20 mM imidazole). Bound material was eluted with NiNTA elution buffer (50 mM sodium phosphate pH7.4, 300 mM NaCl, 250-500 mM imidazole). Fractions containing the target protein were identified by SDS-PAGE and coomassie staining. Peak fractions were pooled and dialysed against PBS prior to further use.

In a 20 mL vial with magnetic stirrer was placed a solution of FGF21 modified to include the NNAA (S)-2-amino-6 ((prop-2-ynyloxy)carbonylamino)hexanoic acid (Lys-Alkyne) at position 131 (SEQ ID64) (20 ug/mL, 0.001 mM, 5000 uL). To this was added a solution of 20K linear PEG bis-azide (60 mg/mL, 1.67 mL). A solution of SDS (20%, 250 uL) and a solution of DTT (250 mM, 60 uL) were added. A DMSO solution of TBTA (80 mM, 7.96 uL) and an aqueous solution of copper sulfate (80 mM, 94 uL). The vial was capped and the reaction was allowed to stir overnight. The mixture was centrifuged (10000 g, 15 min) and the supernatant retained. The reaction mixture was assessed by SDS-PAGE and a clear molecular weight shift was observed consistent with the conjugation of 20 kDa PEG to the polypeptide (FIG. 7A).

Figure 7:
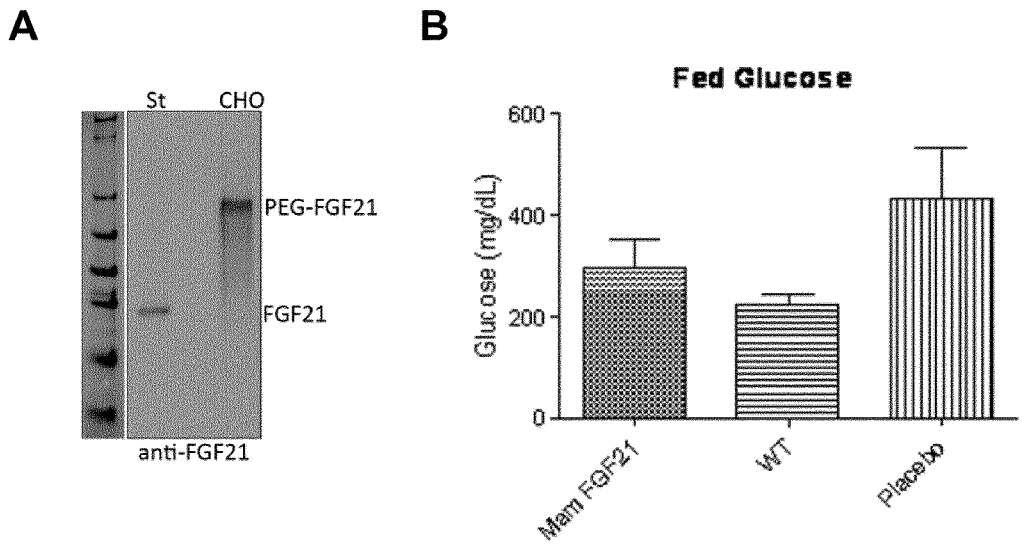
FIG. 7. Evidence that FGF21 containing a propargyl-lysine nnAA at position R131 is efficiently PEGylated and retains function in vivo.

To assess the potency of the PEGylated FGF21 constructs obese, db/db mice were treated daily with 0.25 mg/Kg FGF21 or 20K PEG-FGF21 and glucose levels measured in fed mice after three treatments using a handheld glucose monitor, (FIG. 7B).

The homozygous db/db mouse (B6.BKS(D)-Leprdb/j, Jackson labs) is a well characterized animal model for diabetes and becomes obese after 3-4 weeks of age. The animals also display elevated plasma insulin, blood sugar, and delayed wound healing. In this study, 7-8 week old, male db/db mice were fed Lab Diet 5053 Rodent Diet 20 ad libitum. Mice were acclimatized for seven days and subsequently administered PEGylated FGF21, unmodified FGF21 and vehicle (PBS) subcutaneously daily for eleven days.

Each mouse was administered 0.25 mg/Kg of PEG-FGF21 or unmodified FGF21 daily for three days. Fed glucose blood levels were determined by tail clip bleeding one hour after compound administration on day 3, and glucose levels measured by a handheld glucose meter (Bayer). The data shows that the PEGylation of FGF21 at amino acid residue 131 has the same potency of wild type FGF21 and shows improved glucose level maintenance as compared to placebo controls.

Example 6: Preparation of Amino Acids and Decoy Amino Acids

2-{[(benzyloxy)carbonyl]amino}-6-{[(prop-2-en-1-yloxy)carbonyl]amino}hexanoic acid (Formula VIIA.4, BaChem), 2-{[(9H-fluoren-9-ylmethoxy)carbonyl]amino}-6-{[(prop-2-en-1-yloxy)carbonyl]amino}hexanoic acid (Formula VIIA.5, BaChem), 6-{[(tert-butoxy)carbonyl]amino}hexanoic acid (Formula VIIB.4) were purchased from commercial vendors.

Preparation of Decoy nnAAs of Formula VIIA

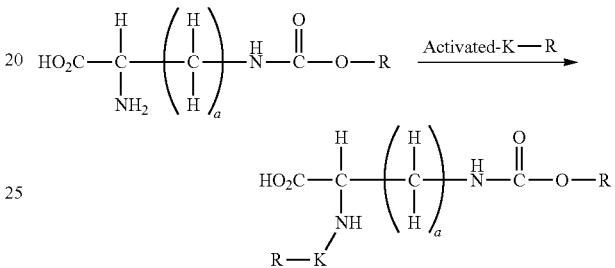

Formula VII analogs are readily prepared by acylating the α-amino group of the starting amino acid with an activated electrophile. This is done by treatment of the starting material with an acid chloride, activated ester, anhydride or sulfonyl chloride. The product can then be utilized for cell line development.

Preparation of Decoy Amino Acids of Formula VIIB:

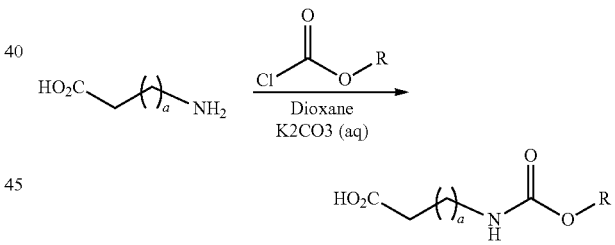

Preparation of 6-{[(prop-2-en-1-yloxy)carbonyl] amino}hexanoic acid (Formula VIIB.1)

In a 20 mL vial with magnetic stirrer was placed 6-aminocaproic acid (280 mg), sodium hydroxide (1M, 5.3 mL) and dioxane (2 mL). Allyl chloroformate (228 uL) was added and mixture stirred for 3 h. The mixture was treated with 1M citric acid until pH was acidic. The mixture was extracted with ethyl acetate (×3) and the organic layers retained. The organic layers were combined, dried with sodium sulfate, filtered and concentrated. Analytical MS: m/z (ES+) calculated 215.1 (M+H)+. found 216.1.

Preparation of 6{[(2-chloroethoxy)carbonyl] amino}hexanoic acid (Formula VIIB.3)

In a 20 mL vial with magnetic stirrer was placed 6-aminocaproic acid (1180 mg), sodium hydroxide (1M, 22.5 mL)

and dioxane (23 mL). 2-chloroethyl chloroformate (932 uL) was added and mixture stirred for 3 h. The mixture was treated with excess 1M citric acid until pH was acidic. The mixture was extracted with ethyl acetate (×3) and organic layers retained. The organic layers were combined, dried with sodium sulfate, filtered and concentrated. Analytical MS: m/z (ES+) calculated 237.1 (M+H)+. found 238.1.

Preparation of 6-{[(2-azidoethoxy)carbonyl]amino}hexanoic acid (Formula VIIB.6)

In a 20 mL vial with magnetic stirrer was placed 6-{[(2-chloroethoxy) carbonyl]amino} hexanoic acid (250 mg) and DMSO (5 mL). Sodium azide was added (2-chloroethyl chloroformate (70 mg) was heated to 60 C and stirred for 20 h. The mixture was diluted with water (5 mL) and poured onto 1M citric acid (10 mL). The mixture was extracted with ethyl acetate (×3) and organic layers retained. The organic layers were combined and washed with 5% lithium chloride. The organic layer was dried with sodium sulfate, filtered and concentrated. Analytical MS: m/z (ES+) calculated 244.1 (M+H)+. found 245.2.

Preparation of 6-{[(prop-2-yn-1-yloxy)carbonyl]amino}hexanoic acid (Formula VIIB.5)

In a 20 mL vial with magnetic stirrer was placed 6-aminocaproic acid (220 mg), sodium hydroxide (1M, 4.2 mL) and dioxane (2 mL). Propargyl chloroformate (163 uL) was added and mixture stirred for 3 h. The mixture was treated with excess 1M citric acid until pH was acidic. The mixture was extracted with ethyl acetate (×3) and organic layers retained. The organic layers were combined, dried with sodium sulfate, filtered and concentrated. Analytical MS: m/z (ES+) calculated 213.1 (M+H)+. found 214.1.

Preparation of 5-{[(prop-2-en-1-yloxy)carbonyl]amino}pentanoic acid (Formula VIIB.2)

In a 500 mL round bottomed flask with magnetic stirrer was placed 5-aminovaleric acid (15.0 g), water (100 mL) and 2N sodium carbonate (40 mL). Allyl chloroformate (8.2 mL) in dioxane (100 mL) was added dropwise and the final mixture stirred for 3 h. The mixture was acidified with 2N HCl (~50 mL). The mixture was extracted with ethyl acetate (4×100 mL) and the organic layers retained. The organic layers were combined, dried with sodium sulfate, filtered and concentrated. Analytical MS: m/z (ES+) calculated 201.1 (M+H)+. found 202.1.

Example 7. Preparation of Formula V and VI Analogs

Preparation of Preparation of (S)-2-amino-6((2-oxo-2-phenylacetamide)hexanoic acid (Formula V.6)

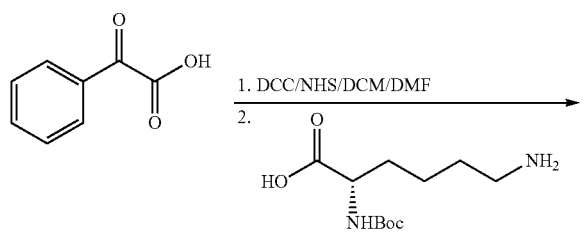

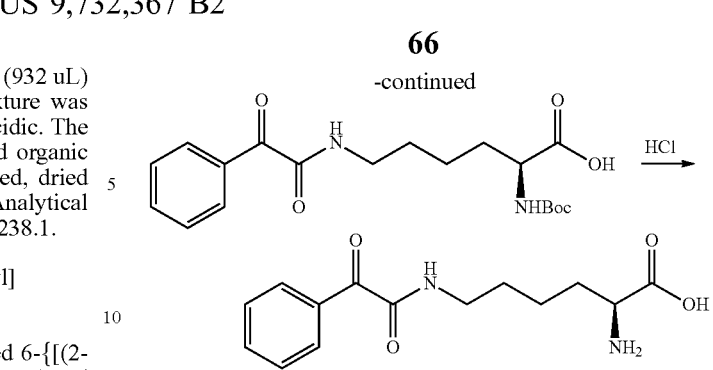

In a 50 mL round bottomed flask with magnetic stirrer was dissolved pyruvic acid (3.5 g, 23.3 mmol) in a 2:1 mixture of dichloromethane and DMF (20 mL). To this mixture was added DCC (5.7 g, 27.6 mmol) and NHS (3.2 g, 27.6 mmol). The mixture was heated to 50 C for 30 min with stirring. The solution was allowed to cool and then added through a filter to a suspension of N-Boc-Lysine (5.2 g, 21.2 mmol) in DMF (20 mL) in a separate 100 mL round bottomed flask with magnetic stirrer. Triethyl amine (8.8 mL, 63.6 mmol) was added after addition of the activated ester, and the mixture was stirred overnight. The mixture was partitioned between ethyl acetate and citric acid. The layers were separated and the aqueous layer was extracted 4 times with ethyl acetate. The organic layers were combined, dried over sodium sulfate and concentrated. The resulting residue was further purified by flash chromatography to afford the final N-Boc lysine derivative as an oil.

In a 100 mL roundbottomed flask was placed the keto-N-Boc lysine derivative (4 g, 10.6 mmol) in acetonitrile (50 mL). To this was added a solution of hydrochloric acid (15 mL, 4N in dioxane). The solution was stirred for 2 h and concentrated. Final purification by flash chromatography afforded the target amino acid. Analytical MS: m/z (ES+) calculated 278.1 (M+H)+. found 279.1.

Preparation of (2S)-2-amino-6-(2-azidoacetamido)hexanoic acid (Formula V.8)

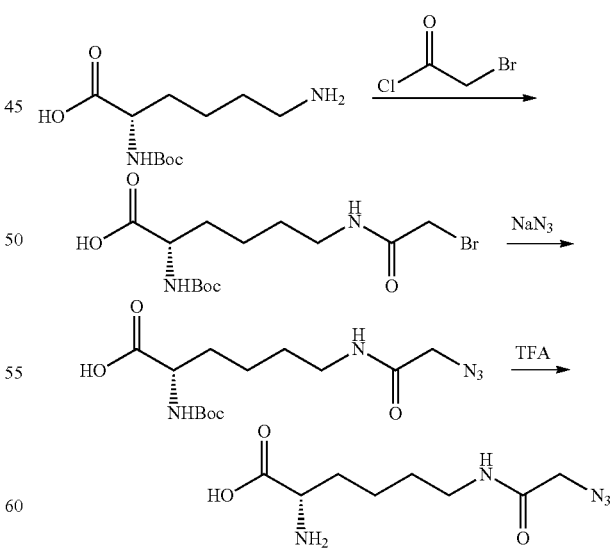

In a 25 mL roundbottomed flask was placed N-Boc-Lysine (500 mg, 2.0 mmol) suspended in dioxane (5 mL). Saturated NaHCO₃ was added (2 mL) and the solution was cooled to 0° C. Bromoacetyl chloride (169 uL, 2.0 mmol) in dioxane (2 mL) was added slowly. The solution was allowed to stir at 0 C for 1 h and then at room temperature for 4 h. The solution was transferred to a extraction funnel and partitioned between water and ether. The organic layer was removed and the aqueous layer made acidic (pH=2) with citric acid. The aqueous layer was extracted with ethyl acetate (3×50 mL), the organic layers combined and dried over sodium sulfate, filtered and concentrated. The resulting residue was carried forward into the next step.

In a 50 mL round bottomed flask was placed the crude N-Boc-ε-2-bromoacetyl-lysine (740 mg, 2.0 mmol) in dioxane (10 mL). To this was added a solution of sodium azide (10 mL, 1M). The solution was stirred at 60° C. overnight. The mixture was partitioned between citric acid (1M, 50 mL) and ethyl acetate (100 mL). The organic layer was retained, and the aqueous layer extracted 3 additional times. The organic layers were combined, dried over sodium sulfate and concentrated to an oil.

The crude N-Boc-ε-2-azido-acetyl-lysine was dissolved in acetonitrile (10 mL) and TFA (2 mL) was added. The mixture was stirred for 2 h and then concentrated. The solution was treated with toluene (10 mL) and concentrated (2×) and acetonitrile (10 mL) and concentrated (2×). The residue was dried overnight under vacuum. The residue was taken up in MeOH and precipitated with methyl-t-butyl ether. The viscous oil was isolated by centrifugation, the supernatant was disposed. Analytical MS: m/z (ES+) calculated 229.1 (M+H)+. found 230.1.

Preparation of (2S)-2-amino-6-(pent-4-enamido)hexanoic acid (Formula V.5)

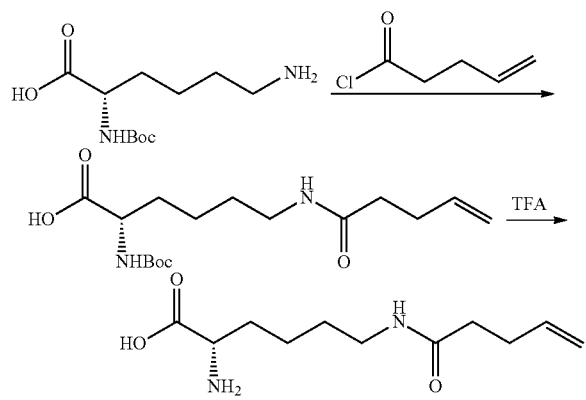

In a 25 mL roundbottomed flask was placed N-Boc-Lysine (500 mg, 2.0 mmol) suspended in dioxane (10 mL). 1M K$_2$CO$_3$ was added (5 mL) and the solution was cooled to 0 C. 4-pentenoyl chloride (224 uL, 2.0 mmol) in dioxane (2 mL) was added slowly. The solution was allowed to stir at 0 C for 1 h and then at room temperature for 4 h. The solution was transferred to a extraction funnel and partitioned between water and ether. The organic layer was removed and the aqueous layer made acidic (pH=2) with citric acid. The aqueous layer was extracted with ethyl acetate (3×50 mL), the organic layers combined and dried over sodium sulfate, filtered and concentrated. The resulting residue was carried forward into the next step.

The crude N-Boc-ε-N-4-pentenoyl amide-lysine was placed in a 50 mL round bottomed flask with acetonitrile (5 mL) and TFA (2 mL) and magnetically stirred for 2 h. The mixture was concentrated. The solution was treated with toluene (10 mL) and concentrated (2×) and acetonitrile (10 mL) and concentrated (2×). The residue was dried overnight under vacuum. The residue was taken up in MeOH and precipitated with methyl-t-butyl ether. The viscous oil was isolated by centrifugation, the supernatant was disposed. Analytical MS: m/z (ES+) calculated 229.2 (M+H)+. found 229.1.

Preparation of Hydroxy-Norleucine Derivatives (Formula VI.1 and Formula VI.2)

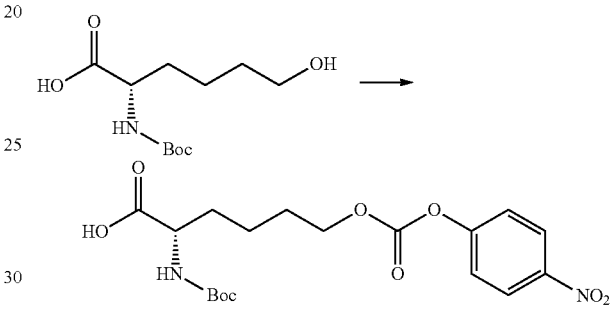

In a 100 mL roundbottomed flask with magnetic stirring was placed N-Boc-Hydroxyl Norleucine (1 g, 4.1 mmol) and acetonitrile (50 mL). The mixture was cooled to 0° C. and p-nitrophenylchloroformate (979 mg, 4.9 mmol) and Pyridine (2 mL) was added and the mixture stirred overnight. The mixture was concentrated and purified by flash chromatography. (Silica, DCM/MeOH gradient).

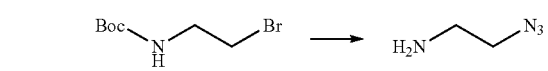

In a 100 mL roundbottomed flask with magnetic stirring was placed 2-N-Boc-ethylbromide (1 g, 4.4 mmol) in 25 mL of dioxane. To this was added a solution of sodium azide (1M, 22.2 mmol). The solution was stirred at 60° C. overnight. The mixture was partitioned between water and ethyl acetate. The ethyl acetate layer was retained and the aqueous layer was extracted with ethyl acetate three additional times. The organic layers were combined, dried over sodium sulfate and concentrated to an oil.

The oil was taken up in acetonitrile (35 mL) and HCL in dioxane was added (4M, 10 mL). The mixture was stirred for two hours and concentrated under vacuum.

Preparation of (2S)-2-amino-6-{[(2-azidoethyl)carbamoyl]oxy}hexanoic acid (Formula VI.1)

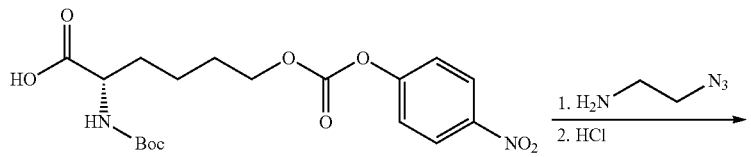

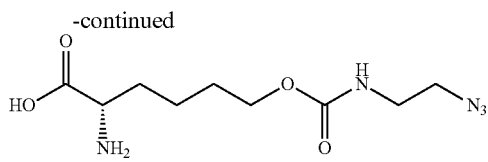

In a 50 mL round bottomed flask was placed the N-Boc-Norleucine p-nitrophenyl carbonate (503 mg, 1.2 mmoL) in dioxane (10 mL). To this was added a solution of the amino-azide (105 mg, 1.2 mmol) in dioxane (5 mL) and pyridine (1 mL). The solution was stirred overnight. The mixture was partitioned between ethyl acetate and 500 mM citric acid. The ethyl acetate layer was retained and the aqueous layer was extracted with ethyl acetate three additional times.

The organic layers were combined, dried over sodium sulfate and concentrated to an oil. The oil was further purified by flash chromatography.

The isolated Boc-protected amino acid was taken up in acetonitrile (15 mL) and treated with HCl in dioxane (4M, 5 mL). The mixture was stirred for two hours and concentrated under vacuum.

Preparation of (2S)-2-amino-6-{[(prop-2-yn-1-yl)carbamoyl]oxy}hexanoic acid (Formula VI.2)

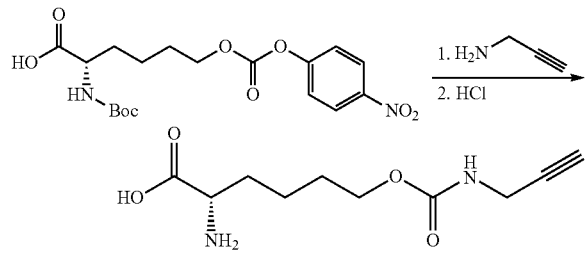

In a 50 mL round bottomed flask was placed the N-Boc-Norleucine p-nitrophenyl carbonate (337 mg, 0.8 mmoL) in dioxane (10 mL). To this was added a solution of the amino-azide (135 mg, 2.4 mmol) in dioxane (5 mL). The solution was stirred overnight. The mixture was partitioned between ethyl acetate and 500 mM citric acid. The ethyl acetate layer was retained and the aqueous layer was extracted with ethyl acetate three additional times. The organic layers were combined, dried over sodium sulfate and concentrated to an oil. The oil was further purified by flash chromatography.

The isolated Boc-protected amino acid was taken up in acetonitrile (15 mL) and treated with HCl in dioxane (4M, 5 mL). The mixture was stirred for two hours and concentrated under vacuum.

Example 8: Anti-Her2-Toxin Conjugation

The anti-Her2 antibody was obtained as follows.

The variable regions of the mouse antibody 4D5 directed to the extracellular domain of Her2 was generated by gene synthesis using overlapping oligomers and cloned into a shuttle vector. The variable regions were then grafted onto the human frameworks encoded by pFUSE-CHIg-hG1 and pFUSE-CHLIg-hK (Invivogen) to generate a mouse-human hybrid. Amber codons were introduced into the heavy chain (gamma) at positions 274 and 359 (SEQ ID 47 and SEQ ID 49 respectively) and the light chain (Kappa) at positions 70 and 81 (SEQ ID 53 and SEQ ID55 respectively) by site directed mutagenesis. Clones containing the amber codon were identified by DNA sequencing. To generate an integrating construct in pOptivec for this IgG, the promoters and ORF for the heavy chain was amplified by PCR and cloned by restriction enzyme digestion and ligation into pOptivec. The light chain and a single copy of the tRNA were joined by two step PCR method using overlapping oligomers and cloned into available sites into the pOptivec plasmid containing the heavy chain.

Expression and Purification

An antibody directed against HER2 was generated by gene synthesis of the Herceptin CDRs and the IgG1 framework modified to enable the integration of a nnAA at one or two sites and their subsequent conjugation. The murine CDRs of Herceptin were cloned into pFUSE-CHIg-hG1 (heavy chain) and pFUSE-CHLIg-hK (Light chain)(Invivogen) to generate a humanized antibody. The resulting vector pairs pFuse-4D5gamma and pFUSE-4D5kappa served for cotransfection and expression of the wildtype anti-Her2 IgG by transient transfections (SEQ ID 45, SEQ ID 46, heavy chain; SEQ ID 51, SEQ ID 52, light chain). The sites for nnAA incorporation were generated by introducing an amber codon at the desired sites by site-directed mutagenesis and mutants screened by sequencing. This resulted in a heavy chain clone containing an amber codon at position 274 (pFuse-4D5gamma_K274am) (SEQ ID 47). Amber sites were also constructed in pFUSE-4D5kappa. First the termination codon was replaced from an amber codon to an ochre stop codon to generate the vector pFUSE-4D5kappa_TAA. An amber codon at position D70 was introduced by site directed mutagenesis (SEQ ID 53). By pairing these different vectors antibodies containing a single nnAA or two nnAAs can be generated.

Transient expression of target antibodies containing a nnAA were performed in HEK293 cells stably expressing pylRS. This cell line was generated by transfection of a vector containing the pylRS gene in pCEP4 (Life Technologies) and selection by growth in medium containing hygromycinB (DMEM (Life Technologies), 2 mM glutamax, 1 mM sodium pyruvate, 6 mM glutamine, 1× non essential amino acids (Gibco CAT#11140-050), 10% fetal calf serum, and 0.2 mg/mL hygromycin). Surviving cells were cloned by limiting dilution and clones demonstrating high functional activity of the pylRS were expanded. This was achieved by transiently transfecting the different clones with a vector encoding tRNApyl and a reporter construct GFPY40 containing an amber codon at position Y40 in the presence of ALOC nnAA. Fluorescence levels were quantified in these cells using an Accuri flow cytometer and high functioning clones isolated. Expression of the anti-Her2 antibodies was performed using standard transfection conditions. Cells were plated to approximately 90% confluence and grown at 37° C. The following day, the plated cells were incubated with the appropriate DNA previously treated with a lipophilic reagent (Lipofectamine 2000, 293 fectin (invitrogen), according to the specific manufacturer's instructions. Following 2-5 days of growth in the presence of 1-2 mM Lys-azide, the growth medium was harvested and either used directly or the expressed proteins purified by an appropriate method. For expression of IgG, cells were grown in medium containing low IgG fetal bovine serum. In each case 0.1 volumes of 10×PBS was added to the expression supernatant to equilibrate the salts and pH of the sample and antibodies purified by protein A affinity chromatography. Briefly, expression supernatants were passaged through a 1 mL or 5 mL nProtein A sepharose Fast Flow column (GE). Bound material was washed with 5-10 column volumes of PBS and eluted with 3-5 volumes of 0.1 M glycine pH3.0. Fractions were subsequently neutralized by the addition of 0.05 volumes of 20×PBS to achieve a neutral pH. Elution fractions were analysed by SDS-PAGE and coomassie staining and peak protein fractions pooled and dialysed to PBS at 4° C. for 16 hours. IgGs containing a lys azide as a nnAA are referred to as AzAb.

Preparation of CYTOTOXIN-ALKYNE Derivatives

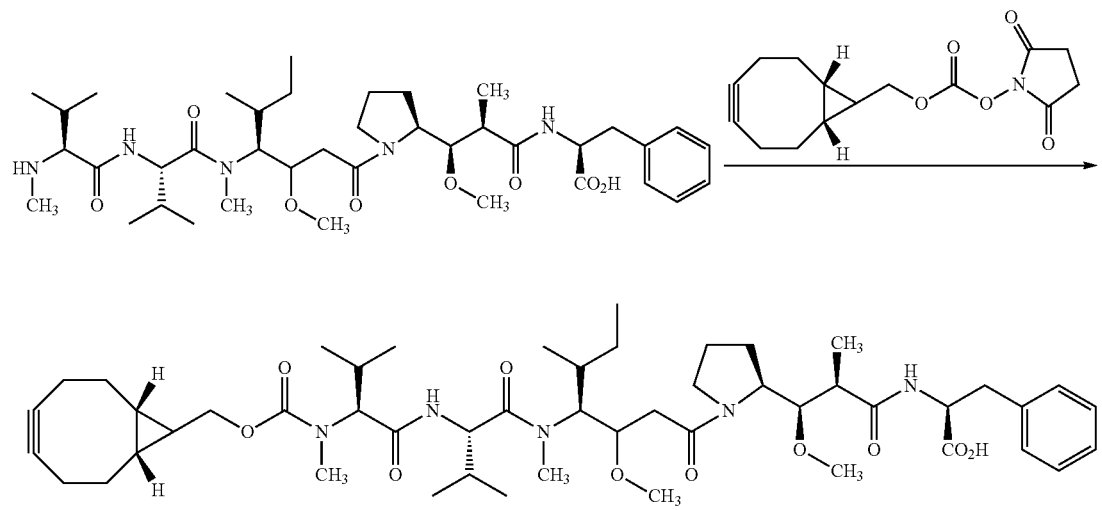

Preparation of MMAF-ALKYNE Derivative.

Monomethyl auristatin F (MMAF) (6 mg, 8.2 umol) was placed in a small vial, and DMSO (450 uL) was added. A solution of BCN carbonate in DMSO (82.6 ug/uL, 84 uL, 2.4 mg, 8.2 umol) was added to the MMAF solution. Triethylamine (2.5 uL, 18 umol) was added, the vial capped and the reaction stirred for 4 h. Analytical MS: m/z (ES+) calculated 907.1 (M+H)+. found 908.6.

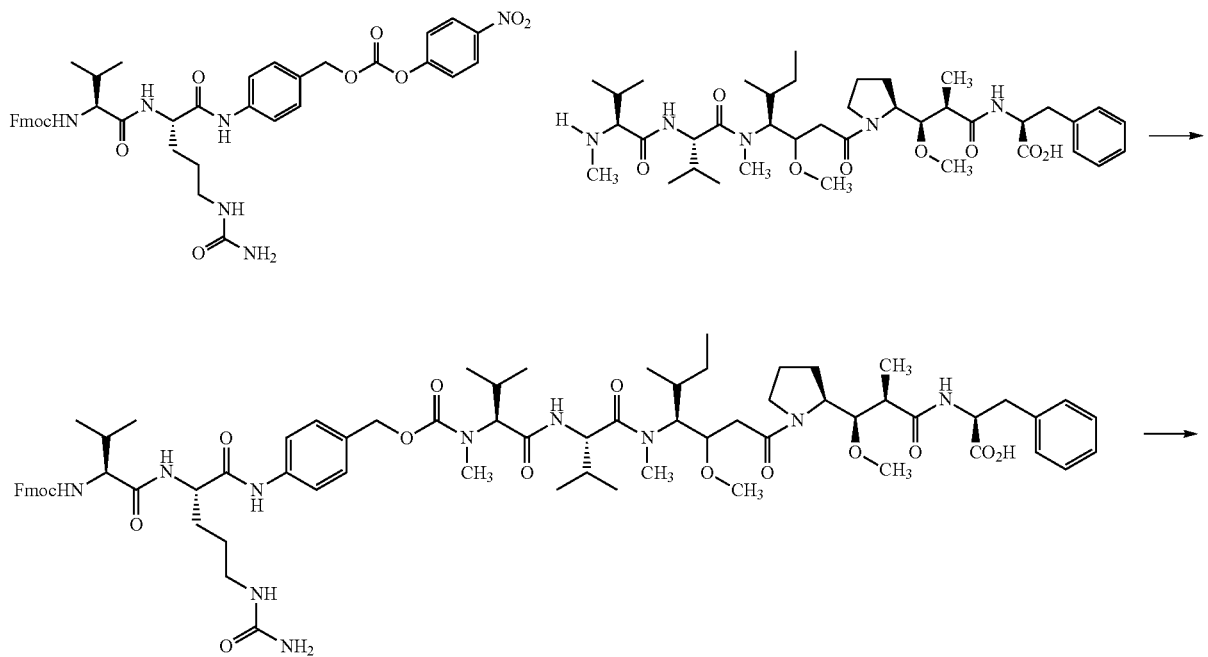

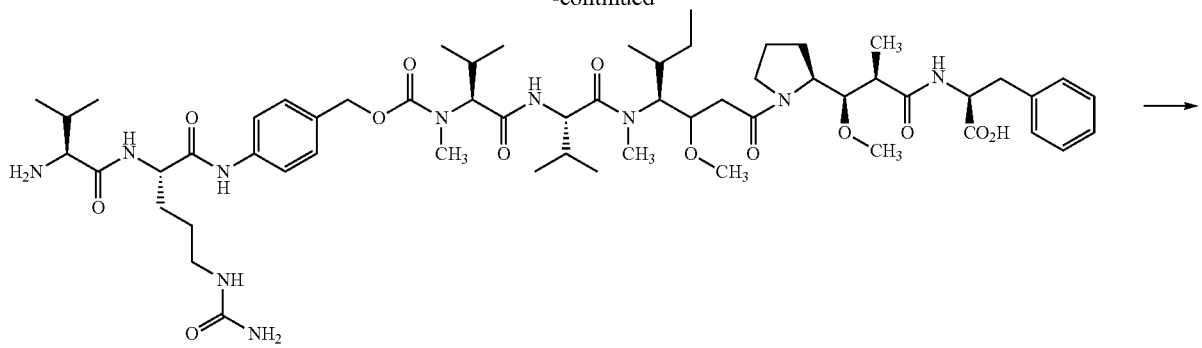

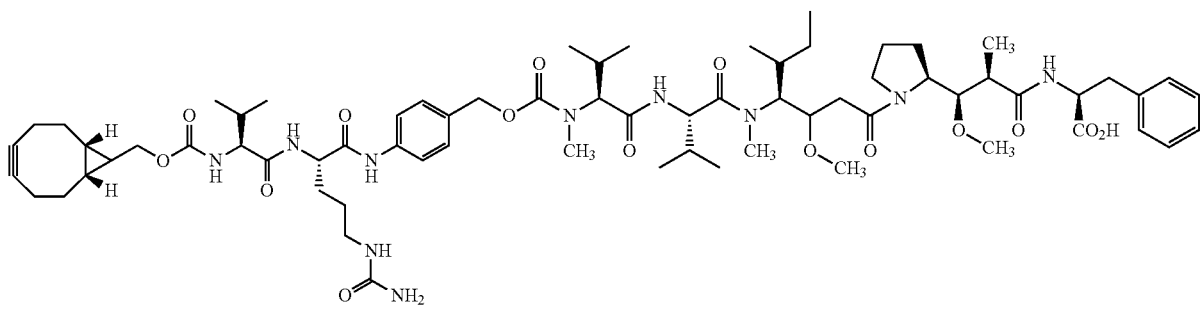

Preparation of MMAF-Valine-Citruline-p-Amino-Benzoyl-Carbonate (VCP)-Cyclooctyne Derivative.

In a 4 mL vial with magnetic stirrer was placed MMAF (5 mg, 6.84 umol) and the dipeptide val-cit-PABC-Fmoc (5.24 mg, 6.84 umol). To this mixture was added a DMSO (350 uL). A DMSO solution of ethyl(hydroxyimino)cyanoacetate (40 mg/mL, 25 uL), and an aqueous solution of potassium tert-butoxide (60 mg/mL, 25 uL) was added, the vial was capped and allowed to stir overnight. Analytical MS: m/z (ES+) calculated 1358 (M+H)+. found 1359.8. The crude mixture was used directly in the next step.

The crude MMAF-VCP-Fmoc was treated taken up in 400 uL of dichloromethane and treated with 400 uL of diisopropylamine. The mixture was stirred for 2 h, transferred to a roundbottomed flask with methanol and concentrated. The material was treated with heptanes (2 mL) and concentrated, the sequence was repeated with isopropanol to remove excess diisopropylamine. The material was concentrated under high vacuum overnight and carried on to the next step. Analytical MS: m/z (ES+) calculated 1136.7 (M+H)+. found 1137.6.

The crude MMAF-VCP-NH2 was taken up in DMF (420 uL) and treated with a solution of ALKYNE carbonate (40 mg/mL, 50 uL) and triethylamine (2.8 uL). The mixture was stirred for 8 h at room temperature. Analytical MS: m/z (ES+) calculated 1312.8 (M+H)+. found 1313.7.

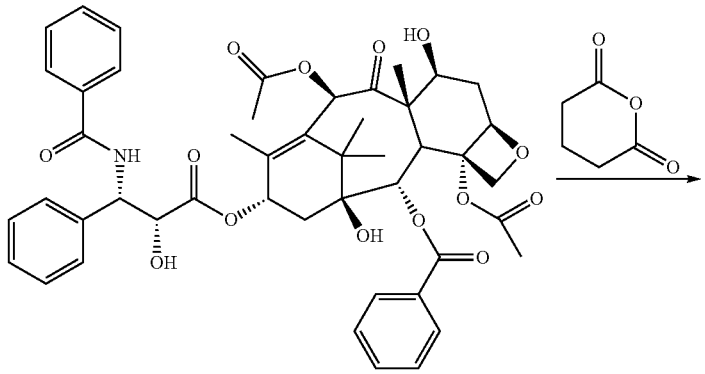

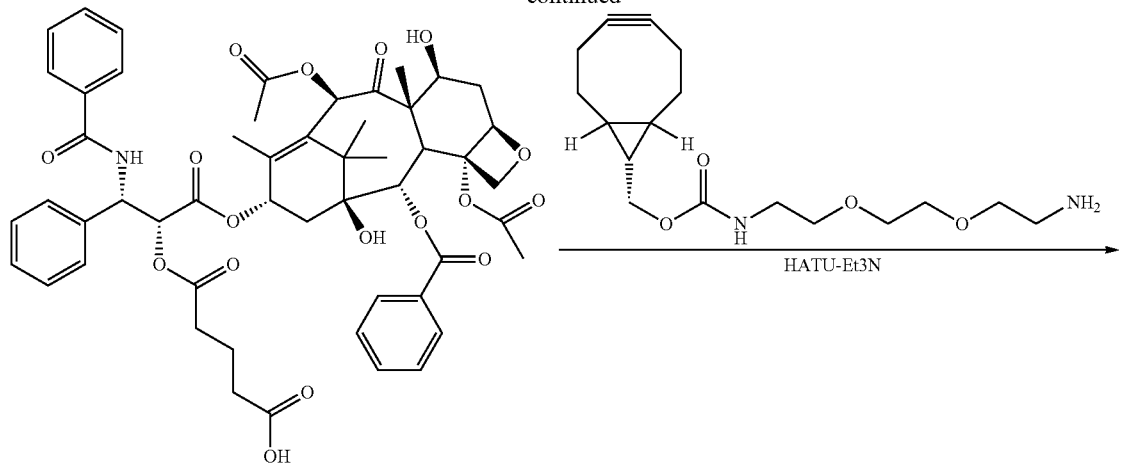

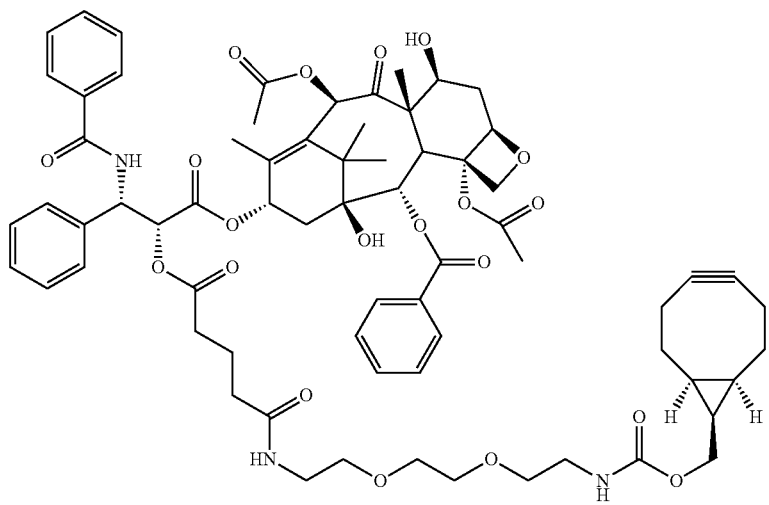

Preparation of Paclitaxel-Cyclooctyne Derivative.

Paclitaxel (500 mg, 590 umol) and glutaric anhydride were placed in a 50 mL round bottomed flask with magnetic stir and pyridine (10 mL) was added. The solution was stirred overnight. The mixture was concentrated to an oil and purified by column chromatography on silica gel (hexane/acetone elution) affording the desired product. Analytical MS: m/z (ES+) calculated 968.0 (M+H)+. found 969.1.

A solution of taxol-glutaric acid conjugate in DMF (15.6 ug/uL, 321 uL, 5 mg, 5.2 umol) was placed in a small vial with magnetic stir bar. A solution of HATU coupling agent (46.1 ug/uL, 50 uL, 2.3 mg, 6.2 umol), a solution of cyclooctyne-amine (34 ug/uL, 50 uL, 1.7 mg, 5.2 umol) and triethylamine (1.6 uL, 11.4 umol) were added in succession. The vial was capped shut and stirred overnight. Analytical MS: m/z (ES+) calculated 1273.6 (M+H)+. found 1274.4.

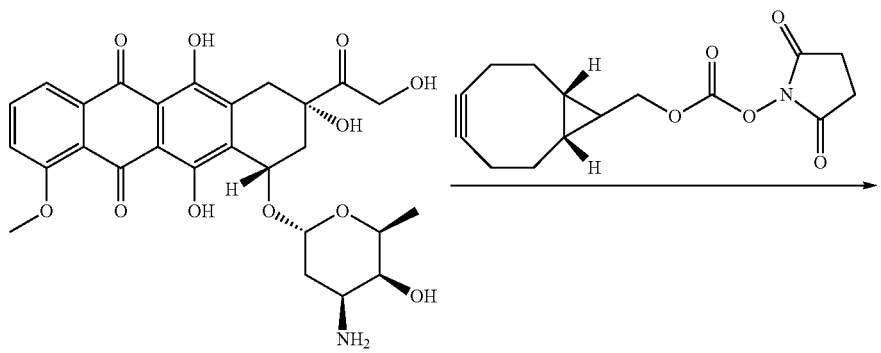

-continued

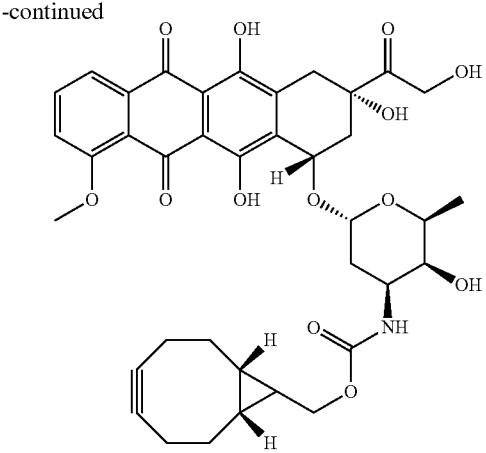

Preparation of a Doxorubicin-Cyclooctyne Derivative.

A doxorubicin solution (12.5 ug/uL, 320 uL, 4 mg, 7.4 umol) was placed in a small vial with small magnetic stir bar. A solution of cyclooctyne carbonate in DMSO (28.5 ug/uL, 63 uL, 1.8 mg, 7.4 umol) was added to the vial. Triethylamine (2.2 uL, 16 umol) was added, the vial capped and the reaction stirred for 4 h. Analytical MS: m/z (ES+) calculated 719.7 (M+H)+. found 720.5.

Figure 58:
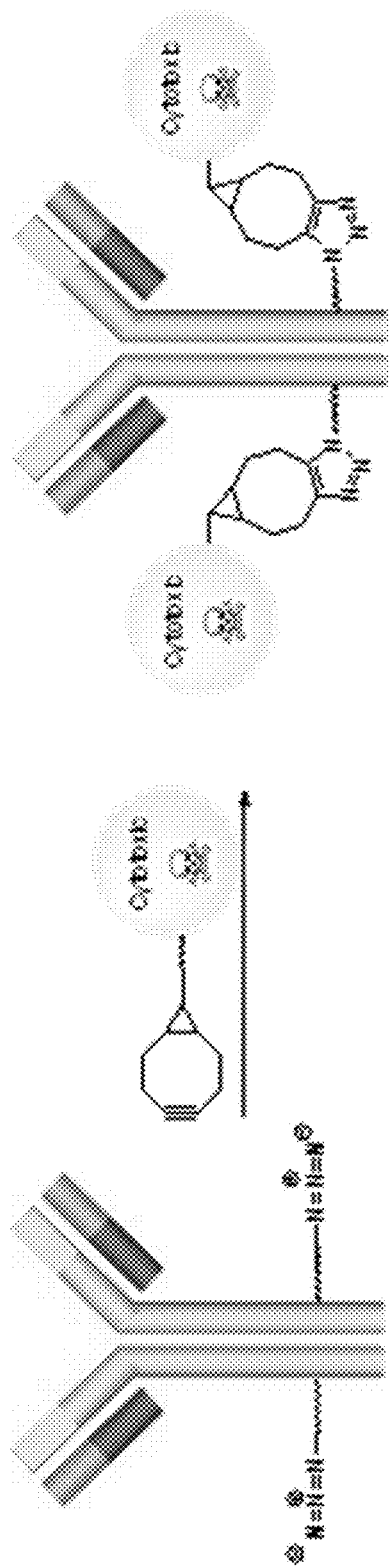
FIG. 58. A schematic showing conjugation of anti-Her2 Antibody having nnAA lys-azide incorporated at position 274 of heavy chain (Anti-Her2-LysAzide274h) with monomethyl auristatin F (MMAF)-clyclooctyne derivative.

Conjugation of Anti-Her2 Antibody, nnAA Lys-Azide Incorporated at Position 274 of Heavy Chain (Anti-Her2-LysAzide274h) with MMAF-Cyclooctyne Derivative. (See FIG. 58)

In a 200 uL PCR tube was placed a solution of phosphates (50 mM, pH=7.4, 3 uL) and a solution of the anti-Her2 Antibody (Anti-Her2-LysAzide274h) (11.43 uL, 2.1 mg/mL). To this was added a DMSO solution of the MMAF-ALKYNE derivative (1.1 uL, 14.5 mMol), the tube was capped and vortexed. The mixture was allowed to stand for 4 h. The reaction mixture was then treated with a solution of azidohomoalanine (AHA, 250 mM in 1M HEPES, 6.4 uL), vortexed and allowed to stand for 60 min. The mixture was then desalted through a ZEBA (Pierce) mini spin column to afford the final ADC solution (0.21 mg/mL)

A cell-based fluorescence assay was used to show that the 4D5 IgG and conjugated 4D5-MMAF bound and internalized into cells expressing Her2 epitope. The breast cancer cell lines A345, or SKBR3 and EL4 and EL4 cells, stably transfected with a construct for the expression of Her2, were grown in complete RPMI-1640 or DMEM. Cells were dissociated, counted and harvested by centrifugation. For each assay approximately 200,000-500,000 cells were incubated with PBS containing 0.5% BSA for 1 hour at RT. Cells were then treated with 1 ug of purified 4D5 IgG or 4D5 IgG-MMAF conjugate in the presence of absence of 0.1% sodium azide for 1 hour at 37° C. Cells were washed and incubated with an anti-Human IgG-phycoerythrin conjugate for 1 hour at 37° C., washed with PBS, and resuspended in PBS or PBS containing 50% Trypan Blue and analysed by flow cytometry (Accuri).

Cell viability and cell death assays. The effect of the anti-Her2-MMAF conjugate on tumor cell viability was assessed using an MTS assay. Briefly, cells were plated onto 96 well plates (5000 cells per well of SKBR3, MDA-MD, and MCF7) in 50 uL of RPMI 1640 lacking phenol red and containing 10% fetal bovine serum (FBS). Different concentrations of the antibody conjugates and controls were added in 50 uL of RPMI1640 containing FBS to the cells for three days at 37° C. in a humidified environment of 5% CO2. Cell viability was analysed by the addition of 20 uL of complete MTS (Pierce) and color allowed to develop for 1-3 hours at 37° C. The absorbance of each well at 490 nm was recorded using a plate reader (Molecular Dynamics) (FIG. 8B)

Conjugation of Anti-Her2 Antibody (Anti-Her2-LysAzide274h) with MMAF-Valine-Citruline-p-Amino-Benzoyl-Carbonate-Cyclooctyne Derivative In a 200 uL PCR tube was placed a solution of phosphates (50 mM, pH=7.4, 3 uL) and a solution of the anti-Her2 Antibody (NNAA lys-azide incorporated at position 274 of heavy chain) (11.43 uL, 2.1 mg/mL). To this was added a DMSO solution of the MMAF-ALKYNE derivative (1.23 uL, 13 mMol), the tube was capped and vortexed. The mixture was allowed to stand for 4 h. The reaction mixture was then treated with a solution of azidohomoalanine (AHA, 250 mM in 1M HEPES, 6.4 uL), vortexed and allowed to stand for 60 min. The mixture was then desalted through a ZEBA (Pierce) mini spin column to afford the final ADC solution (0.21 mg/mL)

Conjugation of Anti-Her2 Antibody (Anti-Her2-LysAzide274h) with Paclitaxel-Cyclooctyne Derivative In a 200 uL PCR tube was placed a solution of phosphates (50 mM, pH=7.4, 3 uL) and a solution of the anti-Her2 Antibody (Anti-Her2-LysAzide274h) (11.43 uL, 2.1 mg/mL). To this was added a DMSO solution of the Paclitaxel-ALKYNE derivative (1.24 uL, 12.9 mMol), the tube was capped and vortexed. The mixture was allowed to stand for 4 h. The reaction mixture was then treated with a solution of azidohomoalanine (AHA, 250 mM in 1M HEPES, 6.4 uL), vortexed and allowed to stand for 60 min. The mixture was then desalted through a ZEBA (Pierce) mini spin column to afford the final ADC solution.

Example 9: PEGylation to Anti-Her2 Antibody (Anti-Her2-LysAzide274h)

Figure 59:
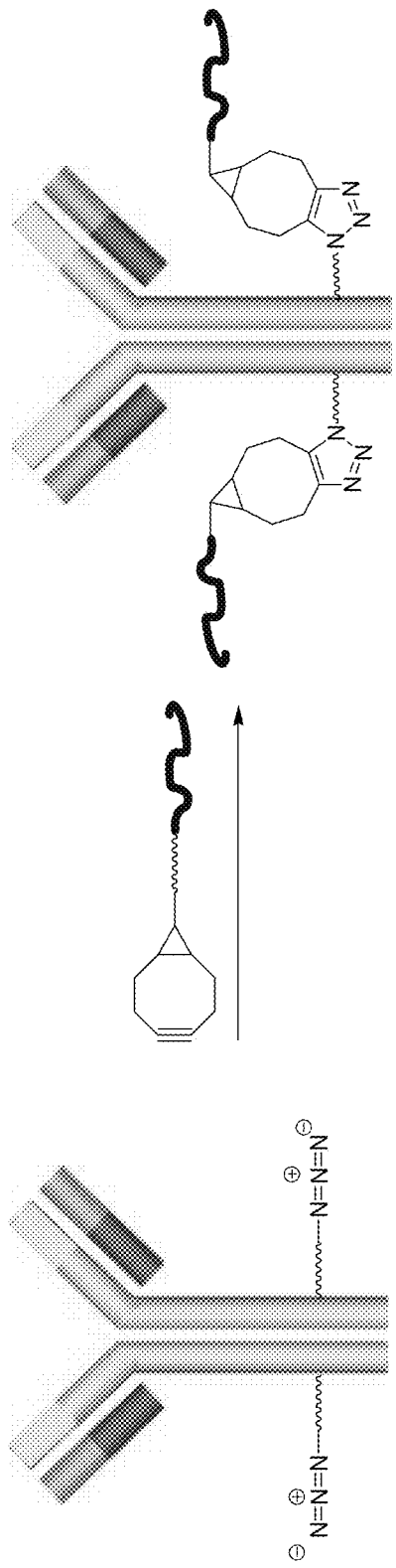
FIG. 59. A schematic showing PEGylation with 20K Linear PEG-cyclooctyne to anti-Her2 Antibody (Anti-Her2-LysAzide274h).

PEGylation with 20K Linear PEG-Cyclooctyne to Anti-Her2 Antibody (Anti-Her2-LysAzide274h) (See FIG. 59)

In a 200 uL PCR tube was placed phosphate buffer (50 mM, pH=7.4, 1 uL). A solution of azide containing antibody (AzAb-2, 2.1 mg/mL, 1.07 uL) was added followed by a solution of 20KPEG cyclooctyne (60 mg/mL, 1.0 uL). The solution was mixed vigorously on a vortexer (Fisher). The tube was placed on a PCR tube centrifuge for a few seconds to place all liquids into the bottom of the tube. The mixture was allowed to stand for 4 h.

Figure 9:
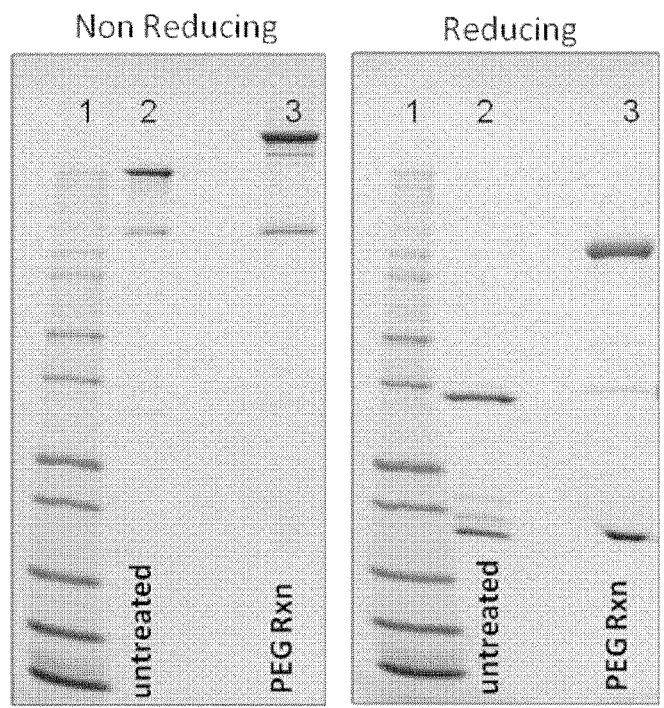
FIG. 9. Non Reducing gel of anti-Her2 Antibody containing an azide reacting with 20K PEG Cyclo-Alkyne (A) and Reducing gel of anti-Her2 Antibody containing an azide reacting with 20K PEG Cyclo-ALKYNE (B)

The solution was diluted with water (7 uL) to bring the final volume to ~10 uL. The solution was then partitioned into 5 uL and added to 5 uL of either reducing or non-reducing gel loading buffer. The mixture was mixed and heated to 95 C for 3 minutes. The samples were then loaded onto SDS-PAGE gels (4-20% Tris-Gly, Invitrogen). SDS-PAGE (reducing and non-reducing) indicated that the PEGylation occurred with a high degree of conversion with nearly all starting being converted to the bis-PEGylated species. Non reducing gel (FIG. 9A) lane 2: anti-Her2 Antibody (NNAA lys-azide incorporated at position 274 of heavy chain) untreated, Lane 3: anti-Her2 Antibody (NNAA lys-azide incorporated at position 274 of heavy chain) treated with 20KPEG linear PEG cyclooctyne. A clear molecular shift is observed in the PEG treated Azide-Antibody to a dominant single species, consistent with the anticipated with molecular weight shift of inclusion of two PEG chains. PDSI indicated a high degree conversion (93% bis PEGylation, 6.9% mono-PEGylation, no starting material). Reducing gel (FIG. 9B) Lane 2: anti-Her2 Antibody (NNAA lys-azide incorporated at position 274 of heavy chain), Lane 3: anti-Her2 Antibody (NNAA lys-azide incorporated at position 274 of heavy chain) treated with 20KPEG linear PEG alkyne. A clear molecular weight shift of the heavy chain in the PEG treated antibody (Lane 3) was observed, speaking to the specificity for the azide containing heavy chain and the degree of conversion with the PEG conjugation (96.7%, densitometry).

PEGylation with 20KPEG Cyclooctyne to Anti-Her2 Antibody with nnAA Lys-Azide Incorporated at Position 274 of Heavy Chain and Position 70 of Light Chain (Anti-Her2-LysAzide274h70l)

In a 200 uL PCR tube was placed a solution of the Anti-Her2-LysAzide274h70l antibody 0.5 mg/mL, 4.5 uL). A solution of 20KPEG cyclooctyne (60 mg/mL, 1.0 uL) was added and the solution mixed vigorously on a vortexer (Fisher). The tube was placed on a PCR tube centrifuge for a few seconds to place all liquids into the bottom of the tube. The mixture was allowed to stand for 18 h.

Figure 10:
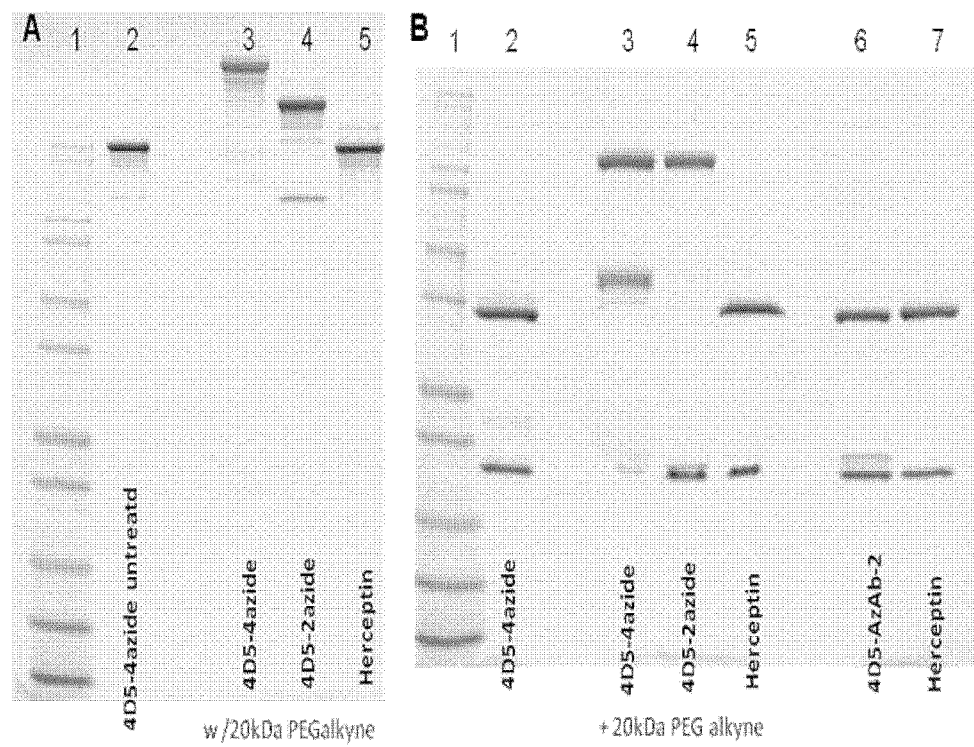
FIG. 10. Non-reducing SDS-PAGE gel of 20KPEGylation of Anti-Her2-LysAzide274h70l (A) and Reducing SDS-PAGE gel of 20K PEGylation of 4D5 AzAb-4 (B)

The solution was diluted with water (4.5 uL) to bring the final volume to ~10 uL. The solution was then partitioned into 5 uL and added to 5 uL of either reducing or non-reducing gel loading buffer. The gel samples were mixed and heated to 95 C for 3 minutes. The samples were then loaded onto SDS-PAGE gels (4-20% Tris-Gly, Invitrogen). SDS-PAGE (non-reducing) indicated that the PEGylation occurred with a high degree of conversion with nearly all starting antibody converted to the tetra-PEGylated species. Non reducing gel (FIG. 10A lane 2: anti-Her2 Antibody (Anti-Her2-LysAzide274h70l) untreated, Lane 3-5: All treated with 20K linear PEG cyclooctyne Lane 3: anti-Her2 Antibody (Anti-Her2-LysAzide274h), Lane 4: anti-Her2 Antibody (Anti-Her2-LysAzide274h), Lane 5: Herceptin (no azides) negative control, Lane 6: anti-Her2 Antibody (Anti-Her2-LysAzide274h) untreated and Lane 7: Herceptin untreated. A clear molecular weight shift is observed from the single band of the untreated 4D5 AzAb-4 to the tetra-PEGylated species which is dominant. This tetra-PEGylated species is larger than the bis-PEGylated species (Lane 4). The non-reducing gel also shows the specificity of the reaction for azide containing antibodies, with Herceptin, containing no azides, showing no reactivity. PDSI indicated a high degree conversion (86% bis PEGylation, 14 tris-PEGylation, no starting material). Reducing gel (FIG. 10B) lane 2: anti-Her2 Antibody (Anti-Her2-LysAzide274h70l) untreated, Lane 3-5: All treated with 20K linear PEG cyclooctyne Lane 3: anti-Her2 Antibody (Anti-Her2-LysAzide274h70l), Lane 4: anti-Her2 Antibody (Anti-Her2-LysAzide274h), Lane 5: Herceptin (no azides) negative control, Lane 6: anti-Her2 Antibody (Anti-Her2-LysAzide274h) untreated and Lane 7: Herceptin untreated. The reducing gel shows that both the heavy and light chains (lane 3) underwent a clear molecular shift, consistent with the addition of a single 20KPEG chain to each subunit of the antibody. The bands are distinct, indicating the reaction took place only at the azide site and no additional PEGylation took place, as indicated by the absence of additional higher MW bands. Comparison to the anti-Her2 Antibody (Anti-Her2-LysAzide274h) which shares an azide in the same position of the heavy chain indicates the same Molecular weight shift for both bands and the same running time through the gel. The non-azide containing herceptin when treated with the 20KPEG alkyne showed no reactivity. The conjugation efficiency for the anti-Her2 Antibody (Anti-Her2-LysAzide274h70l) was also high, the gel showing little to no evidence of the unmodified heavy or light chains.

Example 10: PEGylation of her2 Antibodies Via Copper Catalyzed Click

Figure 60:
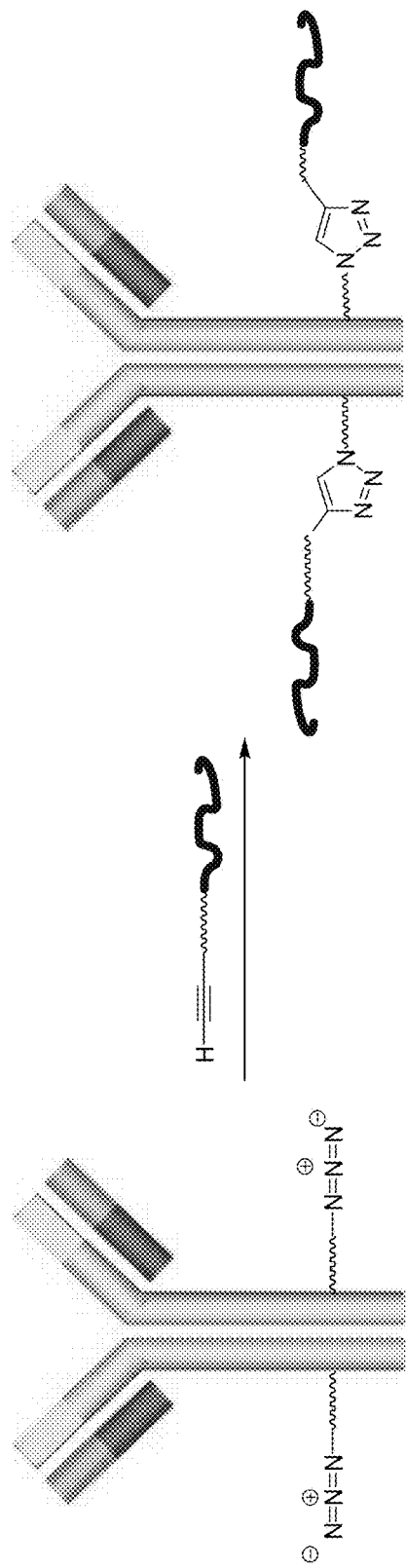
FIG. 60. A schematic showing PEGylation with 20KPEG alkyne to anti-Her2 Antibody (Anti-Her2-LysAzide274h).

PEGylation with 20KPEG Alkyne to Anti-Her2 Antibody (Anti-Her2-LysAzide274h) (See FIG. 60)

In a 200 uL PCR tube was placed a dichloromethane solution of tris[(1-benzyl-1H-1,2,3-triazol-4-yl)methyl]amine (TBTA, 10 mM, 1.5 uL). The solvent was evaporated under a stream of nitrogen, and a solution of 4D5 AzAb-2 (3.5 mg/mL, 2.14 uL) was added. An aqueous solution of 20KPEG alkyne was added (60 mg/mL, 1.67 uL), followed by an aqueous solution of cysteine (20 mM, 0.5 uL). Finally, a solution of copper sulfate (10 mM, 0.75 uL) was added and the mixture was vortexed gently to mix components, then allowed to stand for 4 h.

Figure 11:
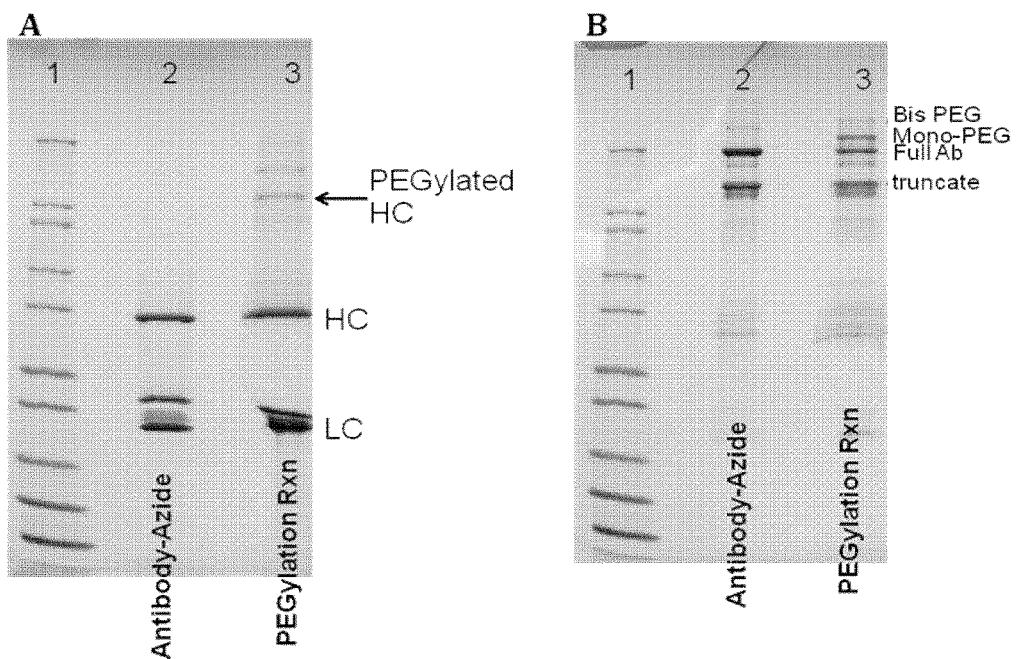
FIG. 11. Reducing gel of anti-Her2 Antibody containing an azide reacting with 20K PEG terminal alkyne in the presence of Copper (A) and Non Reducing gel of V anti-Her2 Antibody containing an azide reacting with 20K PEG terminal alkyne in the presence of Copper (B)

The solution was split (2.5 uL), with half being added to 7.5 uL of reducing gel loading buffer, and half being added to 7.5 uL of non-reducing gel loading buffer. The samples were heated to 95 C for 3 min and then loaded onto SDS-PAGE gels (4-20% Tris-Gly, Invitrogen) and run. Non reducing gel (FIG. 11B) lane 2: anti-Her2 Antibody (Anti-Her2-LysAzide274h) untreated, Lane 3: anti-Her2 Antibody (Anti-Her2-LysAzide274h) treated with 20KPEG linear PEG alkyne. A mixture of unreacted anti-Her2 Antibody (NNAA lys-azide incorporated at position 274 of heavy chain, a higher molecular weight band identified as the inclusion of one 20KPEG chain and a higher molecular weight band identified as the bis-PEGylated species were observed in the non-reducing gel (lane 3). PDSI indicated a modest conversion between the mono and bis PEGylated species. (5.3% bis PEGylation, 37% mono-PEGylation, 58% unmodified Ab). Reducing gel (FIG. 11A) Lane 2: antibody untreated, Lane 3: antibody treated with 20KPEG linear PEG alkyne. Gel analysis by PDSI indicated a modest amount (10%) of the heavy chain PEGylated. The reaction was specific for the heavy chain as the light chain appears unaltered.

Figure 32:
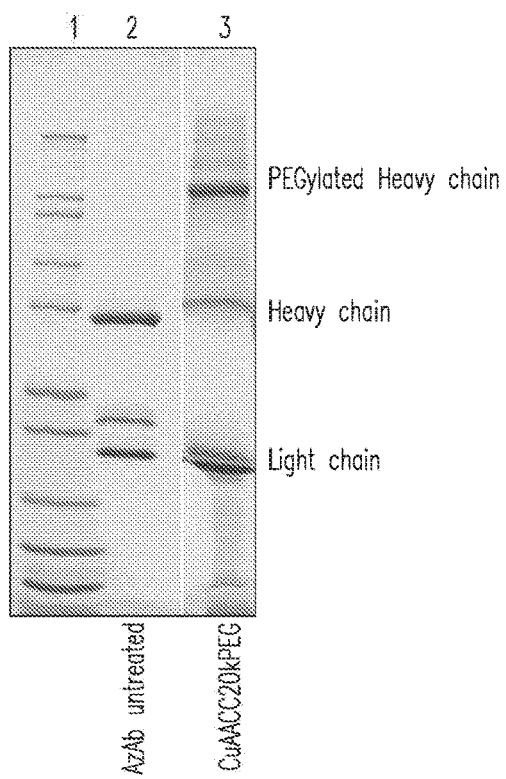
FIG. 32. SDS-PAGE analysis of reaction mixture of 20 kDa PEGylation of 4D5-2AzAb(HC274) under CuAAC conditions and TBTA FIG. 33. SDS PAGE analysis of the product of a 20kPEGylation to 4D5 AzAb with CuAAC and THPTA FIG. 34. A, B, PAGE analysis of 2 kDa PEGylation of 4D5-2AzAb (HC274) with CuAAC/THPTA under reducing and non reducing conditions. C, HIC chromatogram of the final reaction mixture of 2 kDa PEGylation of 4D5-AzAb FIG. 35. In vitro cytotoxic effect of DAR4 4D5-AF ADC's FIG. 36. In vitro cytotoxic effect of 4D5-Amanitin ADC's FIG. 37. In vitro cytotoxic effect of 4D5-AF ADC's obtained via CUAAC and SPAAC chemistries.

Additional examples of 20 kDa PEGylation of 4D5-AzAb (HC274) under CuAAC conditions utilizing TBTA conditions are demonstrated in FIG. 32. When compared to the untreated AzAb, the PEGylation occurred in a site specific manner to the azide bearing heavy chain as indicated by a significant molecular weight shift of this band.

PEGylation with 20K Linear PEG-Cyclooctyne to Anti-PSMA scFv with NNAA Substituted at Position 117 (Anti-PSMAscFV-117)

An scFv directed to PSMA was generated by grafting the CDRs of the antibody J591 (BANDER) onto a scFv framework. The scFv to PSMA was generated by gene synthesis using overlapping oligomers and PCR and the product cloned into pJ201 to yield pJ201-PSMA. An expression construct pCDNA3.1-PSMA was generated by excising the ORF of the scFv by restriction enzyme digest (XhoI and NotI) and the DNA fragment purified. The plasmid pCDNA3.1 was cut with the same enzymes and the PSMA scFv fragment inserted using T4 DNA ligase to produce pCDNA3.1-J591scFv containing a scFv to PSMA under control of the CMV promoter and containing an in frame 3' 5×Pro-6×His tag (encoding PPPPPHHHHHH, SEQ ID 81). To incorporate an amber codon into this scFv, site-directed mutagenesis was used to insert an amber stop codon following the last 3' codon of the scFv, but prior to the 5×Pro-6×His tag. The resulting constructs named anti-PSMAscFV-117. Clones containing the amber codon were identified by DNA sequencing.

Transient expression of the anti-PSMAscFv-117 containing a nnAA were performed in HEK293 cells stably expressing pylRS. This cell line was generated by transfection of a vector containing the pylRS gene in pCEP4 (Life Technologies) and selection by growth in medium containing hygromycin DMEM B (DMEM (DMEM (Life Technologies), 2 mM glutamax, 1 mM sodium pyruvate, 6 mM glutamine, 1× non essential amino acids (Gibco CAT#11140-050), 10% fetal calf serum, and 0.2 mg/mL hygromycin). Surviving cells were cloned by limiting dilution and clones demonstrating high functional activity of the pylRS were expanded. This was achieved by transiently transfecting the different clones with a vector encoding tRNApyl and a reporter construct GFPY40 containing an amber codon at position Y40 in the presence of ALOC nnAA. Fluorescence levels were quantified in these cells using an Accuri flow cytometer and high functioning clones isolated. Expression of anti-PSMAscFv117 was performed using standard transfection conditions. Cells were plated to approximately 90% confluence and grown at 37° C. The following day, the plated cells were incubated with the appropriate DNA previously treated with a lipophilic reagent (Lipofectamine 2000, 293 fectin (invitrogen), according to the specific manufacturer's instructions. Following 2-5 days of growth in the presence of 1-2 mM Lys-azide, the growth medium was harvested and either used directly or the expressed proteins purified. Briefly, Expressed scFvs described here were purified from growth medium following transient expression of eukaryotic cells. In each case 0.1 volumes of 10×PBS was added to the expression supernatant to equilibrate the salts and pH of the sample. The expression supernatant was dialysed to PBS at 4° C. for 16 h. Protein was bound to Nickle-NTA beads (GE Healthcare) by batch binding or gravity flow and washed extensively with wash buffer (50 mM sodium phosphate pH7.4, 300 mM NaCl, 20 mM imidazole). Bound material was eluted with (50 mM sodium phosphate pH7.4, 300 mM NaCl, 250-500 mM imidazole). Fractions containing the target protein were identified by SDS-PAGE and coomassie staining. Peak fractions were pooled and dialysed against PBS prior to further use.

In a 200 uL PCR tube was placed a solution of anti-PSMA scFv with NNAA substituted at position 117 (0.3 mg/mL, 3.6 uL) was added followed by a solution of 20KPEG cyclooctyne (60 mg/mL, 1.0 uL). The solution was mixed vigorously on a vortexer (Fisher). The tube was placed on a PCR tube centrifuge for a few seconds to place all liquids into the bottom of the tube. The mixture was allowed to stand for 4 h.

The solution was diluted with reducing gel buffer (6 uL) to bring the final volume to ~10 uL. The samples were then loaded onto SDS-PAGE gels (4-20% Tris-Gly, Invitrogen). SDS-PAGE (reducing) indicated that the PEGylation was successful consuming the majority of the anti-PSMA scFv band. Reducing gel (FIG. 12A) Lane 2: anti-PSMA scFv with NNAA lys-azide incorporated at position 117, untreated. Lane 3: anti-PSMA scFv with NNAA lys-azide incorporated at position treated with 20KPEG linear PEG cyclooctyne To determine whether J591-scFv was functional and bound PSMA a cell based fluorescence assay was used. Prostate cancer PC3 (PSMA negative) and LNCaP (PSMA positive) and the breast cancer cell line A345 were grown in RPMI-1640. Cells were dissociated, counted and harvested by centrifugation. For each assay 500,000 cells were incubated with PBS containing 0.5% BSA for 1 hour at RT. Cells were then treated with 200 uL of a pCDNA3.1-J591 transfection supernatant and washed with PBS. The cells were then incubated with a Mouse anti-6×HIS antibody at 1 ug/mL (Clontech) for 1 hour at RT. Cells were washed with PBS and incubated with a Phycoerythrin conjugated anti-Mouse antibody (Miltenyi) for 30 mins at RT. Cells were washed with PBS and analysed by flow cytometry (Accuri). Internalization assays were conducted above with the following modifications: Purified PSMA was utilized for internalization assays. During the incubation with the anti-PSMA scFv a cohort of cells was also treated with sodium azide (0.1%) at 4° C. for 1 hour to inhibit the internalization of cell surface markers. Other incubations were conducted at 37° C. In addition after the final wash, surface staining was inhibited by the addition of Trypan Blue to quench the phycoerythrin signal.

Figure 61:
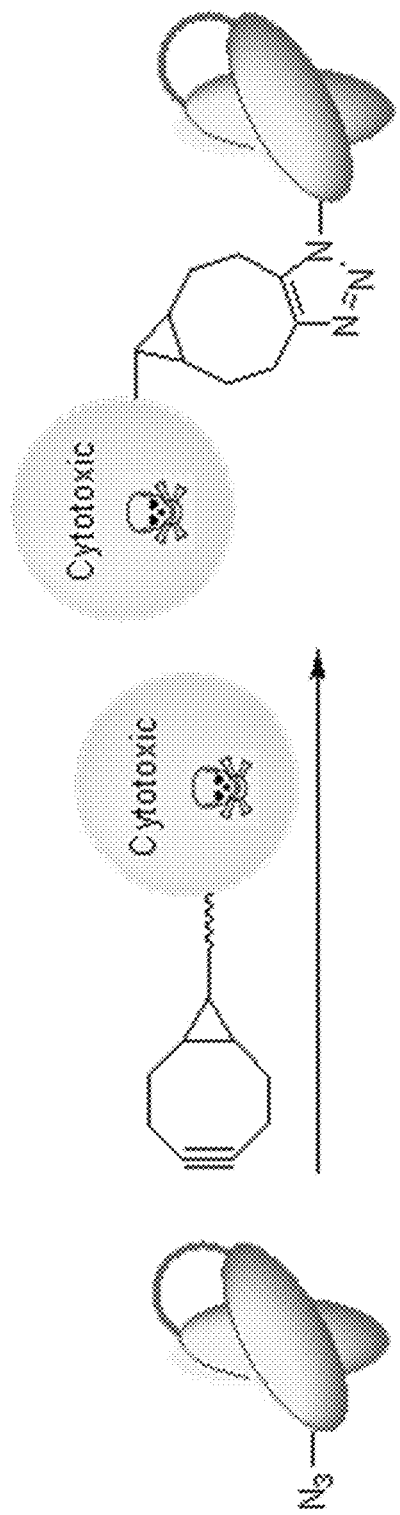
FIG. 61. A schematic showing conjugation of anti PSMA scFv with NNAA substituted at position 117 (anti-PSMAscFV-117) with monomethyl auristatin F (MMAF)-valine-citruline-p-amino-benzoyl-carbonate-cyclooctyne derivative.

Conjugation of Anti PSMA scFv with NNAA Substituted at Position 117 (Anti-PSMAscFV-117) with MMAF-Valine-Citruline-p-Amino-Benzoyl-Carbonate-Cyclooctyne Derivative (See FIG. 61)

Figure 12:
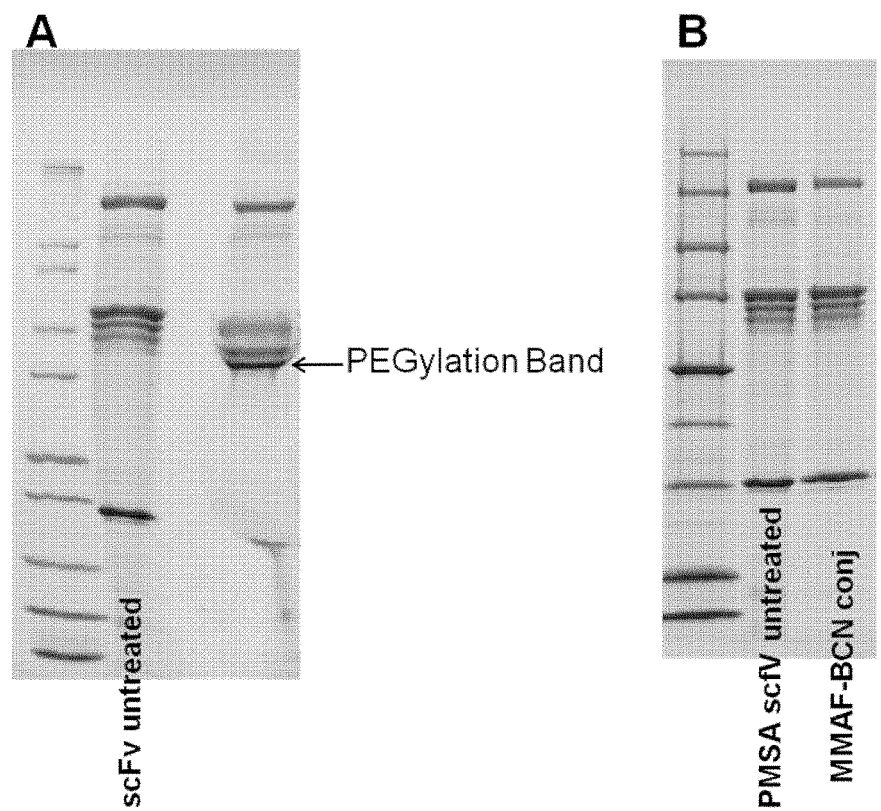
FIG. 12. Reducing gel of anti-PSMA scFv incorporating Lys-Azide conjugated to 20K linear PEG cyclooctyne (A) and Reducing gel of anti-PSMA scFv with nnAA Lys-Azide conjugated to MMAF-VCP-cyclooctyne (B)

In a 200 uL PCR tube was placed a solution of phosphates (50 mM, pH=7.4, 1 uL) and a solution of the anti-PSMAscFV-117 (40.5 uL, 2.1 mg/mL). To this was added a DMSO solution of the MMAF-valine-citruline-p-amino-benzoyl-carbonate-cyclooctyne derivative (3.46 uL, 13 mMol), the tube was capped and vortexed. The mixture was allowed to stand for 4 h. The reaction mixture was then treated with a solution of azidohomoalanine (AHA, 250 mM in 1M HEPES, 20 uL), vortexed and allowed to stand for 60 min. The mixture was then desalted through a ZEBA (Pierce) mini spin column to afford the final scFv-drug conjugate solution. Examination of the reaction mixture by SDS-PAGE (reducing) indicated a small molecular weight shift of the main PSMA band consistent with the conjugation of the drug moiety to protein. The slight shift in PAGE gel is also observed with a separate scFv construct, 28D2 (FIG. 12).

Example 11: Testing of Decoy Amino Acids

Effective dnnAAs were identified by their ability to compete with a high affinity substrate for pylRS (lys-azide) in an in vitro assay, for their ability to reduce background amber suppression levels observed with a reporter protein, and for their ability to improve the viability and function of cells previously selected for high pylRS/tRNA activity.

Figure 13:
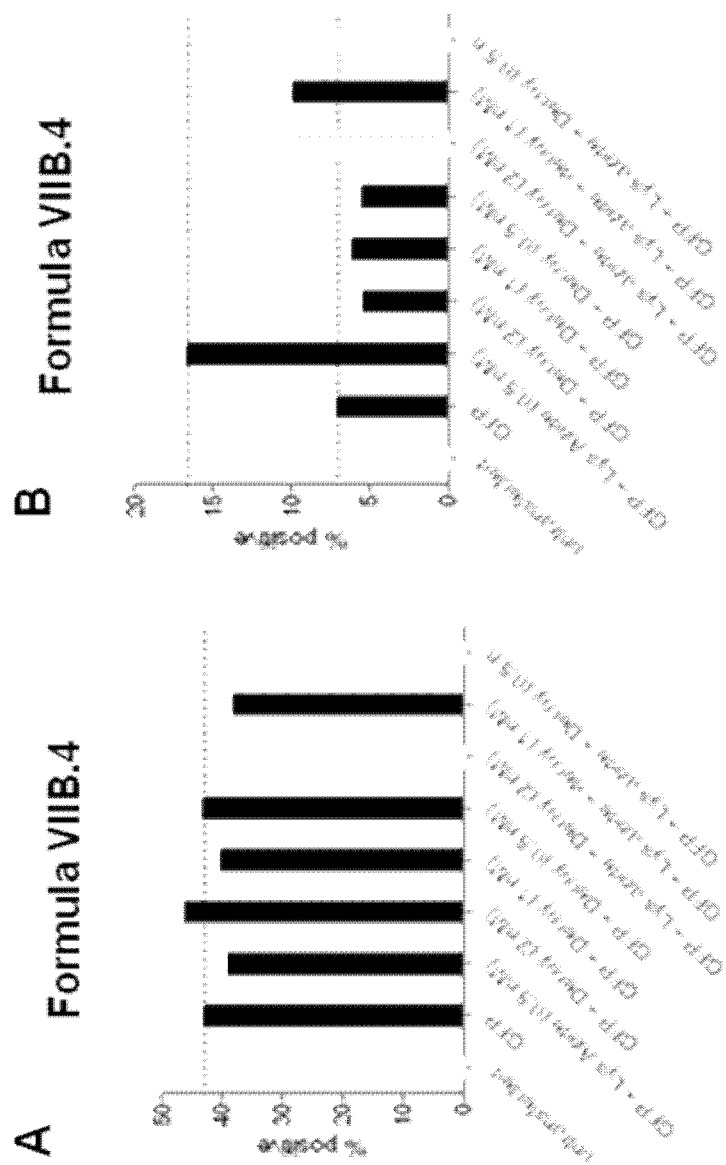
FIG. 13. In vitro functional assays examine the function and specificity of decoy nnAA competition with lys azide.

To identify analogues that could effectively compete for pylRS binding with lys-azide, dnnAAs were first tested for function in an in vitro functional assay based on the ability of cells expressing WT pylRS and tRNApyl to introduce a nnAA at a target site in the reporter protein GFPY40. This reporter contains an amber codon in its open reading frame that, in the absence of amber suppression, generates a truncated protein that is not fluorescent. In the event of amber suppression, a full length GFP protein is generated that is detectable by fluorescence detection methods. In this assay, HEK293 cells stably expressing pylRS, were transiently transfected with a tRNA expression construct and the GFPY40 reporter cassette. Cells were then incubated with 0.5 mM lys azide in the presence or absence of different concentrations of dnnAA ranging from 0.5 mM to 2 mM. GFP fluorescence levels were then quantified by flow cytometry. For this assay the proportion of fluorescent cells in each condition was determined and plotted. As the dnnAAs are expected to compete with the nnAA (lys-azide) for pylRS/tRNA binding, an effective dnnAA should reduce or prevent the expression of full length GFP (as described above dnnAAs can be delivered by the tRNA to the amber site, but cannot propagate protein synthesis). Several dnnAAs of Formula VII were tested: with the dnnAAs Formula VIIB.4 (FIG. 13) increasing concentration of the dnnAA led to a concomitant reduction in the number of fluorescent cells suggesting a dose-related effect (FIGS. 13 A and B). To determine whether the dnnAA enabled amber codon readthrough, transfected cells were also incubated with the dnnAA alone and GFP expression monitored by flow cytometry dnnAA of Formula VIIB.4 did not induce GFP expression. To control for non-specific effects of the dnnAAs, cells transfected with a reporter protein lacking an amber codon, thus producing wildtype GFP (GFPwt) independent of amber suppression, were also monitored in the presence of dnnAA (FIG. 13 A). dnnAA of Formula VIIB.4 (FIG. 13 A), showed no effect on protein expression, suggesting that the inhibition of amber suppression by this latter dnnAA is specific.

Figure 14:
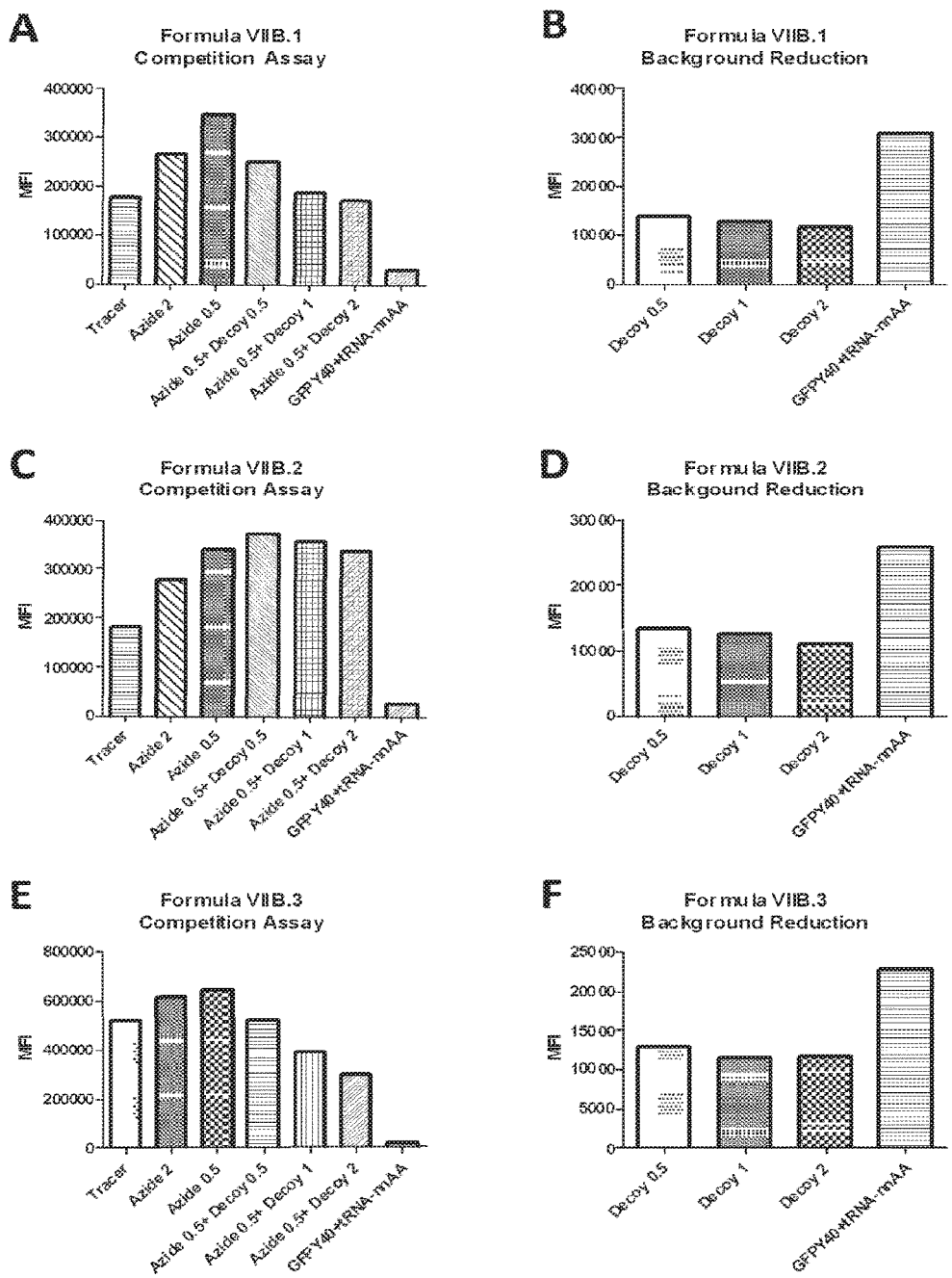
FIG. 14. In vitro functional assays examine the efficacy of dnnAAs function in competition with lys azide and their effect on background amber suppression in cells containing pylRS/tRNA.
Figure 14:
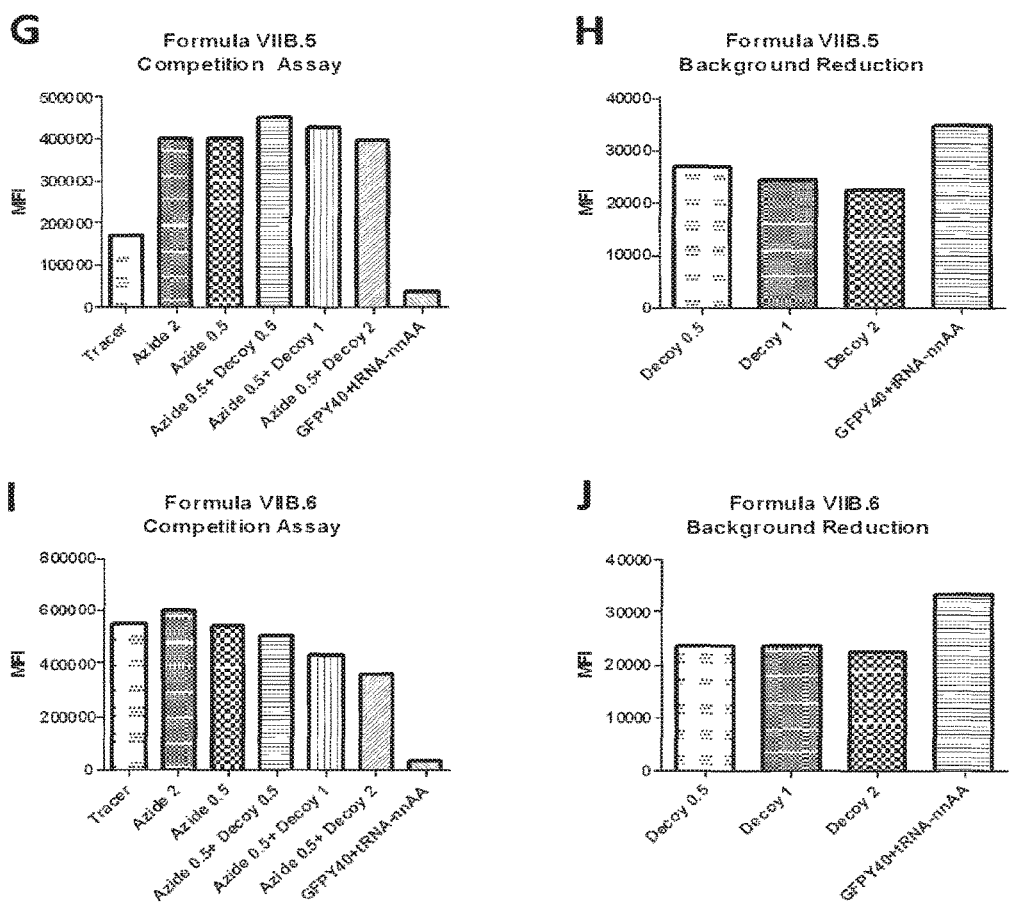

A similar in vitro assay was used to gauge the effectiveness of the dnnAAs of Formula VIIB listed in Table 1 where a description of the amino acids tested and a summary of the results are shown For this assay the geometric mean fluorescence intensity of each sample was determined by flow cytometry and plotted. For each dnnAA tested control cells transfected with wild type GFP were measured as a positive control. In addition cells transfected with the reporter GFPY40 and exposed to 0.5 mM lys azide or 2 mM lys azide were used to determine maximal GFP expression levels in the absence of an inhibitor. In each case robust GFP expression levels were observed. To test whether any of the dnnAA could reduce the efficacy of GFP expression, cells were incubated in the presence of 0.5 mM, 1 mM and 2 mM lys azide. A reduction of GFP expression concomitant with increased dnnAA concentrations was observed in all cases (FIG. 14). dnnAAs of Formula VIIB.1, Formula VIIB.3 and Formula VIIB.6 showed the greatest reduction of GFP expression relative to samples lacking dnnAA (FIG. 14A, E, I). Their inhibition of GFP expression increased with increasing concentrations of the dnnAA suggesting that these are specific high affinity substrates for pylRS. dnnAAs of Formula VIIB.2 and Formula VIIB.5 also showed a reduction in GFP expression with increasing concentrations of dnnAA (FIG. 14C,G). However, the relative reduction in GFP expression was much lower suggesting that these amino acid analogues have low affinity for the pylRS. Thus, dnnAAs of the present invention can compete with the lys-azide nnAA for binding to the pylRS and interfere with the physiological mechanism of nnAA introduction. Cells transfected with the pylRS/tRNA pair and the GFPY40 reporter construct but not exposed to either lys-azide or a dnnAA were used to determine levels of background amber suppression and used as a negative control. In each case low GFP expression levels were observed.

The competitive assay for dnnAA inhibition in the presence of a high affinity substrate identified dnnAAs that compete for binding with to the pylRS and thus are specific inhibitors of the pylRS/tRNA. However, the decoy nnAA is intended to reduce the levels of background amber suppression in the absence of nnAA. To determine if background amber suppression levels could be reduced, we incubated cells containing the GFPY40 reporter construct and the pylRS/tRNApyl pair in medium containing one of the dnnAAs. To do this, HEK293 cells stably expressing pylRS were transiently transfected with a tRNA expression construct and the GFPY40 reporter cassette. After 3 days of incubation, cells were assayed for expression of GFP by flow cytometry and geometric mean fluorescence intensity of the samples determined. We have previously observed that cells containing the full complement of the pylRS/tRNA amber suppression system show detectable expression of the GFP reporter construct that is above what is observed in cells lacking the amber suppression system. This observation suggests that there is non-orthogonal activity derived from the pylRS/tRNA pair that leads to higher amber suppression levels than in cells lacking the pylRS/tRNA pair. To identify dnnAAs capable of reducing background amber suppression levels the transfected cells were incubated with each of the dnnAAs at 0.5 mM, 1 mM and 2 mM and GFP levels measured by flow cytometry. The dnnAAs of Formula VIIB.1, Formula VIIB.3, Formula VIIB.6, Formula VIIB.2, and Formula VIIB.5 all showed reduction in the background amber suppression levels (FIG. 14D, F, J, D) relative to control samples (cells not containing dnnAA (FIG. 14A-J; GFPY40+tRNA-nnAA)).

The decrease in background amber suppression dependent GFP expression was dose dependent and improved as the dnnAA concentration increased. Interestingly, one of the dnnAA, of Formula VIIB.2 showed very efficient inhibition of background amber suppression in this assay, reducing GFP fluorescence levels by 57.7% relative to control samples but had not been identified as a strong competitor of lys-azide. This suggests that the dnnAA of Formula VIIB.2 may have low affinity for the pylRS that is easily displaced by lys-azide. This feature is an attractive characteristic for platform development as it enables the repression of background amber suppression but the system can be activated upon addition of a strong pylRS substrate such as lys-azide. These data suggests that the dnnAA can occupy the pylRS-tRNA pair and prevent amber suppression with natural amino acids. Formula VIIB.1 (62.5% resuction), Formula VIIB.3 (49.7%), Formula VIIB.6 (32%), and Formula VIIB.5 (35%) and Formula VIIB.4 (46.3%) were also effective in reducing background amber suppression levels in this assay. Their efficacy was quantified by the reduction in GFP expression relative to a control sample (not exposed to dnnAA) and the data are summarized in Table 1.

Table 1—Decoy nnAA of Formula VIIB

TABLE 1

Decoy nnAA of Formula VIIB

| Structure | IUPAC name | Formula | % Reduction at 2 mM Decoy |
|---|---|---|---|
| 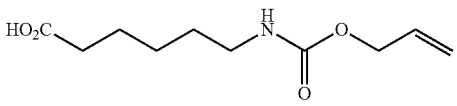 | 6-{[(prop-2-en-1-yloxy)carbonyl]amino}hexanoic acid | VIIB.1 | 62.5 |
| 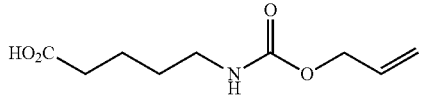 | 5-{[(prop-2-en-1-yloxy)carbonyl]amino}pentanoic acid | VIIB.2 | 57.7 |
| 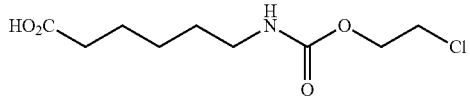 [SMILES: O=C(O)CCCCCNC(=O)OCCCl] | 6-{[(2-chloroethoxy)carbonyl]amino}hexanoic acid | VIIB.3 | 49.7 |
| 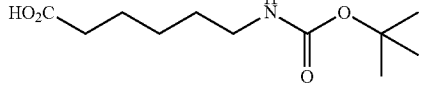 | 6-{[(tert-butoxy)carbonyl]amino}hexanoic acid | VIIB.4 | 46.3 |
| 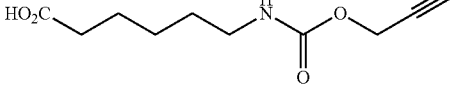 | 6-{[(prop-2-yn-1-yloxy)carbonyl]amino}hexanoic acid | VIIB.5 | 35.0 |
| 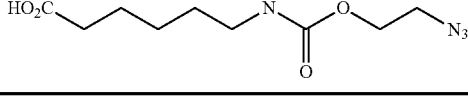 | 6-{[(2-azidoethoxy)carbonyl]amino}hexanoic acid | VIIB.6 | 32.7 |

Figure 15:
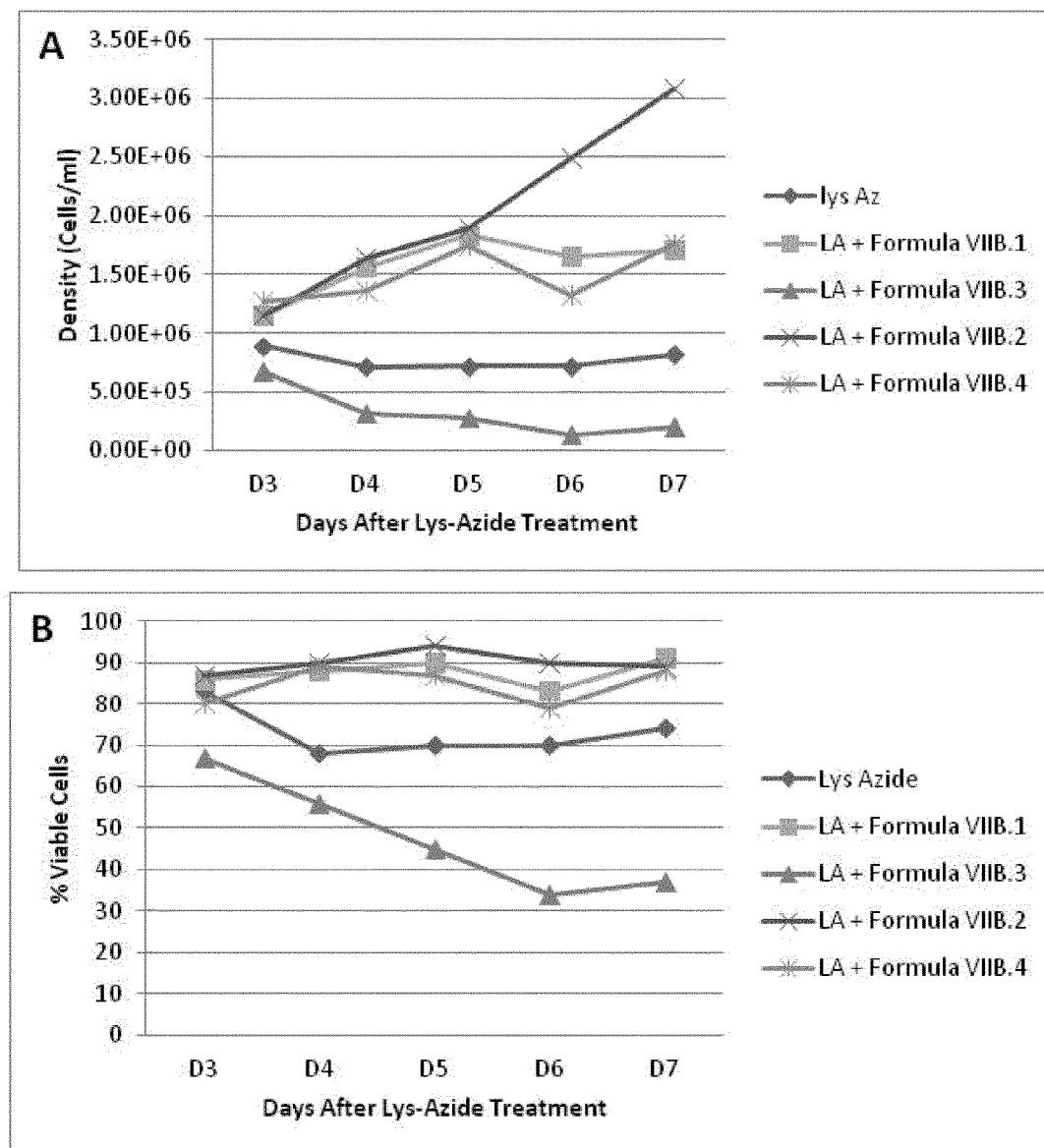
FIG. 15. Growth rate and viability assay of pylRS/tRNA containing cells grown in the presence or absence of decoy nnAA.

Example 12. Effect of Decoy nnAA of the Invention on Platform Cell Line Viability To examine whether the dnnAAs of the invention could function to improve the viability of cells containing pylRS and tRNApyl we monitored the growth and viability of a cell line, stably expressing pylRS and tRNApyl. For this assay CHO cells stably expressing pylRS and tRNApyl and an IgG directed against her2/neu containing an amber codon in the heavy chain, shown to effectively incorporate nnAA into the expressed IgG thus producing an antibody containing a nnAA, were used for this experiment. Despite a high expression level of pylRS/tRNApyl pair, this cell line has very robust cell growth characteristics when grown in medium lacking nnAA. The presence of a highly expressed target containing an amber codon likely has a protective effect on the cells by supplying them with high levels of amber codons that absorb the amber suppression activity and protects the cells from the effects of background amber suppression at essential genes. However, upon addition of the nnAA (lys-azide) to the growth medium, and activation of the amber suppression machinery, a decrease in cell growth rate is observed. That is, the cell density of the culture appears to remain stable, suggesting that activation of the amber suppression machinery results in a cytostatic effect. To determine whether a dnnAA can rescue this effect, cells cultured in serum free medium were grown to a cell density of $0.5\times10^6$ cells/mL and subsequently treated with 0.5 mM lys azide alone or in combination with 2 Mm dnnAA. Cell viability and cell numbers were monitored daily over seven days. Cells treated with lys azide alone reached a cell density just below $1\times10^6$ cells/mL on day 3 after nnAA addition and remained at this density for the remainder of the assay (seven days) (FIG. 15A) The lack of growth was not likely due to loss of viability as the culture retained high viability throughout the experiment (~70% viable cells) (FIG. 15B) Cultures treated with 2 mM Compound of formula VIIB.4, or 2 mM Formula VIIB.1 in combination with 0.5 mM lys-azide supported continued growth of the culture that reached over $1.5\times10^6$ cells/mL and retained a cell viability of 90%. Cells treated with the dnnAA of Formula VIIB.2 showed cell densitied over $3\times10^6$ and viability well over 90% for the duration of the assay. In contrast, cells treated with Formula VIIB.3 showed a decrease in cell viability over the course of the assay ($<0.5\times10^6$ cell/mL) and poor viability (30-40% by day 6). These data suggest that dnnAAs, of Formula VIIB.2, Formula VIIB.4, and Formula VIIB.1 prevent the cytostatic effects induced the activation of the amber suppression system. Cells grown in presence of the dnnAA of Formula VIIB.2 showed linear cell growth over time and reaching cell densities of $3\times10^6$, over the seven days. These data point the dnnAA of Formula VIIB.2 as the most efficient competitor of lys-azide for pylRS/tRNA function.

Figure 16:
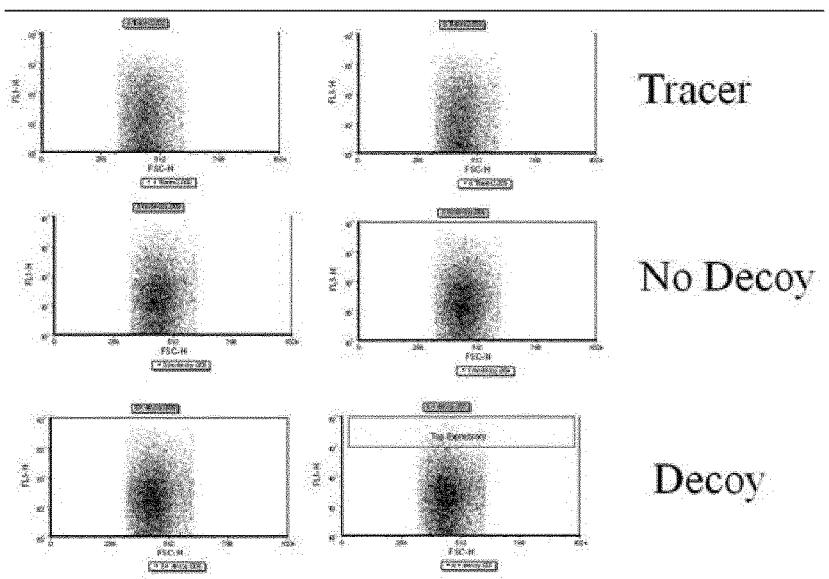
FIG. 16. Population analyses of pylRS/tRNA function in cells treated with decoy nnAA.

The data above showed that the dnnAA of Formula VIIB.2 is an efficient inhibitor of pylRS/tRNA and was shown to reduce the effects of amber suppression dependent cytostasis in a cell containing a highly active amber suppression machinery and expressing a target gene in the presence of nnAA. However, the intended use of the dnnAA is in protecting cells with highly active amber suppression machinery during their development and isolation. Thus, we next asked whether the dnnAA could improve the viability and performance of a cell pool enriched for a highly active amber suppression machinery (platform cell line). To do this a platform cell line, selected for high activity of the amber suppression machinery was grown in the presence or absence of dnnAA for several passages and subsequently seeded into 96-well plates at ten cells per well and grown in the presence or absence of dnnAA (Formula VIIB.2). Each plate was incubated for several days and cells harvested, pooled and counted. Interestingly, plates incubated with decoy nnAA showed higher cell numbers than those grown in the absence of dnnAA ($1.66 \times 10^6$, and $1.5 \times 10^6$ cells/mL without dnnAA and 3.0 and $3.7 \times 10^6$ cells/mL from cultures grown in dnnAA). This two fold increase in cell numbers may be due to the protective effects of the dnnAA. To examine the activity of the cells grown under these conditions, $0.5 \times 10^6$ cells pooled from each plate were seeded into a 6-well plate and transfected with a GFPY40 reporter construct in the absence of dnnAA and with lys-azide. After 24 hours the fluorescence intensity of the cells in each sample was analysed by flow cytometry. The data were gated to include single cells and plotted to display the intensity of each event (scatter plot, FIG. 16). The number of events falling within the top 10% of the GFP intensity spectrum were determined for each sample (Table 2). Cells grown in the presence of a dnnAA showed higher numbers of events falling within the established gate (n=139 no decoy and n=175 with decoy (Formula VIIB.2). This suggests that more high activity cells were preserved by growth in decoy nnAA containing medium. An additional metric was utilized to quantify the performance of cells by isolating the geometric mean for the top 300 events (Top 300) with highest GFP expression. Under this metric dnnAA incubated cells show improvement of performance over cells grown in the absence of dnnAA (GM=954 without decoy; GM=1142 with decoy (Formula VIIB.2). Cells from both groups were also transfected with a construct encoding wild type GFP. The same analyses were performed on this group. These data are summarized in Table 2 and indicate that cells grown in dnnAA (Formula VIIB.2) containing medium show higher numbers of highly fluorescent cells and higher fluorescence levels relative to the same cell line grown in the absence of dnnAA.

TABLE 2 dnnAA (Formula VIIB.2) increases amber suppression activity in platform cell population:

| Sample | Top 300 (GM) | # events in top gate |
|---|---|---|
| 1 - Tracer | 343 | 25 |
| 6 - Tracer | 529 | 59 |
| 1 No decoy | 1024 | 153 |
| 3 No decoy | 885 | 125 |
| 5 Decoy | 1149 | 179 |
| 6 Decoy | 1135 | 171 |

Figure 17:
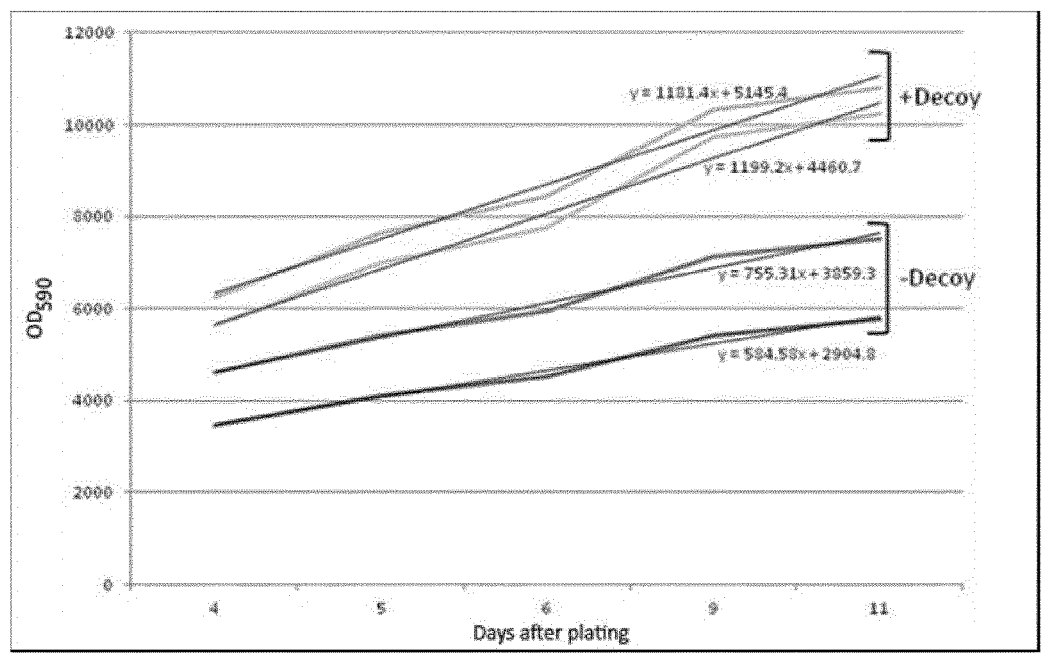
FIG. 17. Growth rates of cells containing the pylRS/tRNA pair examined in cultures treated with decoy nnAA.

The dnnAA appeared to preserve the viability of the platform cells, but also preserved cells with higher levels of amber suppression functionality. To further assess the effect of dnnAA on cell growth characteristics of a platform cell line containing a highly active amber suppression system we conducted a kinetic growth assay. To do this, the platform cell line was incubated in the presence or absence of dnnAA in 96-well plates as described above. Cells from each plate were pooled and seeded at 1000 cells per well in a 96 well plate in triplicate and cells incubated for four days. On the fourth day Alamar Blue dye was added to the cells and viability assayed by fluorescence emission. Alamar Blue serves as a convenient indicator of cell viability. Viable cells metabolize Alamar Blue producing resofurin which is a highly fluorescent dye. Fluorescence levels were monitored on days 5, 6, 9, and 11 and the fluorescence values plotted (FIG. 17). Decoy grown cells showed improved cell viability compared to cells grown in the absence of dnnAA. This was shown by fitting a line over the plotted growth rate and the slopes for each calculated. Cells grown in decoy nnAA containing medium showed faster growth rates (Avg slope=1190) than cells grown in the absence (Avg slope=669) of dnnAA. These data show that the use of a dnnAA protects the cells from the chronic effects of amber suppression and improves cell viability and growth of the culture. Taken together, these data point to dnnAAs as essential components for the development of platform cell lines and the preservation of cells with high amber suppression activity.

Example 13: Translational Testing of Novel Pyrrolysine Analogs as nnAAs with a GFP Assay An in vitro cell based assay was developed to assess the compatibility of the pylRS/tRNA pair and the pyrrolysine analogs of the present invention (nnAAs) by and the efficiency of nnAAs integration into a target protein. For this, HEK293 cells stably expressing pylRS (3H7) were transiently transfected with plasmids for the expression of tRNApyl and a reporter construct encoding GFPY40 (containing amber codon in place of tyrosine at amino acid residue number 40 (where 1 is the initiator methionine)) using standard transfection protocols. Transfected cells were incubated with nnAAs at 2 mM for 2-3 days GFP production was analyzed qualitatively by visual inspection under the microscope. The GFP fluorescence was quantified by flow cytometry using an Accuri flow cytometer and the geometric mean of the fluorescent cells determined.

This cell based assay was used to determine whether the different nnAAs were suitable substrates for the pylRS and allowed its translation into a target protein. Cells expressing the PylRS/tRNApyl pair and containing a vector encoding the GFPY40 reporter gene were incubated in the presence of the nnAAs. nnAAs that are readily utilized by the PylRS/tRNApyl pair support the translation of the nnAA into the amber site of GFP and allow read-through of the gene producing full length GFP (fluorescent protein). The fluorescence intensity of the cells depends on the efficiency of nnAA incorporation. Thus, nnAAs that are poorly utilized produce weakly fluorescent or non-fluorescing cells. Microscopic observation identified a number of nnAAs usable by the pylRS (Table 1, Positive GFP). Furthermore, the relative expression levels in each sample was compared to those generated by substrates known to be efficiently utilized by pylRS. Formula V.1 (MFI=931,289), Formula V.2 (MFI=1,676,250) and Formula V.3 (MFI=2,250,000) (see Table 3) supported high levels of GFP expression with a geometric mean.

Analog Formulae VI.1 and VI.3 and of the present invention were found by the inventors to be incorporated in the GFP reporter gene and yield green cells under the experimental conditions used. Among these, the analog of Formula VI.1 supported high levels of GFP expression (MFI 904206) and represents an analogue that is efficiently utilized by the pylRS/tRNA pair under the experimental conditions tested (see Table 4).

TABLE 3

Formula V analog GFP results

| Formula | IUPAC Name | Positive GFP | MFI |
|---|---|---|---|
| V.1 | (2S)-2-amino-6-{[(2-azidoethoxy)carbonyl]amino}hexanoic acid | Yes | 931289 |
| V.2 | (2S)-2-amino-6-{[(prop-2-yn-1-yloxy)carbonyl]amino}hexanoic acid | Yes | 1676250 |
| V.3 | (2S)-2-amino-6-{[(prop-2-en-1-yloxy)carbonyl]amino}hexanoic acid | Yes | 2250000 |

TABLE 4

Formula VI analog GFP results

| Formula | IUPAC Name | Positive GFP Assay | MFI |
|---|---|---|---|
| VI.1 | (2S)-2-amino-6-{[(2-azidoethyl)carbamoyl]oxy}hexanoic acid | Yes | 904206 |
| VI.3 | (2S)-2-amino-6-{[(prop-2-en-1-yl)carbamoyl]oxy}hexanoic acid | Yes | |

Construction and Expression of Anti-Her2 Antibody

A full length anti-Her2 antibody containing two non natural amino acids (one in each heavy chain) (4D5-2AZ ab) was expressed in mammalian cells. A nnAA, containing an azide moiety, was incorporated at the selected sites and purified by affinity chromatography using either protein A resin (GE Healthcare) or by IgSelect (GE Healthcare, 17096901). The purified material was then concentrated and subjected to a conjugation reaction.

An antibody directed to the extracellular domain of Her2/neu was generated by cloning the variable regions of both the heavy and light chains of the mouse antibody 4D5 into vectors containing genes encoding human IgG. The variable regions of 4D5 were generated by gene synthesis using overlapping oligomers and cloned into the human IgG1 frameworks encoded by pFUSE-CHIg-hG1 (IgG1 heavy chain; gamma) and pFUSE-CHLIg-hK (light chain; kappa; Invivogen) to generate a mouse-human hybrid. Amber codons were introduced into the heavy chain (gamma) at positions K274 by site directed mutagenesis. Clones containing the amber codon were identified by DNA sequencing. To generate an integrating construct the promoters and ORF for the heavy chain was amplified by PCR and cloned by restriction enzyme digestion and ligation into pOptivec (Life Technologies). The light chain and a single copy of the tRNA were joined by two step PCR method using overlapping oligomers and cloned into available sites into the pOptivec plasmid containing the heavy chain. The construct was then transfected into a CHO cell line containing the pylRS/tRNA pair and stably transfected cell lines showing high expression of the IgG selected. This represents a second example of a cell line stably expressing a mAb containing a nnAA indicating that the process has wide applicability for the use in the expression of mAbs. This cell line was utilized to generate IgG containing the nnAAs described above. The cells were grown to a density of $1$-$2 \times 10^6$ cells/mL in Excel DHFR-medium (Sigma-Aldrich) and nnAA added to culture to a final concentration of 1 mM. Cells were incubated for 5 days and IgG purified from the growth medium. Supernatants were harvested and subjected to centrifugation to collect suspended cells and other debris. The supernatant was then filtered through a 0.22 um filter to remove any particulate material prior to application to a chromatography column. The filtered supernatant was applied to a 1 mL-5 mL prepacked HiTrap protein A Sepharose at 1-5 mL/min flow rate using an AKTA chromatography system. The bound material and resin were washed with PBS to remove loosely bound proteins and the bound material eluted with 100 mM glycine (pH 3.0) at a flow rate of 1 mL/min. Peak fractions containing the target protein were neutralized with 0.1 fraction volumes of 1M Tris-HCl (pH8.0).

All constructs were dialyzed to PBS at 4° C. for 16 hours into the final phosphate buffer. The antibody with Formula VI.1 as nnAA incorporated into both of its heavy chains at position 274 was called "4D5-2AzAb-HC274-(2S)-2-amino-6-{[(2-azidoethyl)carbamoyl]oxy}hexanoic acid".

Figure 18:
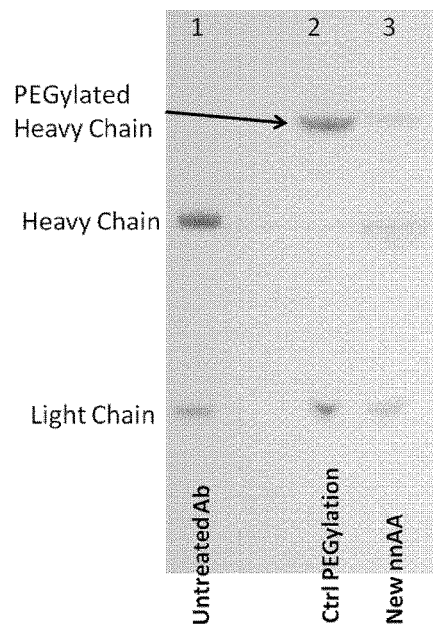
FIG. 18. PEGylation of azide containing monoclonal antibodies. Lane 1: Untreated Antibody, Lane 2: Antibody with pyrrolysine analog Formula V.1 incorporated into heavy chain and subjected to PEGylation conditions; Lane 3: Antibody with pyrrolysine analog Formula VI.1 incorporated into heavy chain and subjected to PEGylation conditions.

PEGylation of 4D5-2AzAb-HC274-(2S)-2-amino-6-{[(2-azidoethyl)carbamoyl]oxy}hexanoic acid In a 200 uL PCR tube was placed phosphate buffer (5 uL, 500 mM, pH=7.4). A solution of 4D5-2AzAb-HC274-(2S)-2-amino-6-{[(2-azidoethyl)carbamoyl]oxy}hexanoic acid (Formula VI.1). (10 uL, 0.55 mg/mL) was added followed by a solution of 20KPEG cyclooctyne (3.3, 60 mg/mL). The solution was mixed vigorously on a vortexer. The mixture was allowed to stand overnight. The mixture was diluted to 200 uL and applied to Protein-A magnetic beads. The mixture was vortexed and allowed to rotate to mix the beads for 90 min. The beads were immobilized and the run through material disposed. The beads were washed with PBS (2×) and then suspended in reducing gel buffer. Vortexed and then heated to 95 C for 3 min. The suspension was loaded directly onto an SDS-PAGE gel. Commassie staining of the SDS-PAGE gel indicated the selective PEGylation of the Heavy chain (FIG. 18, Lane 3).

Figure 19:
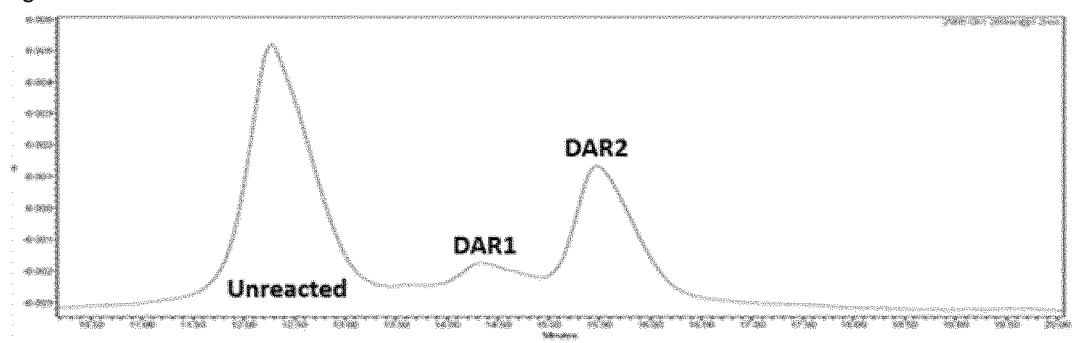
FIG. 19. HIC chromatogram of a 4D5-Auristatin F antibody drug conjugate with the antibody originally containing the pyrrolysine analog Formula VI.1, incorporated into the heavy chain.

Conjugation of 4D5-2AzAb-HC274-(2S)-2-amino-6-{[(2-azidoethyl)carbamoyl]oxy}hexanoic acid with Fluorescence dye by SPAAC In a 200 uL PCR tube was placed phosphate buffer (65 uL, 50 mM, pH=7.4). A solution of 4D5-2AzAb-HC274-(2S)-2-amino-6-{[(2-azidoethyl)carbamoyl]oxy}hexanoic acid (30 uL, 0.55 mg/mL) was added followed by a solution DMCO-Fluor 488 cyclooctyne (5.4, 5 mM in DMSO, click chemistry tools). The solution was mixed vigorously on a vortexer. The mixture was allowed to stand for 24 h. The mixture was analyzed by HIC chromatography (Tosoh TSK-gel Butyl NPR with a gradient of 1M Sodium sulfate to phosphate buffer) showing the conjugation had occurred and resulted in a mixture of DAR1 and DAR 2 species (FIG. 19).

Example 14: Additional nnAA Data

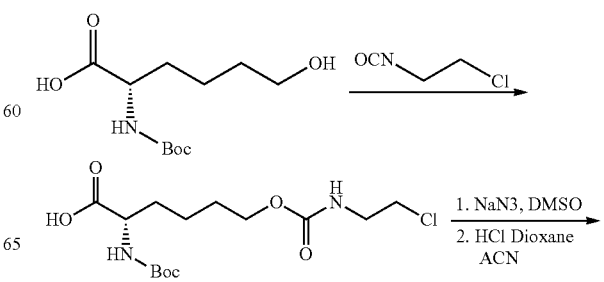

-continued

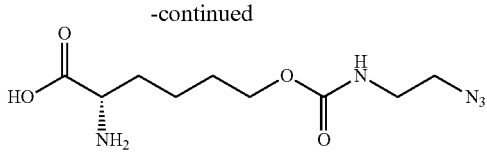

Alternative Preparation of (2S)-2-amino-6-[[(2-azidoethyl)carbamoyl]oxy]hexanoic acid, Formula VI.1

Step 1:

In a 4 mL vial with magnetic stirrer was placed Boc-N-6-hydroxynorleucine (50 mg, 1 eq) and DMF (1 mL). To this was added 2-chloroethyl isocyanate (17.3 mg, 1.0 eq) and pyridine (32.3 uL, 2 eq). The vial was capped and allowed to stir for 5 h. The solution was transferred to a extraction funnel, diluted with ethylacetate and 100 mM citric acid. The mixture shaken and the layers separated. The aqueous layer was extracted with ethyl acetate two additional times. The organic layers combined, washed with 5% lithium chloride, dried with sodium sulfate, filtered and concentrated. The product was taken forward into the next step directly. Analytical MS: m/z (ES+) calculated 352.1 (M+H)+. found 352.1.

Step 2:

In a 4 mL vial with magnetic stirrer was placed the crude chloro derivative from above and DMSO (1 mL). Sodium azide (130 mg, 5 eq) and pyridine (32.3 uL, 2 eq) were added to the mixture and the vial was capped. The mixture was stirred overnight at 60° C. The mixture was transferred to an extraction funnel and diluted with 100 mM citric acid and ethyl acetate. The mixture was shaken and the layers separated. The aqueous layer was extracted with ethyl acetate two additional times. The organic layers combined, washed with 5% lithium chloride, dried with sodium sulfate, filtered and concentrated. The product was carried on to the next step. Analytical MS: m/z (ES+) calculated 359.2 (M+H)+. found 360.2.

Final Step:

In a 20 mL vial was placed the crude Boc protected amino acid and acetonitrile (2 mL). To this was added a solution of hydrochloric acid in dioxane (4N, 2.5 mL). The solution was stirred for 2 h and then concentrated under reduced pressure. The mixture was lyophilized to a semi solid and used in translational testing. Analytical MS: m/z (ES+) calculated 259.1 (M+H)+. found 260.2.

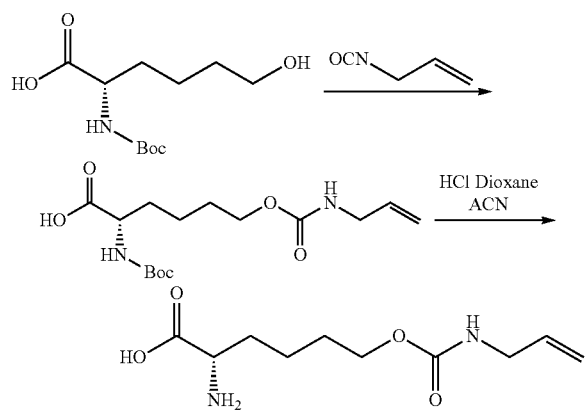

Preparation of (2S)-2-amino-6-{[(prop-2-en-1-yl)carbamoyl]amino}hexanoic acid, Formula VI.3

In a 4 mL vial with magnetic stirrer was placed Boc-N-6-hydroxynorleucine (50 mg, 1 eq) and DMF (1.5 mL). To this was added allyl isocyanate (18.0 uL, 1.0 eq) and pyridine (32.3 uL, 2 eq). The vial was capped and allowed to stir for 4 h. The solution was transferred to an extraction funnel, diluted with ethylacetate and 100 mM citric acid. The mixture shaken and the layers separated. The aqueous layer was extracted with ethyl acetate two additional times. The organic layers were combined, washed with 5% lithium chloride, dried with sodium sulfate, filtered and concentrated. The product was identified by mass spectrometry and taken forward into the next step directly. Analytical MS: m/z (ES+) calculated 330.2 (M+H)+. found 331.3.

In a 20 mL vial was placed the crude hydroxyl leucine-allyl carbamate derivative in acetonitrile (2 mL). To this was added a solution of hydrochloric acid in dioxane (4N, 2.5 mL). The solution was stirred for 2 h and then concentrated under reduced pressure. The mixture was lyophilized to a semi solid and used in translational testing. The product was confirmed by mass spectrometry. Additional purification could be done with ion exchange chromatography (DOWEX-50). Analytical MS: m/z (ES+) calculated 230.1 (M+H)+. found 231.2.

Example 15: IgG First Stable Cell Line

A cell line expressing Herceptin, capable of introducing a NNAA at position 274 was constructed. DG44 CHO cells were transfected with two vectors, one containing the expression cassette for the heavy chain in pOptivec, and one for the light chain in pcDNA3.1 (hygro+) of Herceptin, and containing an amber codon at position H274. Cells were selected in medium containing hygromycin and subsequently selected for expression by growth in medium containing Methotrexate. High expressing clones of the truncated IgG were isolated by cloning. The best expressing clone was transfected with a vector enconding pylRS and 18 copies of the U6-tRNApyl (pMOAV-2 puro). Transfected cells were selected by virtue of antibiotic resistance and cells showing the highest amber suppression activity identified through ELISA assays quantifying their full length IgG expression after exposing clones to nnAA (lys-Azide). A clone showing stable expression of IgG containing nnAA at 12 ug/mL was isolated. This data illustrates a third example of the construction of a mAb expressing cell line capable of nnAA incorporation by the pylRS/tRNA pair. In addition, this approach differs from the methods utilized previously in the order of introduction of the functional elements.

Example 16: IgG Positional Mutations for Introduction of nnAAs

Example 5, the introduction of a mutation at heavy chain position 274 in the anti-IL6 and Anti Her2 antibodies and the successful conjugation of the modified antibodies to various molecules were described.

Here, new IgG positional mutants and generation of DAR2 and DAR4 ADCs are described, from introduction of the mutation onto the cDNA to Cytotoxicity data of the ADCs.

Figure 20:
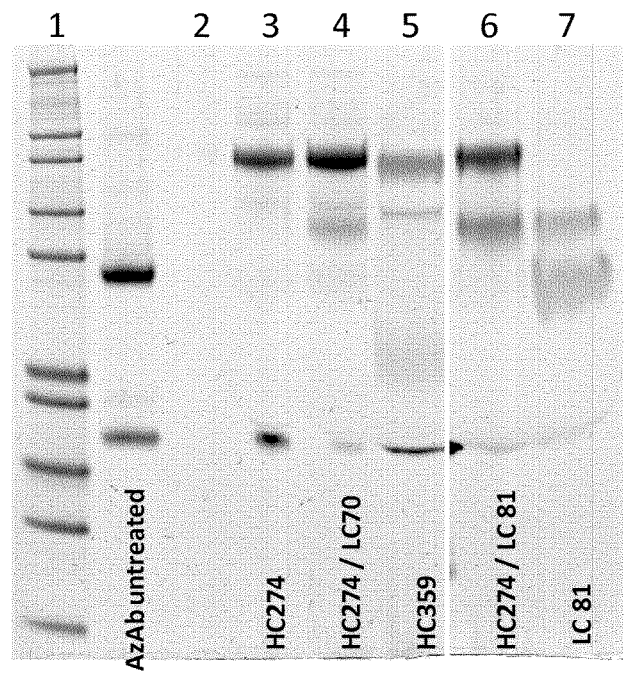
FIG. 20. SDS PAGE analysis of PEGylated 4D5 positional mutants

4D5 anti Her2 antibody was constructed with amber stop codons placed individually at positions H274 and H359 of the heavy chain and L70 and L81 of the light chain. The H274, H359 and L81 were expressed as individual mutants and H274 was also expressed with either L70 or L81 as double mutant in HEK293 cells. These 4D5 mutants were co-expressed with Pyl-tRNA in HEK cells stably expressing PylRS. The supernatants were purified on protein A and mAbs were PEGylated and analyzed by PAGE (FIG. 20). The data indicate that PEGylation occurs efficiently at each position, with conjugation to multiple positions simultaneously occurring as exemplified by the DAR4 species present in the reaction mix. 4D5-AzAb (HC274) and 4D5-4AzAb (HC359) undergo a clear molecular weight shift as a result of site specific PEGylation in the SDS-PAGE gel. Likewise, 4D5-AzAb (LC81) also shows a similar increase in molecular weight as observable on PAGE gel. The heavy chain remains untouched (though distorted by residual PEG moving through the gel). The HC274 and LC81 mutant containing four azides (4D5-AzAb (HC274-LC81)) also readily PEGylated and was detectable by SDS-PAGE gel. Both the heavy and light chains show significant molecular shifts, similar to those of the antibodies containing two azides (FIG. 20).

PEGylation of Positional Mutants

PEGylation of 20K Linear PEG-Cyclooctyne to 4D5-AzAb (LC81)

In a 200 uL PCR tube was placed a solution of 4D5-2AzAh (LC81) (8 uL, 0.106 mg/mL) was added followed by a solution of 20KPEG cyclooctyne (2.0 uL, 60 mg/mL). The solution was mixed vigorously on a vortexer. The tube was placed on a PCR tube centrifuge for a few seconds to place all liquids into the bottom of the tube. The mixture was allowed to stand for 24 h and then analyzed by SDS-PAGE (FIG. 20). Modification of the light chain was evident by a clear molecular weight shift consistent with the incorporation of a 20 kDa MW PEG (Lane 7).

PEGylation of 20K Linear PEG-Cyclooctyne to 4D5-AzAb (HC359)

In a 200 uL PCR tube was placed a solution of 4D5-AzAb (HC359) (8 uL, 0.145 mg/mL) was added followed by a solution of 20KPEG cyclooctyne (2.0 uL, 60 mg/mL). The solution was mixed vigorously on a vortexer. The tube was placed on a PCR tube centrifuge for a few seconds to place all liquids into the bottom of the tube. The mixture was allowed to stand for 24 h and then analyzed by SDS-PAGE (FIG. 20) The Azide containing antibodies with the azide at position 359 showed a clear molecular weight shift, specific to the heavy chain, as a result of site specific PEGylation (Lane 5).

PEGylation of 20KPEG Cyclooctyne to 4D5-AzAb (HC274: LC70)

In a 200 uL PCR tube was placed a solution of 4D5-AzAb(HC274: LC70) (2 uL, 0.47 mg/mL). A solution of 20KPEG cyclooctyne (1.0 uL, 60 mg/mL) was added and the solution mixed vigorously on a vortexer. The tube was placed on a PCR tube centrifuge for a few seconds to place all liquids into the bottom of the tube. The mixture was allowed to stand for 24 h and then analyzed by SDS-PAGE (FIG. 20). Both the heavy and light chains experience a clear molecular weight increase in the PAGE gel as a result of having a single PEG attached site specifically by the conjugation (Lane 6).

Conjugation of Cytotoxic Agents to Positional Mutants

Figure 21:
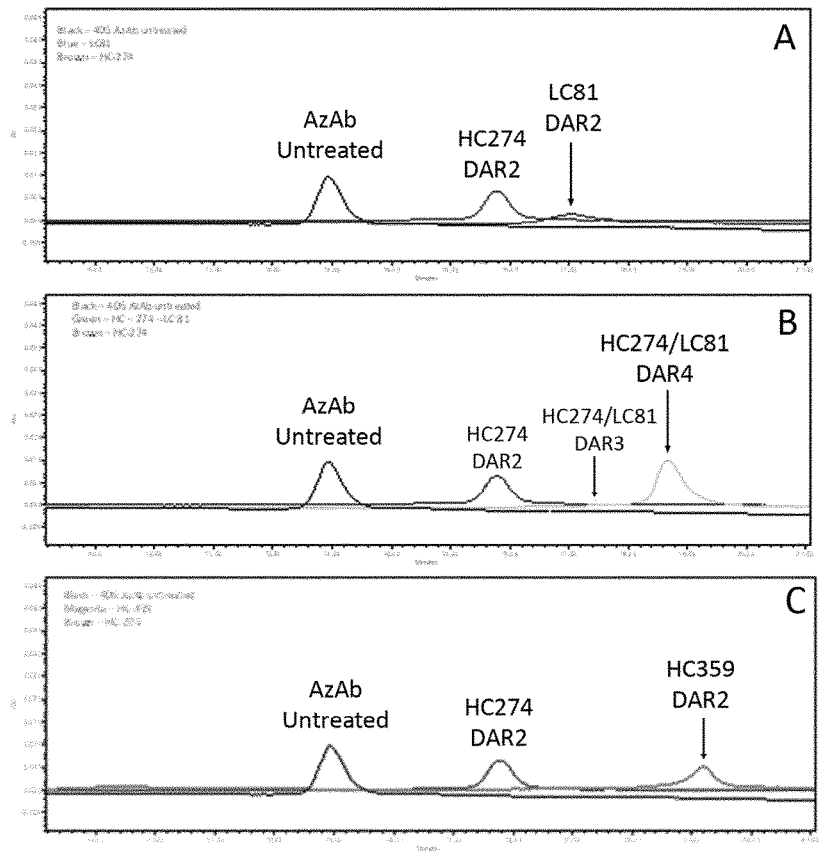
FIG. 21. Reaction analysis of Auristatin conjugation to 4D5-AzAb's with the azide incorporated at different positions by HIC chromatography.
Figure 22:
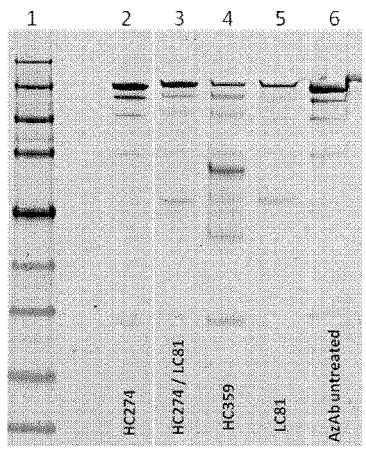
FIG. 22. SDS-PAGE of ADCs derived from positional mutants of 4D5 azide

Conjugation of 4D5-AzAb (LC81) with AF-Cyclooctyne derivative. In a 200 uL PCR tube was placed a solution of 4D5-AzAb (LC81) (150 uL, 0.106 mg/mL) and a DMSO solution of AF-Cylcooctyne (20 uL, 0.5 mMol), the tube was capped and vortexed and allowed to stand for 24 h. The reaction mixture was then treated with a solution of azidohomoalanine (AHA, 250 mM in 1M HEPES, 20 uL), vortexed and allowed to stand for 2 h. The mixture was then desalted through two mini ZEBA (Pierce) spin column to afford the final ADC solution. The mixture was analyzed by SDS-PAGE (FIG. 22) and HIC chromatography (FIG. 21). The resulting conjugate appeared as a single species in the HIC chromatogram and was slightly more hydrophobic than the HC274 variant as determined by retention time. SDS-PAGE (Non-reducing) indicated a slight increase in MW as a result of conjugating the drug (FIG. 22).

Conjugation of 4D5-AzAb (HC359) with AF-Cyclooctyne Derivative

In a 200 ul PCR tube was placed a solution of 4D5-AzAb (HC359) (150 uL, 0.145 mg/mL) and a DMSO solution of AF-Cyclooctyne (20 uL, 0.75 mMol), the tube was capped and vortexed and allowed to stand for 24 h. The reaction mixture was then treated with a solution of azidohomoalanine (AHA, 250 mM in 1M HEPES, 20 uL), vortexed and allowed to stand for 2 h. The mixture was then desalted through two mini ZEBA (Pierce) spin column to afford the final ADC solution. The mixture was analyzed by HIC chromatography (FIG. 21). The resulting conjugate appeared as a single species in the HIC chromatogram and was significantly more hydrophobic than the HC274 variant as determined by retention time. SDS-PAGE also indicated the formation of a band which was higher in molecular weight than the parent antibody for the HC359 variant.

Conjugation of 4D5-AzAb (HC274: LC81) with AF-Cyclooctyne Derivative

In a 200 uL PCR tube was placed a solution of 4D5-AzAb (HC274: LC81) (150 uL, 0.187 mg/mL) and a DMSO solution of AF-Cylcooctyne (20 uL, 1 mMol), the tube was capped and vortexed and allowed to stand for 24 h. The reaction mixture was then treated with a solution of azidohomoalanine (AHA, 250 mM in 1M HEPES, 20 uL), vortexed and allowed to stand for 2 h. The mixture was then desalted through two mini ZEBA (Pierce) spin column to afford the final ADC solution. The mixture was analyzed by SDS-PAGE (FIG. 22) and HIC chromatography (FIG. 21). The resulting conjugate appeared as a predominantly single species in the HIC chromatogram and was significantly more hydrophobic than the DAR2 HC274. An increase in molecular weight was also observed in the SDS-PAGE under non reducing conditions.

Conjugation of 4D5-AzAb (HC274: LC70) with AF-Cyclooctyne Derivative

In a 200 uL PCR tube was placed a solution of 4D5-AzAb (HC274: LC74) (50 uL, 0.47 mg/mL) and a DMSO solution of AF-Cylcooctyne (5 uL, 3 mMol), the tube was capped and vortexed and allowed to stand for 24 h. The reaction mixture was then treated with a solution of azidohomoalanine (AHA, 250 mM in 1M HEPES, 20 uL), vortexed and allowed to stand for 2 h. The mixture was then desalted through two mini ZEBA (Pierce) spin column to afford the final ADC solution. The mixture was analyzed by SDS-PAGE (FIG. 22). An increase in molecular weight was observed in the SDS-PAGE under non reducing conditions.

In Vitro Cytotoxic Activity

The ADC's generated as described above were tested for cytotoxic activity in SKOV3 and HCC1954 and PC3 tumor cell lines which are standard target cells for testing the activity of anti Her2 antibodies and ADC cell lines. SKOV3 and HCC1954 express high levels of Her2, while PC3 expresses Her2 at low level: the cytotoxic activity was calculated as the concentration of ADC to kill 50% of the tumor cells in vitro as described in Table 5. Notably, Herceptin alone exerts no cytotoxic effect on any of the cell lines tested.

TABLE 5 the EC50 (in nM) are shown which represent the concentration of the drug to kill 50% of the tumor cells in vitro:

|  | EC$_{50}$ nM | | |
| --- | --- | --- | --- |
|  | PC3 | HCC1954 | SKOV3 |
| HC-274 | DNC | 0.02123 | 0.1869 |
| HC-274/LC-70 | DNC | 0.03059 | 0.1083 |
| HC-274/LC-81 | DNC | 0.01493 | 0.05233 |
| HC-359 | 1.327 | 0.02414 | 0.1604 |
| LC-81 | 1.133 | 0.04365 | 0.201 |
| AF | 103.5 | 18.81 | 69.39 |
| Herceptin | DNC | 0 | 0 |

Figure 23:
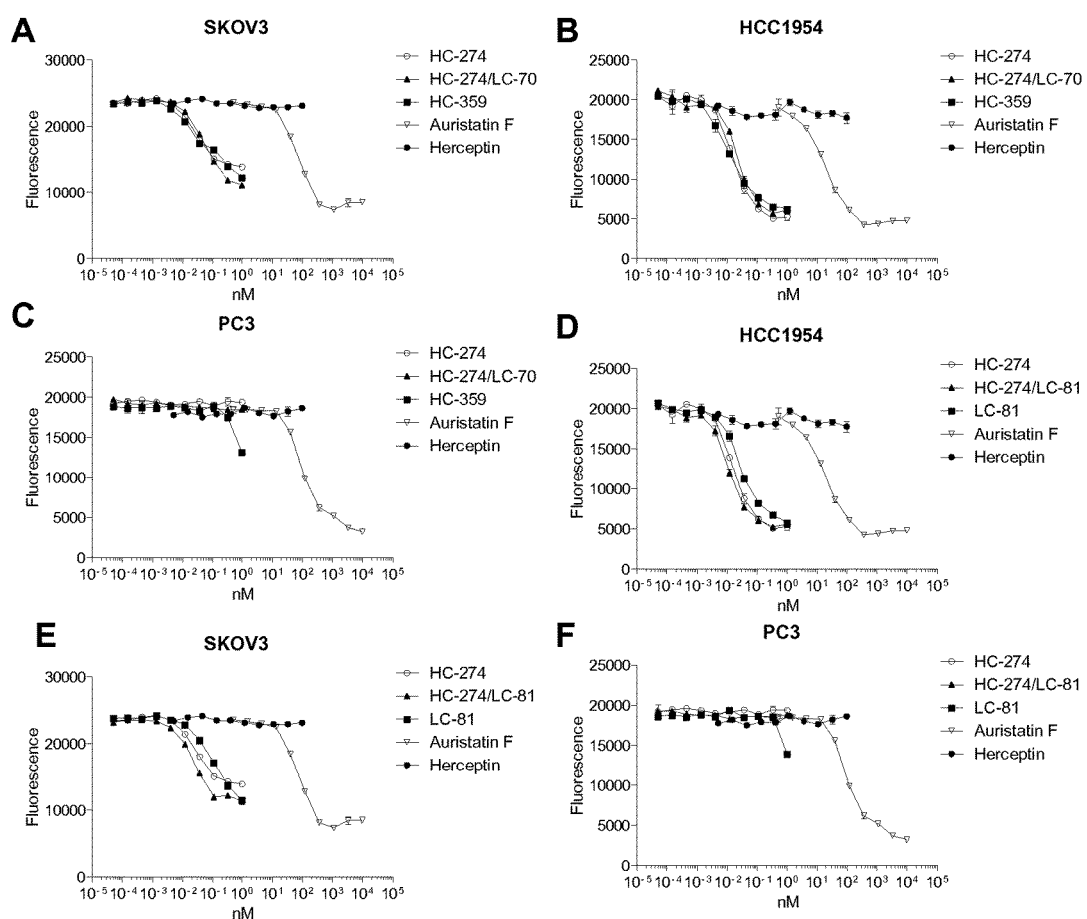
FIG. 23. Potency and selectivity assessment of positional variants of 4D5-2AzAb Auristatin antibody drug conjugates by an in vitro cytotoxicity assay versus high and low express Her2 cell lines.

As shown in FIG. 23 D, E, F, for each positional mutant, DAR2 and DAR4 ADCs were compared. In each Her2 positive tumor cell line, the DAR4 ADC was more potent than either DAR2, confirming the delivery of more drug with the DAR4 than the DAR2 ADC.

FIG. 23 shows the cytotoxicity assay from which the EC50 values in Table 5 were derived.

FIG. 23A shows the tumor cytotoxic activity of the 4D5-AzAb (HC274)-AF and 4D5-AzAb (HC359)-AF DAR2 ADC's as well as the 4D5-AzAb (HC274,LC-70)-AF DAR4 ADC in the SKOV3 tumor cell line. These cells are resistant to Herceptin alone but efficiently killed by the ADC with toxin conjugated at different positions. Clearly, the ADC greatly lowers that concentration of AF required to kill the tumor cells, presumably by efficiently targeting all of the AF directly to the cell, as compared to passive diffusion.

FIG. 23B shows the tumor cytotoxic activity of the 4D5-AzAb (HC274)-AF and 4D5-AzAb (HC359)-AF DAR2 ADC's as well as of the 4D5-AzAb (HC274,LC-70)-AF in HCC1954 cells. Similarly to SKOV3 cells, HCC1954 cells are resistant to Herceptin, but efficiently killed by the ADC, with toxin conjugated at different positions.

FIG. 23C shows the tumor cytotoxic activity of 4D5-AzAb (HC274)-AF and 4D5-AzAb (HC359)-AF DAR2 ADC's as well as the 4D5-AzAb (HC274,LC-70)-AF DAR4 ADC in the PC3 tumor cell line which expresses very low levels of Her2 and is much more resistant to tumor killing by the ADC, as seen in this figure as well as Table 5.

FIG. 23D shows the tumor cytotoxic activity in HCC1954 cells, a Her2 overexpressing tumor cell line, of the 4D5-AzAb (HC274)-AF and 4D5-AzAb (LC-81)-AF DAR2 ADC's as well as the 4D5-AzAb (HC274,LC-81)-AF DAR4 ADC. As seen in the figure as well as Table 5, the DAR4 ADC is more potent that either DAR2 constituents.

FIG. 23E shows the tumor cytotoxic activity in SKOV3 cells, a Her2 overexpressing tumor cell line, of the 4D5-AzAb (HC274)-AF and 4D5-AzAb (LC-81)-AF DAR2 ADC's as well as the 4D5-AzAb (HC274,LC-81)-AF. As seen in the figure as well as Table 5, the DAR4 ADC is more potent that either DAR2 constituents.

FIG. 23F shows the tumor cytotoxic activity in PC3 cells, a tumor cell line that expresses very low Her2, of the 4D5-AzAb (HC274)-AF and 4D5-AzAb (LC-81)-AF DAR2 ADC's as well as the 4D5-AzAb (HC274,LC-81)-AF. As seen in the figure as well as Table 5, there is very little or no activity of these ADC against this target.

Example 17: Pharmacokinetics, Stability, and In Vivo Anti Tumor Activity of Antibodies Conjugated at HC274 Position Conjugation of Anti-Her2 Antibody (4D5 AzAb (HC274)) with DBCO-Fluor 488

Figure 24:
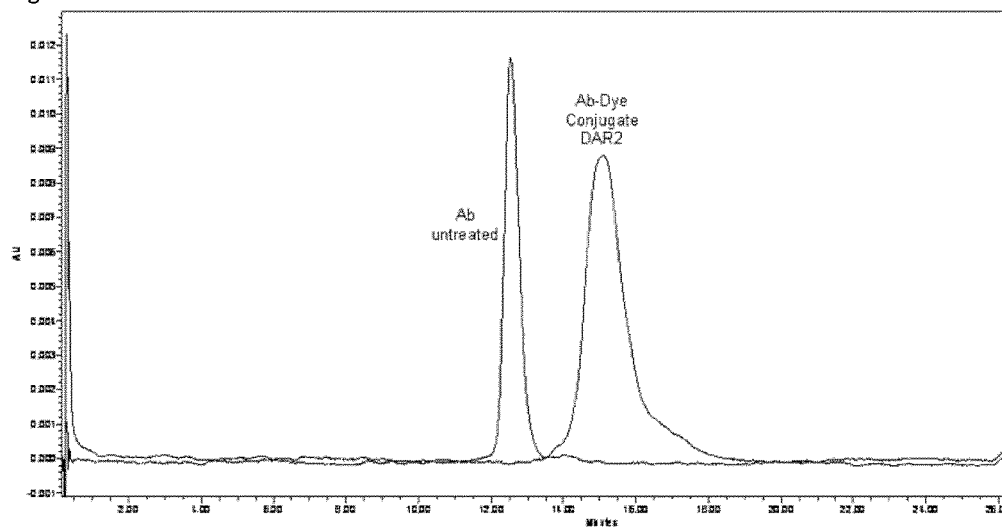
FIG. 24. Reaction analysis of 4D5-2AzAb(HC274) conjugation to a fluorescent dye by HIC chromatography.

In a 1000 uL HPLC vial equipped with magnetic stirrer was placed a solution of phosphates (511 uL, 50 mM, pH=7.4) and a solution of the 4D5-AzAb (164 uL, 6.87 mg/mL). To this was added a DMSO solution DBCO-Fluor 488 (75 uL, 10 mM in DMSO) the tube was capped and stirred for 24 h The reaction mixture was then treated with a solution of azidohomoalanine (AHA, 250 mM in 1M HEPES, 50 uL), and stirred for 2 h. The mixture was then desalted through a ZEBA (Pierce) 2 mL spin column to afford the final antibody-dye conjugate. The material was assessed by HIC chromatography and SDS-PAGE. HIC chromatography indicated the formation of a single major species, consistent with the addition of two dye molecules per antibody (FIG. 24).

Rats were injected IV with 4D5 AzAb (HC274)-DBCO-Fluor 488 or Herceptin at a dose of 1 mg/kg, and serum levels of the two molecules were monitored for 11. days using an anti-IgG ELISA.

Figure 25:
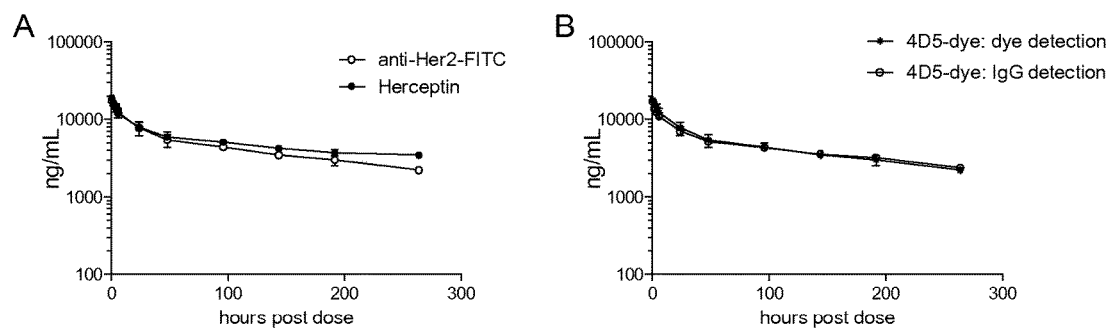
FIG. 25. Pharmacokinetics and stability of 4D5 modified at position H274

As shown in FIG. 25A, the modification of IgG at the constant heavy chain position 274 does not affect the pharmacokinetic profile as measured by serum levels and when compared to unmodified Herceptin.

The rat neonatal Fc receptor for IgG recognizes the human IgG Fc domain at the same residues as the human FcRn. Modified human IgG such as the ADC's of the present invention, will be retained in vivo for extended periods of time, due to the function of the rat FcRn, as long as the interaction of the conjugate and the FcRn remains intact. These data demonstrate that HC-274 modified IgG retains a long in vivo half life in rat, indicating that the FcRn Interaction is not blocked by the conjugate. The same residues on 4D5 that interact with the rat FcRn are also responsible for the interaction with human FcRn. These data show that the ADC with a conjugate at HC-274 will interact with the human FcRn and therefore retain a long half life in man.

The same sera collected for the PK analysis shown in FIG. 25A were tested for the presence of the FITC conjugate on the 4D5 IgG (FIG. 25B) by a quantitative ELISA assay in which the antibody is captured by Her2 extracellular domain protein coated on plastic ELISA wells. After incubation, the wells are washed and incubated with anti-FITC antibody conjugated to HRP. After incubation, the wells are washed and HRP substrate added. This ELISA measures the amount of FITC remaining on the ADC, and is reported as ng/ml of ADC with all the FITC intact, as shown in FIG. 25B. The 4D5 ADC in the sera with DAR2 is the same level as the untreated ADC, indicating no loss of FITC. The data clearly indicate that the dye is completely retained and stable in vivo in rat for the full 11 days of the study.

Conjugation of 4D5-AzAb (HC274) with AF-Cycloalkyne Derivative.

Figure 26:
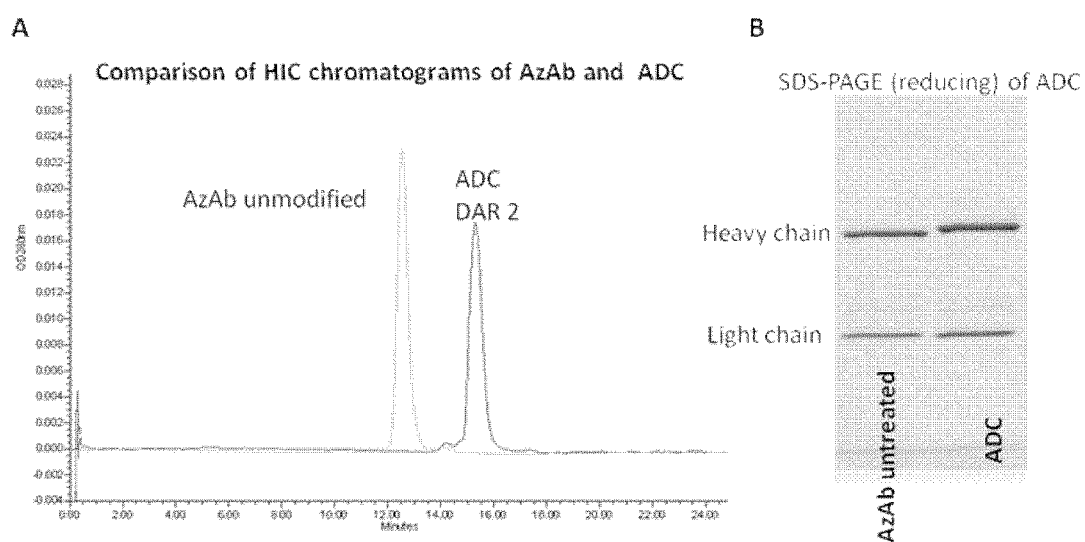
FIG. 26. Overlay of HIC chromatograms of unconjugated antibody and 4D5-2AzAb(HC274)-Auristatin F antibody drug conjugate prepared with Auristatin Cyclooctyne derivative.

In a 1000 mL HPLC tube with magnetic stirrer was placed a solution of phosphates (24 uL, 50 mM, pH=7.4) and a solution of the 4D5-AzAb (149 uL, 6.87 mg/mL). To this was added a DMSO solution of 5 (27.2 uL, 2 mMol), the tube was capped and vortexed. The mixture was allowed to stand for 24 h. The reaction mixture was then treated with a solution of azidohomoalanine (AHA, 250 mM in 1M HEPES, 50 uL), vortexed and allowed to stand for 60 min. The mixture was then desalted through a ZEBA (Pierce) 2 mL spin column to afford the final ADC solution. The mixture was analyzed by HIC chromatography and SDS-PAGE (FIGS. 26A and B). HIC chromatography indicated the formation of a major species consistent with two auristatin molecules being added per antibody. SDS-PAGE (reducing) indicated a small molecular weight shift to the heavy chain consistent with the addition of a auristatin molecule being added.

In Vitro Activity

Figure 27:
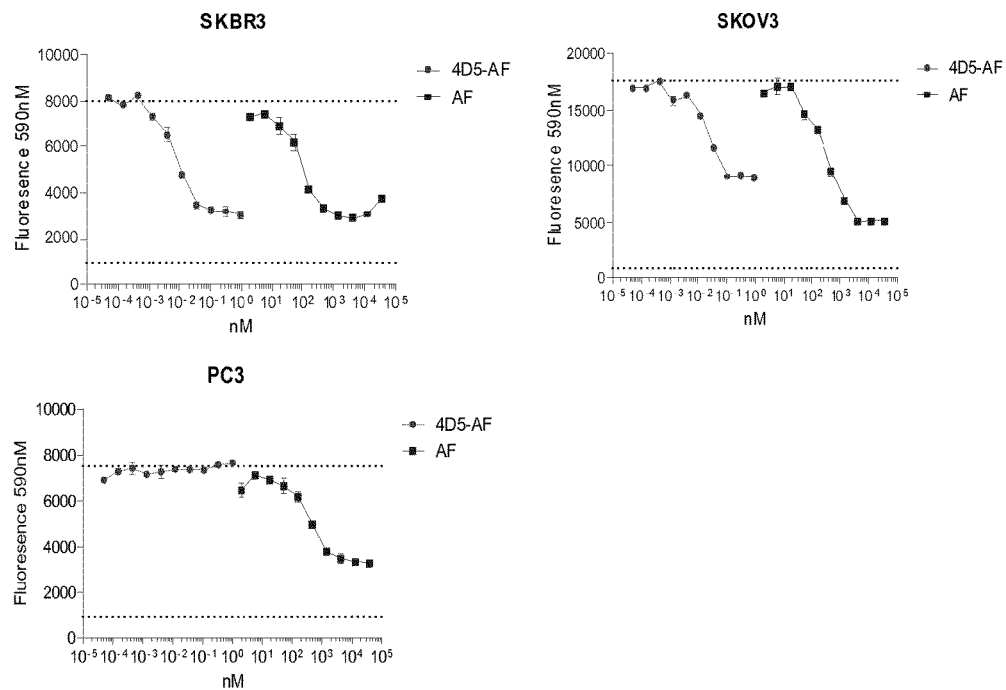
FIG. 27. In vitro antitumor activity of 4D5-2AzAb (HC274)-AF conjugate against Her2 positive tumor cell lines FIG. 28. In vivo antitumor activity of 4D5-2AzAb (HC274)-AF. Tumor progression expressed as the mean tumor size for each group (A) or the percent survival (B).

4D5-AzAb (HC274)-AF was tested for its in vitro potency on Her2 positive cell lines. The Her2 over expressing cell lines, SKBR3 and SKOV3 were compared to PC3, a cell line that expresses very low level of Her2. 4D5-AzAb (HC274)-AF was compared to auristatin (AF) alone. The ADC specifically killed the SKBR3 and SKOV3 cells that overexpress Her2 but did not kill PC3 cells which expresses very little Her2. The potency of this ADC against the 3 target cell lines is shown in Table 6. These values were calculated on the cytotoxicity data shown in FIG. 27. While the ADC shows picomolar potency against SKOV3 and SKBR3, it is inactive against PC3, even though that cell line is quite sensitive to auristatin alone. This demonstrates the specificity of these ADC for cells that express high levels of Her2.

TABLE 6

Potency of 4D5 auristatin conjugate for Her2 positive tumor cell lines in vitro:

| | $EC_{50}$ nM | | |
|---|---|---|---|
| | PC3 | SKOV3 | SKBR3 |
| 4D5-AF | — | 0.019 | 0.0074 |
| Auristatin | 336 | 287 | 71 |

In Vivo Antitumor Activity

Figure 28:
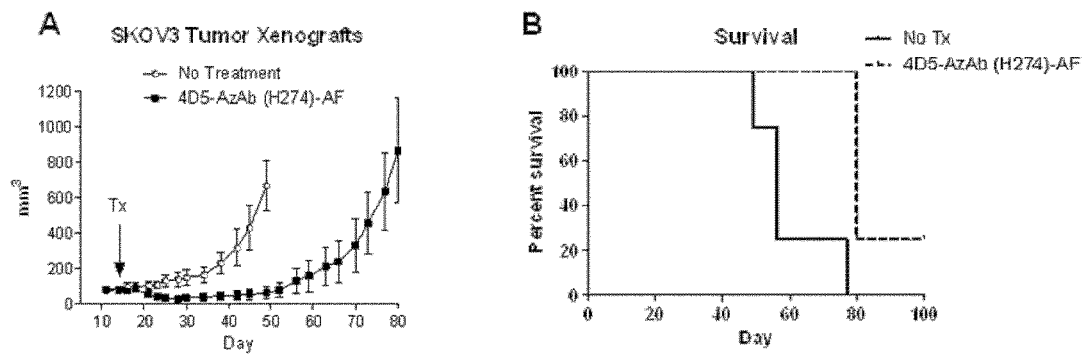

SKOV3 tumor cell line is derived from human ovarian carcinoma overexpressing Her2 but resistant to Herceptin; tumors derived from SKOV3 cells were established in scid mice. The tumors reached approximately 100 mm³ within 2 weeks, and at that time, the mice were randomized and half the mice (n=4/group) were treated with a single subcutaneous injection of 6 mg/kg of the 4D5-2AzAb (HC274)-AF ADC (FIG. 28). Tumor progression was followed by caliper measurement of the tumor size. All the treated mice showed highly significant delay in tumor progression after a short period of tumor shrinkage. One mouse was completely cured while the other three mice eventually relapsed (FIG. 28B). Tumor progression was monitored for up to 80 days to ensure that the single cured mouse did not relapse.

This example demonstrates that the 4D5-AF ADC is retained in circulation in vivo, stable to metabolic degradation, but available to deliver potent toxic activity specifically to the cytoplasm of the target tumor cells.

Example 18:—Generation of Bispecific Antibodies/Antibody Fragments and Characterization Preparation of 4D5 AzAb-0.5KPEG Intermediate. In a 200 uL PCR tube was placed phosphate buffer solution (34.3 uL, 50 mM, pH=7.4). To this was added a solution of 4D5 2-AzAb(HC274) (23.61 uL, 13 mg/mL) and a solution of bis-cyclooctyne linker (2.04 uL, 20 mM in dioxane, 500 kDa). The mixture was vortexed intermittently over a 24 h period. The mixture was purified by CHT resin to afford the functionalized intermediate.

28D2 scFv-AHA is derived from the anti-IL6 antibody in Example 4. A full SEQ ID and description of preparation can be found in WO12032181. Briefly, the antibody fragment, 28D2 scFv-AHA is expressed in e. coli and the nnAA azidohomoalanine is incorporated at the C-Terminus of the sequence. The protein is isolated from the fermentation and purified by nickel affinity chromatography.

Preparation of 4D5 AzAb (HC274)-28D2 (scFv) Bispecific

Figure 29:
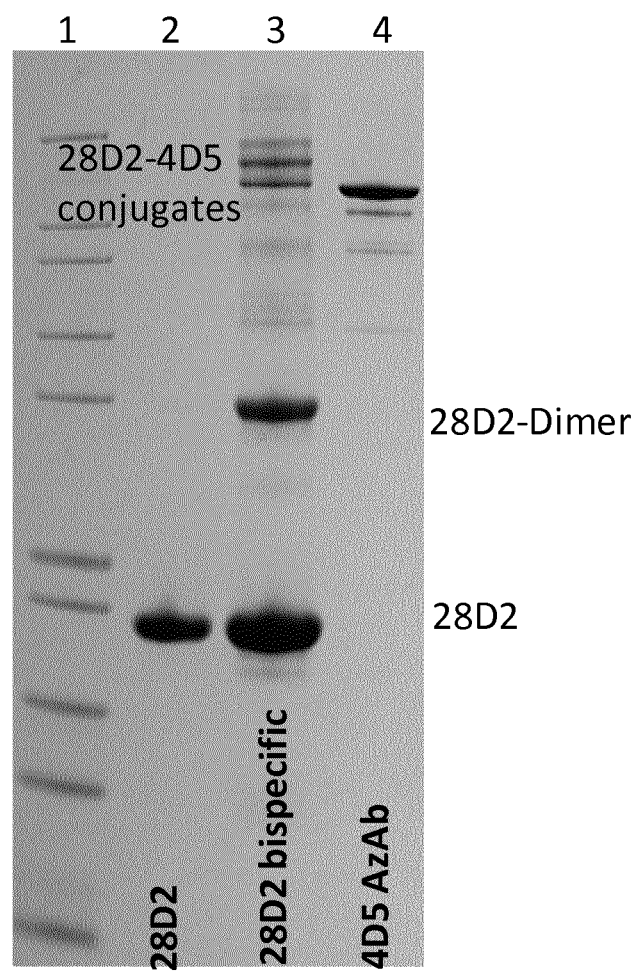
FIG. 29. SDS PAGE analysis of 4D5-2AzAb/FGF21 bispecific. Lane 1: MW Markers, Lane 2: FGF21 untreated, Lane 3: 4D5-FGF21 bispecific reaction, Lane 4: 4D5-2AzAb.
Figure 30:
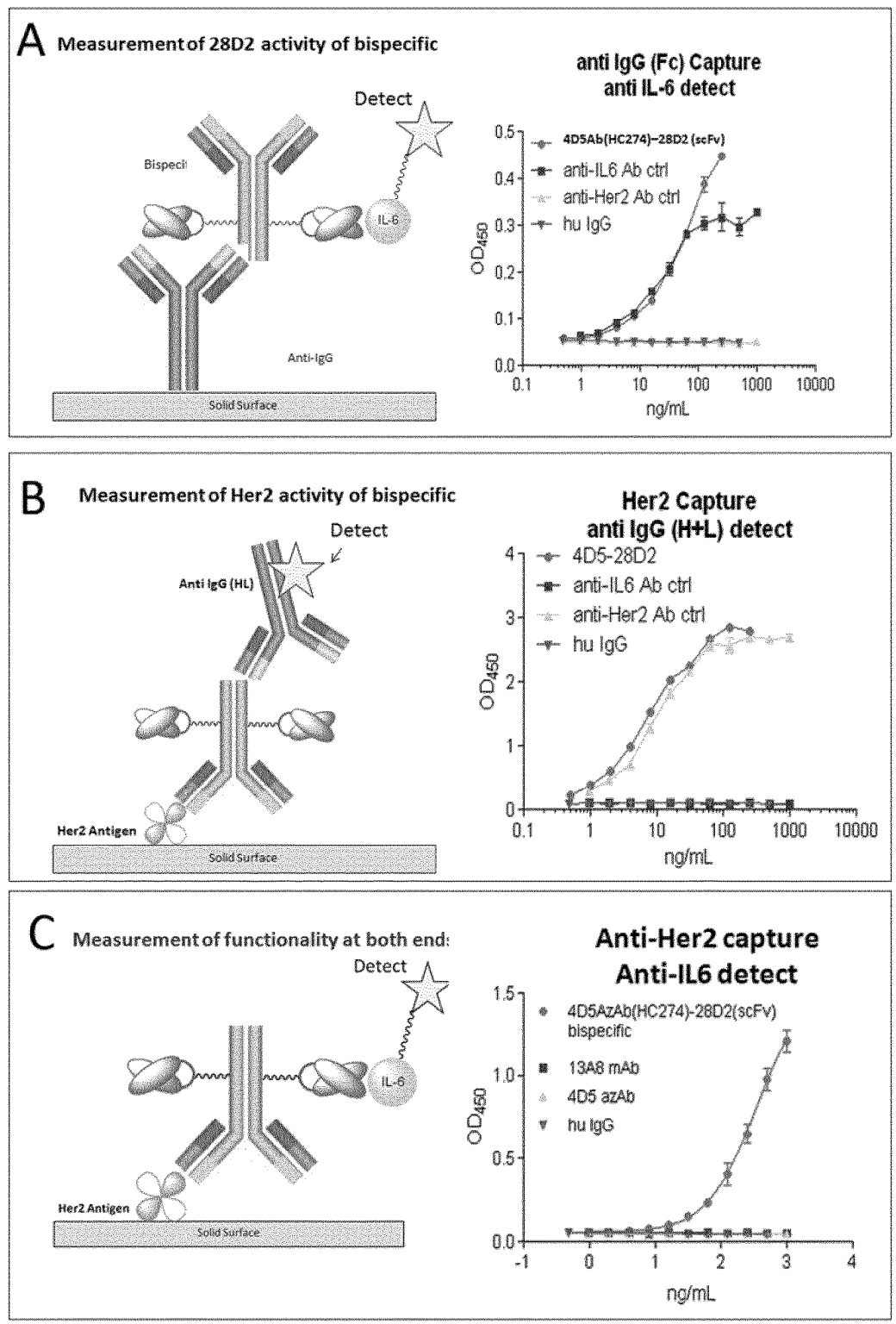
FIG. 30. ELISA assay scheme and data for the detection of a bi-specific antibody constructed with a full length mAb containing a nnAA at position H274 (anti-Her2) and a scFv directed against IL6. A) ELISA showing capture of the full length mAb (4D5) and detection of the bispecific using IL6. B) ELISA showing functional binding of the full length mAb (4D5) to the extracellular domain of Her 2. and subsequent detection of the mAb. C) ELISA assay showing functional binding of the mAb to the Her2 extracellular domain and scFv binding to IL6.

In a 200 uL PCR tube was placed 4D5-0.5KPEG conjugate (37.5 uL, 2 mg/mL) and a solution of 28D2 scFv-AHA (22 uL, 4.6 mg/mL). The mixture was capped, vortexed and allowed to stand for 24 h. The mixture was purified by Protein A magnetic Beads (GE), analyzed by SDS-PAGE (FIG. 29). SDS-PAGE indicated the formation of two distinct bands higher in molecular weight than the starting azide containing antibody which would be consistent with the addition of one and two scFv molecules.

In the ELISA assay, an anti IgG antibody was affixed to a solid surface. The Her2-anti-IL6 bispecific was captured on the Fc region of the bispecific. The bispecific was then assessed for function by the addition of IL-6 which was detected in turn by biotin labeling.

In one ELISA assay, the ability of the bispecific to bind the Her2 antigen was probed. The bispecific was found to have a similar level of antigen affinity to the control 4D5 AzAb (HC274) antibody (FIG. 30C).

In a second ELISA assay, the ability of the bispecific to bind to IL-6 was probed. In this version of the ELISA, the bispecific was captured on the ELISA plates by anti-IgG interaction. The IL-6 affinity was then investigated. It was found that the bispecific possessed a similar level of affinity for IL-6 as a full length antibody, 13A8 (FIG. 30B).

In the final ELISA assay, the ability of the bispecific to function at both ends at the same time was probed. The bispecific was captured ELISA plate by the antibody affinity for the Her2 antigen. The IL-6 activity was then probed. It was found the bispecific possessed high affinity for the Her2 antigen and IL-6 at the same time. The control antibodies were unable to show similar bifunctional activity (FIG. 30A).

The FGF21 polypeptide (FGF21-AHA(s86)) was expressed in e. coli and modified at position 86 of SEQ ID 62 to incorporate azidohomoalanine to replace serine. The modified protein was isolated as inclusion bodies and purified by nickel affinity chromatography.

Preparation of 4D5 AzAb-FGF21 (Cytokine) Bispecific

Figure 31:
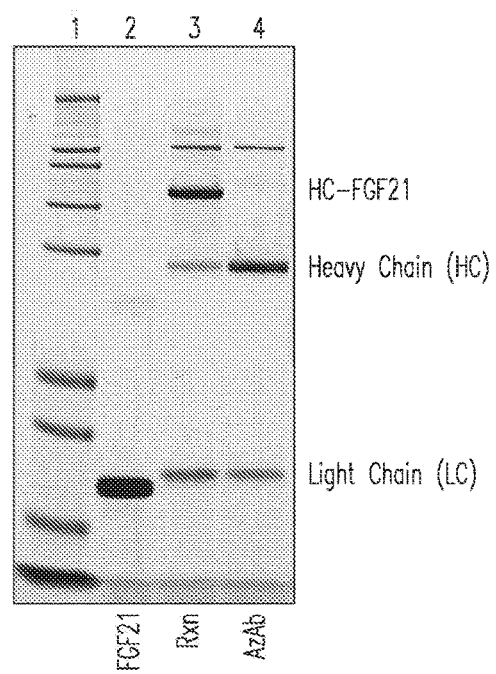
FIG. 31. SDS PAGE analysis of 4D5 AzAb-FGF21 bispecific

In a 200 uL PCR tube was a solution of the Antibody-Linker intermediate (3.0 uL, 2 mg/mL) and a solution of FGF21-AHA (S86)(28.6 uL, 2.8 mg/mL). The tube was capped and incubated at 37 C for 24 h. The mixture was purified by Protein A magnetic beads and analyzed by SDS-PAGE (FIG. 31). A molecular weight shift was observed in the SDS-PAGE gel consistent with the addition of the FGF21 (S86) molecule to the heavy chain by way of the intermediate linker.

Figure 33:
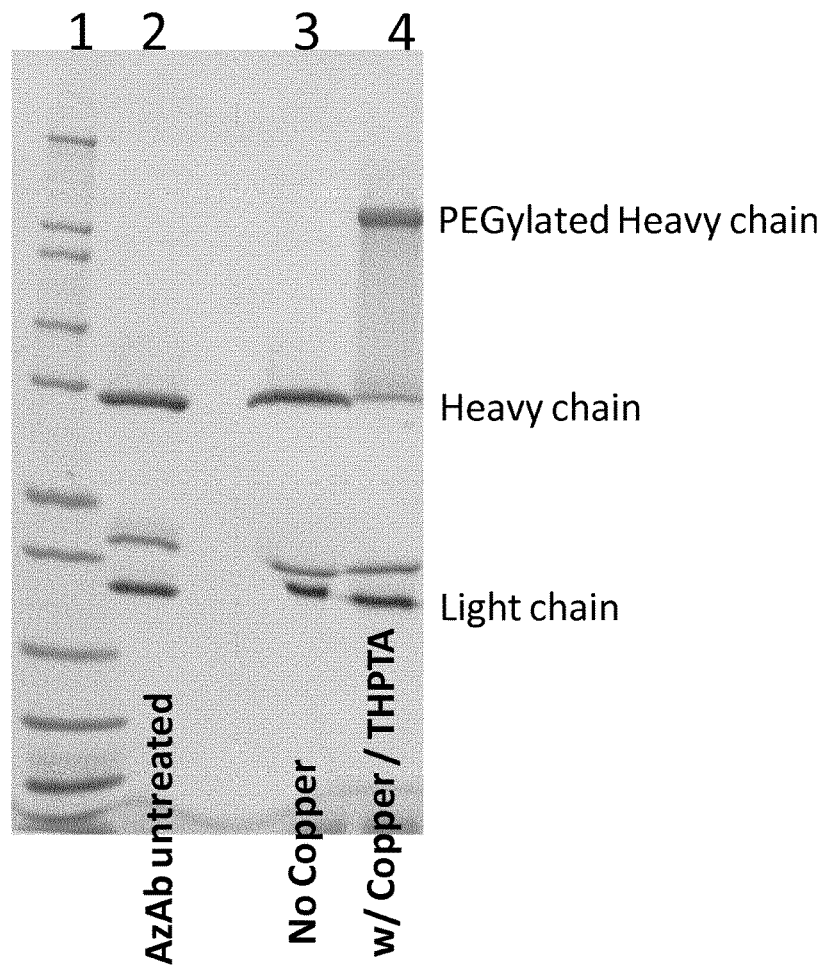
Figure 34:
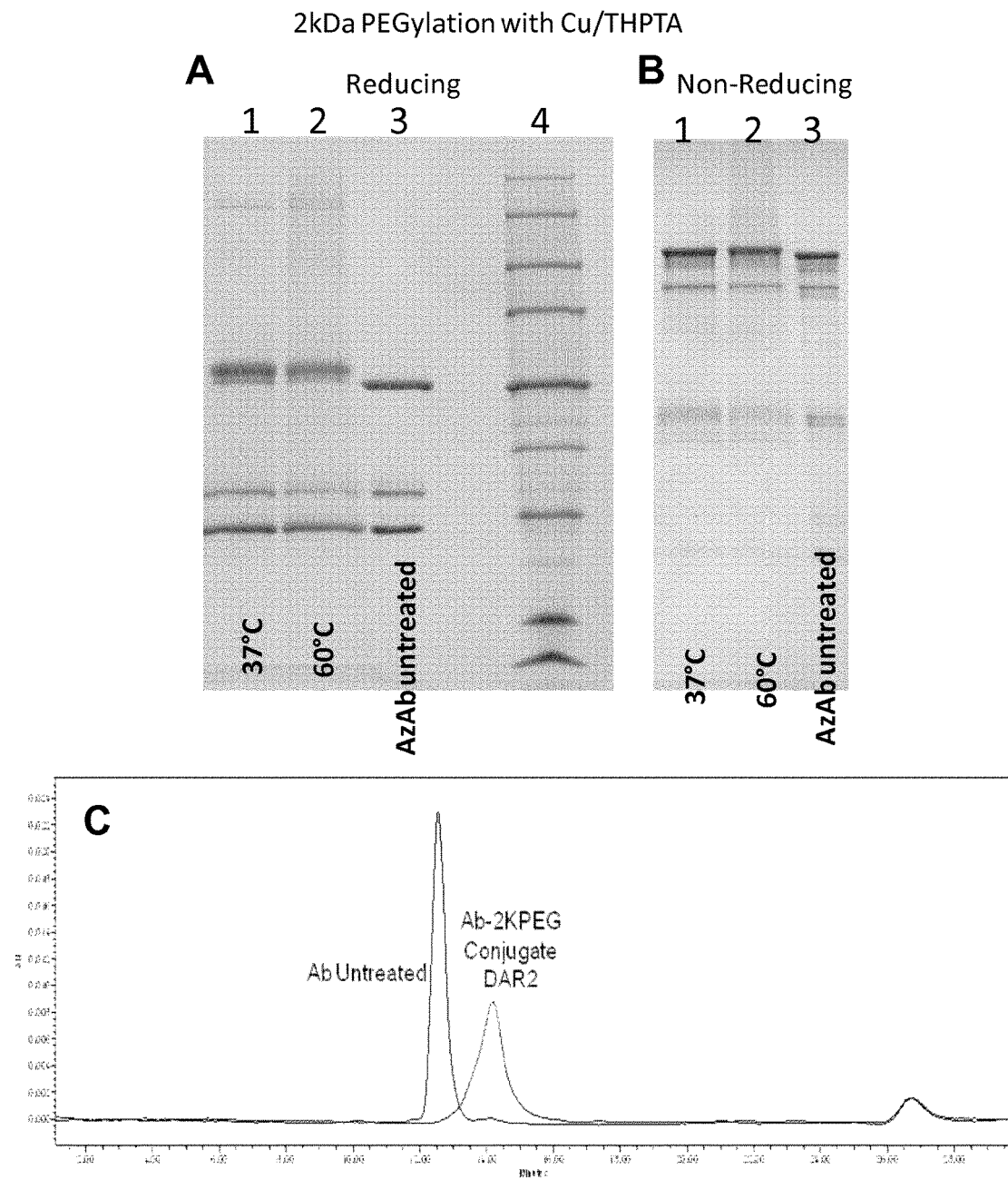

Example 19. PEGylation of 4D5 Azab with Copper Promoted Azide Alkyne Cycloaddition and the Tris(3-Hydroxypropyltriazolylmethyl)Amine (THPTA) Ligand 20 kDA PEGylation with THPTA. In a 200 uL PCR tube was placed a solution of phosphate buffer (3 uL, 150 mM, pH=7.4). To this was added a solution of 4D5 azide containing antibody (6.5 uL, 4.6 mg/mL) and a solution of 20 kDa PEG alkyne (4 uL, 60 mg/mL). In a separate tube was placed a solution of copper sulfate (2.0 uL, 10 mM), and solutions of THPTA (2.5 uL, 40 mM), amino guanidine (1.0 uL, 100 mM) and sodium ascorbate (1.0 uL, 100 mM). The tube was capped, vortexed and allowed to stand for 10 min. The entire copper complex was added to the AzAb-Alkyne solution. The final mixture was capped, vortexed and allowed to incubate for 2 h at 37° C. or 50° C. The reaction was analyzed by SDS-PAGE (FIG. 33). SDS-PAGE indicated a molecular weight shift of the heavy chain consistent with the addition of a 20 kDa PEG. 2 kDA PEGylation with THPTA. In a 200 uL PCR tube was placed a solution of 4D5 azide containing antibody (4.9 uL, 13 mg/mL) and a solution of 20 kDa PEG alkyne (4.2 uL, 20 mM). In a separate tube was placed a solution of copper sulfate (3.5 uL, 20 mM), and solutions of THPTA (8.8 uL, 40 mM), amino guanidine (3.5 uL, 100 mM) and sodium ascorbate (3.5 uL, 100 mM). The tube was capped, vortexed and allowed to stand for 10 min. A portion of the copper complex (1.93 uL) was added to the AzAb-Alkyne solution. The final mixture was capped, vortexed and allowed to incubate for 2 h at 37° C. or 60° C. The reaction was analyzed by SDS-PAGE (FIG. 34) and HIC chromatography. SDS-PAGE reducing showed a slight increase in molecular weight of the heavy chain consistent with the addition of a 2 kDa molecular weight PEG. SDS-PAGE under non-reducing conditions indicated a small molecular weight shift of the full length antibody consistent with the addition of PEG. Additional confirmation was provided by HIC chromatography (FIG. 34B), which indicated a single major species, consistent with the addition of PEG to the antibody.

Example 20. Preparation of Additional Cytotoxin-Alkyne Derivatives

Preparation of Amanitin-Cyclooctyne Derivative

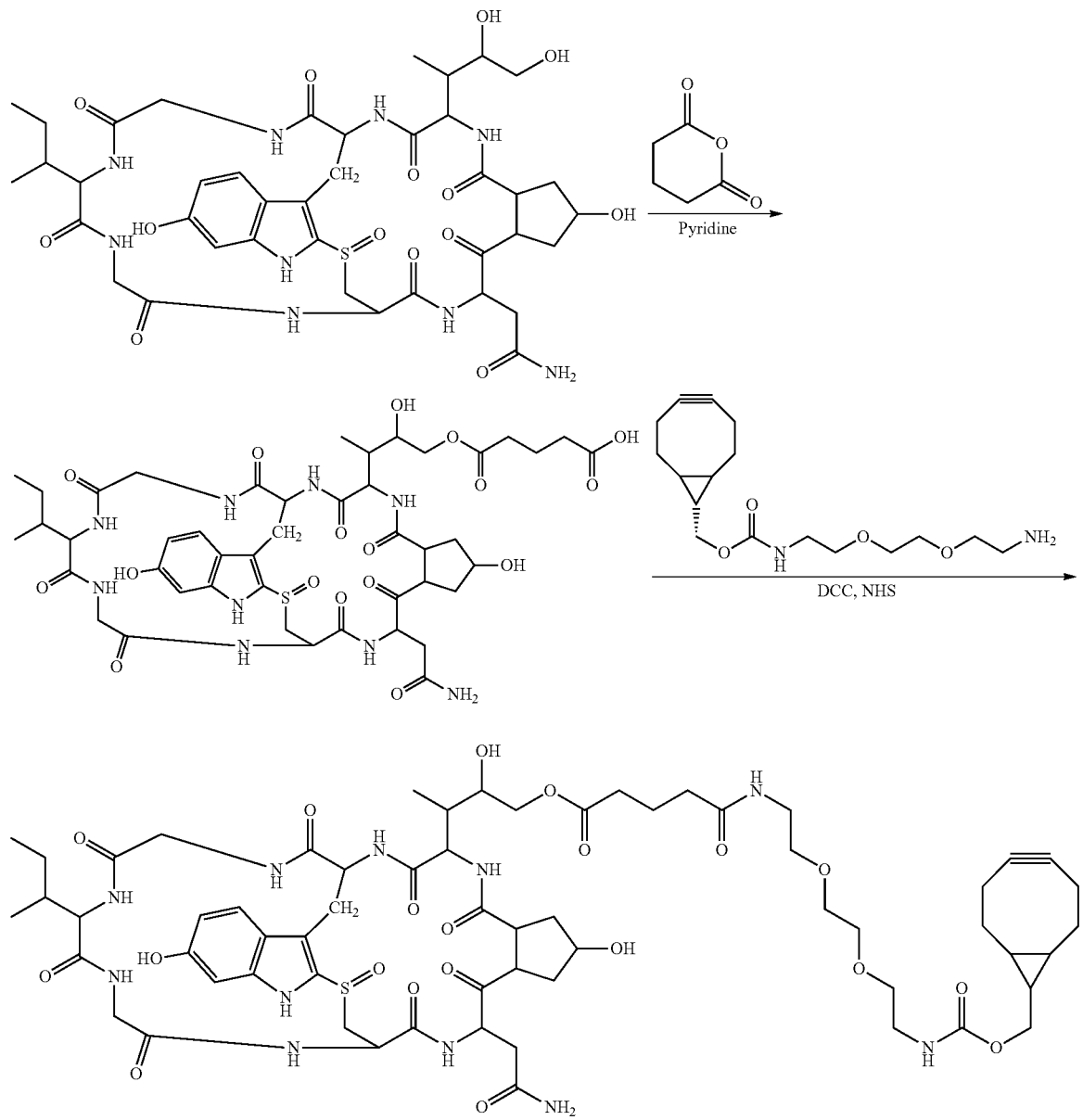

α-Amanitin (5 mg, 5.5 umol) and glutaric anhydride (1.5 mg, 13.2 umol) and pyridine (500 uL) were placed in a 2 mL vial with magnetic stirrer. The solution was stirred overnight. The mixture was concentrated to under vacuum taken up in a small amount of dichloromethane and precipitated in methyl tbutyl ether. The solids were carried forward into the next step. Analytical MS: m/z (ES+) calculated 1031.4 (M+H)+. found 1033.3.

Amanitin-GA (5.6 mg, 5.5 umol), HBTU (4.6 mg), cyclooctyne-amine (1.8 mg) and triethylamine (1.9 uL) were placed in a 5 mL centrifuge tube and dissolved in DMF (1 mL). A small magnetic stir bar was added was added and the mixture was stirred overnight. The mixture was precipitated from Methyl tButyl ether. The solids were isolated by centrifugation. Analytical MS: m/z (ES+) calculated 1337.6 (M+H)+. found 1339.4.

Preparation of Auristatin F-Cyclooctyne Derivative

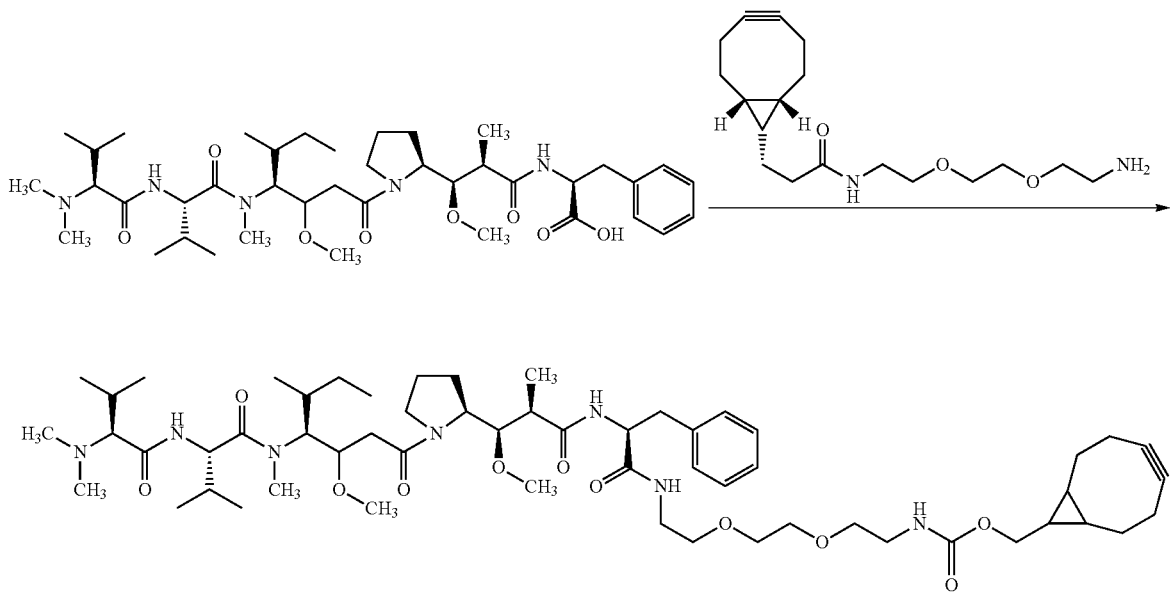

In a 4 mL vial with magnetic stirrer was placed Auristatin F (AF) (5 mg, 10. umol) in DMF (1 mL). To this mixture was added HBTU (7.6 mg, 20 umol), BCN amine (3.2 mg, 10 umol) and triethylamine (3.4 uL, 25 umol). The vial was capped and the mixture allowed was stirred overnight. The solution was purified by reversed phase HPLC (acetonitrile/water 0.1% TFA gradient). The desired fractions pooled and lyophilized to a powder. Analytical MS: m/z (ES+) calculated 1051.7 (M+H)+. found 1052.7.

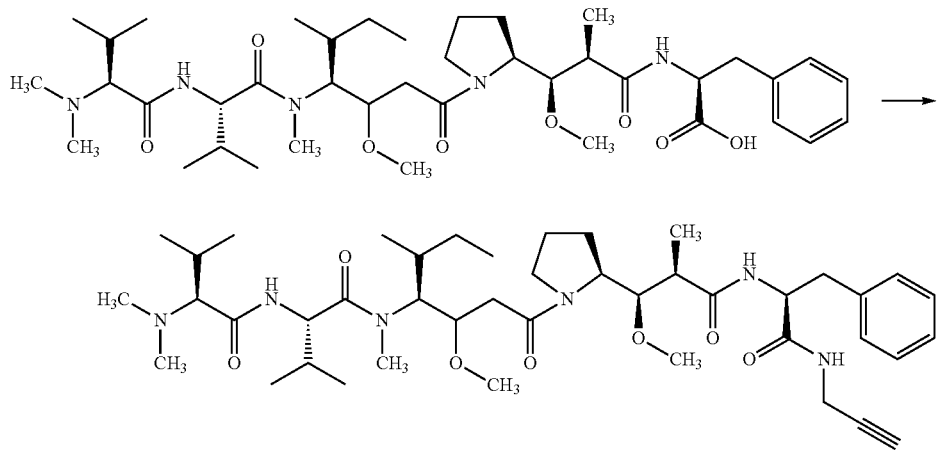

Auristatin F—Propargylamide Derivative AF-PA0

AF-PA0 refers to the PEG spacer between the alkyne and auristatin F. For AF-PA0 there is no PEG spacer, hence the zero. AF-PA3 incorporates three ethylene units between the alkyne and the auristatin F structure.

Figure 35:
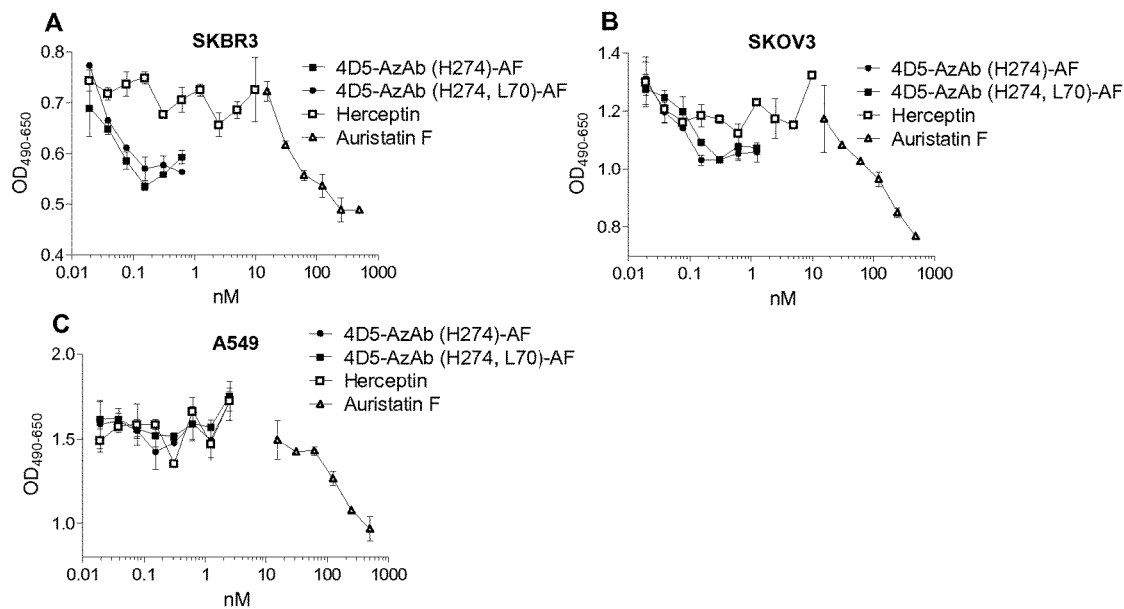

In a 4 mL vial was placed Auristatin F (AF) (6.1 mg, 8.18 umol) in DMF (1 mL). To this mixture was added a solution of HBTU (6.2 mg, 16 umol), propargylamine (0.6 uL, 9 umol) and triethylamine (2.8 uL, 20 umol). The vial was capped and the mixture allowed to incubate overnight. The solution was purified by reversed phase HPLC (acetonitrile/water 0.1% TFA gradient). The desired fractions pooled and lyophilized to a powder. Analytical MS: m/z (ES+) calculated 782.5 (M+H)+. found 783.3.

slightly more potent than the related DAR2 (4D5AzAb (HC274)-AF) compounds described in example 15 and FIG. 23 versus Her2 positive expressing cell lines such as SKOV3 and SKBR3. The compounds showed minimal activity versus a low Her2 expressing cell line such as PC3. Both ADC's were more potent than the unconjugated antibodies or the free drug (FIG. 35, A,B,C) Conjugation of anti-Her2 Antibody (4D5-AzAb (HC274)) with Amanitin-cyclooctyne derivative In a 200 uL PCR tube was placed a solution of phosphates (5 uL, 50 mM, pH=7.4) and a solution of the 4D5-AzAb (HC274) (3.94 uL, 13 mg/mL). To this was added a DMSO solution of amanitin alkyne (1.13 uL, 3 mMol), the tube was capped and vortexed. The mixture was allowed to stand for

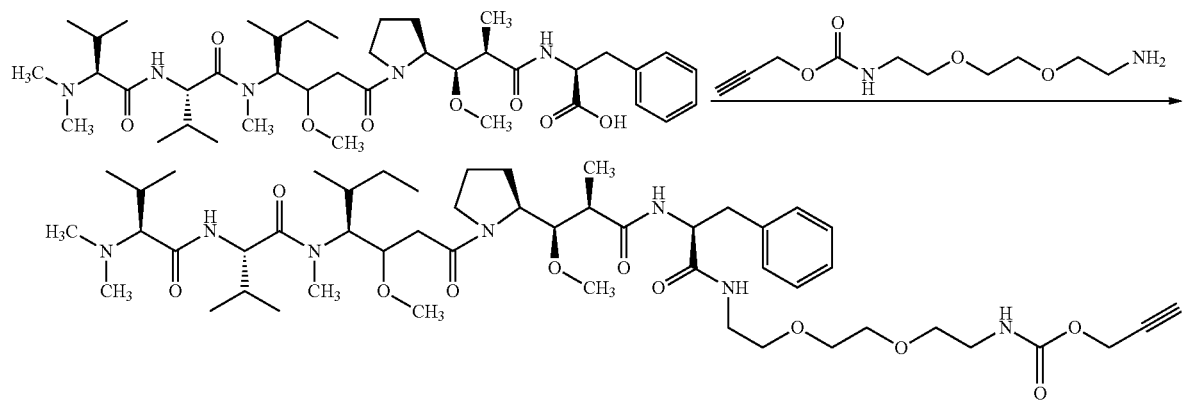

Auristatin F—Propargylamide Derivative AF-PA3

In a 1 mL vial with magnetic stirrer was placed Auristatin F (AF) (4.7 mg, 6.3 umol) in DMF (200 uL). To this mixture was added a solution of HBTU (6.0 mg, 16 umol in 50 uL DMF), prop-2-yn-1-yl N-{2-[2-(2-aminoethoxy)ethoxy]ethyl} carbamate (3.7 mg, 14 umol in 100 uL DMF) and triethylamine (3.7 uL, 25 umol). The vial was capped and the mixture allowed to stir overnight. The solution was purified by reversed phase HPLC (acetonitrile/water 0.1% formic acid gradient). The desired fractions pooled and lyophilized to a powder. Analytical MS: m/z (ES+) calculated 957.6 (M+H)+. found 958.5.

Example 21: Conjugation to Anti-Her2 Antibodies with Toxin-Alkyne Derivatives

Conjugation of 4D5-AzAb (HC274: LC70) with AF-Cyclooctyne Derivative.

In a 200 uL PCR tube was placed a solution of 4D5-AzAb (HC274: LC70) (24 uL, 0.5 mg/mL) and a DMSO solution of AF-Cylcooctyne (0.8 uL, 10 mMol), the tube was capped and vortexed and allowed to stand for 24 h. The reaction mixture was then treated with a solution of azidohomoalanine (AHA, 250 mM in 1M HEPES, 20 uL), vortexed and allowed to stand for 2 h. The mixture was then desalted through ZEBA (Pierce) spin column to afford the final ADC solution. The mixture was analyzed by SDS-PAGE.

4D5-AzAb (HC274: LC70)-AF and 4D5-AzAb (HC274)-AF were assessed by an in vitro potency assay for their ability to kill Her2 positive cells. The in vitro assay is described in example 16. Briefly, the ADC was compared to the unconjugated antibody (herceptin) and the free drug. In the cytotoxicity assay, the DAR4 ADC was found to be 24 h. The reaction mixture was then treated with a solution of azidohomoalanine (AHA, 250 mM in 1M HEPES, 7 uL), vortexed and allowed to stand for 2 h. The mixture was then desalted through a ZEBA (Pierce) mini spin column to afford the final ADC solution 4D5-AzAb (HC274)-Amanitin.

Figure 36:
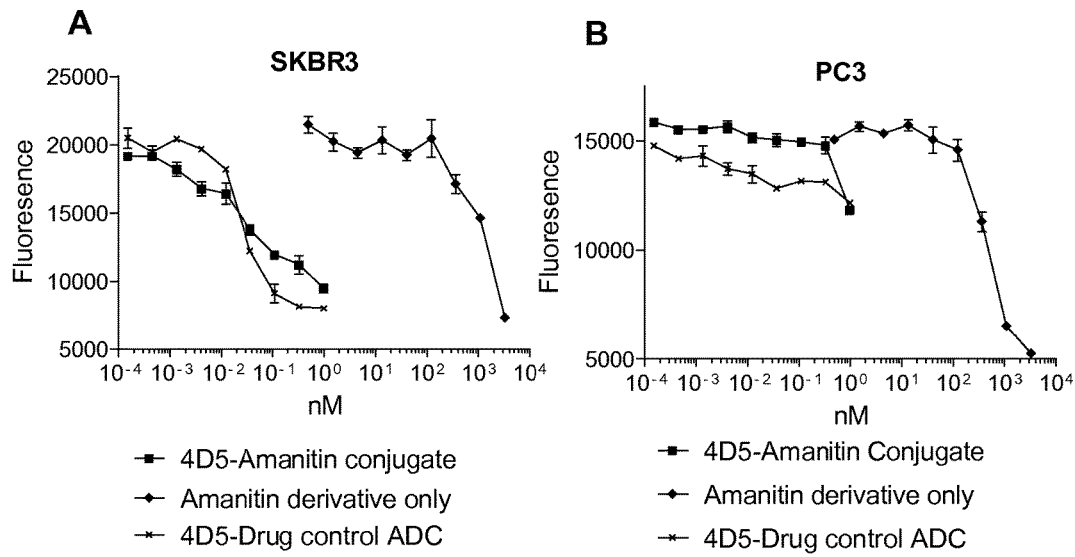

The 4D5-AzAb (HC274)-Amanitin was assessed by an in vitro potency assay for the ability to kill Her2 positive cells. The in vitro assay is described in example 16. Briefly, the ADC was compared to another ADC (4D5AzAb(HC274)-AF) and the free drug. 4D5AzAb(HC274)-amanitin ADC was active in Her2 positive cell lines SKBR3 (FIG. 36A) whilst showed minimal activity in the low Her2 expressing cell line such as PC3 (FIG. 36B). 4D5-AzAb (HC274)-Amanitin was similarly potent as 4D5AzAb(HC274)-AF and more potent than the free drug alone.

Example 22: Conjugation to 4D5 2AzAb (HC274) to AF-Alkyne with CuAAC

Conjugation of 4D5-2AzAb (HC274) with AF-PA0 or AF-PA3. In 200 uL PCR tubes was placed phosphate buffer (3.0 uL, 50-500 mM, pH=7.4), a solution of 4D5-AzAb (HC274) (2.1 uL, 25 m/mL in PBS) and a organic solution of the cytotoxic agent, AF-PA0 or AF-PA3 (0.70 uL, 5 mM, in DMSO or propylene glycol). In a separate tube was placed a solutions of copper sulfate (7 uL, 10-160 mM), THPTA (3.6 uL, 10-160 mM), amino guanidine (7.0 uL, 10-200 mM), and sodium ascorbate (7.0 uL, 50-300 mM). The THPTA-CuSO4 complex was capped, vortexed and allowed to stand for 10 min. The copper complex (1.23 uL per rxn) was added to the AzAb-Alkyne solutions. The final mixture was capped, vortexed and allowed to incubate (4 C to 60 C) for 0.5-18 h. The material was desalted by passing through a Pierce Zeba mini spin column (Cat#89882, MWCO=7000) and treated with 10×PBS. Alternatively, the reactions mixtures are purified by CHT chromatography.

Figure 38:
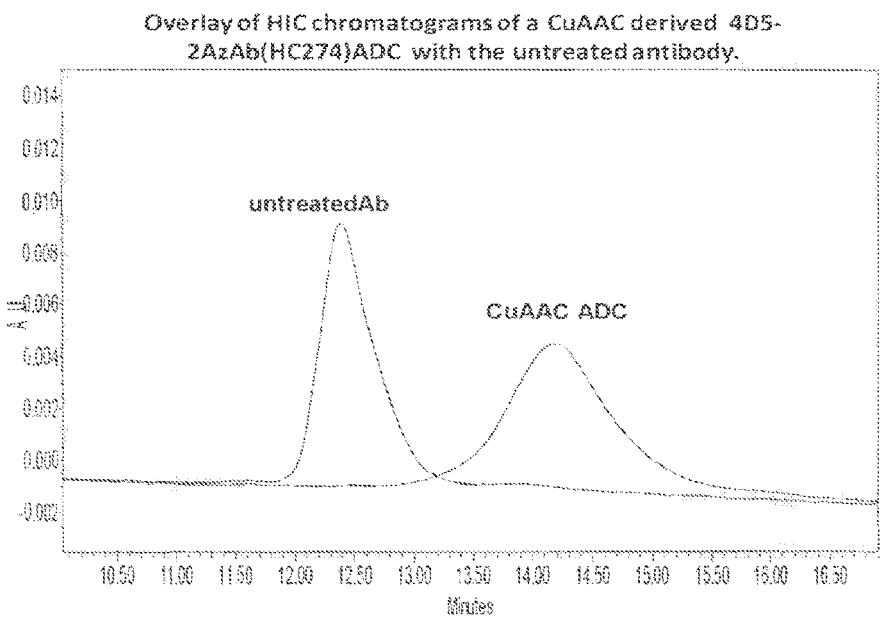
FIG. 38. HIC chromatogram of the reaction mixture of a 4D5-2AzAb(HC274) conjugation to a Auristatin F derivative under CuAAC conditions.

Conjugation of 4D5-2AzAb with AF-PA0 at 1:1 THPTA:CuSO4 Ratio at room temperature. In 200 uL PCR tubes was placed phosphate buffer (2.8 uL, 500 mM, pH=7.4), 4D5-AzAb(HC274) (2.1 uL, 25 mg/mL) and AF-PA0 (0.7 uL, 5 mM, DMSO solution). In separate tubes were placed a solutions of copper sulfate (3.5 uL, 20 mM), THPTA (1.8 uL, 40 mM), amino guanidine (3.5 uL, 100 mM), and sodium ascorbate (5.3 uL, 100 mM). The THPTA-CuSO4 complex was capped, vortexed and allowed to stand for 10 min. The copper complex (1.4 uL) was added to the AzAb-Alkyne solutions. The final mixture was capped, vortexed and allowed to incubate for 1 h at room temperature. The reactions were purified by desalting through a Zeba Spin column (MWCO=7000). Analysis of the reaction by HIC chromatography indicated clean formation of the desired DAR2 product. (FIG. 38).

Figure 37:
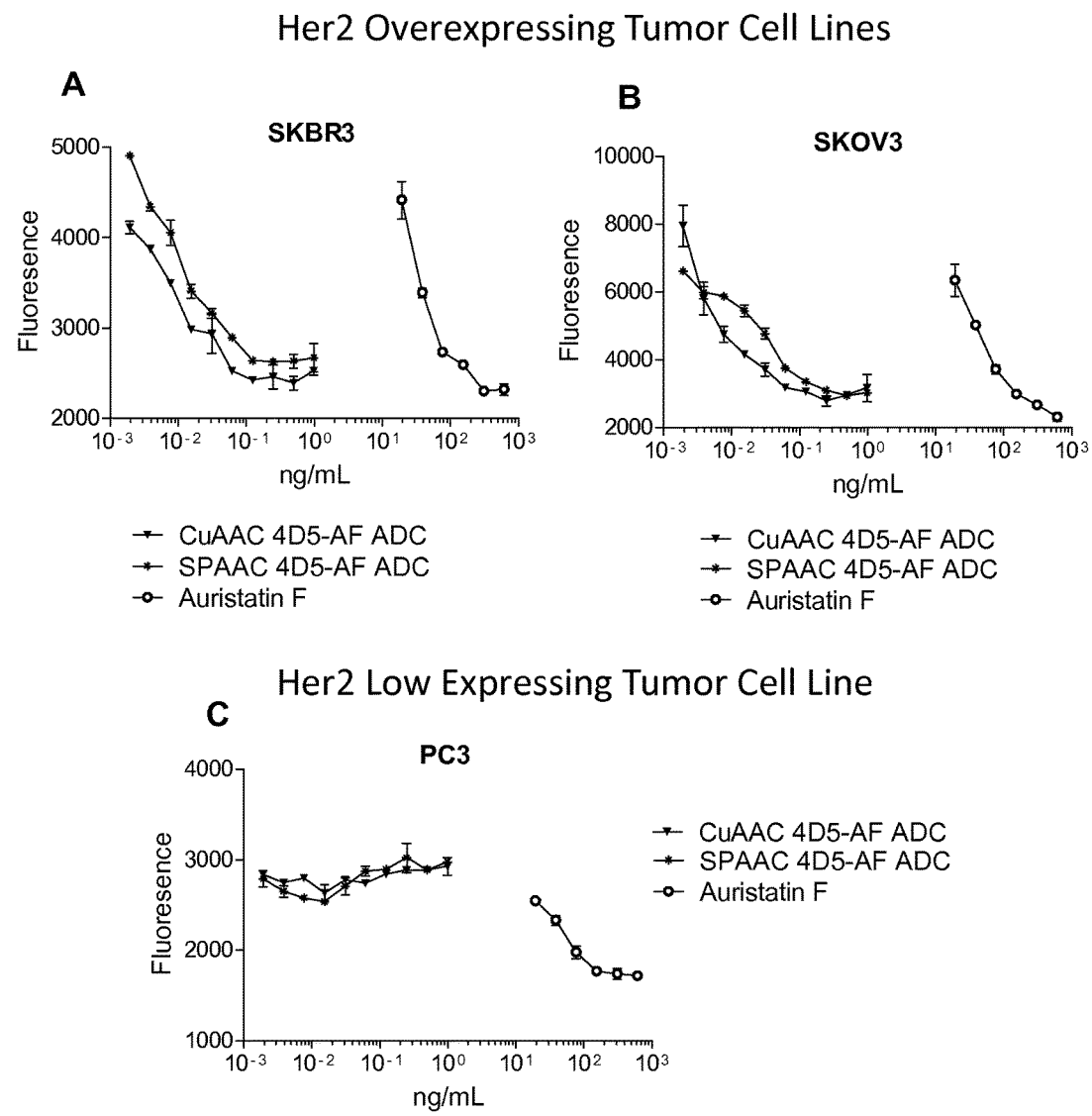

The CuAAC based anti-Her2 auristatin ADC was compared to the related cycloalkyne derived anti-Her2 auristatin ADC by an in vitro assay to measure potency and selectivity for. The in vitro potency assay was run in a similar manner to that described in example 16. The CuAAC based ADC was found to have a similar potency to the cycloalkyne derived ADC versus Her2 positive cell lines such as SKBR3 and SKOV3 (FIG. 37A, B). The same ADC's were tested for selectivity versus a low expressing Her2 cell line, PC3 and found to be non potent (FIG. 37C).

and fractions showing OD280 readings were retained. Peak protein fractions were combined and protein concentrated and buffered exchanged into phosphate buffered saline using an Amicon Ultra-4 concentrator (Millipore). Concentrated samples were processed for conjugation.

Figure 39:
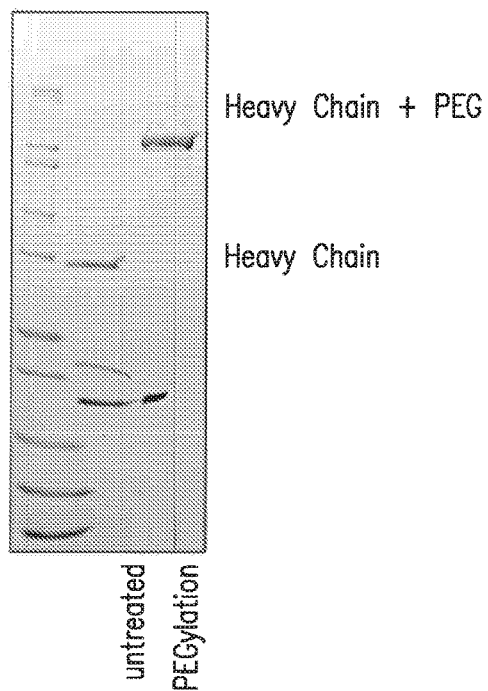
FIG. 39. Gel Mobility assay of site-specifically modified Herceptin AzAb heavy chain with 20 KDa PEG alkyne.

PEGylation of 20K Linear PEG-cycloalkyne to Herceptin-AzAb (HC274). In a 200 uL PCR tube was placed a solution of Herceptin-2AzAb (HC274) (1.0 uL, 2.4 mg/mL) followed by a solution of 20KPEG cyclooctyne (1.0 uL, 60 mg/mL). The solution was mixed vigorously on a vortexer. The tube was placed on a PCR tube centrifuge for a few seconds to place all liquids into the bottom of the tube. The mixture was allowed to stand for 4 h and then analyzed by SDS-PAGE. SDS-PAGE (reducing) indicated the 20 kDa PEG alkyne was site specifically conjugated to the azide of the heavy chain with excellent efficiency, with minimal to no unreacted heavy chain remaining (FIG. 39).

Conjugation of Herceptin-AzAb(HC274) with AF-Cyclooctyne derivative. In a 200 uL PCR tube was placed a solution of the Herceptin-2AzAb (19 uL, 4.8 mg/mL). To this was added a DMSO solution of AF-cyclooctyne derivative (1.5 uL, 5 mMol), the tube was capped and vortexed. The mixture was allowed to stand for 24 h. The reaction mixture was then treated with a solution of azidohomoalanine (AHA, 250 mM in 1M HEPES, 10 uL), vortexed and allowed to stand for 60 min. The mixture was then desalted through a ZEBA (Pierce) 2 mL spin column to afford the final ADC solution. Analysis by HIC chromatography indi-

TABLE 7

Summary of CuAAC condition utilized for AzAb conjugations:

| Rxn Component | Azide containing proteins | Alkyne substrate | Copper Source | Copper stabilizing Ligand | Reducing Agents |
|---|---|---|---|---|---|
| Examples | PSMA-azide scFv-azide α-IL6 AzAb α-Her2 AzAb | Cytoxic agents Dye PEG (2-20 kDa) Protein-PEG Conjugates | CuSO4 CuI CuCl2 Cu(Ac)2 CuBr | THPTA TBTA MES ET3N | BME Cysteine TCEP Sodium ascorbate Sodium bisulfite Hydrazine hydroxylamine |
| Conc Range (mM) | 0.001-0.1 | 0.001-5 | 0.1-10 | 0.2-20 | 0.1-30 |

Example 23 Generation of Herceptin ADC and Conjugation

Figure 40:
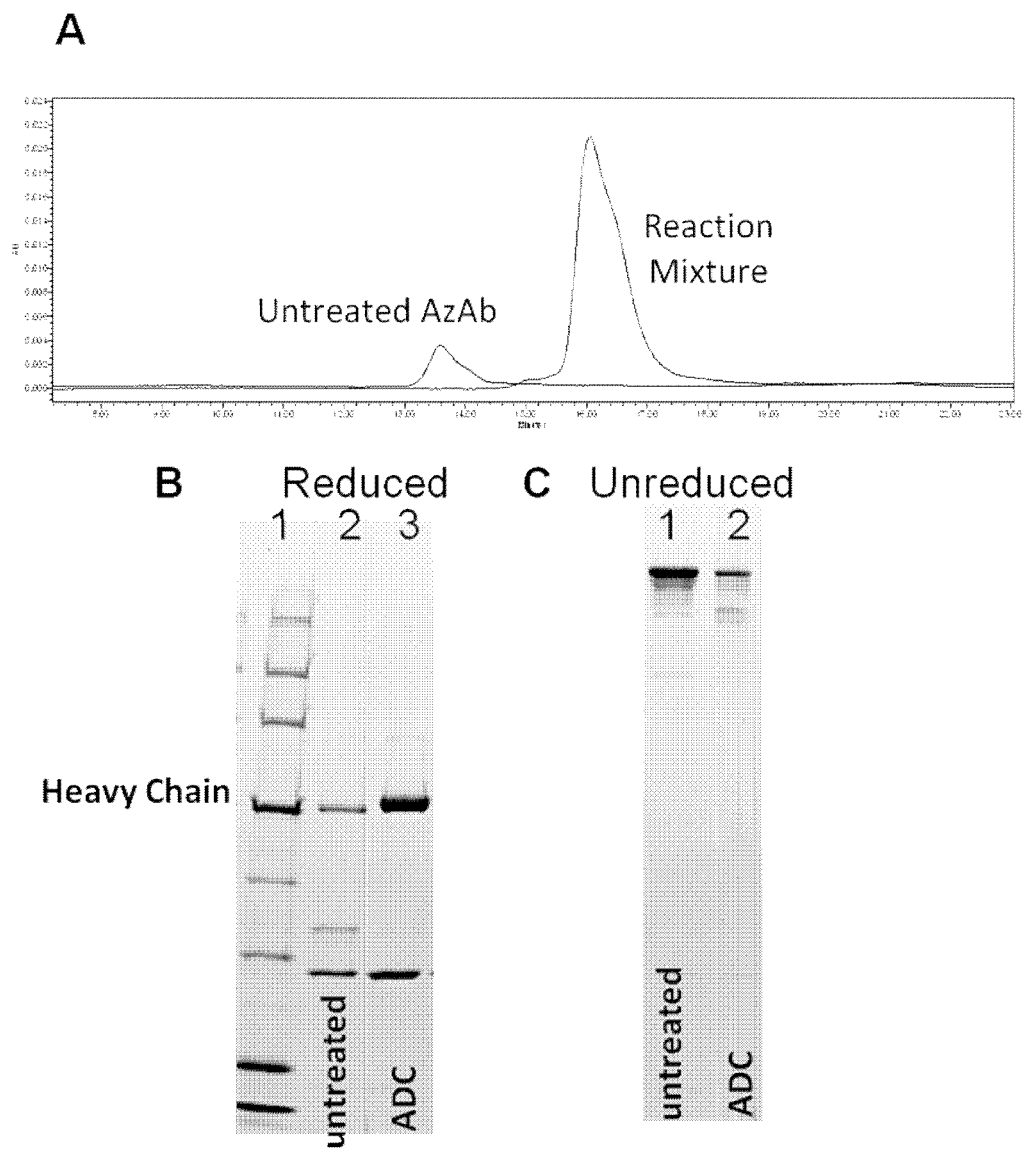
FIG. 40. Analysis of Herceptin AzAb conjugated to Auristatin F-cyclooctyne. A) HIC analyses of the untreated Herceptin-AzAb and the product of the conjugation reaction. B) Gel mobility assays of untreated and conjugation reactions by SDS-PAGE under reducing (B) and non-reducing conditions (C).

The cell line described in Example 15 was used to generate an anti-Her2 azAb antibody derived from Herceptin (SEQ ID 74 and 75, light chain; SEQ ID 76, 77, heavy chain) modified to contain a nnAA at position 274 of the heavy chain (mutant heavy chain, SEQ ID 76,77; unmodified light chain as per SEQ ID 78,79), Herceptin AzAb (HC274). 3×10$^6$ cells/mL were seeded into 125 mL of Excell DHFR-medium and exposed to lys-azide for 7 days. The medium was collected and cells harvested by centrifugation (1000×g for 10 min). 12.5 mL of 10× phosphate buffered saline (10×PBS; Life Technologies) was added and medium passed three times over a 300 ul (packed volume) IgSelect resin (GE Healthcare). The bound protein was washed with 10 column volumes of Tris buffered saline containing 0.1% tween-20 (TBS-T pH7.5). Herceptin-AzAb was eluted with 0.1M glycine pH2.5 and 250 ul elution fractions collected. The acid was immediately neutralized with 50 ul 1M Tris pH8.0. Each fraction was analysed by spectrophotometry cated the clean formation of the desired DAR2 product (FIG. 40). Additional analysis by SDS-PAGE (reducing) indicated a small increase in molecular weight of the heavy chain, non reducing PAGE also indicated an increase in molecular weight of the main protein band.

Figure 41:
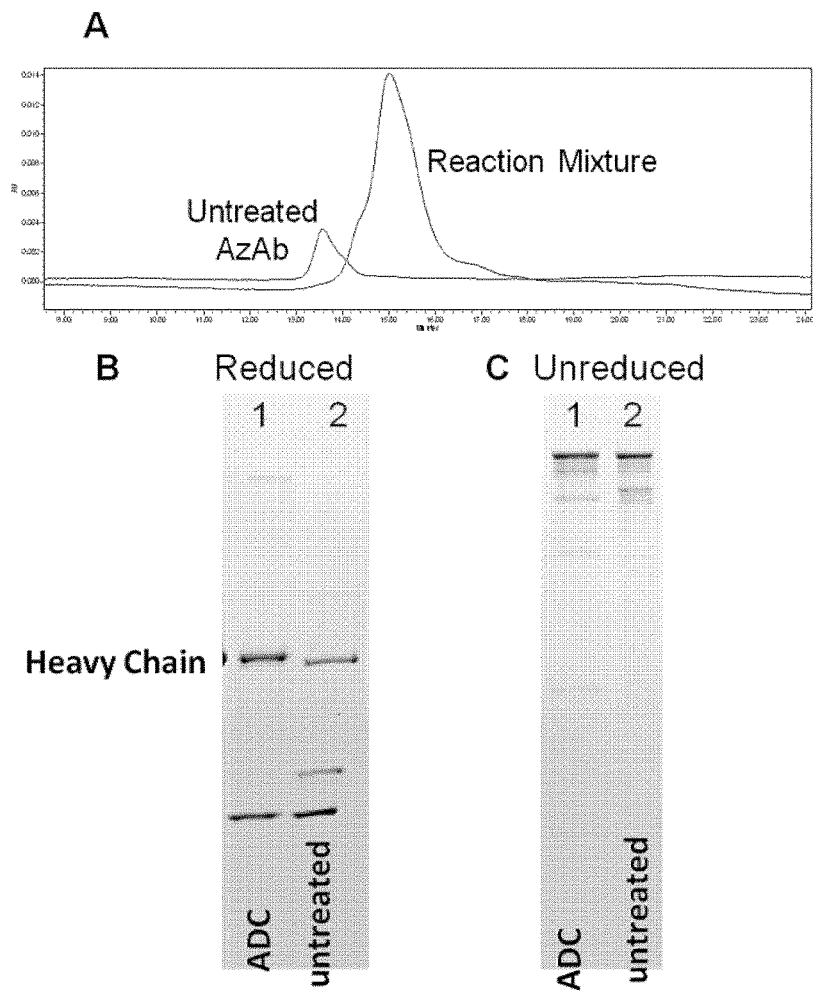
FIG. 41. Analysis of Herceptin AzAb conjugated to Auristatin F-alkyne. A) HIC analyses of the untreated Herceptin-AzAb and the product of the conjugation reaction. B) Gel mobility assays of untreated and conjugation reactions by SDS-PAGE under reducing (B) and non-reducing conditions (C).

Conjugation of Herceptin-2AzAb with AF-PA0 under CuAAC conditions. The conjugation was done under conditions described in example 22. The reactions were purified by desalting through a Zeba Spin column (MWCO=7000). Analysis of the reaction by HIC chromatography indicated clean formation of the desired DAR2 product (FIG. 41). Additional analysis by SDS-PAGE (reducing) indicated a small increase in molecular weight due to conjugation of the drug to this subunit. Additional PAGE (non-reducing) analysis also indicated a molecular weight increase of the main protein band (FIG. 41).

In Vitro Cytotoxic Activity

The ADC's generated as described above were tested for cytotoxic activity in SKOV3 and a PC3 tumor cell lines which are standard target cells for testing the activity of anti Her2 antibodies and ADC cell lines. SKOV3 cells express high levels of Her2, while PC3 cells express Her2 at low level. Briefly, for each assay 1000 cells are seeded into each well of a 96 well plate and incubated with a titration of Auristatin F alone, or Herceptin-AF conjugates generated by either SPAAC or CUAAC chemistry. The drug treated cells are incubated at 37 C for 3 days in 100 ul medium. 20 ul of Alamar Blue (Life Technologies) is added to each well and the cells incubated for 16-24 hours and an OD 450 nm determined for each well. The cytotoxic activity of the conjugates was calculated as the concentration of ADC to kill 50% of the tumor cells in vitro as described in Table 8.

TABLE 8

Potency of Herceptin ADC against different tumor cell lines

| | $EC_{50}$ nM | | | | |
|---|---|---|---|---|---|
| | PC3 | SKOV3 | HCC1954 | BT474 | SKBR3 |
| Herceptin-CUAAC-AF ADC | NA | 0.03 | 0.023 | 0.069 | 0.017 |
| Herceptin-SPAAC-AF ADC | NA | 0.026 | 0.023 | 0.062 | 0.017 |
| Auristatin F | 166.2 | 23.48 | 12.9 | 58.81 | 33.27 |

Figure 42:
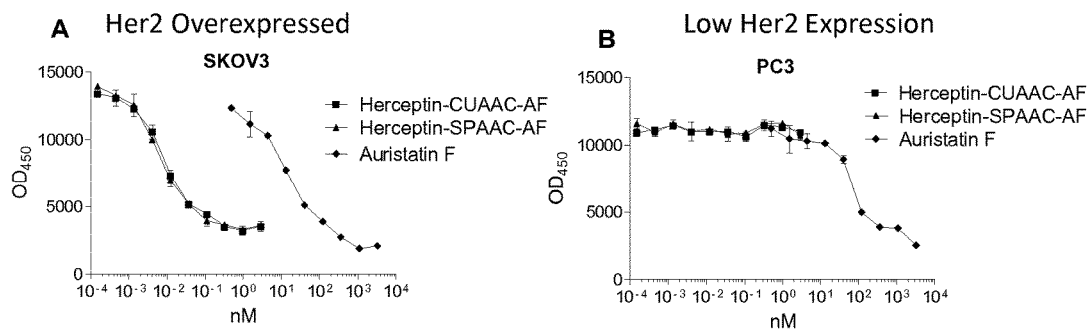
FIG. 42. In vitro cytotoxicity of Herceptin ADCs

As shown in FIGS. 42 A and B, Herceptin-AzAb (HC274)-AF ADCs constructed with CUAAC or SPAAC conjugation chemistries were compared. In each case the Herceptin ADC was potent in SKOV3 cells (Her2 positive tumor cell line), but did not affect PC3 cells.

FIGS. 42A and B shows the cytotoxicity assay from which the EC50 values in Table 8 were derived.

FIG. 42A shows the tumor cytotoxic activity of the Herceptin-AzAb (HC274)-CUUAC-AF and Herceptin-AzAb SPAAC-AF in the SKOV3 tumor cell line. These cells are efficiently killed by the ADC with toxin conjugated generated by the different conjugation chemistries. Clearly, the ADC greatly lowers that concentration of Auristatin F required to kill the tumor cells, presumably by efficiently targeting all of the AF directly to the cell, as compared to passive diffusion. FIG. 42B shows the effect of the Herceptin conjugates on PC3 cells. Here, both SPAAC and CUUAC generated conjugates did not show cytotoxicity at the examined concentrations. These data show specific targeting and activity of the Herceptin ADCs generated by both CUUAC and SPPAAC conjugation methods.

REFERENCES

1. Blight et aL. 2004 Nature. 431 333-335 (2004)
2. Chen, P., 2009 Agnew Chem Int Ed Engl. 48, 4052-55.
3. Hancock et AL. JACS 2010, 132, 14819-24
4. Hecht et al., 1978 JBC 253, 4517-20.
5. Herold et al., 2008 PNAS 105, 18507-12.
6. Kavran et al., 2007 PNAS 104, 11268-73.
7. Kohrer et al., 2001 PNAS 98, 14310-15;
8. Kohrer et al., Chem & Biol., (2003) 10, 1095-1102;
9. Liebman SW. and Sherman, F. 1976 Genetics, 82, 233-249.
10. Liebman, S W et al., 1976 Genetics 82, 251-272.
11. Liu W. et al. 2007, Nature methods, 4; 239-244.
12. Mukai et al 2008 BBRC 371, 818-823
13. Naykova et al. 2003 J Mol. Evol. 57:520-532.
14. Neumann et al. 2008 Nat. Chem. Biol. 4, 232-234.
15. Nguyen et al., 2009 *J. Am. Chem. Soc.* 131 (25), pp 8720-8721
16. Nozawa 2009, Nature. 457 1163-67.
17. Pettit et al., 1997 Fortschr. Chem. Org. Naturst 70, 1-79
18. Sakamoto, K. 2002 Nucl. Acid Res. 30, 4692-4699.
19. Shan L. et al., J Gene Med. (2006) 8, 1400-1406.
20. Senter P. et al., 2003 Blood 102, 1458-65.
21. Takimoto j. 2009, Mol. Biosystems, 5, 931-34.
22. Wang w. Nature Neuro. 2007, 8; 1063-1072.
23. Ye, S. 2008, JBC 283, 1525-1533.
24. Yanagisawa 2008 Chem & Biol. 15, 1187-1197.
25. Wang et Al, 2011 Aijun Wang, Natalie Winblade Nairn, Marcello Marelli and Kenneth Grabstein (2012). Protein Engineering with Non-Natural Amino Acids, Protein Engineering, Prof. Pravin Kaumaya (Ed.), ISBN: 978-953-51-0037-9, InTech, Available from: http://www.intechopen.com/books/protein-engineering/protein-engineering-with-nonnatural-amino-acids
26. Fekner, T., Li, X., & Chan, M. K. (2010). Pyrrolysine Analogs for Translational Incorporation into Proteins. *European Journal of Organic Chemistry*, 4171-4179.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A process for stabilizing a eukaryotic cell line which expresses PylRS and tRNAPyl, wherein the cell line is capable of incorporating a gene encoding a target protein and wherein said target protein comprises one or more non-natural amino acids encoded by an amber codon, wherein said process comprises culturing said cell line in the presence of a decoy amino acid of:

(a) formula VIIA:

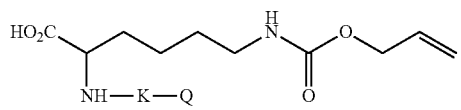

wherein K is CO or SO$_2$;
Q=H, C$_{1-6}$alkyl, aryl, heteroaryl, -OC$_{1-6}$alkyl, -OCH$_2$aryl, -OCH$_2$heteroaryl, C$_{2-6}$alkenyl or -OC$_{2-6}$alkenyl; or (b) formula VIIB:

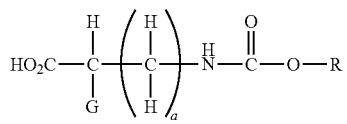

wherein G=H;
a=4 or 5; and
R=C$_{1-6}$alkyl, C$_{2-6}$alkenyl, CH$_2$aryl, C$_{2-6}$alkynyl, C$_{1-6}$haloalkyl or C$_{1-6}$azidoalkyl,
wherein the viability of said eukaryotic cell line is enhanced in comparison to the viability of said eukaryotic cell line cultured in the absence of said decoy amino acid.

2. A process according to claim 1 wherein the decoy amino acid is selected from:

Formula VIIB.1

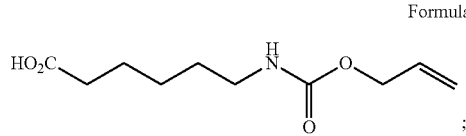

Formula VIIB.2

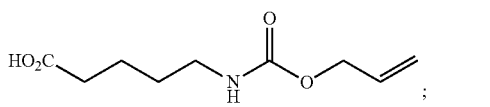

Formula VIIB.3

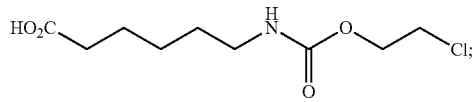 [SMILES: [N-]=[N+]=NCCOC(=O)NCCCCCC(=O)O]

Formula VIIB.4

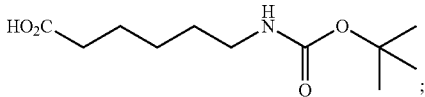

Formula VIIB.5

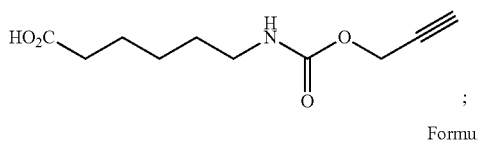

; and

Formula VIIB.6

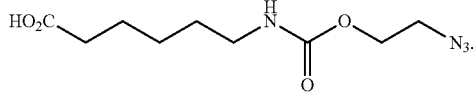

3. A process according to claim 1 wherein the expression of tRNAPyl occurs under the control of a repressible promoter.

4. A process according to claim 1 wherein the eukaryotic cell line is a mammalian cell line is selected from CHO, HEK293, PERC6, COS-1, COS-7, HeLa, VERO, mouse hybridoma and mouse myeloma cell lines.

5. A process according to claim 1 wherein the nonsense codon is an amber codon.

6. A process according to claim 1 wherein the compound of formula VII is a compound of formula VIIA:

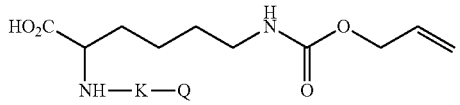

wherein K is CO or SO2;
Q=—H, C1-6alkyl, aryl, heteroaryl OC1-6alkyl, —OCH2aryl, —OCH2heteroaryl, —C2-6alkenyl or —OC2-6alkenyl.

* * * * *

SEQUENCE LISTING

```
<160> NUMBER OF SEQ ID NOS: 84

<210> SEQ ID NO 1
<211> LENGTH: 454
<212> TYPE: PRT
<213> ORGANISM: Methanosarcina mazei

<400> SEQUENCE: 1

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45
```

```
Asn Asn Ser Arg Ser Ser Arg Thr Ala Arg Ala Leu Arg His His Lys
    50              55                  60

Tyr Arg Lys Thr Cys Lys Arg Cys Arg Val Ser Asp Glu Asp Leu Asn
65              70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
                100                 105                 110

Ala Arg Ala Pro Lys Pro Leu Glu Asn Thr Glu Ala Ala Gln Ala Gln
                115                 120                 125

Pro Ser Gly Ser Lys Phe Ser Pro Ala Ile Pro Val Ser Thr Gln Glu
                130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
                180                 185                 190

Ser Gln Thr Asp Arg Leu Glu Val Leu Leu Asn Pro Lys Asp Glu Ile
                195                 200                 205

Ser Leu Asn Ser Gly Lys Pro Phe Arg Glu Leu Glu Ser Glu Leu Leu
                210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
                260                 265                 270

Ile Glu Arg Met Gly Ile Asp Asn Asp Thr Glu Leu Ser Lys Gln Ile
                275                 280                 285

Phe Arg Val Asp Lys Asn Phe Cys Leu Arg Pro Met Leu Ala Pro Asn
                290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
                340                 345                 350

Gly Cys Thr Arg Glu Asn Leu Glu Ser Ile Ile Thr Asp Phe Leu Asn
                355                 360                 365

His Leu Gly Ile Asp Phe Lys Ile Val Gly Asp Ser Cys Met Val Tyr
                370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
                420                 425                 430

Asp Phe Lys Asn Ile Lys Arg Ala Ala Arg Ser Glu Ser Tyr Tyr Asn
                435                 440                 445

Gly Ile Ser Thr Asn Leu
        450
```

```
<210> SEQ ID NO 2
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PylRS Methanosarcina mazei Y384F mutant amino
      acid sequence

<400> SEQUENCE: 2

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65              70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350
```

```
Gly Cys Thr Arg Glu Asn Leu Glu Ser Ile Ile Thr Asp Phe Leu Asn
            355                 360                 365

His Leu Gly Ile Asp Phe Lys Ile Val Gly Asp Ser Cys Met Val Phe
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 3
<211> LENGTH: 419
<212> TYPE: PRT
<213> ORGANISM: Methanosarcina barkeri

<400> SEQUENCE: 3

Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Ala Pro Lys Val Lys Lys Ala Met Pro Lys Ser Val Ser
            100                 105                 110

Arg Ala Pro Lys Pro Leu Glu Asn Pro Val Ser Ala Lys Ala Ser Thr
        115                 120                 125

Asp Thr Ser Arg Ser Val Pro Ser Pro Ala Lys Ser Thr Pro Asn Ser
    130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Asp Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270
```

```
Tyr Leu Arg Lys Leu Asp Arg Ile Leu Pro Asp Pro Ile Lys Ile Phe
            275                 280                 285

Glu Val Gly Pro Cys Tyr Arg Lys Glu Ser Asp Gly Lys Glu His Leu
        290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Pro Leu Asp Arg Glu Trp Gly Ile Asp Lys Pro Trp Ile Gly
370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 4
<211> LENGTH: 288
<212> TYPE: PRT
<213> ORGANISM: Desulfitobacterium hafniense

<400> SEQUENCE: 4

Met Phe Leu Thr Arg Arg Asp Pro Pro Leu Ser Ser Phe Trp Thr Lys
1               5                   10                  15

Val Gln Tyr Gln Arg Leu Lys Glu Leu Asn Ala Ser Gly Glu Gln Leu
            20                  25                  30

Glu Met Gly Phe Ser Asp Ala Leu Ser Arg Asp Arg Ala Phe Gln Gly
        35                  40                  45

Ile Glu His Gln Leu Met Ser Gln Gly Lys Arg His Leu Glu Gln Leu
    50                  55                  60

Arg Thr Val Lys His Arg Pro Ala Leu Leu Glu Leu Glu Glu Lys Leu
65                  70                  75                  80

Ala Lys Ala Leu His Gln Gln Gly Phe Val Gln Val Val Thr Pro Thr
                85                  90                  95

Ile Ile Thr Lys Ser Ala Leu Ala Lys Met Thr Ile Gly Glu Asp His
            100                 105                 110

Pro Leu Phe Ser Gln Val Phe Trp Leu Asp Gly Lys Lys Cys Leu Arg
        115                 120                 125

Pro Met Leu Ala Pro Asn Leu Tyr Thr Leu Trp Arg Glu Leu Glu Arg
    130                 135                 140

Leu Trp Asp Lys Pro Ile Arg Ile Phe Glu Ile Gly Thr Cys Tyr Arg
145                 150                 155                 160

Lys Glu Ser Gln Gly Ala Gln His Leu Asn Glu Phe Thr Met Leu Asn
                165                 170                 175

Leu Thr Glu Leu Gly Thr Pro Leu Glu Glu Arg His Gln Arg Leu Glu
            180                 185                 190

Asp Met Ala Arg Trp Val Leu Glu Ala Ala Gly Ile Arg Glu Phe Glu
        195                 200                 205

Leu Val Thr Glu Ser Ser Val Val Tyr Gly Asp Thr Val Asp Val Met
    210                 215                 220
```

```
Lys Gly Asp Leu Glu Leu Ala Ser Gly Ala Met Gly Pro His Phe Leu
225                 230                 235                 240

Asp Glu Lys Trp Glu Ile Phe Asp Pro Trp Val Gly Leu Gly Phe Gly
            245                 250                 255

Leu Glu Arg Leu Leu Met Ile Arg Glu Gly Thr Gln His Val Gln Ser
        260                 265                 270

Met Ala Arg Ser Leu Ser Tyr Leu Asp Gly Val Arg Leu Asn Ile Asn
        275                 280                 285

<210> SEQ ID NO 5
<211> LENGTH: 443
<212> TYPE: PRT
<213> ORGANISM: Methanosarcina acetivorans

<400> SEQUENCE: 5

Met Asp Lys Lys Pro Leu Asp Thr Leu Ile Ser Ala Thr Gly Leu Trp
1               5                   10                  15

Met Ser Arg Thr Gly Met Ile His Lys Ile Lys His His Glu Val Ser
            20                  25                  30

Arg Ser Lys Ile Tyr Ile Glu Met Ala Cys Gly Glu Arg Leu Val Val
        35                  40                  45

Asn Asn Ser Arg Ser Ser Arg Thr Ala Arg Ala Leu Arg His His Lys
    50                  55                  60

Tyr Arg Lys Thr Cys Arg His Cys Arg Val Ser Asp Glu Asp Ile Asn
65                  70                  75                  80

Asn Phe Leu Thr Lys Thr Ser Glu Glu Lys Thr Thr Val Lys Val Lys
                85                  90                  95

Val Val Ser Ala Pro Arg Val Arg Lys Ala Met Pro Lys Ser Val Ala
            100                 105                 110

Arg Ala Pro Lys Pro Leu Glu Ala Thr Ala Gln Val Pro Leu Ser Gly
        115                 120                 125

Ser Lys Pro Ala Pro Ala Thr Pro Val Ser Ala Pro Ala Gln Ala Pro
    130                 135                 140

Ala Pro Ser Thr Gly Ser Ala Ser Ala Thr Ser Ala Ser Ala Gln Arg
145                 150                 155                 160

Met Ala Asn Ser Ala Ala Ala Pro Ala Ala Pro Val Pro Thr Ser Ala
            165                 170                 175

Pro Ala Leu Thr Lys Gly Gln Leu Asp Arg Leu Glu Gly Leu Leu Ser
        180                 185                 190

Pro Lys Asp Glu Ile Ser Leu Asp Ser Glu Lys Pro Phe Arg Glu Leu
    195                 200                 205

Glu Ser Glu Leu Leu Ser Arg Arg Lys Lys Asp Leu Lys Arg Ile Tyr
    210                 215                 220

Ala Glu Glu Arg Glu Asn Tyr Leu Gly Lys Leu Glu Arg Glu Ile Thr
225                 230                 235                 240

Lys Phe Phe Val Asp Arg Gly Phe Leu Glu Ile Lys Ser Pro Ile Leu
            245                 250                 255

Ile Pro Ala Glu Tyr Val Glu Arg Met Gly Ile Asn Ser Asp Thr Glu
        260                 265                 270

Leu Ser Lys Gln Val Phe Arg Ile Asp Lys Asn Phe Cys Leu Arg Pro
    275                 280                 285

Met Leu Ala Pro Asn Leu Tyr Asn Tyr Leu Arg Lys Leu Asp Arg Ala
    290                 295                 300

Leu Pro Asp Pro Ile Lys Ile Phe Glu Ile Gly Pro Cys Tyr Arg Lys
```

```
           305                 310                 315                 320
Glu Ser Asp Gly Lys Glu His Leu Glu Glu Phe Thr Met Leu Asn Phe
                325                 330                 335

Cys Gln Met Gly Ser Gly Cys Thr Arg Glu Asn Leu Glu Ala Ile Ile
                340                 345                 350

Thr Glu Phe Leu Asn His Leu Gly Ile Asp Phe Glu Ile Ile Gly Asp
                355                 360                 365

Ser Cys Met Val Tyr Gly Asn Thr Leu Asp Val Met His Asp Asp Leu
                370                 375                 380

Glu Leu Ser Ser Ala Val Val Gly Pro Val Pro Leu Asp Arg Glu Trp
385                 390                 395                 400

Gly Ile Asp Lys Pro Trp Ile Gly Ala Gly Phe Gly Leu Glu Arg Leu
                405                 410                 415

Leu Lys Val Met His Gly Phe Lys Asn Ile Lys Arg Ala Ala Arg Ser
                420                 425                 430

Glu Ser Tyr Tyr Asn Gly Ile Ser Thr Asn Leu
                435                 440

<210> SEQ ID NO 6
<211> LENGTH: 416
<212> TYPE: PRT
<213> ORGANISM: Methanococcoides burtonii

<400> SEQUENCE: 6

Met Glu Lys Gln Leu Leu Asp Val Leu Val Glu Leu Asn Gly Val Trp
1               5                   10                  15

Leu Ser Arg Ser Gly Leu Leu His Gly Ile Arg Asn Phe Glu Ile Thr
                20                  25                  30

Thr Lys His Ile His Ile Glu Thr Asp Cys Gly Ala Arg Phe Thr Val
                35                  40                  45

Arg Asn Ser Arg Ser Ser Arg Ser Ala Arg Ser Leu Arg His Asn Lys
                50                  55                  60

Tyr Arg Lys Pro Cys Lys Arg Cys Arg Pro Ala Asp Glu Gln Ile Asp
65                  70                  75                  80

Arg Phe Val Lys Lys Thr Phe Lys Glu Lys Arg Gln Thr Val Ser Val
                85                  90                  95

Phe Ser Ser Pro Lys Lys His Val Pro Lys Lys Pro Lys Val Ala Val
                100                 105                 110

Ile Lys Ser Phe Ser Ile Ser Thr Pro Ser Pro Lys Glu Ala Ser Val
                115                 120                 125

Ser Asn Ser Ile Pro Thr Pro Ser Ile Ser Val Val Lys Asp Glu Val
                130                 135                 140

Lys Val Pro Glu Val Lys Tyr Thr Pro Ser Gln Ile Glu Arg Leu Lys
145                 150                 155                 160

Thr Leu Met Ser Pro Asp Asp Lys Ile Pro Ile Gln Asp Glu Leu Pro
                165                 170                 175

Glu Phe Lys Val Leu Glu Lys Glu Leu Ile Gln Arg Arg Asp Asp
                180                 185                 190

Leu Lys Lys Met Tyr Glu Glu Asp Arg Glu Asp Arg Leu Gly Lys Leu
                195                 200                 205

Glu Arg Asp Ile Thr Glu Phe Phe Val Asp Arg Gly Phe Leu Glu Ile
                210                 215                 220

Lys Ser Pro Ile Met Ile Pro Phe Glu Tyr Ile Glu Arg Met Gly Ile
225                 230                 235                 240
```

```
Asp Lys Asp Asp His Leu Asn Lys Gln Ile Phe Arg Val Asp Glu Ser
            245                 250                 255
Met Cys Leu Arg Pro Met Leu Ala Pro Cys Leu Tyr Asn Tyr Leu Arg
        260                 265                 270
Lys Leu Asp Lys Val Leu Pro Asp Pro Ile Arg Ile Phe Glu Ile Gly
    275                 280                 285
Pro Cys Tyr Arg Lys Glu Ser Asp Gly Ser Ser His Leu Glu Glu Phe
290                 295                 300
Thr Met Val Asn Phe Cys Gln Met Gly Ser Gly Cys Thr Arg Glu Asn
305                 310                 315                 320
Met Glu Ala Leu Ile Asp Glu Phe Leu Glu His Leu Gly Ile Glu Tyr
            325                 330                 335
Glu Ile Glu Ala Asp Asn Cys Met Val Tyr Gly Asp Thr Ile Asp Ile
        340                 345                 350
Met His Gly Asp Leu Glu Leu Ser Ser Ala Val Val Gly Pro Ile Pro
    355                 360                 365
Leu Asp Arg Glu Trp Gly Val Asn Lys Pro Trp Met Gly Ala Gly Phe
370                 375                 380
Gly Leu Glu Arg Leu Leu Lys Val Arg His Asn Tyr Thr Asn Ile Arg
385                 390                 395                 400
Arg Ala Ser Arg Ser Glu Leu Tyr Tyr Asn Gly Ile Asn Thr Asn Leu
            405                 410                 415

<210> SEQ ID NO 7
<211> LENGTH: 478
<212> TYPE: PRT
<213> ORGANISM: Methanosarcina thermophila

<400> SEQUENCE: 7

Met Asp Lys Lys Pro Leu Asn Thr Leu Ile Ser Ala Thr Gly Leu Trp
1               5                   10                  15
Met Ser Arg Thr Gly Lys Leu His Lys Ile Arg His His Glu Val Ser
            20                  25                  30
Lys Arg Lys Ile Tyr Ile Glu Met Glu Cys Gly Glu Arg Leu Val Val
        35                  40                  45
Asn Asn Ser Arg Ser Cys Arg Ala Ala Arg Ala Leu Arg His His Lys
    50                  55                  60
Tyr Arg Lys Ile Cys Lys His Cys Arg Val Ser Asp Glu Asp Leu Asn
65                  70                  75                  80
Lys Phe Leu Thr Arg Thr Asn Glu Asp Lys Ser Asn Ala Lys Val Thr
            85                  90                  95
Val Val Ser Ala Pro Lys Ile Arg Lys Val Met Pro Lys Ser Val Ala
        100                 105                 110
Arg Thr Pro Lys Pro Leu Glu Asn Thr Ala Pro Val Gln Thr Leu Pro
    115                 120                 125
Ser Glu Ser Gln Pro Ala Pro Thr Thr Pro Ile Ser Ala Ser Thr Thr
130                 135                 140
Ala Pro Ala Ser Thr Ser Thr Thr Ala Pro Ala Pro Ala Ser Thr Thr
145                 150                 155                 160
Ala Pro Ala Pro Ala Ser Thr Thr Ala Pro Ala Ser Ala Ser Thr Thr
            165                 170                 175
Ile Ser Thr Ser Ala Met Pro Ala Ser Thr Ser Ala Gln Gly Thr Thr
        180                 185                 190
Lys Phe Asn Tyr Ile Ser Gly Gly Phe Pro Arg Pro Ile Pro Val Gln
    195                 200                 205
```

```
Ala Ser Ala Pro Ala Leu Thr Lys Ser Gln Ile Asp Arg Leu Gln Gly
        210                 215                 220

Leu Leu Ser Pro Lys Asp Glu Ile Ser Leu Asp Ser Gly Thr Pro Phe
225                 230                 235                 240

Arg Lys Leu Glu Ser Glu Leu Leu Ser Arg Arg Lys Asp Leu Lys
                245                 250                 255

Gln Ile Tyr Ala Glu Glu Arg Glu His Tyr Leu Gly Lys Leu Glu Arg
        260                 265                 270

Glu Ile Thr Lys Phe Phe Val Asp Arg Gly Phe Leu Glu Ile Lys Ser
        275                 280                 285

Pro Ile Leu Ile Pro Met Glu Tyr Ile Glu Arg Met Gly Ile Asp Asn
290                 295                 300

Asp Lys Glu Leu Ser Lys Gln Ile Phe Arg Val Asp Asn Asn Phe Cys
305                 310                 315                 320

Leu Arg Pro Met Leu Ala Pro Asn Leu Tyr Asn Tyr Leu Arg Lys Leu
                325                 330                 335

Asn Arg Ala Leu Pro Asp Pro Ile Lys Ile Phe Glu Ile Gly Pro Cys
                340                 345                 350

Tyr Arg Lys Glu Ser Asp Gly Lys Glu His Leu Glu Glu Phe Thr Met
                355                 360                 365

Leu Asn Phe Cys Gln Met Gly Ser Gly Cys Thr Arg Glu Asn Leu Glu
370                 375                 380

Ala Ile Ile Lys Asp Phe Leu Asp Tyr Leu Gly Ile Asp Phe Glu Ile
385                 390                 395                 400

Val Gly Asp Ser Cys Met Val Tyr Gly Asp Thr Leu Asp Val Met His
                405                 410                 415

Gly Asp Leu Glu Leu Ser Ser Ala Val Val Gly Pro Val Pro Met Asp
                420                 425                 430

Arg Asp Trp Gly Ile Asn Lys Pro Trp Ile Gly Ala Gly Phe Gly Leu
                435                 440                 445

Glu Arg Leu Leu Lys Val Met His Asn Phe Lys Asn Ile Lys Arg Ala
                450                 455                 460

Ser Arg Ser Glu Ser Tyr Tyr Asn Gly Ile Ser Thr Asn Leu
465                 470                 475

<210> SEQ ID NO 8
<211> LENGTH: 427
<212> TYPE: PRT
<213> ORGANISM: Methanosalsum zhilinae

<400> SEQUENCE: 8

Met Thr Arg Arg Ser Leu Glu Ser Leu Val Ser Glu Lys Glu Val Trp
1               5                   10                  15

Leu Ser Arg Lys Gly Leu Leu His Glu Ile Lys Asp Tyr Ser Val Thr
                20                  25                  30

Gln Arg Tyr Ile Asn Ile Tyr Thr Thr Cys Gly Glu Ser Phe Ser Val
        35                  40                  45

Arg Asn Ser Arg Arg Gly Arg Ala Ser Arg Val Leu Arg Asn Asn Lys
    50                  55                  60

Tyr Arg Lys Ile Cys Lys His Cys Lys Val Pro Asp Glu Lys Ile Ser
65                  70                  75                  80

Lys Phe Leu Gln Lys Ala Ser Val Asp Ser Thr Ala Lys Val Lys Val
                85                  90                  95

Val Ser Ser Thr Lys Pro Ser Gln Ser Lys Lys Ala Val Pro Lys Ala
```

```
            100                 105                 110
Val Lys Ala Lys Lys Gly Thr Glu Asn Ser Asn Gly Ser Leu Ile
            115                 120                 125

Gln Ser Lys Val Lys Asp Gln Gly Ser Val Asn Ala Ile Ser Ser Gly
            130                 135                 140

Gln Pro Arg Ser Lys Ile Gln Pro Thr Glu Glu Arg Asn Asn Ile Pro
145                 150                 155                 160

Ala Phe Thr Pro Ser Gln Lys Lys Arg Leu Glu Ala Leu Leu Met Pro
                165                 170                 175

Glu Glu Val Ile Pro Asp Pro Ser Glu Asn Leu Asn Phe Gln Glu Leu
            180                 185                 190

Glu Ser Ser Leu Val Asn Arg Arg Lys Lys Asp Ile Val Lys Ile Tyr
            195                 200                 205

Glu Asp Asp Arg Glu Asn Gln Leu Gly Lys Ile Glu Arg Ile Ile Thr
            210                 215                 220

Lys Phe Phe Val Asp Arg Gly Phe Leu Glu Ile Lys Ser Pro Ile Leu
225                 230                 235                 240

Ile Pro Ile Glu Tyr Ile Glu Arg Met Gly Ile Thr Glu Asp Lys Glu
                245                 250                 255

Leu Phe Glu Gln Val Phe Lys Val Asp Lys Asn Met Cys Leu Arg Pro
            260                 265                 270

Met Leu Ala Pro Gly Leu Tyr Asn His Leu Arg Lys Phe Asp Lys Val
            275                 280                 285

Leu Pro Asp Pro Ile Arg Ile Phe Glu Ile Gly Pro Cys Tyr Arg Lys
            290                 295                 300

Glu Ser Asp Gly Ser Gln His Leu Glu Glu Phe Thr Met Leu Asn Phe
305                 310                 315                 320

Cys Gln Met Gly Ser Met Cys Thr Arg Lys Thr Leu Glu Asn Leu Ile
                325                 330                 335

Asp Glu Leu Leu Glu Phe Met Asp Ile Glu Tyr Glu Ile Val Ser Asp
            340                 345                 350

Asn Cys His Val Tyr Gly Ala Thr Ile Asp Val Leu His Lys Asp Met
            355                 360                 365

Glu Leu Ala Ser Ala Val Val Gly Pro Ile Pro Lys Asp Ala Asp Trp
            370                 375                 380

Gly Ile Thr Lys Pro Trp Ile Gly Ala Gly Phe Gly Leu Glu Arg Leu
385                 390                 395                 400

Leu Lys Val Met His Asn Tyr Lys Asn Ile Arg Arg Ala Ser Arg Ser
                405                 410                 415

Glu Ser Tyr Tyr Asn Gly Ile Thr Thr Asn Leu
            420                 425

<210> SEQ ID NO 9
<211> LENGTH: 414
<212> TYPE: PRT
<213> ORGANISM: Methanohalobium evestigatum

<400> SEQUENCE: 9

Met Ser Lys Lys Ser Leu Ala Ser Leu Ile Ser Asp Leu Gln Val Trp
1               5                   10                  15

Val Ser Arg Ser Gly Leu Leu His Glu Ile Lys Asn Tyr Glu Val Ser
            20                  25                  30

Gln Arg Tyr Ile His Met Glu Met Asp Cys Gly Glu Lys Ile Thr Val
        35                  40                  45
```

```
Arg Asn Ser Arg Asn Ser Arg Thr Ala Arg Ile Leu Arg Lys Lys
 50                  55                  60

Tyr Lys Lys Pro Cys Lys Asn Cys Lys Val Ser Asp Glu Val Ile Asn
 65                  70                  75                  80

Arg Phe Leu Gln Lys His Thr Asp Arg Thr Asp Thr Lys Val Thr Ala
                 85                  90                  95

Phe Ser Tyr Ser Glu Ser Lys Lys Lys Ser Lys Gln Leu Gly His
            100                 105                 110

Lys Lys Lys Lys Gln Ser Lys Val Gln Val Asn Pro Thr Thr Glu Ser
            115                 120                 125

Ile Gln Ser Asn Thr Ser Val Ser Glu Asp Lys Thr Asp Asn Lys Ile
130                 135                 140

Glu Pro Glu Thr Phe Thr Ser Ala Gln Lys Glu Arg Ile Asn Glu Leu
145                 150                 155                 160

Leu Leu Pro Gly Glu Lys Ile Pro Phe Ser Asn Glu Pro Ser Lys Phe
                165                 170                 175

Lys Glu Ile Glu Ser Glu Leu Val Asn Lys Arg Arg Asn Asp Phe Lys
            180                 185                 190

Gln Met Tyr Glu Asn Asp Arg Glu Gln Ile Ala Lys Leu Glu Arg
            195                 200                 205

Thr Ile Ser Gln Phe Phe Val Asp Lys Gly Phe Ile Glu Ile Lys Ala
210                 215                 220

Pro Ile Ile Ile Asp Ile Asp Ser Val Lys Lys Met Gly Ile Asp Thr
225                 230                 235                 240

Asp His Lys Leu Ser Lys Gln Ile Phe Tyr Leu Asp Asn Lys His Cys
                245                 250                 255

Leu Arg Pro Met Leu Ala Pro Gly Leu Tyr Gln Trp Leu Lys Asn Phe
            260                 265                 270

Asp Lys Ile Leu Pro Asp Pro Ile Lys Ile Phe Glu Ile Gly Pro Cys
            275                 280                 285

Tyr Arg Lys Glu Ser Glu Gly Ser Gln His Leu Glu Glu Phe Thr Met
290                 295                 300

Phe Asn Phe Cys Gln Met Gly Ser Gly Ala Asn Arg Glu Asn Leu Leu
305                 310                 315                 320

Asn His Ile Asp Asp Leu Leu Lys His Leu Asn Ile Asp Tyr Lys Ile
                325                 330                 335

Ile Asp Asp Asn Cys His Val Tyr Gly Glu Thr Ile Asp Ile Val His
            340                 345                 350

Gly Asp Leu Glu Leu Ser Ser Ala Val Val Gly Pro Val Pro Ile Asp
            355                 360                 365

Met Asn Trp Gly Ile Asp Lys Thr Trp Ile Gly Ala Gly Leu Gly Leu
370                 375                 380

Glu Arg Leu Leu Lys Val Lys His Gly Tyr Lys Asn Ile Lys Arg Ala
385                 390                 395                 400

Ser Lys Ser His Ser Tyr Tyr Asn Gly Ile Ser Thr Asn Leu
                405                 410

<210> SEQ ID NO 10
<211> LENGTH: 404
<212> TYPE: PRT
<213> ORGANISM: Methanohalophilus mahii

<400> SEQUENCE: 10

Met Glu Arg Lys Pro Leu Asp Leu Leu Ile Asp Thr Asn Gly Val Trp
1               5                   10                  15
```

```
Leu Ser Arg Asn Gly Leu Leu His Gly Val Lys Asn Phe Glu Val Ser
            20                  25                  30

Arg Asn His Ile His Ile Thr Thr Asp Cys Gln Ser Arg Phe Thr Val
            35                  40                  45

Arg Asn Ser Arg Arg Ser Arg Ser Ala Arg Ala Leu Arg Asn Asn Lys
            50                  55                  60

Tyr Arg Lys Ala Cys Lys Asn Cys Lys Leu Ser Asp Glu Arg Ile Thr
 65                  70                  75                  80

Arg Phe Val Thr Lys Asp Phe Gly Arg Gly Ser Gln Ala Arg Val Ile
                     85                  90                  95

Thr Ser Ser Lys Thr Lys Lys Ser Lys Ser Pro Lys Glu Ala Val Val
            100                 105                 110

Lys Ser Val Ser Ser Lys Ala Asn Glu Met Pro Pro Val Val Glu Ala
            115                 120                 125

Lys Lys Glu Lys Pro Val Lys Pro Asp Tyr Thr Pro Ala Gln Lys Lys
            130                 135                 140

Arg Ile Thr Thr Leu Leu Ser Pro Ala Asp Asp Leu Ser Ser Ile Lys
145                 150                 155                 160

Glu Leu Pro Thr Phe Lys Glu Leu Glu Thr Glu Leu Val Lys Lys Arg
                     165                 170                 175

Lys Gln Asp Leu Arg Gln Met Tyr Glu Asp Asp Arg Arg His Gln Leu
            180                 185                 190

Ala Gln Leu Glu Arg Asp Ile Ser Leu Phe Leu Ile Glu Lys Gly Phe
            195                 200                 205

Met Glu Val Arg Thr Ser Val Leu Ile Pro Ala Lys Phe Ile Glu Arg
            210                 215                 220

Met Gly Ile Thr Glu Glu Asp Pro Leu Tyr Lys Gln Ile Phe Arg Val
225                 230                 235                 240

Asp Glu Asn Thr Cys Leu Arg Pro Met Leu Ala Pro Gly Leu Tyr Asn
                     245                 250                 255

Tyr Leu His Asn Phe Asp Asn Ile Met Pro Asp Pro Leu Lys Ile Phe
            260                 265                 270

Glu Ile Gly Thr Cys Tyr Arg Lys Glu Ser Asp Gly Lys Glu His Leu
            275                 280                 285

Glu Glu Phe Thr Met Val Asn Phe Cys Gln Met Gly Ser Gly Cys Thr
            290                 295                 300

Lys Glu Asn Leu Leu Asn Ile Ile Asp Asp Leu Leu Lys Tyr Leu Asn
305                 310                 315                 320

Ile Asp Tyr Glu Val Ile Ser Asp Asn Cys Met Val Tyr Gly Asp Thr
                     325                 330                 335

Ile Asp Ile Met His Gly Asp Met Glu Ile Ser Ser Ala Val Val Gly
            340                 345                 350

Pro Ile Pro Gln Asp Leu Asp Trp Gly Val Thr Lys Pro Trp Met Gly
            355                 360                 365

Ala Gly Met Gly Ile Glu Arg Leu Leu Lys Val Lys His Lys Tyr Thr
            370                 375                 380

Asn Ile Lys Arg Ser Ser Arg Ser Ile Ser Tyr Tyr Asn Gly Ile Thr
385                 390                 395                 400

Thr Asn Leu Arg

<210> SEQ ID NO 11
<211> LENGTH: 277
<212> TYPE: PRT
```

<213> ORGANISM: Desulfotomaculum gibsoniae

<400> SEQUENCE: 11

```
Met Ile Asn Trp Ser Ile Ser Gln Lys Gln Lys Leu Ile Glu Leu Asn
1               5                   10                  15

Gly Lys Ser Glu Leu Leu Asp Leu Arg Phe Gln Asp Lys Gln Lys Arg
            20                  25                  30

Asp Gln Thr Phe Gln Lys Ile Glu Lys Glu Leu Val Lys Lys Asn Lys
        35                  40                  45

Asp His Leu Leu Glu Leu Lys Glu Val Ile His Arg Pro Leu Leu Ser
    50                  55                  60

Ser Leu Glu Ile Gln Leu Ser Asn Leu Leu Cys Lys Thr Gly Phe Val
65                  70                  75                  80

Gln Val Asn Thr Pro Ile Ile Leu Pro Lys Ala Met Leu His Lys Met
                85                  90                  95

Thr Ile Thr Pro Glu His Pro Leu Tyr Lys Gln Val Phe Trp Val Asp
            100                 105                 110

Asn Asn Lys Cys Leu Arg Pro Met Leu Ala Pro Asn Leu Tyr His Tyr
        115                 120                 125

Leu Lys Ile Leu Asp Arg Leu Trp Ser Lys Pro Val Arg Ile Phe Glu
    130                 135                 140

Ile Gly Pro Cys Phe Arg Lys Glu Ser Gln Gly Ala Gln His Leu Asn
145                 150                 155                 160

Glu Phe Thr Met Leu Asn Leu Val Glu Leu Gly Val Asp Lys Gly Lys
                165                 170                 175

Gln Thr Glu Arg Leu Lys Glu Leu Gly Ser Leu Val Met Glu Glu Ile
            180                 185                 190

Gly Val Lys Asn Tyr Glu Phe Val Glu Thr Glu Ser Glu Ile Tyr Gly
        195                 200                 205

Ile Thr Val Asp Val Val Phe Asp Asp Leu Glu Leu Gly Ser Gly Ala
    210                 215                 220

Phe Gly Pro Leu Lys Met Asp Glu Gln Trp Gly Ile Phe Glu Pro Trp
225                 230                 235                 240

Val Gly Ile Gly Phe Gly Leu Glu Arg Leu Ala Met Thr Leu Gln Gly
                245                 250                 255

His Arg Asn Ile Arg Arg Val Gly Arg Gly Leu Thr Tyr Leu Asp Gly
            260                 265                 270

Ser Leu Leu Asn Ile
        275
```

<210> SEQ ID NO 12
<211> LENGTH: 277
<212> TYPE: PRT
<213> ORGANISM: Desulfosporosinus meridiei

<400> SEQUENCE: 12

```
Met Ser Ile Thr Trp Thr Pro Ile Gln Lys Gln Arg Leu Gln Glu Leu
1               5                   10                  15

Asn Ala Ser Glu Val Leu Gln Glu Met Cys Phe Glu Ser His Gln Glu
            20                  25                  30

Arg Asp Arg Ala Tyr Gln Glu Glu His Leu Leu Val Ile Arg Gly
        35                  40                  45

Lys Gln Lys Leu Gln Glu Leu Leu Glu Thr Asn Arg Arg Pro Ser Leu
    50                  55                  60

Ser Val Leu Glu Gln Gln Leu Val Glu Ala Leu Thr Gln Glu Gly Phe
```

```
                65                  70                  75                  80
Val Gln Val Val Thr Pro Thr Ile Ile Ser Lys Thr Ala Leu Ala Lys
                    85                  90                  95

Met Ser Val Ser Asp Asp His Pro Leu Phe Ser Gln Val Phe Trp Leu
                100                 105                 110

Asp Ser Lys Arg Cys Leu Arg Pro Met Leu Ala Pro Asn Leu Tyr Thr
                115                 120                 125

Leu Trp Arg Asp Leu Leu Arg Leu Trp Glu Lys Pro Ile Arg Ile Phe
130                 135                 140

Glu Ile Gly Thr Cys Tyr Arg Lys Glu Ser Lys Gly Ser Leu His Leu
145                 150                 155                 160

Asn Glu Phe Thr Met Leu Asn Leu Thr Glu Leu Gly Leu Pro Leu Asp
                165                 170                 175

Gln Arg His Gln Arg Leu Lys Glu Leu Ala Asp Leu Val Met Asn Thr
                180                 185                 190

Val Gly Ile Asp Asp Tyr Gln Leu Glu Ser Glu Ser Val Val Tyr
                195                 200                 205

Gly Asp Thr Leu Asp Val Val Lys Gly Ile Glu Leu Gly Ser Ser Ala
210                 215                 220

Met Gly Pro His Val Leu Asp Asp Gln Trp Gly Ile Phe Asp Pro Trp
225                 230                 235                 240

Val Gly Ile Gly Phe Gly Leu Glu Arg Leu Leu Met Ile Lys Glu Gly
                245                 250                 255

Ser Gln Asn Val Gln Ser Met Gly Arg Ser Leu Thr Tyr Leu Asn Gly
                260                 265                 270

Val Arg Leu Asn Ile
                275

<210> SEQ ID NO 13
<211> LENGTH: 278
<212> TYPE: PRT
<213> ORGANISM: Desulfotomaculum acetoxidans

<400> SEQUENCE: 13

Met Ser Phe Leu Trp Thr Val Ser Gln Gln Lys Arg Leu Ser Glu Leu
1               5                   10                  15

Asn Ala Ser Glu Glu Lys Asn Met Ser Phe Ser Ser Thr Ser Asp
                20                  25                  30

Arg Glu Ala Ala Tyr Lys Arg Val Glu Met Arg Leu Ile Asn Glu Ser
            35                  40                  45

Lys Gln Arg Leu Asn Lys Leu Arg His Glu Thr Lys Arg Pro Ala Ile
        50                  55                  60

Cys Ala Leu Glu Asn Arg Leu Ala Ala Ala Leu Arg Gly Ala Gly Phe
65                  70                  75                  80

Val Gln Val Ala Thr Pro Val Ile Leu Ser Lys Lys Leu Leu Gly Lys
                85                  90                  95

Met Thr Ile Thr Asp Glu His Ala Leu Phe Ser Gln Val Phe Trp Ile
                100                 105                 110

Glu Glu Asn Lys Cys Leu Arg Pro Met Leu Ala Pro Asn Leu Tyr Tyr
                115                 120                 125

Ile Leu Lys Asp Leu Leu Arg Leu Trp Glu Lys Pro Val Arg Ile Phe
130                 135                 140

Glu Ile Gly Ser Cys Phe Arg Lys Glu Ser Gln Gly Ser Asn His Leu
145                 150                 155                 160
```

```
Asn Glu Phe Thr Met Leu Asn Leu Val Glu Trp Gly Leu Pro Glu Glu
                165                 170                 175

Gln Arg Gln Lys Arg Ile Ser Glu Leu Ala Lys Leu Val Met Asp Glu
            180                 185                 190

Thr Gly Ile Asp Glu Tyr His Leu Glu His Ala Glu Ser Val Val Tyr
        195                 200                 205

Gly Glu Thr Val Asp Val Met His Arg Asp Ile Glu Leu Gly Ser Gly
    210                 215                 220

Ala Leu Gly Pro His Phe Leu Asp Gly Arg Trp Gly Val Val Gly Pro
225                 230                 235                 240

Trp Val Gly Ile Gly Phe Gly Leu Glu Arg Leu Leu Met Val Glu Gln
                245                 250                 255

Gly Gly Gln Asn Val Arg Ser Met Gly Lys Ser Leu Thr Tyr Leu Asp
            260                 265                 270

Gly Val Arg Leu Asn Ile
        275
```

<210> SEQ ID NO 14
<211> LENGTH: 1365
<212> TYPE: DNA
<213> ORGANISM: Methanosarcina mazei

<400> SEQUENCE: 14

```
atggataaaa aaccactaaa cactctgata tctgcaaccg ggctctggat gtccaggacc        60
ggaacaattc ataaaataaa acaccacgaa gtctctcgaa gcaaaatcta tattgaaatg       120
gcatgcggag accaccttgt tgtaaacaac tccaggagca gcaggactgc aagagcgctc       180
aggcaccaca atacaggaa  gacctgcaaa cgctgcaggg tttcggatga ggatctcaat       240
aagttcctca caaggcaaa  cgaagaccag acaagcgtaa agtcaaggt  cgtttctgcc       300
cctaccagaa cgaaaaaggc aatgccaaaa tccgttgcga gaccccgaa  acctcttgag       360
aatacagaag cggcacaggc tcaaccttct ggatctaaat tttcacctgc gataccggtt       420
tccacccaag agtcagtttc tgtcccggca tctgtttcaa catcaatatc aagcatttct       480
acaggagcaa ctgcatccgc actggtaaaa gggaatacga accccattac atccatgtct       540
gcccctgttc aggcaagtgc ccccgcactt acgaagagcc agactgacag gcttgaagtc       600
ctgttaaacc caaagatga  gatttccctg aattccggca gccttcag  ggagcttgag       660
tccgaattgc tctctcgcag aaaaaaagac ctgcagcaga tctacgcgga agaaagggag       720
aattatctgg ggaaactcga gcgtgaaatt accaggttct tgtggacag  ggttttctg       780
gaaataaaat ccccgatcct gatccctctt gagtatatcg aaaggatggg cattgataat       840
gataccgaac tttcaaaaca gatcttcagg gttgacaaga acttctgcct gagacccatg       900
cttgctccaa accttttacaa ctacctgcgc aagcttgaca gggccctgcc tgatccaata       960
aaaattttg  aataggccc  atgctacaga aaagagtccg acggcaaaga acacctcgaa      1020
gagtttacca tgctgaactt ctgccagatg ggatcgggat gcacacggga aaatcttgaa      1080
agcataatta cggacttcct gaaccacctg ggaattgatt tcaagatcgt aggcgattcc      1140
tgcatggtct atgggatac  ccttgatgta atgcacggag acctggaact ttcctctgca      1200
gtagtcggac ccataccgct tgaccgggaa tggggtattg ataaaccctg gataggggca      1260
ggtttcgggc tcgaacgcct tctaaaggtt aaacacgact ttaaaaatat caagagagct      1320
gcaaggtccg agtcttacta taacgggatt tctaccaacc tgtaa                      1365
```

<210> SEQ ID NO 15
<211> LENGTH: 1365
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: PylRS Methanosarcina mazei Y384F mutant nucleotide sequence

<400> SEQUENCE: 15

```
atggataaaa aaccactaaa cactctgata tctgcaaccg gctctggat gtccaggacc      60
ggaacaattc ataaaataaa acaccacgaa gtctctcgaa gcaaaatcta tattgaaatg     120
gcatgcggag accaccttgt tgtaaacaac tccaggagca gcaggactgc aagagcgctc     180
aggcaccaca atacaggaa gacctgcaaa cgctgcaggg tttcggatga ggatctcaat     240
aagttcctca caaaggcaaa cgaagaccag acaagcgtaa aagtcaaggt cgtttctgcc     300
cctaccagaa cgaaaaaggc aatgccaaaa tccgttgcga gaccccgaa acctcttgag     360
aatacagaag cggcacaggc tcaaccttct ggatctaaat tttcacctgc gataccggtt     420
tccacccaag agtcagtttc tgtcccggca tctgtttcaa catcaatatc aagcatttct     480
acaggagcaa ctgcatccgc actggtaaaa gggaatacga accccattac atccatgtct     540
gcccctgttc aggcaagtgc ccccgcactt acgaagagcc agactgacag gcttgaagtc     600
ctgttaaacc caaagatga gatttccctg aattccggca gcctttcag ggagcttgag     660
tccgaattgc tctctcgcag aaaaaaagac ctgcagcaga tctacgcgga agaaaggggag     720
aattatctgg ggaaactcga gcgtgaaatt accaggttct ttgtggacag gggttttctg     780
gaaataaaat ccccgatcct gatccctctt gagtatatcg aaaggatggg cattgataat     840
gataccgaac tttcaaaaca gatcttcagg gttgacaaga acttctgcct gagacccatg     900
cttgctccaa acctttacaa ctacctgcgc aagcttgaca gggccctgcc tgatccaata     960
aaaattttg aaataggccc atgctacaga aaagagtccg acggcaaaga acacctcgaa    1020
gagtttacca tgctgaactt ctgccagatg ggatcgggat gcacacggga aaatcttgaa    1080
agcataatta cggacttcct gaaccacctg ggaattgatt tcaagatcgt aggcgattcc    1140
tgcatggtct ttgggatac ccttgatgta atgcacggag acctggaact ttcctctgca    1200
gtagtcggac ccataccgct tgaccgggaa tggggtattg ataaaccctg atagggca    1260
ggtttcgggc tcgaacgcct tctaaaggtt aaacacgact ttaaaaatat caagagagct    1320
gcaaggtccg agtcttacta taacgggatt tctaccaacc tgtaa               1365
```

<210> SEQ ID NO 16
<211> LENGTH: 1365
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: PylRS Codon optimized Methanosarcina mazei nucleotide sequence

<400> SEQUENCE: 16

```
atggataaaa aaccattgaa tacgctcatt agcgcaactg gctgtggat gagccgtacg      60
ggaacgattc ataaaatcaa gcaccacgaa gtatctcgta gcaaaatcta tcgagatg     120
gcttgcggcg accatctcgt ggtaaacaat agcaggtcct cacggaccgc ccgtgccttg     180
```

| | |
|---|---|
| cgccaccaca aatatcgtaa aacttgtaag agatgtagag tgagcgacga ggatctgaac | 240 |
| aagtttctta caaaggccaa cgaggaccaa accagcgtca aagtcaaggt tgtgagcgcc | 300 |
| ccaacacgca ccaagaaggc catgcccaag tctgttgcgc gggcaccgaa acctctggag | 360 |
| aatactgagg ccgctcaggc ccagcccagc ggttcaaaat tctctcctgc cattccagtt | 420 |
| agcactcaag agtcagtcag cgtgcccgcc tctgtgtcta catccatcag ctctatctcc | 480 |
| accggcgcaa cagcctctgc cctggtgaag ggtaatacga accctatcac gagtatgtcc | 540 |
| gcacccgtgc aagcaagtgc tcccgcactc actaaatccc aaacggaccg gctggaggtc | 600 |
| ctgcttaacc ctaaggatga aatcagcctg aacagtggaa aaccgtttcg agaactggaa | 660 |
| tccgagctct taagccggcg aaagaaagat ttgcaacaga tttacgccga gaacgggaa | 720 |
| aattatctgg gcaagctgga gagagaaatc actaggttct tgtagatag gggctttctg | 780 |
| gagattaaga gtcccatatt gatccctctc gaatacattg agcgtatggg catcgacaac | 840 |
| gacacagaac ttagcaagca gatctttcgg gtggacaaaa acttctgcct caggcctatg | 900 |
| ctggctccaa atctgtacaa ctatcttagg aaactcgacc gggccctgcc cgatcccatt | 960 |
| aaaatcttcg aaattggacc ttgctataga aaggagagcg atggcaagga gcacctggag | 1020 |
| gagtttacta tgctcaattt ctgtcaaatg ggctccggct gcacacgtga aacctcgaa | 1080 |
| tccattataa ccgacttcct gaatcacctg gggattgatt tcaagatcgt gggcgactcc | 1140 |
| tgcatggtgt atggtgatac gttggatgtg atgcacggag atttggaatt gtcaagcgct | 1200 |
| gtggtaggcc ccattcctct cgacagggag tggggtattg acaagccctg atcggcgca | 1260 |
| ggttttggac tggagcgcct gttgaaggtt aagcatgact tcaaaaacat aaagagagcc | 1320 |
| gcacgcagcg aatcctatta taatggaatc agcactaact tgtaa | 1365 |

<210> SEQ ID NO 17
<211> LENGTH: 1260
<212> TYPE: DNA
<213> ORGANISM: Methanosarcina barkeri

<400> SEQUENCE: 17

| | |
|---|---|
| atggataaaa aaccattaga tgttttaata tctgcgaccg ggctctggat gtccaggact | 60 |
| ggcacgctcc acaaaatcaa acactatgag gtctcaagaa gtaaaatata cattgaaatg | 120 |
| gcgtgtggag accatcttgt tgtgaataat tctaggagtt gtagaacagc cagagcattc | 180 |
| agacatcata agtacagaaa aacctgcaaa cgatgtaggg tttcggacga ggatatcaat | 240 |
| aatttcctca caagatcaac tgaaggcaaa accagtgtga agttaaggt agtttctgct | 300 |
| ccaaaggtca aaaagctat gccgaaatca gtttcgaggg ctccaaagcc tctggaaaat | 360 |
| cctgtgtctg caaaggcatc aacggacaca tccagatctg taccttcgcc tgcaaaatca | 420 |
| actccaaatt cgcctgttcc cacatcggct cctgctcctt cacttacaag aagccagctc | 480 |
| gatagggttg aggctctctt aagtccagag gataaaattt ctctgaatat tgcaaagcct | 540 |
| ttcagggaac ttgagtccga acttgtgaca agaagaaaaa acgattttca gcggctctat | 600 |
| accaatgata gagaagacta ccttggtaaa ctcgaacggg acattacgaa atttttcgta | 660 |
| gaccgggatt ttctggagat aaagtctcct atccttattc cggcagaata cgtgagagaa | 720 |
| atgggtatta caatgatac tgaactttca aaacagatct tcagggtgga taaaaatctc | 780 |
| tgcttaaggc caatgcttgc cccgactctt tacaactatc tgcgaaaact cgataggatt | 840 |
| ttaccagatc ctataaagat tttcgaagtc gggccctgtt accggaaaga gtctgacggc | 900 |
| aaagagcacc tggaagaatt taccatggtg aacttctgtc agatgggttc gggatgtact | 960 |

```
cgggaaaatc ttgaatccct catcaaagag tttctggact atctggaaat cgacttcgaa    1020
atcgtaggag attcctgtat ggtctatggg gataccettg atataatgca cggggacctg    1080
gagctttctt cggcagtcgt cgggccagtt cctcttgata gggaatgggg cattgacaaa    1140
ccatggatag gtgcaggttt tgggcttgaa cgcttgctca aggttatgca tggctttaaa    1200
aacattaaga gagcatcaag gtccgaatct tactataatg ggatttcaac caatctatga    1260
```

<210> SEQ ID NO 18
<211> LENGTH: 867
<212> TYPE: DNA
<213> ORGANISM: Desulfitobacterium hafniense

<400> SEQUENCE: 18

```
atgttttaa caaggaggga cccacccttg agcagctttt ggacaaaggt tcaatatcaa     60
cgcctgaaag aactcaatgc ttccggggag cagctggaaa tgggtttttc cgatgcacta    120
agccgtgacc gcgcttttca ggggattgaa catcaactga tgagccaggg aaaacgccat    180
ttggaacagc tgcgcacggt gaagcatcgt cccgccttgc tcgagcttga agagggatta    240
gcgaaggcat tgcaccaaca gggatttgtt caggtggtga ccccgacgat tattacgaag    300
tcggccttgg ctaagatgac cataggggag gaccatcctt tgttttccca ggttttttgg    360
ttggatggga agaaatgttt gcggccgatg ctggctccca atctatacac tttgtggaga    420
gagcttgagc gcctgtggga taagccgatc cggattttcg agattggaac ctgttaccgg    480
aaagagtccc aggggcaca acatctcaat gaatttacca tgctgaatct cacagaactg    540
gggactccgc tggaagagcg gcatcaacgt cttgaagaca tggcccgttg ggtgctggag    600
gctgcgggaa taagggagtt tgagctggtt acgaatcct cggtagttta cggggatacg    660
gtagatgtga tgaagggcga tctggagctg gcttcggggg ccatgggggcc ccacttcctt    720 gatgaaaaat gggagatagt tgatccctgg gtaggcctgg gctttggtct ggaaaggctt    780
ctgatgattc gcgaaggaac acaacatgtt cagagtatgg ccagaagcct gagctatctt    840
gatggagtac gcttaaatat caattga                                        867
```

<210> SEQ ID NO 19
<211> LENGTH: 1332
<212> TYPE: DNA
<213> ORGANISM: Methanosarcina acetivorans

<400> SEQUENCE: 19

```
atggataaaa aaccgctaga cactctgata tctgcaaccg ggctctggat gtccaggacc     60
ggaatgattc acaaaatcaa gcaccatgaa gtttcaagaa gcaagatcta tatcgaaatg    120
gcatgtggag aaaggctcgt tgtaaataac tcccggagca gcaggactgc aagagctctc    180
aggcaccaca aatacagaaa gacctgcaga cactgcaggg tttcggacga ggatattaac    240
aacttcctca caaagaccag cgaagagaaa accaccgtga agtcaaggt tgtttctgct    300 cccagagtca ggaaagccat gccgaaatcc gttgccagag ctccaaaacc gcttgaagcc    360
acagcacagg ttccgctttc cggatcaaaa cctgcaccg caaccccggt ttccgcacct    420
gcacaggctc ccgcaccatc aacaggctcg gcttcggcaa catctgcatc agcacagaga    480
atggcaaact ctgctgcggc tccggctgct cctgttccga cgagtgctcc tgcacttaca    540
aagggccagc ttgacaggct tgaagggctg ttaagtccta agatgagat ttccctggat    600 tccgaaaagc ctttcaggga gcttgagtcc gaactgctct cccggagaaa aaaagacctg    660
```

```
aagcggatct atgccgaaga gagagaaaac tatctgggaa agctcgaacg cgaaattacg    720
aaattctttg tggatagggg ttttctggag atcaagtccc cgattctgat ccctgcggaa    780
tacgtggaga gaatgggcat taacagtgac acggagcttt caaagcaggt ctttagaatc    840
gacaaaaatt tctgtttaag gccaatgtta gccccgaacc tctacaacta cctgcgcaag    900
cttgacagag ccctgcctga cccgataaaa atcttcgaaa tcgggccctg ttacaggaaa    960
gaatcggacg gcaaagaaca cctggaagag tttaccatgc tgaacttctg ccagatgggg    1020
tcaggctgca cacgagaaaa ccttgaagcc ataatcacgg agttcctgaa ccacctgggg    1080
atcgactttg agattatagg ggattcctgc atggtctacg aaataccct tgatgtcatg    1140 cacgacgacc ttgaactttc ttctgcggtc gtagggcccg tccctcttga ccgggaatgg    1200
ggaattgaca gccctggat aggagccggt tcgggcttg aacgcctgct gaaagtcatg    1260
cacggcttca aaaacatcaa aagagctgca aggtccgaat cttactataa cgggatttcc    1320
acaaacctgt aa    1332
```

<210> SEQ ID NO 20
<211> LENGTH: 1251
<212> TYPE: DNA
<213> ORGANISM: Methanococcoides burtonii

<400> SEQUENCE: 20

```
atggaaaagc aattactgga cgttctagta gagctcaacg gagtatggct atcgcgaagc     60
ggattgcttc atgggataag gaactttgag ataaccacta aacatattca cattgagacc    120
gactgtggtg caaggttcac tgtgagaaat tccagatcaa gccgttctgc aagatcatta    180
aggcataaca aatatcgcaa accctgcaaa cgctgtcgtc cggcagatga gcagatcgac    240
cgttttgtta agaagacctt aaagagaaa ggcagactg tcagcgtatt ctccagtccg    300
aagaaacatg tcccgaaaaa gccaaaagtg gctgtcatta aatcctttc tatttctaca    360 cccagcccta aggaggcaag tgtgtcaaac tcaataccaa ctccttctat aagtgtcgta    420
aaagatgaag tgaaagtacc agaagtaaag tacacacctt cacagatcga gagactaaag    480
accctgatgt cccctgatga caagatacca atccaggacg agttacctga gttcaaggtg    540
cttgagaaag aactgataca gaggcgacgt gacgacctta agaagatgta cgaggaagac    600
agaagagacc gtcttggtaa acttgagagg gacataaccg aattcttcgt ggacagagga    660
ttcctggaaa taaaatcacc tataatgata cctttcgaat atatcgaaag gatggggata    720
gacaaggatg atcacctcaa caagcagata ttccgtgttg atgagagcat gtgtctgcga    780
cctatgctgg caccatgcct ttacaattat ctgcgcaaac ttgacaaggt gcttccggac    840
cccataagaa tattcgagat aggaccatgc taccgcaaag aatcagatgg tagcagccat    900
cttgaagagt ttaccatggt gaacttctgc cagatgggat caggatgtac aagagagaac    960
atggaagcgc tcatagatga gttccttgag catcttggaa tagaatacga gatagaggct    1020
gacaactgca tggtctatgg agataccatt gacatcatgc atggcgacct tgaactgtca    1080
tccgcagtgg tagggccaat cccgcttgac agagaatggg gtgtgaataa accgtggatg    1140
ggagcaggat tcggtcttga agactacta aaggtcaggc acaattacac gaacatacgc    1200
cgtgcaagcc gttctgaact atactacaac ggaatcaata cgaatctatg a    1251
```

<210> SEQ ID NO 21
<211> LENGTH: 1437
<212> TYPE: DNA
<213> ORGANISM: Methanosarcina thermophila

<400> SEQUENCE: 21

```
atggataaaa aaccactaaa cactctgata tctgctacag ggctctggat gtccaggacc      60
ggaaagcttc acaaaatcag gcatcatgag gtatcaaaaa ggaaaatcta catcgaaatg     120
gaatgtggag aacggcttgt tgtgaacaat tcccggagct gcagggcagc acgggccctg     180
aggcaccata agtacaggaa gatctgcaaa cactgcaggg tttcagatga ggacctaaac     240
aagttcctca caagaacaaa cgaagacaaa agcaacgcga aagtcacggt agttctgct     300
ccaaaaataa gaaaagtaat gccaaaatca gttgcaagaa ccccaaaacc acttgaaaat     360
acggcaccgg tacagactct gccttctgag tctcaacctg cacccactac accaatttct     420
gcatcaacaa cagcacctgc atcaacttct acaacagcac ctgcaccagc ttctacaaca     480
gcacctgcac cagcttctac aacagcacca gcttctgcat caacaacaat ctccacttcg     540
gcaatgcctg catctacatc agcacaggga acaacaaaat tcaactacat ctccggcggc     600
ttccccagac ccatccctgt tcaggcgagt gctcctgcac ttacaaagag ccagattgac     660
aggcttcaag gtctgttaag cccgaaggat gagatttccc tggattccgg aacgcccttc     720
aggaaacttg agtccgaact gctgtccagg agaagaaagg acctgaagca gatctatgcc     780
gaagaaaggg aacattacct gggaaaactc gaacgcgaga ttacgaaatt ttttgttgat     840
cggggttttc tggagataaa gtccccgatt ctgatcccta tggagtatat tgaaaggatg     900
ggcattgata cgataagga actctcaaag cagatcttca gggttgataa taacttctgc     960
ttaaggccca tgcttgctcc gaatctctac aactacctgc gcaagcttaa tagagccctg    1020
cctgacccga taaaaatctt cgagatcggg ccctgttaca ggaaagagtc tgacggcaaa    1080
gaacacctgg aagagtttac catgctgaat ttctgccaga tggggtcagg ctgcacgcgc    1140
gaaaaccttg aagccataat taagattttc ctggactacc tggggatcga cttcgaaatt    1200
gtaggagact cctgtatggt ctacggggat acccttgatg tcatgcacgg agacctggaa    1260
cttttcctcag cagttgtcgg gcccgtgccc atggaccggg actggggaat aaacaagccc    1320
tggataggg caggtttcgg gctcgaacgc ctgttgaagg ttatgcacaa tttcaagaat    1380
attaaaagag cttcaagatc cgaatcatac tacaacggga tttccaccaa tctgtaa      1437
```

<210> SEQ ID NO 22
<211> LENGTH: 1284
<212> TYPE: DNA
<213> ORGANISM: Methanosalum zhilinae

<400> SEQUENCE: 22

```
atgacaagaa ggtcccttga atctctggta tccgaaaaag aagtctggtt atccagaaaa      60
ggtcttcttc atgaaattaa agattacagt gttacacaga gatatattaa tatctatact     120
acctgcgggg aatcatttc tgtaagaaac tcaagaagag ggagagcttc aagggttta     180
agaaataaca aatataggaa atctgtaaa cattgtaaag tacctgatga aaaaatatct     240
aaattcttac agaaggcaag tgtggattct actgcaaag taaaagtggt ttcatctaca     300
aaaccatctc aatctaagaa agcggtccct aaggctgtaa aagcgaaaaa aagggaaca    360
gaaaacagta atggatctct tatacaatca aaagttaaag atcaagggtc agtcaatgct     420
atatcatcag gacagcctcg atcaaaaatt cagccaacgg aagaaagaaa taatattcct     480
gcattcacac ccagtcagaa aaaaaggctc gaagcactcc ttatgcctga ggaagtcatt     540
cctgatccat ccgaaaatct caatttccag gaacttgaat caagtctggt caaccgaaga     600
```

```
aaaaaagata ttgtaaaaat ctatgaggat gacagagaaa atcaattggg taaaattgaa      660
agaatcataa ctaaattttt tgtagataga ggttttcttg agattaaatc accaattctg      720
atacctattg aatatattga aaggatgggg attacagaag ataaagaatt gttcgaacag      780
gtattcaagg ttgataaaaa catgtgcctt agacctatgc tggcacctgg actgtacaat      840
cacctgagaa agtttgataa agttctaccg gatcctataa ggatatttga aattggcccc      900
tgctatagaa aagaatctga cggaagccag catctggaag agtttacaat gctgaatttc      960
tgccagatgg gatcgatgtg cacacgaaag accctggaaa atttgataga tgaattactg     1020
gaatttatgg atattgaata tgaaatcgta tctgataact gccatgtata tggagctact     1080
attgatgttc ttcacaaaga tatggaactt gcatctgctg ttgttgggcc aattccaaaa     1140
gatgcagact ggggaatcac aaaaccatgg atcggtgctg gatttggtct tgaacgtttg     1200
ctcaaagtca tgcataatta taagaatata agacgtgcga gcagatctga gtcgtattat     1260
aatggcataa ctacaaatct ctaa                                            1284

<210> SEQ ID NO 23
<211> LENGTH: 1245
<212> TYPE: DNA
<213> ORGANISM: Methanohalobium evestigatum

<400> SEQUENCE: 23
atgtctaaaa aatcactggc atcattaata tcagacctcc aagtatgggt ttcaaggagt       60
ggtttactcc atgaaataaa aaattatgaa gtgtcacaaa gatacattca tatggaaatg      120
gattgtgggg aaaaaatcac agtaagaaat tccagaaata gtcgtacagc aagaatatta      180
agacttaaaa aatacaaaaa accctgtaaa aactgcaagg tttctgatga ggttattaac      240 agattttttac aaaaacatac cgacagaact gatacaaaag taactgcttt ttcatattct      300
gaatcaaaga aaagaaatc caagcaactg ggacacaaaa aaagaagca atcaaaagtg      360 caggttaacc ccactactga aagtattcaa tcaaacacat cagtttcaga agataaaaca      420
gacaacaaaa ttgagccaga gacatttact tctgcacaga agaacgaat taatgaacta      480 cttttgcctg gagaaaaaat accattttct aatgaaccat caaatttaa ggaaatagaa      540 tctgaattgg tcaacaaaag gcgaaatgat ttcaaacaga tgtatgaaaa cgaccgagaa      600
gaacaaattg caaacttga gagaactatt tcccaatttt ttgttgataa agggtttata      660
gaaattaaag ccccaataat tattgatatt gattctgtta aaaaaatggg tatcgataca      720
gatcataaat tatcaaaaca aatattttat cttgataata aacactgctt gcgacccatg      780
cttgcaccgg gtctctacca gtggcttaaa aattttgaca aaatcctgcc tgatccgatt      840
aaaatttttg aaatcggacc gtgttatcgg aaagagtcag aaggtagcca gcaccttgaa      900
gaatttacaa tgtttaactt ctgtcaaatg ggttctggtg caaacagaga aaaccttcta      960
aatcatatag atgaccctgtt aaaacatcta acatcgact acaaaataat tgatgataac     1020
tgtcatgttt atggtgagac catagatatc gtccacggtg atttagaact ttcatctgct     1080
gttgtaggtc ctgttccaat cgatatgaac tggggaatcg ataaaacatg gattggtgca     1140
ggattaggac tggaaagatt gctaaaggtt aaacacggat ataaaaatat aaaacgcgcc     1200
agtaaatctc attcatatta taatggtata tcaaccaatc tttaa                     1245

<210> SEQ ID NO 24
<211> LENGTH: 867
<212> TYPE: DNA
<213> ORGANISM: Desulfotomaculum gibsoniae
```

<400> SEQUENCE: 24

```
atgttttta acaaggaggga cccacccttg agcagctttt ggacaaaggt tcaatatcaa    60
cgcctgaaag aactcaatgc ctccggggag cagctggaaa tgggttttc cgatgcacta   120
agccgtgacc gcgcttttca ggggattgaa catcaactga tgagccaggg aaaacgccat   180
ttggaacagc tgcgcacggt gaagcatcgt cccgccttgc tcgagcttga agagaaatta   240
gcgaaagcat tgcaccaaca gggatttgtt caggtggtga ccccgacgat tattacgaag   300
tcggccttgg ctaagatgac catagggagg accatccttt gttttcccca ggttttttgg   360
ttggatggga agaaatgttt gcggccgatg ctggctccca atctatacac tttgtggaga   420
gagcttgagc gcctgtggga taagccgatc cggattttcg agattggaac ctgttaccgg   480
aaagagtccc aggggcaca gcatctcaat gaatttacca tgctgaatct cacgaactg    540
gggactcccc tggaagagcg gcatcaacgt cttgaagaca tggcccgctg ggtgctggaa   600
gctgcgggaa taagggagtt tgagctggtt acggaatcct cggtagttta cggggatacg   660
gtagatgtga tgaagggcga tctggagctg gcttcggggg ccatggggcc ccacttcctt   720
gatgaaaaat gggagatatt tgatccctgg gtaggtctgg gctttggtct ggaaaggctt   780
ctgatgattc gtgaaggaac acaacatgtt cagagtatgg ccagaagcct gagctatctt   840
gatggagtac gcttaaatat caattga                                     867
```

<210> SEQ ID NO 25
<211> LENGTH: 1215
<212> TYPE: DNA
<213> ORGANISM: Methanohalophilus mahii

<400> SEQUENCE: 25

```
atggaaagga aaccactaga tttacttata gacaccaacg gagtgtggct ctctaggaac    60
gggttacttc atggtgtaaa gaacttcgag gtgtcaagaa accatattca tatcactact   120
gactgccaaa gccgctttac agtacgcaat tcaagaagaa gtcgctctgc aagggcgcta   180
cgcaacaata aatatcgcaa agcatgcaaa aactgcaaac tttccgatga gcgtattact   240
cgttttgtca caaaagattt tggcagggga agccaggcac gtgttatcac atcttcaaaa   300
acaaaaaaga gtaaatctcc aaaggaagca gtggtaaaat ctgtatccag caaggcaaat   360
gaaatgccac ctgttgtaga ggcaaaaaaa gaaaagcctg taaaaccgga ttacacgcct   420
gcccagaaga aaaggattac aacactgctt agccctgcag acgaccttag ttcaataaaa   480
gaactcccca ccttcaagga gctggagaca gaacttgtta aaaaagaaa acaagacctg   540
cgccagatgt atgaggatga ccgcagacat cagctggccc agctcgaaag ggacatctcc   600
ctatttttaa tagaaaaagg attcatgaa gtacgtactt ctgtcctgat acctgccaaa   660
ttcattgaaa gaatgggcat cacagaagaa gaccccctct acaagcagat cttccgggtg   720
gatgagaata catgcctgcg gcccatgctt gccccgggat tatataatta tcttcacaat   780
tttgataaca taatgcccga ccccctcaag atattcgaga tcggtacctg ctacagaaag   840
gaatccgacg gcaaagaaca tcttgaagag tttacaatgg ttaatttctg ccagatgggt   900
tcgggatgca caaagaaaaa cctgttaaat attatcgatg acctgctcaa atatctaaac   960
atcgattacg aagtaatctc ggataattgc atggtgtatg agataccat gacataatg   1020
catgggata tggaatatc ttcagccgtt gtgggaccca ttccacagga cctcgactgg  1080
ggagtgacca accctggat gggtgcagga atgggaattg agagattact caaggtaaag  1140
```

-continued

```
cacaaataca caaacataaa gcgctcaagc aggtctattt catactataa cggaattaca    1200
accaatctca ggtga                                                    1215
```

<210> SEQ ID NO 26
<211> LENGTH: 67
<212> TYPE: RNA
<213> ORGANISM: Methanosarcina barkeri

<400> SEQUENCE: 26

```
ggaaaccuga ucauguagau cguggacucu aaauccgcag ccggguagau ucccgggguu    60
uccgcca                                                              67
```

<210> SEQ ID NO 27
<211> LENGTH: 72
<212> TYPE: DNA
<213> ORGANISM: Methanosarcina acetivorans

<400> SEQUENCE: 27

```
ggaaacctga tcatgtagat cgaatggact ctaaatccgt tcagccgggt tagattcccg    60
gggtttccgc ca                                                        72
```

<210> SEQ ID NO 28
<211> LENGTH: 72
<212> TYPE: DNA
<213> ORGANISM: Methanosarcina mazei

<400> SEQUENCE: 28

```
ggaaacctga tcatgtagat cgaatggact ctaaatccgt tcagccgggt tagattcccg    60
gggtttccgc ca                                                        72
```

<210> SEQ ID NO 29
<211> LENGTH: 72
<212> TYPE: DNA
<213> ORGANISM: Methanococcoides burtonii

<400> SEQUENCE: 29

```
ggagacttga tcatgtagat cgaacggact ctaaatcctt tcagccgggt tagattcccg    60
gagtttccgc ca                                                        72
```

<210> SEQ ID NO 30
<211> LENGTH: 67
<212> TYPE: RNA
<213> ORGANISM: Desulfobacterium hafniense

<400> SEQUENCE: 30

```
ggaaaccuga ucauguagau cguggacucu aaauccgcag ccggguagau ucccgggguu    60
uccgcca                                                              67
```

<210> SEQ ID NO 31
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: H1/TO promoter

<400> SEQUENCE: 31

```
aatatttgca tgtcgctatg tgttctggga aatcaccata aacgtgaaat ccctatcagt    60
```
gatagagact tataagttcc ctatcagtga tagagacacc a          101

<210> SEQ ID NO 32
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: U6 snRNA promoter

<400> SEQUENCE: 32
agagggccta tttcccatga ttccttcata tttgcatata cgatacaagg ctgttagaga    60
gataattaga attaatttga ctgtaaacac aaagatatta gtacaaaata cgtgacgtag   120
aaagtaataa tttcttgggt agtttgcagt tttaaaatta tgttttaaaa tggactatca   180
tatgcttacc gtaacttgaa agtatttcga tttcttggct ttatatatct tgtggaaagg   240
acgaaacacc                                                          250

<210> SEQ ID NO 33
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SNR52 promoter

<400> SEQUENCE: 33
tctttgaaaa gataatgtat gattatgctt tcactcatat ttatacagaa acttgatgtt    60
ttctttcgag tatatacaag gtgattacat gtacgtttga agtacaactc tagattttgt   120
agtgccctct tgggctagcg gtaaaggtgc gcatttttc acaccctaca atgttctgtt    180
caaaagattt tggtcaaacg ctgtagaagt gaaagttggt gcgcatgttt cggcgttcga   240
aacttctccg cagtgaaaga taaatgatc                                     269

<210> SEQ ID NO 34
<211> LENGTH: 221
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: H1 promoter

<400> SEQUENCE: 34
gaacgctgac gtcatcaacc cgctccaagg aatcgcgggc ccagtgtcac taggcgggaa    60
cacccagcgc gcgtgcgccc tggcaggaag atggctgtga gggacagggg agtggcgccc   120
tgcaatattt gcatgtcgct atgtgttctg ggaaatcacc ataaacgtga aatgtctttg   180
gatttgggaa tcttataagt tctgtatgag accacagatc t                       221

<210> SEQ ID NO 35
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: U6-tRNApyl construct

<400> SEQUENCE: 35

```
aaggtcgggc aggaagaggg cctatttccc atgattcctt catatttgca tatacgatac      60
aaggctgtta gagagataat tagaattaat ttgactgtaa acacaaagat attagtacaa     120
aatacgtgac gtagaaagta ataatttctt gggtagtttg cagtttttaa aattatgttt     180
taaaatggac tatcatatgc ttaccgtaac ttgaaagtat ttcgatttct tggctttata     240
tatcttgtgg aaaggacgaa acaccgaatt ctctagactc gagggaaacc tgatcatgta     300
gatcgaatgg actctaaatc cgttcagccg ggttagattc ccggggtttc cggacaagtg     360
cggttttttgt tt                                                        372
```

<210> SEQ ID NO 36
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: GFP nucleotide sequence

<400> SEQUENCE: 36

```
atggcctcca aaggagaaga acttttcact ggagttgtcc caattcttgt tgaattagat      60
ggtgatgtta atgggcacaa attttctgtc agtggagagg gtgaaggtga tgctacatac     120
ggaaagctta cccttaaatt tatttgcact actggaaaac tacctgttcc atggccaaca     180
cttgtcacta ctttctctta tggtgttcaa tgcttttccc gttatccgga tcatatgaaa     240
cggcatgact ttttcaagag tgccatgccc gaaggttatg tacaggaacg cactatatct     300
ttcaaagatg acgggaacta caagacgcgt gctgaagtca agtttgaagg tgataccctt     360
gttaatcgta tcgagttaaa aggtattgat tttaagaag atggaaacat tctcggacac     420
aaactcgagt acaactataa ctcacacaat gtatacatca cggcagacaa acaaaagaat     480
ggaatcaaag ctaacttcaa aattcgtcac aacattgaag atggatccgt tcaactagca     540
gaccattatc aacaaaatac tccaattggc gatggccctg tccttttacc agacaaccat     600
tacctgtcga cacaatctgc cctttcgaaa gatcccaacg aaaagcgtga ccacatggtc     660
cttcttgagt ttgtaactgc tgctgggatt acacatggca tggatcaggc aagcctttg      720
tctcaagaag aatccaccct cattgaaaga gcaacggcta caatcaacag catccccatc     780
tctgaagact acagcgtcgc cagcgcagct ctctctagcg acggccgcat cttcactggt     840
gtcaatgtat atcatttac tggggacct tgtgcagaac tcgtggtgct gggcactgct      900
gctgctgcgg cagctggcaa cctgacttgt atcgtcgcga tcggaaatga aacaggggc     960
atcttgagcc cctgcggacg gtgccgacag gtgcttctcg atctgcatcc tgggatcaaa    1020
gccatagtga aggacagtga tggacagccg acggcagttg ggattcgtga attgctgccc    1080
tctggttatg tgtgggaggg ctaa                                          1104
```

<210> SEQ ID NO 37
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GFP amino acid sequence

<400> SEQUENCE: 37

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Gln Ala Lys Pro Leu
225                 230                 235                 240

Ser Gln Glu Glu Ser Thr Leu Ile Glu Arg Ala Thr Ala Thr Ile Asn
                245                 250                 255

Ser Ile Pro Ile Ser Glu Asp Tyr Ser Val Ala Ser Ala Ala Leu Ser
            260                 265                 270

Ser Asp Gly Arg Ile Phe Thr Gly Val Asn Val Tyr His Phe Thr Gly
        275                 280                 285

Gly Pro Cys Ala Glu Leu Val Val Leu Gly Thr Ala Ala Ala Ala Ala
    290                 295                 300

Ala Gly Asn Leu Thr Cys Ile Val Ala Ile Gly Asn Glu Asn Arg Gly
305                 310                 315                 320

Ile Leu Ser Pro Cys Gly Arg Cys Arg Gln Val Leu Leu Asp Leu His
                325                 330                 335

Pro Gly Ile Lys Ala Ile Val Lys Asp Ser Asp Gly Gln Pro Thr Ala
            340                 345                 350

Val Gly Ile Arg Glu Leu Leu Pro Ser Gly Tyr Val Trp Glu Gly
        355                 360                 365
```

<210> SEQ ID NO 38
<211> LENGTH: 367
<212> TYPE: PRT
<213> ORGANISM: Artificial Sequence
<220> FEATURE:
<223> OTHER INFORMATION: Description of Artificial Sequence: Synthetic polypeptide -continued
<220> FEATURE:
<223> OTHER INFORMATION: GFPY40 Amino acid Sequence
<220> FEATURE:
<221> NAME/KEY: MOD_RES
<222> LOCATION: (40)..(40)
<223> OTHER INFORMATION: Xaa is nnAA, a non natural amino acid

<400> SEQUENCE: 38

Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Xaa Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Gln Ala Lys Pro Leu
225                 230                 235                 240

Ser Gln Glu Glu Ser Thr Leu Ile Glu Arg Ala Thr Ala Thr Ile Asn
                245                 250                 255

Ser Ile Pro Ile Ser Glu Asp Tyr Ser Val Ala Ser Ala Ala Leu Ser
            260                 265                 270

Ser Asp Gly Arg Ile Phe Thr Gly Val Asn Val Tyr His Phe Thr Gly
        275                 280                 285

Gly Pro Cys Ala Glu Leu Val Val Leu Gly Thr Ala Ala Ala Ala Ala
290                 295                 300

Ala Gly Asn Leu Thr Cys Ile Val Ala Ile Gly Asn Glu Asn Arg Gly
305                 310                 315                 320

Ile Leu Ser Pro Cys Gly Arg Cys Arg Gln Val Leu Leu Asp Leu His
                325                 330                 335

Pro Gly Ile Lys Ala Ile Val Lys Asp Ser Asp Gly Gln Pro Thr Ala
            340                 345                 350

Val Gly Ile Arg Glu Leu Leu Pro Ser Gly Tyr Val Trp Glu Gly
        355                 360                 365

<210> SEQ ID NO 39
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-IL-6 (28D2) Gamma Nucleotide Sequence

<400> SEQUENCE: 39

```
atggagactg ggctgcgctg gcttctcctg gtcgctgtgc tcaaaggtgt ccagtgtcag      60
tcgctggggg agtccggggg tcgcctggtc acgcctggga caccctgac actcacctgc     120 acagtctctg gattatccct cagtaagaat gcaattgcct gggtccgcca ggctccaggg    180
aagggactgg aatggatcgg aatcatttat gctggtggtg ccacaaccta cgcgagctgg    240
gcgaaaggcc gattcaccat ctccaagtcc tcgaccacgg tggatctgaa gatcaccagt    300
ccgacaacag tggacacggc cacctatttc tgtgccaggg aatatgctgg tgatagttat    360
tatactggat acactcagtt ggatctctgg ggcccaggca ccctggtcac cgtctcgagt    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag gcagccccg agaaccacag gtgtacaccc tgcccccatc ccgggaggag   1140
atgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tga                                 1413
```

<210> SEQ ID NO 40
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-IL-6 (28D2) Gamma Amino acid Sequence

<400> SEQUENCE: 40

```
Met Glu Thr Gly Leu Arg Trp Leu Leu Leu Val Ala Val Leu Lys Gly
1               5                   10                  15

Val Gln Cys Gln Ser Leu Gly Glu Ser Gly Gly Arg Leu Val Thr Pro
            20                  25                  30
```

-continued

```
Gly Thr Pro Leu Thr Leu Thr Cys Thr Val Ser Gly Leu Ser Leu Ser
             35                  40                  45
Lys Asn Ala Ile Ala Trp Val Arg Gln Ala Pro Gly Lys Gly Leu Glu
 50                  55                  60
Trp Ile Gly Ile Ile Tyr Ala Gly Ala Thr Thr Tyr Ala Ser Trp
 65                  70                  75                  80
Ala Lys Gly Arg Phe Thr Ile Ser Lys Ser Thr Thr Val Asp Leu
                 85                  90                  95
Lys Ile Thr Ser Pro Thr Thr Val Asp Thr Ala Thr Tyr Phe Cys Ala
                100                 105                 110
Arg Glu Tyr Ala Gly Asp Ser Tyr Tyr Thr Gly Tyr Thr Gln Leu Asp
                115                 120                 125
Leu Trp Gly Pro Gly Thr Leu Val Thr Val Ser Ser Ala Ser Thr Lys
    130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
        195                 200                 205
Val Thr Val Pro Ser Ser Ser Leu Gly Thr Gln Thr Tyr Ile Cys Asn
            210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
                260                 265                 270
Thr Leu Met Ile Ser Arg Thr Pro Glu Val Thr Cys Val Val Val Asp
            275                 280                 285
Val Ser His Glu Asp Pro Glu Val Lys Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
                340                 345                 350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Glu Glu Met Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
                420                 425                 430
Leu Thr Val Asp Lys Ser Arg Trp Gln Gln Gly Asn Val Phe Ser Cys
            435                 440                 445
Ser Val Met His Glu Ala Leu His Asn His Tyr Thr Gln Lys Ser Leu
```

Ser Leu Ser Pro Gly Lys
465                 470

<210> SEQ ID NO 41
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-IL-6 (28D2) Gamma_amber K274 Nucleotide
      Sequence

<400> SEQUENCE: 41

```
atggagactg ggctgcgctg gcttctcctg gtcgctgtgc tcaaaggtgt ccagtgtcag        60
tcgctggggg agtccggggg tcgcctggtc acgcctggga cccctgac actcacctgc        120
acagtctctg gattatccct cagtaagaat gcaattgcct gggtccgcca ggctccaggg       180
aagggactgg aatggatcgg aatcatttat gctggtggtg ccacaaccta cgcgagctgg       240
gcgaaaggcc gattcaccat ctccaagtcc tcgaccacgg tggatctgaa gatcaccagt       300
ccgacaacag tggacacggc cacctatttc tgtgccaggg aatatgctgg tgatagttat       360
tatactggat acactcagtt ggatctctgg ggcccaggca ccctggtcac cgtctcgagt       420
gctagcacca agggcccatc ggtcttcccc ctggcaccct cctccaagag cacctctggg       480
ggcacagcgg ccctgggctg cctggtcaag gactacttcc ccgaaccggt gacggtgtcg       540
tggaactcag gcgccctgac cagcggcgtg cacaccttcc cggctgtcct acagtcctca       600
ggactctact ccctcagcag cgtggtgacc gtgccctcca gcagcttggg cacccagacc       660
tacatctgca acgtgaatca caagcccagc aacaccaagg tggacaagaa agttgagccc       720
aaatcttgtg acaaaactca cacatgccca ccgtgcccag cacctgaact cctgggggga       780
ccgtcagtct tcctcttccc cccaaaaccc aaggacaccc tcatgatctc ccggacccct       840
gaggtcacat gcgtggtggt ggacgtgagc cacgaagacc ctgaggtcta gttcaactgg       900
tacgtggacg gcgtggaggt gcataatgcc aagacaaagc cgcgggagga gcagtacaac       960
agcacgtacc gtgtggtcag cgtcctcacc gtcctgcacc aggactggct gaatggcaag      1020
gagtacaagt gcaaggtctc caacaaagcc ctcccagccc ccatcgagaa aaccatctcc      1080
aaagccaaag gcagccccg agaaccacag gtgtacaccc tgcccccatc ccgggaggag       1140
atgaccaaga accaggtcag cctgacctgc ctggtcaaag gcttctatcc cagcgacatc      1200
gccgtggagt gggagagcaa tgggcagccg gagaacaact acaagaccac gcctcccgtg      1260
ctggactccg acggctcctt cttcctctac agcaagctca ccgtggacaa gagcaggtgg      1320
cagcagggga acgtcttctc atgctccgtg atgcatgagg ctctgcacaa ccactacacg      1380
cagaagagcc tctccctgtc tccgggtaaa tga                                    1413
```

<210> SEQ ID NO 42
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-IL-6 (28D2) Gamma_amber K274 amino acid
      Sequence
<220> FEATURE:

```
<221> NAME/KEY: MOD_RES
<222> LOCATION: (297)..(297)
<223> OTHER INFORMATION: Xaa is nnAA, a non natural amino acid

<400> SEQUENCE: 42
```

| | | | | | | | | | | | | | | |
|---|---|---|---|---|---|---|---|---|---|---|---|---|---|---|
| Met | Glu | Thr | Gly | Leu | Arg | Trp | Leu | Leu | Leu | Val | Ala | Val | Leu | Lys | Gly |
| 1 | | | | 5 | | | | | 10 | | | | | 15 | |

Val Gln Cys Gln Ser Leu Gly Glu Ser Gly Gly Arg Leu Val Thr Pro
        20                25                30

Gly Thr Pro Leu Thr Leu Thr Cys Thr Val Ser Gly Leu Ser Leu Ser
      35                    40                45

Lys Asn Ala Ile Ala Trp Val Arg Gln Ala Pro Gly Lys Gly Leu Glu
50                    55                60

Trp Ile Gly Ile Ile Tyr Ala Gly Gly Ala Thr Thr Tyr Ala Ser Trp
65                70                75            80

Ala Lys Gly Arg Phe Thr Ile Ser Lys Ser Ser Thr Val Asp Leu
            85                90            95

Lys Ile Thr Ser Pro Thr Thr Val Asp Thr Ala Thr Tyr Phe Cys Ala
          100                105            110

Arg Glu Tyr Ala Gly Asp Ser Tyr Tyr Thr Gly Tyr Thr Gln Leu Asp
        115                120            125

Leu Trp Gly Pro Gly Thr Leu Val Thr Val Ser Ser Ala Ser Thr Lys
130                  135                140

Gly Pro Ser Val Phe Pro Leu Ala Pro Ser Ser Lys Ser Thr Ser Gly
145                  150              155            160

Gly Thr Ala Ala Leu Gly Cys Leu Val Lys Asp Tyr Phe Pro Glu Pro
          165                170            175

Val Thr Val Ser Trp Asn Ser Gly Ala Leu Thr Ser Gly Val His Thr
        180                185            190

Phe Pro Ala Val Leu Gln Ser Ser Gly Leu Tyr Ser Leu Ser Ser Val
        195                200            205

Val Thr Val Pro Ser Ser Ser Leu Gly Thr Gln Thr Tyr Ile Cys Asn
    210                215              220

Val Asn His Lys Pro Ser Asn Thr Lys Val Asp Lys Lys Val Glu Pro
225                  230              235            240

Lys Ser Cys Asp Lys Thr His Thr Cys Pro Pro Cys Pro Ala Pro Glu
          245                250            255

Leu Leu Gly Gly Pro Ser Val Phe Leu Phe Pro Pro Lys Pro Lys Asp
        260                265            270

Thr Leu Met Ile Ser Arg Thr Pro Glu Val Thr Cys Val Val Val Asp
    275                280              285

Val Ser His Glu Asp Pro Glu Val Xaa Phe Asn Trp Tyr Val Asp Gly
    290                295              300

Val Glu Val His Asn Ala Lys Thr Lys Pro Arg Glu Glu Gln Tyr Asn
305                  310              315            320

Ser Thr Tyr Arg Val Val Ser Val Leu Thr Val Leu His Gln Asp Trp
          325                330            335

Leu Asn Gly Lys Glu Tyr Lys Cys Lys Val Ser Asn Lys Ala Leu Pro
        340                345            350

Ala Pro Ile Glu Lys Thr Ile Ser Lys Ala Lys Gly Gln Pro Arg Glu
        355                360            365

Pro Gln Val Tyr Thr Leu Pro Pro Ser Arg Glu Glu Met Thr Lys Asn
    370                375              380

Gln Val Ser Leu Thr Cys Leu Val Lys Gly Phe Tyr Pro Ser Asp Ile

```
                  385                 390                 395                 400
Ala Val Glu Trp Glu Ser Asn Gly Gln Pro Glu Asn Asn Tyr Lys Thr
                        405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys
465                 470

<210> SEQ ID NO 43
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-IL-6 (28D2) Kappa Nucleotide Sequence

<400> SEQUENCE: 43
atggacacga gggcccccac tcagctgctg gggctcctgc tgctctggct cccaggcgcc     60
agatgtgccc ttgtgatgac ccagactcca gcctccgtgt ctgccgctgt gggaggcaca    120
gtgaccatca attgccaggc cagtgaggac cttttagta gtttggcctg gtttcagcag    180
aaaccagggc agcctcccaa actcctgatc tattctgcat ccactctggc atctggggtc    240
ccatcgcggt tcagcggcag tggatctggg acagaattca ctctcaccat cagcgacctg    300
gaatgtgccg atgctgccac ttactactgt ctaggccttt actattatct tactcctgat    360
cctatttatg ggttcggcgg agggaccaag gtggtggtgg tccgtacggt ggctgcacca    420
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagttcg cccgtcacaa agagcttcaa caggggagag    720
tgttaa                                                              726

<210> SEQ ID NO 44
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-IL-6 (28D2) Kappa amino acid Sequence

<400> SEQUENCE: 44

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ala Ser
                20                  25                  30

Val Ser Ala Ala Val Gly Gly Thr Val Thr Ile Asn Cys Gln Ala Ser
            35                  40                  45

Glu Asp Leu Phe Ser Ser Leu Ala Trp Phe Gln Gln Lys Pro Gly Gln
```

```
                 50                  55                  60
Pro Pro Lys Leu Leu Ile Tyr Ser Ala Ser Thr Leu Ala Ser Gly Val
 65                  70                  75                  80

Pro Ser Arg Phe Ser Gly Ser Gly Ser Gly Thr Glu Phe Thr Leu Thr
                     85                  90                  95

Ile Ser Asp Leu Glu Cys Ala Asp Ala Ala Thr Tyr Tyr Cys Leu Gly
                100                 105                 110

Leu Tyr Tyr Tyr Leu Thr Pro Asp Pro Ile Tyr Gly Phe Gly Gly Gly
            115                 120                 125

Thr Lys Val Val Val Val Arg Thr Val Ala Ala Pro Ser Val Phe Ile
        130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 45
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-Her2 (4D5) gamma Nucleotide sequence

<400> SEQUENCE: 45
atggaggctc cgcccagct gctctttctg ctccttctct ggcttcccga cacaaccggt      60
gaggtgcagc tggtggagtc tggcggtggc ttggtacagc cgggcgggtc cctgcgcctc    120
tcctgtgccg cttccggatt caacatcaaa gacacgtata ttcactgggt ccgtcaggca    180
cctggcaagg gtctggagtg ggtgagccgc atttatccta ccaatggtta cactcgctac    240
gccgactctg tgaagggccg cttcaccatc agcgccgaca cgtccaagaa caccctgtat    300
ctgcaaatga acagcctgcg tgccgaggac accgcggtgt attactgcag ccgctggggc    360
ggtgatggct tttacgcgat ggactactgg ggccagggca ccctggtcac cgtctcgagt    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctggggga    780 ccgtcagtct tcctcttccc cccaaaaccc aaggacaccc tcatgatctc ccggaccct    840 gaggtcacat gcgtggtggt ggacgtgagc cacgaagacc ctgaggtcaa gttcaactgg    900
```

```
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag gcagccccg agaaccacag gtgtacaccc tgcccccatc ccgggaggag   1140
atgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tga                                1413
```

<210> SEQ ID NO 46
<211> LENGTH: 470
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Anti-Her2 (4D5) gamma amino acid sequence

<400> SEQUENCE: 46

```
Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Ile Lys Asp Thr Tyr Ile His Trp Val Arg Gln Ala Pro Gly Lys Gly
        50                  55                  60

Leu Glu Trp Val Ser Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Leu Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255
```

```
Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 47
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-Her2 (4D5) gamma_K274amber nucleotide
      sequence

<400> SEQUENCE: 47
atggaggctc cgcccagct  gctctttctg ctccttctct ggcttcccga cacaaccggt      60
gaggtgcagc tggtggagtc tggcggtggc ttggtacagc cgggcgggtc cctgcgcctc     120
tcctgtgccg cttccggatt caacatcaaa gacacgtata ttcactgggt ccgtcaggca     180
cctggcaagg gtctggagtg ggtgagccgc atttatccta ccaatggtta cactcgctac     240
gccgactctg tgaagggccg cttcaccatc agcgccgaca cgtccaagaa caccctgtat     300
ctgcaaatga acagcctgcg tgccgaggac accgcggtgt attactgcag ccgctggggc     360
ggtgatggct tttacgcgat ggactactgg ggccagggca ccctggtcac cgtctcgagt     420
gctagcacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
```

```
tacatctgca acgtgaatca caagcccagc aacaccaagg tggacaagaa agttgagccc       720
aaatcttgtg acaaaactca cacatgccca ccgtgcccag cacctgaact cctgggggga       780
ccgtcagtct tcctcttccc cccaaaaccc aaggacaccc tcatgatctc ccggacccct       840
gaggtcacat gcgtggtggt ggacgtgagc cacgaagacc ctgaggtcta gttcaactgg       900
tacgtggacg gcgtggaggt gcataatgcc aagacaaagc cgcgggagga gcagtacaac       960
agcacgtacc gtgtggtcag cgtcctcacc gtcctgcacc aggactggct gaatggcaag      1020
gagtacaagt gcaaggtctc caacaaagcc ctcccagccc ccatcgagaa aaccatctcc      1080
aaagccaaag gcagccccg agaaccacag gtgtacaccc tgcccccatc ccggaggag         1140 atgaccaaga accaggtcag cctgacctgc ctggtcaaag gcttctatcc cagcgacatc      1200
gccgtggagt gggagagcaa tgggcagccg gagaacaact acaagaccac gcctcccgtg      1260
ctggactccg acggctcctt cttcctctac agcaagctca ccgtggacaa gagcaggtgg      1320
cagcagggga acgtcttctc atgctccgtg atgcatgagg ctctgcacaa ccactacacg      1380
cagaagagcc tctccctgtc tccgggtaaa tga                                    1413

<210> SEQ ID NO 48
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-Her2 (4D5) gamma_K274amber amino acid
      sequence
<220> FEATURE:
<221> NAME/KEY: MOD_RES
<222> LOCATION: (297)..(297)
<223> OTHER INFORMATION: Xaa is nnAA, a non natural amino acid

<400> SEQUENCE: 48

Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ser Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Leu Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190
```

```
Phe Pro Ala Val Leu Gln Ser Ser Gly Leu Tyr Ser Leu Ser Ser Val
            195                 200                 205
Val Thr Val Pro Ser Ser Ser Leu Gly Thr Gln Thr Tyr Ile Cys Asn
        210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
        275                 280                 285
Val Ser His Glu Asp Pro Glu Val Xaa Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Glu Glu Met Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys
465                 470

<210> SEQ ID NO 49
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-Her2 (4D5) gamma_T359amber nucleotide
      sequence

<400> SEQUENCE: 49
atggaggctc cgcccagct gctctttctg ctccttctct ggcttcccga cacaaccggt     60
gaggtgcagc tggtggagtc tggcggtggc ttggtacagc cgggcgggtc cctgcgcctc   120
tcctgtgccg cttccggatt caacatcaaa gacacgtata ttcactgggt ccgtcaggca   180
cctggcaagg gtctggagtg ggtgagccgc atttatccta ccaatggtta cactcgctac   240
gccgactctg tgaagggccg cttcaccatc agcgccgaca cgtccaagaa caccctgtat   300
```

-continued

```
ctgcaaatga acagcctgcg tgccgaggac accgcggtgt attactgcag ccgctggggc   360
ggtgatggct tttacgcgat ggactactgg ggccagggca ccctggtcac cgtctcgagt   420
gctagcacca agggcccatc ggtcttcccc ctggcaccct cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacatctgca acgtgaatca caagcccagc aacaccaagg tggacaagaa agttgagccc   720
aaatcttgtg acaaaactca cacatgccca ccgtgcccag cacctgaact cctgggggga   780
ccgtcagtct tcctcttccc cccaaaaccc aaggacaccc tcatgatctc ccggacccct   840
gaggtcacat gcgtggtggt ggacgtgagc cacgaagacc ctgaggtcaa gttcaactgg   900
tacgtggacg gcgtggaggt gcataatgcc aagacaaagc cgcgggagga gcagtacaac   960
agcacgtacc gtgtggtcag cgtcctcacc gtcctgcacc aggactggct gaatggcaag  1020
gagtacaagt gcaaggtctc caacaaagcc ctcccagccc ccatcgagaa aaccatctcc  1080
aaagccaaag ggcagccccg agaaccacag gtgtacaccc tgcccccatc ccgggaggag  1140
atgtagaaga accaggtcag cctgacctgc ctggtcaaag gcttctatcc cagcgacatc  1200
gccgtggagt gggagagcaa tgggcagccg gagaacaact acaagaccac gcctcccgtg  1260
ctggactccg acggctcctt cttcctctac agcaagctca ccgtggacaa gagcaggtgg  1320
cagcagggga acgtcttctc atgctccgtg atgcatgagg ctctgcacaa ccactacacg  1380
cagaagagcc tctccctgtc tccgggtaaa tga                               1413
```

<210> SEQ ID NO 50
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-Her2 (4D5) gamma_T359amber amino acid
      sequence
<220> FEATURE:
<221> NAME/KEY: MOD_RES
<222> LOCATION: (382)..(382)
<223> OTHER INFORMATION: Xaa is nnAA, a non natural amino acid

<400> SEQUENCE: 50

```
Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ser Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Leu Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125
```

Tyr Trp Gly Gln Gly Thr Leu Val Thr Val Ser Ser Ala Ser Thr Lys
            130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Xaa Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 51
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-Her2 (4D5)Kappa nucleotide sequence

<400> SEQUENCE: 51

```
atggaggctc cgcccagct gctctttctg ctccttctct ggcttcccga cacaaccggt      60
gacatccaga tgacccagtc tccatcctcc ctgtctgcat ctgtgggaga ccgtgtcaca     120
atcacttgcc gtgctagcca ggatgtgaat acagcggtgg cctggtatca gcagaaacct    180
ggcaaagccc ctaagctcct gatctattct gcatcctttt tgtacagcgg cgtgccgagc    240
cgcttcagcg gcagccgttc tggtaccgat tcactctca ccatcagctc tctgcaaccg     300
gaagattttg caacttacta ctgtcaacag cactacacca ctcctccgac gttcggccaa    360
gggaccaagg tggaaatcga acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagttcgc ccgtcacaaa gagcttcaac aggggagagt gttaa                    705
```

<210> SEQ ID NO 52
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Anti-Her2 (4D5)Kappa amino acid sequence

<400> SEQUENCE: 52

```
Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Glu Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220
```

-continued

Val Thr Lys Ser Phe Asn Arg Gly Glu Cys
225                 230

<210> SEQ ID NO 53
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-Her2 Kappa D70amber nucleotide sequence

<400> SEQUENCE: 53
atggaggctc cgcccagct gctctttctg ctccttctct ggcttcccga cacaaccggt      60
gacatccaga tgacccagtc tccatcctcc ctgtctgcat ctgtgggaga ccgtgtcaca     120
atcacttgcc gtgctagcca ggatgtgaat acagcggtgg cctggtatca gcagaaacct    180
ggcaaagccc ctaagctcct gatctattct gcatcctttt tgtacagcgg cgtgccgagc    240
cgcttcagcg gcagccgttc tggtacctag ttcactctca ccatcagctc tctgcaaccg    300
gaagattttg caacttacta ctgtcaacag cactacacca ctcctccgac gttcggccaa    360
gggaccaagg tggaaatcga acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagttcgc ccgtcacaaa gagcttcaac aggggagagt gttaa                    705

<210> SEQ ID NO 54
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-Her2 Kappa D70amber amino acid sequence
<220> FEATURE:
<221> NAME/KEY: MOD_RES
<222> LOCATION: (90)..(90)
<223> OTHER INFORMATION: Xaa is nnAA, a non natural amino acid

<400> SEQUENCE: 54

Met Glu Ala Pro Ala Gln Leu Leu Phe Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Xaa Phe Thr Leu Thr Ile Ser
                85                  90                  95

Ser Leu Gln Pro Glu Asp Phe Ala Thr Tyr Tyr Cys Gln Gln His Tyr
            100                 105                 110

```
Thr Thr Pro Pro Thr Phe Gly Gln Gly Thr Lys Val Glu Ile Glu Arg
        115                 120                 125

Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 55
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-Her2 Kappa E81amber nucleotide sequence

<400> SEQUENCE: 55

```
atggaggctc ccgcccagct gctctttctg ctccttctct ggcttcccga cacaaccggt    60
gacatccaga tgacccagtc tccatcctcc ctgtctgcat ctgtgggaga ccgtgtcaca   120
atcacttgcc gtgctagcca ggatgtgaat acagcggtgg cctggtatca gcagaaacct   180
ggcaaagccc ctaagctcct gatctattct gcatcctttt tgtacagcgg cgtgccgagc   240
cgcttcagcg gcagccgttc tggtaccgat ttcactctca ccatcagctc tctgcaaccg   300
taggattttg caacttacta ctgtcaacag cactacacca ctcctccgac gttcggccaa   360
gggaccaagg tggaaatcga acgtacggtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga aaacacaaa gtctacgcct gcgaagtcac ccatcagggc   660
ctgagttcgc ccgtcacaaa gagcttcaac aggggagagt gttaa               705
```

<210> SEQ ID NO 56
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-Her2 Kappa E81amber amino acid sequence
<220> FEATURE:
<221> NAME/KEY: MOD_RES
<222> LOCATION: (101)..(101)
<223> OTHER INFORMATION: Xaa is nnAA, a non natural amino acid

<400> SEQUENCE: 56

Met Glu Ala Pro Ala Gln Leu Leu Phe Leu Leu Leu Leu Trp Leu Pro

```
1               5                   10                  15
Asp Thr Thr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
 50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Xaa Asp Phe Ala Thr Tyr Tyr Cys Gln Gln His Tyr
            100                 105                 110

Thr Thr Pro Pro Thr Phe Gly Gln Gly Thr Lys Val Glu Ile Glu Arg
            115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 57
<211> LENGTH: 825
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-PSMA scFv nucleotide sequence

<400> SEQUENCE: 57
atggaggcgc cagcgcagct tctcttcttg ctcctgctct ggctgccgga cacgacggga      60
gacatcgtca tgactcagtc acacaagttc atgtcgactt cggtgggaga tagggtgtcc     120
atcatttgca aagcaagcca agatgtaggg acagcggtcg actggtatca gcagaagccc     180
ggtcagtccc ctaaactcct catctactgg gcatcgacgc gacacacggg cgtcccggac     240
cgcttcacgg gatcgggatc aggtactgac tttacattga caattacaaa cgtccaatcg     300
gaggaccttg cggattactt ctgtcaacag tacaattcgt atccctgac gttcggggct      360 gggacaaagc tcgacttgaa gggcggtgga gggtcaggtg gaggaggctc cggtggggga     420
gggagcggag gggtggttc ggaggtgcag ttgcagcaat caggcccgga acttaagaaa      480
cccgggacct cagtaagaat cagctgtaag acaagcgggt acacgtttac cgaatatact     540
atccattggg tgaagcagtc gcatggaaaa tcgcttgaat ggatcgggaa cattaatcct     600
aataacgggg gaaccacgta caaccagaag tttgaggata agccacccct tactgtggac     660
```

```
aaatcctcca gcactgccta tatggaattg cggtccctga cctcggagga ttcagccgta    720
tactactgcg cggcaggatg gaattttgat tattgggggc agggaacaac attgacagtc    780
tcgagcggtc cacctcctcc acctcaccat caccatcatc actga                    825
```

<210> SEQ ID NO 58
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-PSMA scFv amino acid sequence

<400> SEQUENCE: 58

```
Met Glu Ala Pro Ala Gln Leu Leu Phe Leu Leu Leu Trp Leu Pro
1               5                   10                  15

Asp Thr Thr Gly Asp Ile Val Met Thr Gln Ser His Lys Phe Met Ser
            20                  25                  30

Thr Ser Val Gly Asp Arg Val Ser Ile Ile Cys Lys Ala Ser Gln Asp
        35                  40                  45

Val Gly Thr Ala Val Asp Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Thr
                85                  90                  95

Asn Val Gln Ser Glu Asp Leu Ala Asp Tyr Phe Cys Gln Gln Tyr Asn
            100                 105                 110

Ser Tyr Pro Leu Thr Phe Gly Ala Gly Thr Lys Leu Asp Leu Lys Gly
        115                 120                 125

Gly Gly Gly Ser Gly Gly Gly Gly Ser Gly Gly Gly Ser Gly Gly
    130                 135                 140

Gly Gly Ser Glu Val Gln Leu Gln Gln Ser Gly Pro Glu Leu Lys Lys
145                 150                 155                 160

Pro Gly Thr Ser Val Arg Ile Ser Cys Lys Thr Ser Gly Tyr Thr Phe
                165                 170                 175

Thr Glu Tyr Thr Ile His Trp Val Lys Gln Ser His Gly Lys Ser Leu
            180                 185                 190

Glu Trp Ile Gly Asn Ile Asn Pro Asn Asn Gly Gly Thr Thr Tyr Asn
        195                 200                 205

Gln Lys Phe Glu Asp Lys Ala Thr Leu Thr Val Asp Lys Ser Ser Ser
    210                 215                 220

Thr Ala Tyr Met Glu Leu Arg Ser Leu Thr Ser Glu Asp Ser Ala Val
225                 230                 235                 240

Tyr Tyr Cys Ala Ala Gly Trp Asn Phe Asp Tyr Trp Gly Gln Gly Thr
                245                 250                 255

Thr Leu Thr Val Ser Ser Gly Pro Pro Pro Pro His His His
            260                 265                 270

His His
```

<210> SEQ ID NO 59
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Anti-PSMA scFv_117amber nucleotide sequence

<400> SEQUENCE: 59

```
atggaggcgc cagcgcagct tctcttcttg ctcctgctct ggctgccgga cacgacggga      60
gacatcgtca tgactcagtc acacaagttc atgtcgactt cggtgggaga tagggtgtcc     120
atcatttgca aagcaagcca agatgtaggg acagcggtcg actggtatca gcagaagccc     180
ggtcagtccc ctaaactcct catctactgg gcatcgacgc gacacacggg cgtcccggac     240
cgcttcacgg gatcgggatc aggtactgac tttacattga caattacaaa cgtccaatcg     300
gaggaccttg cggattactt ctgtcaacag tacaattcgt atcccctgac gttcggggct     360
gggacaaagc tcgacttgaa gggcggtgga gggtcaggtg gaggaggctc cggtggggga     420
gggagcggag ggggtggttc ggaggtgcag ttgcagcaat caggcccgga acttaagaaa     480
cccgggacct cagtaagaat cagctgtaag acaagcgggt acacgtttac cgaatatact     540
atccattggg tgaagcagtc gcatggaaaa tcgcttgaat ggatcgggaa cattaatcct     600
aataacgggg gaaccacgta caaccagaag tttgaggata agccaccct tactgtggac     660
aaatcctcca gcactgccta tatggaattg cggtccctga cctcggagga ttcagccgta     720
tactactgcg cggcaggatg gaattttgat tattgggggc agggaacaac attgacagtc     780
tcgagctagg gtccacctcc tccacctcac catcaccatc atcactga                  828
```

<210> SEQ ID NO 60
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-PSMA scFv_amber amino acid sequence
<220> FEATURE:
<221> NAME/KEY: MOD_RES
<222> LOCATION: (263)..(263)
<223> OTHER INFORMATION: Xaa is nnAA, a non natural amino acid

<400> SEQUENCE: 60

```
Met Glu Ala Pro Ala Gln Leu Leu Phe Leu Leu Leu Trp Leu Pro
1               5                   10                  15

Asp Thr Thr Gly Asp Ile Val Met Thr Gln Ser His Lys Phe Met Ser
                20                  25                  30

Thr Ser Val Gly Asp Arg Val Ser Ile Ile Cys Lys Ala Ser Gln Asp
            35                  40                  45

Val Gly Thr Ala Val Asp Trp Tyr Gln Gln Lys Pro Gly Gln Ser Pro
        50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Thr
                85                  90                  95

Asn Val Gln Ser Glu Asp Leu Ala Asp Tyr Phe Cys Gln Gln Tyr Asn
            100                 105                 110

Ser Tyr Pro Leu Thr Phe Gly Ala Gly Thr Lys Leu Asp Leu Lys Gly
        115                 120                 125

Gly Gly Gly Ser Gly Gly Gly Gly Ser Gly Gly Gly Ser Gly Gly
    130                 135                 140

Gly Gly Ser Glu Val Gln Leu Gln Gln Ser Gly Pro Glu Leu Lys Lys
```

```
                    145                 150                 155                 160
Pro Gly Thr Ser Val Arg Ile Ser Cys Lys Thr Ser Gly Tyr Thr Phe
                165                 170                 175

Thr Glu Tyr Thr Ile His Trp Val Lys Gln Ser His Gly Lys Ser Leu
                180                 185                 190

Glu Trp Ile Gly Asn Ile Asn Pro Asn Asn Gly Gly Thr Thr Tyr Asn
                195                 200                 205

Gln Lys Phe Glu Asp Lys Ala Thr Leu Thr Val Asp Lys Ser Ser Ser
                210                 215                 220

Thr Ala Tyr Met Glu Leu Arg Ser Leu Thr Ser Glu Asp Ser Ala Val
225                 230                 235                 240

Tyr Tyr Cys Ala Ala Gly Trp Asn Phe Asp Tyr Trp Gly Gln Gly Thr
                245                 250                 255

Thr Leu Thr Val Ser Ser Xaa Gly Pro Pro Pro Pro His His His
                260                 265                 270

His His His
        275

<210> SEQ ID NO 61
<211> LENGTH: 612
<212> TYPE: DNA
<213> ORGANISM: Homo sapiens

<400> SEQUENCE: 61
atgtctgcac ttctgatcct agctcttgtt ggagctgcag ttgctaagct tcaccatcac      60
catcaccatc cgattccaga ctcatctccg ttgctgcagt tggcgggca ggtgcggcag      120 cgctatctgt acaccgacga cgcacagcaa acagaggctc atcttgaaat ccgggaggat      180
ggcactgttg gcggtgcggc ggatcagagt cccgagtcac tgcttcaact taaggccttg      240
aaaccaggag tgattcaaat cctcggtgtg aaaacgagta gattcctctg ccaaaggccc      300
gatggcgccc tgtacggaag cctccacttc gaccctgagg catgtagctt cgcgaactc      360 ctgttggaag atgggtataa cgtctatcag tccgaggcac acggccttcc tctccacctc      420
cccgggaata agtcaccgca cagggacccc gctccaaggg gtcccgcacg attcctgccc      480
ttgccagggc tgccaccgc cctgccagaa ccgcctggaa ttctggcccc tcagccacct      540
gacgtcgggt ctagcgaccc cctgagtatg gtaggaccta gccagggcag atccccctcc      600
tacgcctcct aa                                                         612

<210> SEQ ID NO 62
<211> LENGTH: 219
<212> TYPE: PRT
<213> ORGANISM: Homo sapiens

<400> SEQUENCE: 62

Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
                20                  25                  30

Asp Asp Asp Asp Lys Ser His Pro Ile Pro Asp Ser Ser Pro Leu Leu
            35                  40                  45

Gln Phe Gly Gly Gln Val Arg Gln Arg Tyr Leu Tyr Thr Asp Asp Ala
        50                  55                  60

Gln Gln Thr Glu Ala His Leu Glu Ile Arg Glu Asp Gly Thr Val Gly
65                  70                  75                  80
```

```
Gly Ala Ala Asp Gln Ser Pro Glu Ser Leu Gln Leu Lys Ala Leu
                85                  90                  95
Lys Pro Gly Val Ile Gln Ile Leu Gly Val Lys Thr Ser Arg Phe Leu
            100                 105                 110
Cys Gln Arg Pro Asp Gly Ala Leu Tyr Gly Ser Leu His Phe Asp Pro
        115                 120                 125
Glu Ala Cys Ser Phe Arg Glu Leu Leu Leu Glu Asp Gly Tyr Asn Val
    130                 135                 140
Tyr Gln Ser Glu Ala His Gly Leu Pro Leu His Leu Pro Gly Asn Lys
145                 150                 155                 160
Ser Pro His Arg Asp Pro Ala Pro Arg Gly Pro Ala Arg Phe Leu Pro
                165                 170                 175
Leu Pro Gly Leu Pro Pro Ala Leu Pro Glu Pro Pro Gly Ile Leu Ala
            180                 185                 190
Pro Gln Pro Pro Asp Val Gly Ser Ser Asp Pro Leu Ser Met Val Gly
        195                 200                 205
Pro Ser Gln Gly Arg Ser Pro Ser Tyr Ala Ser
    210                 215
```

<210> SEQ ID NO 63
<211> LENGTH: 612
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: FGF21 R131amber nucleotide sequence

<400> SEQUENCE: 63

```
atgtctgcac ttctgatcct agctcttgtt ggagctgcag ttgctaagct tcaccatcac     60
catcaccatc cgattccaga ctcatctccg ttgctgcagt ttggcgggca ggtgcggcag    120
cgctatctgt acaccgacga cgcacagcaa acagaggctc atcttgaaat ccgggaggat    180
ggcactgttg gcggtgcggc ggatcagagt cccgagtcac tgcttcaact taaggccttg    240
aaaccaggag tgattcaaat cctcggtgtg aaaacgagta gattcctctg ccaaaggccc    300
gatggcgccc tgtacggaag cctccacttc gaccctgagg catgtagctt cgcgaactc     360
ctgttggaag atgggtataa cgtctatcag tccgaggcac acggccttcc tctccacctc    420
cccgggaata agtcaccgca cagggacccc gctccatagg gtcccgcacg attcctgccc    480
ttgccagggc tgccacccgc cctgccagaa ccgcctggaa ttctggcccc tcagccacct    540
gacgtcgggt ctagcgaccc cctgagtatg gtaggaccta gccagggcag atccccctcc    600
tacgcctcct aa                                                        612
```

<210> SEQ ID NO 64
<211> LENGTH: 219
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: FGF21 R131amber amino acid sequence
<220> FEATURE:
<221> NAME/KEY: MOD_RES
<222> LOCATION: (169)..(169)
<223> OTHER INFORMATION: Xaa is nnAA, a non natural amino acid

<400> SEQUENCE: 64

Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Ser His Pro Ile Pro Asp Ser Ser Pro Leu Leu
        35                  40                  45

Gln Phe Gly Gly Gln Val Arg Gln Arg Tyr Leu Tyr Thr Asp Asp Ala
    50                  55                  60

Gln Gln Thr Glu Ala His Leu Glu Ile Arg Glu Asp Gly Thr Val Gly
65                  70                  75                  80

Gly Ala Ala Asp Gln Ser Pro Glu Ser Leu Leu Gln Leu Lys Ala Leu
                85                  90                  95

Lys Pro Gly Val Ile Gln Ile Leu Gly Val Lys Thr Ser Arg Phe Leu
            100                 105                 110

Cys Gln Arg Pro Asp Gly Ala Leu Tyr Gly Ser Leu His Phe Asp Pro
        115                 120                 125

Glu Ala Cys Ser Phe Arg Glu Leu Leu Leu Glu Asp Gly Tyr Asn Val
    130                 135                 140

Tyr Gln Ser Glu Ala His Gly Leu Pro Leu His Leu Pro Gly Asn Lys
145                 150                 155                 160

Ser Pro His Arg Asp Pro Ala Pro Xaa Gly Pro Ala Arg Phe Leu Pro
                165                 170                 175

Leu Pro Gly Leu Pro Pro Ala Leu Pro Glu Pro Pro Gly Ile Leu Ala
            180                 185                 190

Pro Gln Pro Pro Asp Val Gly Ser Ser Asp Pro Leu Ser Met Val Gly
        195                 200                 205

Pro Ser Gln Gly Arg Ser Pro Ser Tyr Ala Ser
    210                 215

<210> SEQ ID NO 65
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: FGF21 F12amber nucleotide sequence

<400> SEQUENCE: 65
atgtctgctc ttctgatact cgccttggta ggggctgctg ttgccgacta taaggatcac      60
gacggcgatt acaaggacca tgatatcgat tacaaagatg acgacgacaa gtctcatccg     120
attccagact catctccgtt gctgcagtag ggcgggcagg tgcggcagcg ctatctgtac     180
accgacgacg cacagcaaac agaggctcat cttgaaatcc gggaggatgg cactgttggc     240
ggtgcggcgg atcagagtcc cgagtcactg cttcaactta aggccttgaa accaggagtg     300
attcaaatcc tcggtgtgaa aacgagtaga ttcctctgcc aaaggcccga tggcgccctg     360
tacggaagcc tccacttcga ccctgaggca tgtagctttc gcgaactcct gttggaagat     420
gggtataacg tctatcagtc cgaggcacac ggccttcctc tccacctccc cgggaataag     480
tcaccgcaca gggaccccgc tccaaggggt cccgcacgat tcctgccctt gccagggctg     540
ccacccgccc tgccagaacc gcctggaatt ctggcccctc agccacctga cgtcgggtct     600
agcgaccccc tgagtatggt aggacctagc cagggcagat cccctcctc cgcctcctaa     660

<210> SEQ ID NO 66

<211> LENGTH: 219
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: FGF21 F12amber amino acid sequence
<220> FEATURE:
<221> NAME/KEY: MOD_RES
<222> LOCATION: (50)..(50)
<223> OTHER INFORMATION: Xaa is nnAA, a non natural amino acid

<400> SEQUENCE: 66

Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Ser His Pro Ile Pro Asp Ser Ser Pro Leu Leu
        35                  40                  45

Gln Xaa Gly Gly Gln Val Arg Gln Arg Tyr Leu Tyr Thr Asp Asp Ala
    50                  55                  60

Gln Gln Thr Glu Ala His Leu Glu Ile Arg Glu Asp Gly Thr Val Gly
65                  70                  75                  80

Gly Ala Ala Asp Gln Ser Pro Glu Ser Leu Leu Gln Leu Lys Ala Leu
                85                  90                  95

Lys Pro Gly Val Ile Gln Ile Leu Gly Val Lys Thr Ser Arg Phe Leu
            100                 105                 110

Cys Gln Arg Pro Asp Gly Ala Leu Tyr Gly Ser Leu His Phe Asp Pro
        115                 120                 125

Glu Ala Cys Ser Phe Arg Glu Leu Leu Leu Glu Asp Gly Tyr Asn Val
    130                 135                 140

Tyr Gln Ser Glu Ala His Gly Leu Pro Leu His Leu Pro Gly Asn Lys
145                 150                 155                 160

Ser Pro His Arg Asp Pro Ala Pro Arg Gly Pro Ala Arg Phe Leu Pro
                165                 170                 175

Leu Pro Gly Leu Pro Pro Ala Leu Pro Glu Pro Pro Gly Ile Leu Ala
            180                 185                 190

Pro Gln Pro Pro Asp Val Gly Ser Ser Asp Pro Leu Ser Met Val Gly
        195                 200                 205

Pro Ser Gln Gly Arg Ser Pro Ser Tyr Ala Ser
    210                 215

<210> SEQ ID NO 67
<211> LENGTH: 612
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: FGF21 L60amber nucleotide sequence

<400> SEQUENCE: 67
atgtctgcac ttctgatcct agctcttgtt ggagctgcag ttgctaagct tcaccatcac      60
catcaccatc cgattccaga ctcatctccg ttgctgcagt ttggcgggca ggtgcggcag     120
cgctatctgt acaccgacga cgcacagcaa acagaggctc atcttgaaat ccgggaggat     180
ggcactgttg gcggtgcggc ggatcagagt cccgagtcac tgcttcaact taaggccttg     240
aaaccaggag tgattcaaat ctagggtgtg aaaacgagta gattcctctg ccaaaggccc     300

-continued

```
gatggcgccc tgtacggaag cctccacttc gaccctgagg catgtagctt tcgcgaactc    360
ctgttggaag atgggtataa cgtctatcag tccgaggcac acggccttcc tctccacctc    420
cccgggaata agtcaccgca cagggacccc gctccaaggg gtcccgcacg attcctgccc    480
ttgccagggc tgccacccgc cctgccagaa ccgcctggaa ttctggcccc tcagccacct    540
gacgtcgggt ctagcgaccc cctgagtatg gtaggaccta gccagggcag atccccctcc    600
tacgcctcct aa                                                        612
```

<210> SEQ ID NO 68
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FGF21 L60amber amino acid sequence
<220> FEATURE:
<221> NAME/KEY: MOD_RES
<222> LOCATION: (104)..(104)
<223> OTHER INFORMATION: Xaa is nnAA, a non natural amino acid

<400> SEQUENCE: 68

```
Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Ser His Pro Ile Pro Asp Ser Ser Pro Leu Leu
        35                  40                  45

Gln Phe Gly Gly Gln Val Arg Gln Arg Tyr Leu Tyr Thr Asp Asp Ala
    50                  55                  60

Gln Gln Thr Glu Ala His Leu Glu Ile Arg Glu Asp Gly Thr Val Gly
65                  70                  75                  80

Gly Ala Ala Asp Gln Ser Pro Glu Ser Leu Leu Gln Leu Lys Ala Leu
                85                  90                  95

Lys Pro Gly Val Ile Gln Ile Xaa Gly Val Lys Thr Ser Arg Phe Leu
            100                 105                 110

Cys Gln Arg Pro Asp Gly Ala Leu Tyr Gly Ser Leu His Phe Asp Pro
        115                 120                 125

Glu Ala Cys Ser Phe Arg Glu Leu Leu Leu Glu Asp Gly Tyr Asn Val
    130                 135                 140

Tyr Gln Ser Glu Ala His Gly Leu Pro Leu His Leu Pro Gly Asn Lys
145                 150                 155                 160

Ser Pro His Arg Asp Pro Ala Pro Arg Gly Pro Ala Arg Phe Leu Pro
                165                 170                 175

Leu Pro Gly Leu Pro Pro Ala Leu Pro Glu Pro Pro Gly Ile Leu Ala
            180                 185                 190

Pro Gln Pro Pro Asp Val Gly Ser Ser Asp Pro Leu Ser Met Val Gly
        195                 200                 205

Pro Ser Gln Gly Arg Ser Pro Ser Tyr Ala Ser
    210                 215
```

<210> SEQ ID NO 69
<211> LENGTH: 612
<212> TYPE: DNA
<213> ORGANISM: Artificial Sequence
<220> FEATURE:
<223> OTHER INFORMATION: Description of Artificial Sequence: Synthetic -continued

```
<220> FEATURE:
<223> OTHER INFORMATION: FGF21P 90amber nucleotide sequence

<400> SEQUENCE: 69
atgtctgcac ttctgatcct agctcttgtt ggagctgcag ttgctaagct tcaccatcac      60
catcaccatc cgattccaga ctcatctccg ttgctgcagt ttggcgggca ggtgcggcag     120
cgctatctgt acaccgacga cgcacagcaa acagaggctc atcttgaaat ccggaggat      180 ggcactgttg gcggtgcggc ggatcagagt cccgagtcac tgcttcaact taaggccttg     240
aaaccaggag tgattcaaat cctcggtgtg aaaacgagta gattcctctg ccaaaggccc     300
gatggcgccc tgtacggaag cctccacttc gactaggagg catgtagctt cgcgaactc      360 ctgttggaag atgggtataa cgtctatcag tccgaggcac acggccttcc tctccacctc     420
cccgggaata agtcaccgca cagggacccc gctccaaggg gtcccgcacg attcctgccc     480
ttgccagggc tgccacccgc cctgccagaa ccgcctggaa ttctggcccc tcagccacct     540
gacgtcgggt ctagcgaccc cctgagtatg gtaggaccta gccagggcag atcccctcc      600 tacgcctcct aa                                                         612

<210> SEQ ID NO 70
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FGF21 P90amber amino acid sequence
<220> FEATURE:
<221> NAME/KEY: MOD_RES
<222> LOCATION: (128)..(128)
<223> OTHER INFORMATION: Xaa is nnAA, a non natural amino acid

<400> SEQUENCE: 70

Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Ser His Pro Ile Pro Asp Ser Ser Pro Leu Leu
        35                  40                  45

Gln Phe Gly Gly Gln Val Arg Gln Arg Tyr Leu Tyr Thr Asp Asp Ala
    50                  55                  60

Gln Gln Thr Glu Ala His Leu Glu Ile Arg Glu Asp Gly Thr Val Gly
65                  70                  75                  80

Gly Ala Ala Asp Gln Ser Pro Glu Ser Leu Leu Gln Leu Lys Ala Leu
                85                  90                  95

Lys Pro Gly Val Ile Gln Ile Leu Gly Val Lys Thr Ser Arg Phe Leu
            100                 105                 110

Cys Gln Arg Pro Asp Gly Ala Leu Tyr Gly Ser Leu His Phe Asp Xaa
        115                 120                 125

Glu Ala Cys Ser Phe Arg Glu Leu Leu Leu Glu Asp Gly Tyr Asn Val
    130                 135                 140

Tyr Gln Ser Glu Ala His Gly Leu Pro Leu His Leu Pro Gly Asn Lys
145                 150                 155                 160

Ser Pro His Arg Asp Pro Ala Pro Arg Gly Pro Ala Arg Phe Leu Pro
                165                 170                 175

Leu Pro Gly Leu Pro Pro Ala Leu Pro Glu Pro Pro Gly Ile Leu Ala
```

```
                      180                 185                 190
Pro Gln Pro Pro Asp Val Gly Ser Ser Asp Pro Leu Ser Met Val Gly
            195                 200                 205

Pro Ser Gln Gly Arg Ser Pro Ser Tyr Ala Ser
            210                 215

<210> SEQ ID NO 71
<211> LENGTH: 612
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: FGF21 P140amber nucleotide sequence

<400> SEQUENCE: 71
atgtctgcac ttctgatcct agctcttgtt ggagctgcag ttgctaagct tcaccatcac      60
catcaccatc cgattccaga ctcatctccg ttgctgcagt ttggcgggca ggtgcggcag     120
cgctatctgt acaccgacga cgcacagcaa acagaggctc atcttgaaat ccgggaggat     180
ggcactgttg gcggtgcggc ggatcagagt cccgagtcac tgcttcaact taaggccttg     240
aaaccaggag tgattcaaat cctcggtgtg aaaacgagta gattcctctg ccaaaggccc     300
gatggcgccc tgtacggaag cctccacttc gaccctgagg catgtagctt cgcgaactc     360 ctgttggaag atgggtataa cgtctatcag tccgaggcac acggccttcc tctccacctc     420
cccgggaata agtcaccgca cagggacccc gctccaaggg gtcccgcacg attcctgccc     480 ttgtagggc tgccacccgc cctgccagaa ccgcctggaa ttctggcccc tcagccacct     540
gacgtcgggt ctagcgaccc cctgagtatg gtaggaccta gccagggcag atccccctcc     600
tacgcctcct aa                                                         612

<210> SEQ ID NO 72
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FGF21 P140amber amino acid sequence
<220> FEATURE:
<221> NAME/KEY: MOD_RES
<222> LOCATION: (178)..(178)
<223> OTHER INFORMATION: Xaa is nnAA, a non natural amino acid

<400> SEQUENCE: 72

Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Ser His Pro Ile Pro Asp Ser Ser Pro Leu Leu
        35                  40                  45

Gln Phe Gly Gly Gln Val Arg Gln Arg Tyr Leu Tyr Thr Asp Asp Ala
    50                  55                  60

Gln Gln Thr Glu Ala His Leu Glu Ile Arg Glu Asp Gly Thr Val Gly
65                  70                  75                  80

Gly Ala Ala Asp Gln Ser Pro Glu Ser Leu Leu Gln Leu Lys Ala Leu
                85                  90                  95

Lys Pro Gly Val Ile Gln Ile Leu Gly Val Lys Thr Ser Arg Phe Leu
```

|  |  | 100 |  |  | 105 |  |  | 110 |  |
|---|---|---|---|---|---|---|---|---|---|

Cys Gln Arg Pro Asp Gly Ala Leu Tyr Gly Ser Leu His Phe Asp Pro
        115            120              125

Glu Ala Cys Ser Phe Arg Glu Leu Leu Leu Glu Asp Gly Tyr Asn Val
  130                135              140

Tyr Gln Ser Glu Ala His Gly Leu Pro Leu His Leu Pro Gly Asn Lys
145              150              155              160

Ser Pro His Arg Asp Pro Ala Pro Arg Gly Pro Ala Arg Phe Leu Pro
        165            170              175

Leu Xaa Gly Leu Pro Pro Ala Leu Pro Glu Pro Pro Gly Ile Leu Ala
        180            185              190

Pro Gln Pro Pro Asp Val Gly Ser Ser Asp Pro Leu Ser Met Val Gly
        195            200              205

Pro Ser Gln Gly Arg Ser Pro Ser Tyr Ala Ser
        210            215

<210> SEQ ID NO 73
<211> LENGTH: 1104
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: GFPY40 Nucleotide Sequence

<400> SEQUENCE: 73

| | |
|---|---|
| atggcctcca aaggagaaga acttttcact ggagttgtcc caattcttgt tgaattagat | 60 |
| ggtgatgtta atgggcacaa attttctgtc agtggagagg gtgaaggtga tgctacatag | 120 |
| ggaaagctta cccttaaatt tatttgcact actggaaaac tacctgttcc atggccaaca | 180 |
| cttgtcacta ctttctctta tggtgttcaa tgcttttccc gttatccgga tcatatgaaa | 240 |
| cggcatgact ttttcaagag tgccatgccc gaaggttatg tacaggaacg cactatatct | 300 |
| ttcaaagatg acgggaacta caagacgcgt gctgaagtca agtttgaagg tgataccctt | 360 |
| gttaatcgta tcgagttaaa aggtattgat tttaaagaag atggaaacat tctcggacac | 420 |
| aaactcgagt acaactataa ctcacacaat gtatacatca cggcagacaa acaaaagaat | 480 |
| ggaatcaaag ctaacttcaa aattcgtcac aacattgaag atggatccgt tcaactagca | 540 |
| gaccattatc aacaaaatac tccaattggc gatggccctg tcctttacc agacaaccat | 600 |
| tacctgtcga cacaatctgc cctttcgaaa gatcccaacg aaaagcgtga ccacatggtc | 660 |
| cttcttgagt ttgtaactgc tgctgggatt acacatggca tggatcaggc caagcctttg | 720 |
| tctcaagaag aatccaccct cattgaaaga gcaacggcta caatcaacag catccccatc | 780 |
| tctgaagact acagcgtcgc cagcgcagct ctctctagcg acggccgcat cttcactggt | 840 |
| gtcaatgtat atcatttac tggggggacct tgtgcagaac tcgtggtgct gggcactgct | 900 |
| gctgctgcgg cagctggcaa cctgacttgt atcgtcgcga tcgaaatga aacaggggc | 960 |
| atcttgagcc cctgcggacg gtgccgacag gtgcttctcg atctgcatcc tgggatcaaa | 1020 |
| gccatagtga aggacagtga tggacagccg acggcagttg ggattcgtga attgctgccc | 1080 |
| tctggttatg tgtgggaggg ctaa | 1104 |

<210> SEQ ID NO 74
<211> LENGTH: 1416
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: Herceptin Nucleotide sequence Gamma Chain

<400> SEQUENCE: 74
atggaggctc ccgcccagct gctctttctg ctccttctct ggcttcccga cacaaccggt      60
gaggtgcagc tggtggagtc tggcggtggc ttggtacagc cgggcgggtc cctgcgcctc     120
tcctgtgccg cttccggatt caacatcaaa gacacgtata ttcactgggt ccgtcaggca     180
cctggcaagg gtctggagtg ggtggcccgc atttatccta ccaatggtta cactcgctac     240
gccgactctg tgaagggccg cttcaccatc agcgccgaca cgtccaagaa caccgcttat     300
ctgcaaatga acagcctgcg tgccgaggac accgcggtgt attactgcag ccgctggggc     360
ggtgatggct tttacgcgat ggactactgg ggccagggca ccctggtcac cgtctcgagt     420
gctagcacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagaa agttgagccc     720
cctaaatctt gtgacaaaac tcacacatgc ccaccgtgcc cagcacctga actcctgggg     780
ggaccgtcag tcttcctctt ccccccaaaa cccaaggaca ccctcatgat ctcccggacc     840
cctgaggtca catgcgtggt ggtggacgtg agccacgaag accctgaggt caagttcaac     900
tggtacgtgg acggcgtgga ggtgcataat gccaagacaa agccgcggga ggagcagtac     960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca aagggcagcc ccgagaacca caggtgtaca ccctgccccc atcccgggac    1140
gagctcacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcatg aggctctgca caaccactac    1380
acgcagaaga gcctctccct gtctccgggt aaataa                              1416

<210> SEQ ID NO 75
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Herceptin amino acid sequence Gamma Chain

<400> SEQUENCE: 75

Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Ile Lys Asp Thr Tyr Ile His Trp Val Arg Gln Ala Pro Gly Lys Gly
```

```
            50                  55                  60
Leu Glu Trp Val Ala Arg Ile Tyr Pro Thr Asn Gly Tyr Thr Arg Tyr
 65                  70                  75                  80

Ala Asp Ser Val Lys Gly Arg Phe Thr Ile Ser Ala Asp Thr Ser Lys
                 85                  90                  95

Asn Thr Ala Tyr Leu Gln Met Asn Ser Leu Arg Ala Glu Asp Thr Ala
                100                 105                 110

Val Tyr Tyr Cys Ser Arg Trp Gly Asp Gly Phe Tyr Ala Met Asp
                115                 120                 125

Tyr Trp Gly Gln Gly Thr Leu Val Thr Val Ser Ser Ala Ser Thr Lys
                130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
                210                 215                 220

Val Asn His Lys Pro Ser Asn Thr Lys Val Asp Lys Lys Val Glu Pro
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val Asp
                290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Asp Glu Leu Thr Lys
                370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly Lys
465                 470
```

<210> SEQ ID NO 76
<211> LENGTH: 1416
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Herceptin H274 Nucleotide sequence Gamma Chain

<400> SEQUENCE: 76

| | | | | | |
|---|---|---|---|---|---|
| atggaggctc | ccgcccagct | gctctttctg | ctccttctct | ggcttcccga | cacaaccggt | 60 |
| gaggtgcagc | tggtggagtc | tggcggtggc | ttggtacagc | cgggcgggtc | cctgcgcctc | 120 |
| tcctgtgccg | cttccggatt | caacatcaaa | gacacgtata | ttcactgggt | ccgtcaggca | 180 |
| cctggcaagg | gtctggagtg | ggtggcccgc | atttatccta | ccaatggtta | cactcgctac | 240 |
| gccgactctg | tgaagggccg | cttcaccatc | agcgccgaca | cgtccaagaa | caccgcttat | 300 |
| ctgcaaatga | acagcctgcg | tgccgaggac | accgcggtgt | attactgcag | ccgctggggc | 360 |
| ggtgatggct | tttacgcgat | ggactactgg | ggccagggca | ccctggtcac | cgtctcgagt | 420 |
| gctagcacca | agggcccatc | ggtcttcccc | ctggcaccct | cctccaagag | cacctctggg | 480 |
| ggcacagcgg | ccctgggctg | cctggtcaag | gactacttcc | ccgaaccggt | gacggtgtcg | 540 |
| tggaactcag | gcgccctgac | cagcggcgtg | cacaccttcc | cggctgtcct | acagtcctca | 600 |
| ggactctact | ccctcagcag | cgtggtgacc | gtgccctcca | gcagcttggg | cacccagacc | 660 |
| tacatctgca | acgtgaatca | caagcccagc | aacaccaagg | tggacaagaa | agttgagccc | 720 |
| cctaaatctt | gtgacaaaac | tcacacatgc | ccaccgtgcc | cagcacctga | actcctgggg | 780 |
| ggaccgtcag | tcttcctctt | ccccccaaaa | cccaaggaca | ccctcatgat | ctcccggacc | 840 |
| cctgaggtca | catgcgtggt | ggtggacgtg | agccacgaag | accctgaggt | ctagttcaac | 900 |
| tggtacgtgg | acggcgtgga | ggtgcataat | gccaagacaa | agccgcggga | ggagcagtac | 960 |
| aacagcacgt | accgtgtggt | cagcgtcctc | accgtcctgc | accaggactg | gctgaatggc | 1020 |
| aaggagtaca | agtgcaaggt | ctccaacaaa | gccctcccag | cccccatcga | gaaaaccatc | 1080 |
| tccaaagcca | aagggcagcc | ccgagaacca | caggtgtaca | ccctgccccc | atcccgggac | 1140 |
| gagctcacca | agaaccaggt | cagcctgacc | tgcctggtca | aaggcttcta | tcccagcgac | 1200 |
| atcgccgtgg | agtgggagag | caatgggcag | ccggagaaca | actacaagac | cacgcctccc | 1260 |
| gtgctggact | ccgacggctc | cttcttcctc | tacagcaagc | tcaccgtgga | caagagcagg | 1320 |
| tggcagcagg | ggaacgtctt | ctcatgctcc | gtgatgcatg | aggctctgca | caaccactac | 1380 |
| acgcagaaga | gcctctccct | gtctccgggt | aaataa | | | 1416 |

<210> SEQ ID NO 77
<211> LENGTH: 471
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Herceptin 274 amino acid sequence Gamma Chain
<220> FEATURE:
<221> NAME/KEY: MOD_RES
<222> LOCATION: (298)..(298)
<223> OTHER INFORMATION: Xaa is nnAA, a non natural amino acid

<400> SEQUENCE: 77

```
Met Glu Ala Pro Ala Gln Leu Leu Phe Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
                35                  40                  45

Ile Lys Asp Thr Tyr Ile His Trp Val Arg Gln Ala Pro Gly Lys Gly
50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
                100                 105                 110

Val Tyr Tyr Cys Ser Arg Trp Gly Gly Asp Gly Phe Tyr Ala Met Asp
                115                 120                 125

Tyr Trp Gly Gln Gly Thr Leu Val Thr Val Ser Ala Ser Thr Lys
            130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
                210                 215                 220

Val Asn His Lys Pro Ser Asn Thr Lys Val Asp Lys Lys Val Glu Pro
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Xaa Phe Asn Trp Tyr Val Asp
                290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Asp Glu Leu Thr Lys
                370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
```

Lys Leu Thr Val Asp Lys Ser Arg Trp Gln Gln Gly Asn Val Phe Ser
            420                 425                 430
                    435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 78
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Herceptin nucleotide sequence Kappa Chain

<400> SEQUENCE: 78
atggaggctc cgcccagct gctctttctg ctccttctct ggcttcccga cacaaccggt      60
gacatccaga tgacccagtc tccatcctcc ctgtctgcat ctgtgggaga ccgtgtcaca     120
atcacttgcc gtgctagcca ggatgtgaat acagcggtgg cctggtatca gcagaaacct    180
ggcaaagccc ctaagctcct gatctattct gcatcctttt tgtacagcgg cgtgccgagc    240
cgcttcagcg gcagccgttc tggtaccgat ttcactctca ccatcagctc tctgcaaccg    300
gaagattttg caacttacta ctgtcaacag cactacacca ctcctccgac gttcggccaa    360
gggaccaagg tggaaatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag cacccctgacg    600 ctgagcaaag cagactacga gaaacacaaa gtctacgcct gcgaagtcac ccatcagggc    660
ctgagttcgc ccgtcacaaa gagcttcaac aggggagagt gttaa                    705

<210> SEQ ID NO 79
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Herceptin amino acid sequence Kappa Chain

<400> SEQUENCE: 79

Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
        50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

-continued

```
Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 80
<211> LENGTH: 23
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<223> OTHER INFORMATION: 3 x Flag tag sequence

<400> SEQUENCE: 80

```
Asp Tyr Lys Asp His Asp Gly Asp Tyr Lys Asp His Asp Ile Asp Tyr
1               5                   10                  15

Lys Asp Asp Asp Asp Lys Ser
            20
```

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<223> OTHER INFORMATION: 5xPro-6xHis tag

<400> SEQUENCE: 81

```
Pro Pro Pro Pro Pro His His His His His His
1               5                   10
```

<210> SEQ ID NO 82
<211> LENGTH: 330
<212> TYPE: PRT
<213> ORGANISM: Homo sapiens

<400> SEQUENCE: 82

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 83
<211> LENGTH: 17
<212> TYPE: PRT
<213> ORGANISM: Homo sapiens

<400> SEQUENCE: 83

Ser Gly Ser Arg Ser Gly Thr Asp Phe Thr Leu Thr Ile Ser Ser Leu
1               5                   10                  15

Gln

<210> SEQ ID NO 84
<211> LENGTH: 15
<212> TYPE: PRT
<213> ORGANISM: Homo sapiens

<400> SEQUENCE: 84

Ser Ser Leu Gln Pro Glu Asp Phe Ala Thr Tyr Tyr Cys Gln Gln
1               5                   10                  15
```